(12) United States Patent
Danishefsky et al.

(10) Patent No.: US 8,110,590 B2
(45) Date of Patent: Feb. 7, 2012

(54) SYNTHESIS OF EPOTHILONES, INTERMEDIATES THERETO AND ANALOGUES THEREOF

(75) Inventors: Samuel J. Danishefsky, Englewood, NJ (US); Alexey Rivkin, New York, NY (US); Yoshimura Fumikiko, New York, NY (US); Ting-Chao Chou, Paramus, NJ (US); Ana E. Gabarda, New York, NY (US); Huajin Dong, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 12/604,127

(22) Filed: Oct. 22, 2009

(65) Prior Publication Data

US 2010/0197746 A1 Aug. 5, 2010

Related U.S. Application Data

(63) Continuation of application No. 10/435,408, filed on May 9, 2003, now Pat. No. 7,649,006, which is a continuation-in-part of application No. 10/402,004, filed on Mar. 28, 2003, now Pat. No. 6,921,769.

(60) Provisional application No. 60/456,159, filed on Mar. 20, 2003, provisional application No. 60/423,129, filed on Nov. 1, 2002, provisional application No. 60/408,589, filed on Sep. 6, 2002, provisional application No. 60/405,823, filed on Aug. 23, 2002.

(51) Int. Cl.
*A61K 31/427* (2006.01)
(52) U.S. Cl. ...................................................... 514/365
(58) Field of Classification Search .................... None
See application file for complete search history.

(56) References Cited

U.S. PATENT DOCUMENTS

| 5,021,430 | A | 6/1991 | Ksander |
| 5,917,084 | A | 6/1999 | Jiang |
| 5,969,145 | A | 10/1999 | Schinzer et al. |
| 6,043,372 | A | 3/2000 | Schinzer et al. |
| 6,090,601 | A | 7/2000 | Gustafsson et al. |
| 6,096,757 | A | 8/2000 | Bishop et al. |
| 6,117,659 | A | 9/2000 | Ashley et al. |
| 6,121,029 | A | 9/2000 | Schupp et al. |
| 6,156,905 | A | 12/2000 | Schinzer et al. |
| 6,204,388 | B1 | 3/2001 | Danishefsky et al. |
| 6,211,412 | B1 | 4/2001 | Georg et al. |
| 6,221,641 | B1 | 4/2001 | Khosla et al. |
| 6,242,469 | B1 | 6/2001 | Danishefsky et al. |
| 6,251,636 | B1 | 6/2001 | Betlach et al. |
| 6,262,094 | B1 | 7/2001 | Hoefle et al. |
| 6,262,107 | B1 | 7/2001 | Li et al. |
| 6,280,999 | B1 | 8/2001 | Gustafsson et al. |
| 6,284,781 | B1 | 9/2001 | Danishefsky et al. |
| 6,288,237 | B1 | 9/2001 | Hoefle et al. |
| 6,291,684 | B1 | 9/2001 | Borzilleri et al. |
| 6,300,355 | B1 | 10/2001 | Danishefsky et al. |
| 6,302,838 | B1 | 10/2001 | O'Reilly et al. |
| 6,303,342 | B1 | 10/2001 | Julien et al. |
| 6,303,767 | B1 | 10/2001 | Betlach et al. |
| 6,316,630 | B1 | 11/2001 | Danishefsky et al. |
| 6,320,045 | B1 | 11/2001 | Kim et al. |
| 6,350,878 | B1 | 2/2002 | Altmann et al. |
| 6,359,140 | B1 | 3/2002 | Hofle et al. |
| 6,365,749 | B1 | 4/2002 | Kim et al. |
| 6,369,234 | B1 | 4/2002 | Danishefsky et al. |
| 6,380,227 | B1 | 4/2002 | Mutz |
| 6,380,394 | B1 | 4/2002 | Nicolaou et al. |
| 6,380,395 | B1 | 4/2002 | Vite et al. |
| 6,383,787 | B1 | 5/2002 | Schupp et al. |
| 6,384,230 | B1 | 5/2002 | Mulzer et al. |
| 6,387,927 | B1 | 5/2002 | Altmann et al. |
| 6,399,638 | B1 | 6/2002 | Vite et al. |
| 6,407,103 | B2 | 6/2002 | Nugiel et al. |
| 6,410,301 | B1 | 6/2002 | Julien et al. |
| 6,419,692 | B1 | 7/2002 | Yang et al. |
| 6,441,186 | B1 | 8/2002 | Nicolaou et al. |

(Continued)

FOREIGN PATENT DOCUMENTS

DE 4138042 A1 5/1993
(Continued)

OTHER PUBLICATIONS

U.S. Appl. No. 60/032,864, filed Dec. 13, 1996, Nicolau et al.
U.S. Appl. No. 08/856,533, filed May 14, 1997, Nicolau et al.
U.S. Appl. No. 10/004,571, filed Dec. 4, 2001, Danishefsky et al.
Abraham, et al., "Phase I Trial and Pharmacokinetic Study of BMS-247550, an Epothilone B Analog, Administered Intravenously on a Daily Schedule for Five Days", *Journal of Clinical Oncology*, 21(9): 1866-1873, 2003.

(Continued)

*Primary Examiner* — Kamal Saeed
(74) *Attorney, Agent, or Firm* — Brenda Herschbach Jarrell; Kristen C. Buteau; Choate, Hall & Stewart LLP

(57) ABSTRACT

The present invention provides compounds of formula (I):

(I)

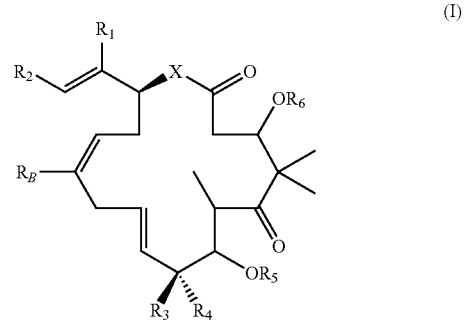

as described generally and in classes and subclasses herein. The present invention additionally provides pharmaceutical compositions comprising compounds of formula (I) and provides methods of treating cancer comprising administering a compound of formula (I).

50 Claims, 70 Drawing Sheets

U.S. PATENT DOCUMENTS

| | | |
|---|---|---|
| 6,457,303 B1 | 10/2002 | Georg et al. |
| 6,489,314 B1 | 12/2002 | Ashley et al. |
| 6,498,257 B1 | 12/2002 | Vite et al. |
| 6,515,017 B1 | 2/2003 | Li et al. |
| 6,518,421 B1 | 2/2003 | Li et al. |
| 6,525,197 B1 | 2/2003 | Furstner et al. |
| 6,531,497 B1 | 3/2003 | Nicolaou et al. |
| 6,537,988 B2 | 3/2003 | Lee |
| 6,538,038 B1 | 3/2003 | Pero et al. |
| 6,544,544 B2 | 4/2003 | Hunter et al. |
| 6,576,651 B2 | 6/2003 | Bandyopadhyay et al. |
| 6,593,115 B2 | 7/2003 | Vite et al. |
| 6,596,875 B2 | 7/2003 | White et al. |
| 6,603,015 B2 | 8/2003 | Georg et al. |
| 6,603,023 B2 | 8/2003 | Danishefsky et al. |
| 6,605,599 B1 | 8/2003 | Vite et al. |
| 6,605,726 B1 | 8/2003 | Mulzer et al. |
| 6,610,736 B1 | 8/2003 | Klar et al. |
| 6,613,912 B2 | 9/2003 | Hoefle et al. |
| 6,624,310 B1 | 9/2003 | Hoefle et al. |
| 6,625,666 B1 | 9/2003 | Kim |
| 6,670,384 B2 | 12/2003 | Bandyopadhyay et al. |
| 6,683,100 B2 | 1/2004 | van Hoogevest |
| 6,686,380 B2 | 2/2004 | Lee |
| 6,689,802 B2 | 2/2004 | DiMarco et al. |
| 6,719,540 B2 | 4/2004 | Regueiro-Ren et al. |
| 6,723,854 B2 | 4/2004 | Danishefsky et al. |
| 6,727,276 B2 | 4/2004 | Lee |
| 6,730,699 B2 | 5/2004 | Li et al. |
| 6,730,803 B2 | 5/2004 | Iwasaki et al. |
| 6,780,620 B1 | 8/2004 | Li et al. |
| 6,800,653 B2 | 10/2004 | Regueiro-Ren et al. |
| 6,906,188 B2 | 6/2005 | White et al. |
| 6,958,401 B2 | 10/2005 | White et al. |
| 7,145,018 B2 | 12/2006 | White et al. |
| 2001/0031880 A1 | 10/2001 | Borzilleri et al. |
| 2001/0034452 A1 | 10/2001 | Hoefle et al. |
| 2001/0051356 A1 | 12/2001 | Khosla et al. |
| 2002/0002162 A1 | 1/2002 | Lee |
| 2002/0002194 A1 | 1/2002 | Danishefsky et al. |
| 2002/0004229 A1 | 1/2002 | Santi et al. |
| 2002/0010328 A1 | 1/2002 | Reeves et al. |
| 2002/0028839 A1 | 3/2002 | O'Reilly et al. |
| 2002/0042109 A1 | 4/2002 | Vite et al. |
| 2002/0045220 A1 | 4/2002 | Khosla et al. |
| 2002/0045609 A1 | 4/2002 | Ashley et al. |
| 2002/0052028 A1 | 5/2002 | Santi et al. |
| 2002/0058286 A1 | 5/2002 | Danishefsky et al. |
| 2002/0058817 A1 | 5/2002 | Danishefsky et al. |
| 2002/0062030 A1 | 5/2002 | White et al. |
| 2002/0065295 A1 | 5/2002 | Chu et al. |
| 2002/0086812 A1 | 7/2002 | Schweinfest et al. |
| 2002/0091269 A1 | 7/2002 | Avery |
| 2002/0094991 A1 | 7/2002 | Gallaher |
| 2002/0115686 A1 | 8/2002 | Hoogevest |
| 2002/0119202 A1 | 8/2002 | Hunter et al. |
| 2002/0137152 A1 | 9/2002 | Santi et al. |
| 2002/0143026 A1 | 10/2002 | Lombardo et al. |
| 2002/0143038 A1 | 10/2002 | Bandyopadhyay et al. |
| 2002/0147197 A1 | 10/2002 | Newman et al. |
| 2002/0156110 A1 | 10/2002 | Arslanian et al. |
| 2002/0156289 A1 | 10/2002 | Georg et al. |
| 2002/0164377 A1 | 11/2002 | Hunter et al. |
| 2002/0165256 A1 | 11/2002 | Hofmann et al. |
| 2002/0165257 A1 | 11/2002 | Lee |
| 2002/0165258 A1 | 11/2002 | Lee |
| 2002/0165265 A1 | 11/2002 | Hunter et al. |
| 2002/0165415 A1 | 11/2002 | Georg et al. |
| 2002/0169125 A1 | 11/2002 | Leung et al. |
| 2002/0169135 A1 | 11/2002 | Pardee et al. |
| 2002/0169190 A1 | 11/2002 | Bandyopadhyay et al. |
| 2002/0177615 A1 | 11/2002 | Bandyopadhyay et al. |
| 2002/0192778 A1 | 12/2002 | Schupp et al. |
| 2002/0193361 A1 | 12/2002 | Ashley et al. |
| 2002/0197261 A1 | 12/2002 | Li et al. |
| 2002/0198141 A1 | 12/2002 | McChesney et al. |
| 2003/0003094 A1 | 1/2003 | Hunter et al. |
| 2003/0004209 A1 | 1/2003 | Hunter et al. |
| 2003/0004338 A1 | 1/2003 | Li et al. |
| 2003/0023082 A1 | 1/2003 | Ashley et al. |
| 2003/0036177 A1 | 2/2003 | Strohhacker |
| 2003/0036515 A1 | 2/2003 | Pardee et al. |
| 2003/0045711 A1 | 3/2003 | Ashley et al. |
| 2003/0049841 A1 | 3/2003 | Short et al. |
| 2003/0054977 A1 | 3/2003 | Kumar et al. |
| 2003/0060623 A1 | 3/2003 | Vite et al. |
| 2003/0069277 A1 | 4/2003 | Danishefsky et al. |
| 2003/0073205 A1 | 4/2003 | Arslanian et al. |
| 2003/0073615 A1 | 4/2003 | Li et al. |
| 2003/0073617 A1 | 4/2003 | Li et al. |
| 2003/0073677 A1 | 4/2003 | Lee |
| 2003/0087888 A1 | 5/2003 | Regueiro-Ren et al. |
| 2003/0096381 A1 | 5/2003 | Julien et al. |
| 2003/0105330 A1 | 6/2003 | Danishefsky et al. |
| 2003/0109500 A1 | 6/2003 | Pero et al. |
| 2003/0113335 A1 | 6/2003 | Li et al. |
| 2003/0114363 A1 | 6/2003 | Li et al. |
| 2003/0114450 A1 | 6/2003 | Santi et al. |
| 2003/0114504 A1 | 6/2003 | Webster et al. |
| 2003/0114518 A1 | 6/2003 | Li et al. |
| 2003/0124055 A1 | 7/2003 | Li et al. |
| 2003/0125362 A1 | 7/2003 | Danishefsky et al. |
| 2003/0130170 A1 | 7/2003 | Li et al. |
| 2003/0130178 A1 | 7/2003 | Li et al. |
| 2003/0134883 A1 | 7/2003 | Myles et al. |
| 2003/0139460 A1 | 7/2003 | Schwede et al. |
| 2003/0144523 A1 | 7/2003 | Klar et al. |
| 2003/0144533 A1 | 7/2003 | Iwasaki et al. |
| 2003/0147807 A1 | 8/2003 | Li et al. |
| 2003/0149281 A1 | 8/2003 | Westermann et al. |
| 2003/0158412 A1 | 8/2003 | Westermann et al. |
| 2003/0166507 A1 | 9/2003 | Li et al. |
| 2003/0171596 A1 | 9/2003 | Danishefsky et al. |
| 2003/0176320 A1 | 9/2003 | Li et al. |
| 2003/0176368 A1 | 9/2003 | Danishefsky et al. |
| 2003/0176473 A1 | 9/2003 | Taylor et al. |
| 2003/0176710 A1 | 9/2003 | Klar et al. |
| 2003/0180760 A1 | 9/2003 | Basch et al. |
| 2003/0186965 A1 | 10/2003 | Vite et al. |
| 2003/0186983 A1 | 10/2003 | Mastalerz et al. |
| 2003/0187039 A1 | 10/2003 | Favreau et al. |
| 2003/0187273 A1 | 10/2003 | White et al. |
| 2003/0191089 A1 | 10/2003 | Regueiro-Ren et al. |
| 2003/0194787 A1 | 10/2003 | Hofmann et al. |
| 2003/0203876 A1 | 10/2003 | Hoogevest |
| 2003/0203929 A1 | 10/2003 | Ghosh |
| 2003/0203938 A1 | 10/2003 | Nicolaou et al. |
| 2003/0208080 A1 | 11/2003 | Danishefsky et al. |
| 2004/0006087 A1 | 1/2004 | Cutler et al. |
| 2004/0023345 A1 | 2/2004 | Vite et al. |
| 2004/0024032 A1 | 2/2004 | Voi et al. |
| 2004/0024033 A1 | 2/2004 | O'Reilly et al. |
| 2004/0030147 A1 | 2/2004 | White et al. |
| 2004/0038324 A1 | 2/2004 | Atadja et al. |
| 2004/0039026 A1 | 2/2004 | Nicoloou et al. |
| 2004/0044203 A1 | 3/2004 | Wittman et al. |
| 2004/0044221 A1 | 3/2004 | Danishefsky et al. |
| 2004/0049051 A1 | 3/2004 | Hoefle et al. |
| 2004/0053910 A1 | 3/2004 | Danishefsky et al. |
| 2004/0053978 A1 | 3/2004 | Lee et al. |
| 2004/0053995 A1 | 3/2004 | Danishefsky et al. |
| 2004/0054186 A1 | 3/2004 | Das et al. |
| 2004/0054188 A1 | 3/2004 | Kusters et al. |
| 2004/0058899 A1 | 3/2004 | Klimko |
| 2004/0058969 A1 | 3/2004 | Buchmann et al. |
| 2004/0062810 A1 | 4/2004 | Hunter et al. |
| 2004/0063707 A1 | 4/2004 | Bhide et al. |
| 2004/0063708 A1 | 4/2004 | Bhide et al. |
| 2004/0063712 A1 | 4/2004 | Salvati et al. |
| 2004/0063715 A1 | 4/2004 | Paruch et al. |
| 2004/0072760 A1 | 4/2004 | Carboni et al. |
| 2004/0072832 A1 | 4/2004 | Bhide et al. |
| 2004/0072835 A1 | 4/2004 | Paruch et al. |
| 2004/0072870 A1 | 4/2004 | Nicolaou et al. |
| 2004/0072882 A1 | 4/2004 | Johnson et al. |
| 2004/0073026 A1 | 4/2004 | Das et al. |
| 2004/0076672 A1 | 4/2004 | Hunter et al. |

| | | | | | | |
|---|---|---|---|---|---|---|
| 2004/0077696 | A1 | 4/2004 | Borzilleri et al. | EP | 1275648 A1 | 1/2003 |
| 2004/0077875 | A1 | 4/2004 | Das et al. | EP | 1340498 A1 | 9/2003 |
| 2004/0082651 | A1 | 4/2004 | Wessjohann et al. | EP | 1386922 A2 | 2/2004 |
| 2004/0087610 | A1 | 5/2004 | Pardee et al. | EP | 1407784 A1 | 4/2004 |
| 2004/0087634 | A1 | 5/2004 | Hoefle et al. | EP | 1428826 A2 | 6/2004 |
| 2004/0092478 | A1 | 5/2004 | Rothermel et al. | EP | 1440973 A2 | 7/2004 |
| 2004/0092514 | A1 | 5/2004 | Velaparthi et al. | WO | WO-9310121 | 5/1993 |
| 2004/0092560 | A1 | 5/2004 | Hoefle et al. | WO | WO-9310121 A1 | 5/1993 |
| 2004/0097516 | A1 | 5/2004 | Dwyer et al. | WO | WO-9503035 | 2/1995 |
| 2004/0097517 | A1 | 5/2004 | Dwyer et al. | WO | WO-9719086 A1 | 5/1997 |
| 2004/0102451 | A1 | 5/2004 | Guzi et al. | WO | WO-9808849 A1 | 3/1998 |
| 2004/0102452 | A1 | 5/2004 | Guzi et al. | WO | WO-9822461 A1 | 5/1998 |
| 2004/0102495 | A1 | 5/2004 | Danishefsky et al. | WO | WO-9825929 A1 | 6/1998 |
| 2004/0106624 | A1 | 6/2004 | Guzi et al. | WO | WO-9838192 A1 | 9/1998 |
| 2004/0106985 | A1 | 6/2004 | Jang | WO | WO-9847891 | 10/1998 |
| 2004/0116442 | A1 | 6/2004 | Guzi et al. | WO | WO-9854966 | 12/1998 |
| 2004/0126379 | A1 | 7/2004 | Adolf et al. | WO | WO-9901124 A1 | 1/1999 |
| 2004/0127432 | A1 | 7/2004 | Nicolaou et al. | WO | WO-9902514 A2 | 1/1999 |
| 2004/0132146 | A1 | 7/2004 | Benigni et al. | WO | WO-9903848 | 1/1999 |
| 2004/0132692 | A1 | 7/2004 | Sherrill et al. | WO | WO-9903848 A1 | 1/1999 |
| 2004/0132736 | A1 | 7/2004 | Guzi et al. | WO | WO-9907692 | 2/1999 |
| 2004/0132754 | A1 | 7/2004 | Brandt et al. | WO | WO-9907692 A2 | 2/1999 |
| 2004/0133271 | A1 | 7/2004 | Jang | WO | WO-9927890 | 6/1999 |
| 2004/0142931 | A1 | 7/2004 | Vite et al. | WO | WO-9928324 | 6/1999 |
| 2004/0142990 | A1 | 7/2004 | Hofmann et al. | WO | WO-9939694 | 8/1999 |
| 2004/0152708 | A1 | 8/2004 | Li et al. | WO | WO-9942602 | 8/1999 |
| 2004/0157897 | A1 | 8/2004 | DiMarco et al. | WO | WO-9943320 | 9/1999 |
| 2004/0167083 | A1 | 8/2004 | Bosslet et al. | WO | WO-9943653 | 9/1999 |
| 2004/0167097 | A1 | 8/2004 | Zhou et al. | WO | WO-9954318 | 10/1999 |
| 2004/0176429 | A1 | 9/2004 | Li et al. | WO | WO-9954319 | 10/1999 |
| 2004/0192621 | A1 | 9/2004 | Nihei et al. | WO | WO-9954330 | 10/1999 |
| 2005/0192440 | A1 | 9/2005 | White et al. | WO | WO-9958534 | 11/1999 |
| | | | | WO | WO-9959985 | 11/1999 |
| FOREIGN PATENT DOCUMENTS | | | | WO | WO-9965913 | 12/1999 |
| DE | 19542986.9 | | 5/1997 | WO | WO-9966028 | 12/1999 |
| DE | 19607702 A1 | | 9/1997 | WO | WO-9967252 | 12/1999 |
| DE | 19636343 C1 | | 10/1997 | WO | WO-9967253 | 12/1999 |
| DE | 19638870 A1 | | 3/1998 | WO | WO-0000485 A1 | 1/2000 |
| DE | 19639456.2 | | 3/1998 | WO | WO-0031247 A2 | 6/2000 |
| DE | 19645361 A1 | | 4/1998 | WO | WO-0037473 A1 | 6/2000 |
| DE | 19645362 A1 | | 4/1998 | WO | WO-0039276 A2 | 7/2000 |
| DE | 19701758 A1 | | 7/1998 | WO | WO-0047584 A2 | 8/2000 |
| DE | 19713970 A1 | | 10/1998 | WO | WO-0049019 A2 | 8/2000 |
| DE | 19720312 A1 | | 11/1998 | WO | WO-0049020 A2 | 8/2000 |
| DE | 19821954 A1 | | 11/1998 | WO | WO-0049021 A2 | 8/2000 |
| DE | 19726627 A1 | | 12/1998 | WO | WO-0050423 A1 | 8/2000 |
| DE | 19735574 A1 | | 2/1999 | WO | WO-0057874 A1 | 10/2000 |
| DE | 19735575 A1 | | 2/1999 | WO | WO-0058254 A1 | 10/2000 |
| DE | 19735578 A1 | | 2/1999 | WO | WO-0066589 A1 | 11/2000 |
| DE | 19833750 A1 | | 2/1999 | WO | WO-0071521 A1 | 11/2000 |
| DE | 19744135 C1 | | 3/1999 | WO | WO-0107439 A2 | 2/2001 |
| DE | 19749717 A1 | | 5/1999 | WO | WO-0110412 A1 | 2/2001 |
| DE | 19751200 A1 | | 5/1999 | WO | WO-0127308 A2 | 4/2001 |
| DE | 19813821 A1 | | 9/1999 | WO | WO-0164650 A2 | 9/2001 |
| DE | 19830060 A1 | | 2/2000 | WO | WO-0166154 A2 | 9/2001 |
| DE | 19846493 A1 | | 4/2000 | WO | WO-0170716 A1 | 9/2001 |
| DE | 19849464 A1 | | 4/2000 | WO | WO-0173103 A2 | 10/2001 |
| DE | 19907588 A1 | | 8/2000 | WO | WO-0181341 A2 | 11/2001 |
| DE | 19908760 A1 | | 8/2000 | WO | WO-0183800 A2 | 11/2001 |
| DE | 19908763 A1 | | 8/2000 | WO | WO-0192255 A2 | 12/2001 |
| DE | 19908765 A1 | | 8/2000 | WO | WO-0230356 | 4/2002 |
| DE | 19908767 A1 | | 10/2000 | WO | WO-0232844 | 4/2002 |
| DE | 19923001 A1 | | 11/2000 | WO | WO-0242432 | 5/2002 |
| DE | 19930111 A1 | | 1/2001 | WO | WO-0242432 A2 | 5/2002 |
| DE | 19954228 A1 | | 9/2001 | WO | WO-0246196 | 6/2002 |
| DE | 10015836 A1 | | 10/2001 | WO | WO-0246196 A1 | 6/2002 |
| DE | 10020517 A1 | | 10/2001 | WO | WO-02058699 | 8/2002 |
| DE | 10020899 A1 | | 10/2001 | WO | WO-02058700 A1 | 8/2002 |
| DE | 19954230 A1 | | 11/2001 | WO | WO-02058701 A1 | 8/2002 |
| DE | 10051136 A1 | | 4/2002 | WO | WO-02060904 A2 | 8/2002 |
| EP | 0903348 A1 | | 3/1999 | WO | WO-02062338 A1 | 8/2002 |
| EP | 0975622 B1 | | 2/2000 | WO | WO-02066033 A1 | 8/2002 |
| EP | 0975638 B1 | | 2/2000 | WO | WO-02066038 A1 | 8/2002 |
| EP | 1001951 B1 | | 5/2000 | WO | WO-02067941 A2 | 9/2002 |
| EP | 1043369 A1 | | 10/2000 | WO | WO-02072085 A1 | 9/2002 |
| EP | 1080082 B1 | | 3/2001 | WO | WO-02072858 A2 | 9/2002 |
| EP | 1121364 B1 | | 8/2001 | WO | WO-02074042 A2 | 9/2002 |
| EP | 1186606 A1 | | 3/2002 | WO | WO-02080846 A2 | 10/2002 |
| EP | 1201666 A2 | | 5/2002 | WO | WO-02096281 A1 | 12/2002 |

| | | |
|---|---|---|
| WO | WO-02098868 A1 | 12/2002 |
| WO | WO-03007924 A2 | 1/2003 |
| WO | WO-03014063 A2 | 2/2003 |
| WO | WO-03014068 A1 | 2/2003 |
| WO | WO-0322844 A2 | 3/2003 |
| WO | WO-03018002 A2 | 3/2003 |
| WO | WO-03026744 A1 | 4/2003 |
| WO | WO-03029195 A1 | 4/2003 |
| WO | WO-03029260 A1 | 4/2003 |
| WO | WO-03042217 A2 | 5/2003 |
| WO | WO-03045324 A2 | 6/2003 |
| WO | WO-03049734 A1 | 6/2003 |
| WO | WO-03053949 A1 | 7/2003 |
| WO | WO-03057217 A1 | 7/2003 |
| WO | WO-03057830 A2 | 7/2003 |
| WO | WO-03070170 A2 | 8/2003 |
| WO | WO-03074053 A1 | 9/2003 |
| WO | WO-03074521 A1 | 9/2003 |
| WO | WO-03075899 A2 | 9/2003 |
| WO | WO-03076445 A2 | 9/2003 |
| WO | WO-03077903 A1 | 9/2003 |
| WO | WO-03078411 A1 | 9/2003 |
| WO | WO-03084536 A1 | 10/2003 |
| WO | WO-03096975 A2 | 11/2003 |
| WO | WO-03103712 A1 | 12/2003 |
| WO | WO-03105828 A1 | 12/2003 |
| WO | WO-2004007476 A1 | 1/2004 |
| WO | WO-2004012735 A2 | 2/2004 |
| WO | WO-2004014919 A1 | 2/2004 |
| WO | WO-2004016269 A1 | 2/2004 |
| WO | WO-2004017943 A2 | 3/2004 |
| WO | WO-2004018000 A2 | 3/2004 |
| WO | WO-2004018478 A2 | 3/2004 |
| WO | WO-2004018635 A2 | 3/2004 |
| WO | WO-2004022062 A1 | 3/2004 |
| WO | WO-2004022080 A2 | 3/2004 |
| WO | WO-2004022559 A1 | 3/2004 |
| WO | WO-2004022560 A1 | 3/2004 |
| WO | WO-2004024735 A2 | 3/2004 |
| WO | WO-2004025254 A2 | 3/2004 |
| WO | WO-2004026229 A2 | 4/2004 |
| WO | WO-2004026254 A2 | 4/2004 |
| WO | WO-2004026310 A1 | 4/2004 |
| WO | WO-2004026867 A2 | 4/2004 |
| WO | WO-2004026872 A1 | 4/2004 |
| WO | WO-2004026877 A1 | 4/2004 |
| WO | WO-2004028582 A1 | 4/2004 |
| WO | WO-2004028610 A2 | 4/2004 |
| WO | WO-2004030620 A2 | 4/2004 |
| WO | WO-2004030627 A2 | 4/2004 |
| WO | WO-2004032866 A2 | 4/2004 |
| WO | WO-2004032872 A2 | 4/2004 |
| WO | WO-2004032923 A1 | 4/2004 |
| WO | WO-2004035050 A1 | 4/2004 |
| WO | WO-2004043363 A2 | 5/2004 |
| WO | WO-2004043400 A2 | 5/2004 |
| WO | WO-2004043454 A1 | 5/2004 |
| WO | WO-2004043954 A2 | 5/2004 |
| WO | WO-2004048372 A1 | 6/2004 |
| WO | WO-2004050057 A2 | 6/2004 |
| WO | WO-2004050089 A1 | 6/2004 |
| WO | WO-2004052237 A2 | 6/2004 |
| WO | WO-2004052361 A1 | 6/2004 |
| WO | WO-2004052401 A2 | 6/2004 |
| WO | WO-2004054514 A2 | 7/2004 |
| WO | WO-2004054622 A1 | 7/2004 |
| WO | WO-2004054624 A1 | 7/2004 |
| WO | WO-2004056832 A2 | 7/2004 |
| WO | WO-2004061116 A2 | 7/2004 |
| WO | WO-2004063151 A2 | 7/2004 |
| WO | WO-2004078978 A1 | 9/2004 |
| WO | WO-2004080458 A1 | 9/2004 |
| WO | WO-2004085421 A2 | 10/2004 |
| WO | WO-2004087045 A2 | 10/2004 |

OTHER PUBLICATIONS

Agrawal, et al., "Treatment of Recurrent Cervical Adenocarcinoma with BMS-247550, an Epothilone B Analog", *Gynecologic Oncology*, 90: 96-99, 2003.

Ahmed et al., "Total Synthesis of the Microtubule Stabilizing Antitumor Agent Laulimalide and Some Nonnatural Analogues: The Power of Sharpless' Asymmedtric Epoxidation" *J. Org. Chem.* 68:3026-3042, 2003.

Altaha, et al., "Epothilones: A Novel Class of Non-Taxane Microtubule-Stabilizing Agents", *Current Pharmaceutical Design*, 8: 1707-1712, 2002.

Altmann et al., "Epothilone B and Its Analogs—A New Family of Anticancer Agents" *Mini-Rev. Med. Chem.* 3:149-158, 2003.

Altmann et al., "Epothilones and Related Structures—A New Class of Microtubule Inhibitors with Potent in vivo Antitumor Activity" *Biochim. Biophys. Acta*, 1470(3):M79-M91, 2000.

Altmann et al., "Epothilones and Their Analogs-Potential New Weapons in the Fight Against Cancer" *Chimia*, 54:612-621, 2000.

Altmann et al., "Microtubule-Stabilizing Agents: A Growing Class of Important Anticancer Drugs" *Curr. Opin. Chem. Biol.*, 5(4):424-431, Aug. 2001.

Altmann et al., "Synthesis and Biological Evaluation of Highly Potent Analogues of Epothilones B and D" *Bioorg. Med. Chem. Lett.* 10(24):2765-2768, 2000.

Altmann, K., "Microtubule-Stabilizing Agents: A Growing Class of Important Anticancer Drugs", *Current Opinion in Chemical Biology*, 5: 424-431, 2001.

Appendino et al., "The Synthesis of Epothilones: Highlights from a Year's Race" *Chemtracts* 11(9):678-696, 1998.

Arslanian et al., "A New Cytotoxic Epothilone from Modified Polyketide Synthases Heterologously Expresssed in *Myxococcus xanthus*" *J. Nat. Prod.* 65:1061-1064, 2002.

Avila et al., "The Use of Microtubule Poisons on Tumor Cells" *Cancer J.* 10(6):315-318, 1997.

Awada et al., "New Cytotoxic Agents and Molecular-Targeted Therapies in the Treatment of Metastatic" *Breast Cancer Review* 4-15, 2002.

Baggiolini et al., "Stereocontrolled Total Synthesis of 1α, 25-Dihydroxycholecalciferol and 1α, 25-Dihydroxyergocalciferol" *J. Org. Chem.* 51:3098-3108, 1986.

Baik et al., "Diastereoselective Cobalt-Catalyzed Aldol and Michael Cycloreductions" *J. Am. Chem. Soc.* 123:5112-5113, 2001.

Balog et al., "A Novel Aldol Condensation with 2-Methyl-4-Pentenal and Its Application to an Improved Total Synthesis of Epothilone B" *Angew. Chem. Int. Ed.* 37(19):2675-2678, 1998.

Balog et al., "Stereoselective Syntheses and Evaluation of Compounds in the 8-Desmethylepothilone A Series: Some Surprising Observations . . . " *Tetrahedron Letters* 38:26 4529-4532 (1997).

Balog et al., "Total Synthesis of Epothilone A" *Angew. Chem. Int. Ed.* 61:2801-2803, 1996.

Bayes, et al., "Gateways to Clinical Trials", *Methods Find Exp Clin. Pharmacol.* 25(1): 53-76, 2003.

Bellemin-Laponnaz et al., "The Kinetic Resolution of Allylic Alchols by a Non-Enzymatic Acylation Catalyst: Application to Natural Product Synthesis" *Chem. Commun.* 12:1009-1010, 2000.

Bertinato et al., "Studies Toward a Synthesis of Epothilone A: Stereocontrolled Assembly of the Acyl Region and Models for Macrocyclization" *J. Org. Chem.* 61:8000-8001, 1996.

Beyer et al., "Metabolic Diversity in Myxobacteria" *Biochim. Biophys. Acta* 1445(2):185-195, 1999.

Bijoy, P. et al., "Synthetic Studies Directed Towards Epothilone A: . . . ", *Tetrahedron Letters* 39:209-212 (1998).

Biswas et al., "Highly Concise Routes to Epothilones: The Total Synthesis and Evaluation of Epothilone 490" *J. Am. Chem. Soc.* 124:9825-9832, 2002.

Blum et al., "In vivo Metabolism of Epothilone B in Tumor-Bearing Nude Mice: Identification of Three New Epothilone B Metabolites by Capillary High-Pressure Liquid Chromatography/Mass Spectrometry/Tandem Mass Spectrometry" *Rapid Commun. Mass Spectrom.* 15(1):41-49, 2001.

Bocci et al., "Protracted Low-Dose Effects on Human Endothelial Cell Proliferation and Survival in Vitro Reveal a Selective Antiangiogenic Window for Various Chemotherapeutic Drugs" *Cancer Research* 62:6938-6943, 2002.

Boddy et al., "Epothilone C. Macrolactonization and Hydrolysis Are Catalyzed by the Isolated Thioesterase Domain of Epothilone Polyketide Synthase" *J. Am. Chem. Soc.* 125:3428-3429, 2002.

Bode et al., "Stereoselective Syntheses of Epothilones A and B via Directed Nitrile Oxide Cycloaddition" *J. Am. Chem. Soc.* 123(15):3611-3612, 2001.

Bode et al., "Stereoselective Syntheses of Epothilones A and B via Nitrile Oxide Cycloadditions and Related Studies" *J. Org. Chem.*, 66(19):6410-6424, 2001.

Bollag et al., "Epothilones, a New Class of MT-stabilizing Agents with a Taxol-Like Mechanism of Action" *Cancer Research* 55:2325-2333, 1995.

Bollag et al., "Epothilones: Novel Microtubule Stabilizing Agents" *Expert Opin. Invest. Drugs* 6(7):867-873, 1997.

Bollag, et al., "Epothilones, A New Class of Microtubule-Stabilizing Agents with a Taxol-Like Mechanism of Action", *Chemstracts—Organic Chemistry*, 11: 671-677, 1998.

Bornscheuer, et al., "Directed Evolution of an Esterase for the Stereoselective Resolution of a Key Intermediate in the Synthesis of Epothilones", *Biotechnol Bioeng.* 58: 554-559, 1998.

Borzilleri et al., "A Novel Application of a Pd(0)-Catalyzed Nucleophilic Substitution Reaction to the Regio and Stereoselective Synthesis of Lactam Analogues of the Epothilone Natural Products" *J. Am. Chem. Soc.* 122(37):8890-8897, 2000.

Borzilleri, et al., "A Novel Application of a Pd(0)-Catalyzed Nucleophilic Substitution Reaction to the Regio—and Stereoselective Synthesis of Lactam Analogues of the Epothilone Natural Products", *Chemtracts—Organic Chemistry*, 14: 401-404, 2001.

Broker, et al., "Late Activation of Apoptotic Pathways Plays a Negligible Role in Mediating the Cytotoxic Effects of Discodermolide and Epothilone B in Non-Small Cell Lung Cancer Cells", *Cancer Research*, 62: 4081-4088, 2002.

Broker, et al., "The Role of New Agents in the Treatment of Non-Small Cell Lung Cancer", *European Journal of Cancer*, 38: 2347-2361, 2002.

Carlomagno et al., "Derivation of Dihedral Angles from Ch-Ch Dipolar-Dipolar Cross-Correlated Relaxation Rates: A C-C Torsion Involving a Quaternary Carbon Atom in Epothilone A Bound to Tubulin" *Angew. Chem. Int. Ed.* 42:2515-2517, 2003.

Carlomagno et al., "The High-Resolution Solution Structure of Epothilone A Bound to Rubulin: An Understanding of the Structure-Activity Relationships for a Powerful Class of Antitumor Agents" *Angew. Chem. Int. Ed.* 42:2511-2515, 2003.

Carreira, "Discovery and Study of New Reaction Chemistry: Applications in Complex Molecule Assembly" *Chimia* 55(10):818-820, 2001.

Casas et al., "BINOLAM, a Recoverable Chiral Ligand for Bifunctional Enantioselective Catalysis: The Asymmetric Synthesis of Cyanohydrins" Organic Letters 4(15):2589-2592, 2002.

Chakraborty, T.K. et al., "Radical-induced Opening of Trisubstituted Epothilones", *Tetrahedron Letters* 39:101-104 (1998).

Chappell, et al., "En Route to a Plant Scale Synthesis of the Promising Antitumor Agent 12,13-Desoxyepothilone B" *Org. Letter.* 2(11): 1633-1636, 2000.

Chen et al., "Epothilone Biosynthesis: Assembly of the Methylthiazolylcarboxy Starter Unit on the EpoB Subunit" *Chem. Biol.* 8(9):899-912, 2001.

Chou et al., "Design and Total Synthesis of a Superior Family of Epothiolone Analogues, which Eliminate Xenograft Tumors to a Nonrelapsable State" Angew. Chem. Int. Ed. Engl. 42:4762-4767, 2003.

Chou et al., "Desoxyepothilone B: An efficacious microtubule-targeted antitumor agent with a promising in vivo profile relative to epothilone B" Proc. Natl. Acad. Sci. USA 95:9642-9647, 1998.

Chou et al., "Quantitative Analysis of Dose-Effect Relationships the Combined Effects of Multiple Drugs or Enzyme Inhibitors" Adv. Enzyme Reg. 22:27-55, 1984.

Chou, et al., "Desoxyepothilone B is curative against human tumor xenografts that are refractory to paclitaxel" Proc. Natl. Acad. Sci. USA 95:15798-15802, 1998.

Claus, E. et al., "Synthesis of the C1-C9 Segment of Epothilones", *Tetrahedron Letters* 38:8:1359-1362(1997).

Corey, et al., "Chemistry of Diimide. Some New Systems for the Hydrogenation of Multiple Bonds" *Tetrahedron Lett.* 347-352 1961.

Correia et al., "Physiochemical Aspects of Tubulin-Interacting Antimitotic Drugs" *Curr. Pharm. Des.* 7(13):1213-1228, 2001.

Costa, et al., "Neue Aspekte Bei Der Therapie des Ovarialkarzinoms—Was Andert Sich Nach Dem ASCO-Meeting 2001?", *Zentralbl Gynakol*, 124: 96-103, 2002.

Costa, et al., "New Aspects by the Therapy of Ovarian Cancer—What Changes After the ASCO Meeting 2001?", Zentralbl Gynakol, 124: 96-103, 2002.

Cowden et al., "Cancer Drugs-Better than Taxol?" *Nature* 387:238-239, 1997.

Danishefsky et al., "A Novel Aldol Condensation with 2-Methyl-4-Pentenal and the Application to an Improved Total Synthesis of Epothilone B" *Angew. Chem. Int. Ed.* 37:2675, 1998.

Danishefsky et al., "Chemical Synthesis and Biological Studies of the Epothilones-Microtubule Stabilizing Agents with Enhanced Activity Against Multidrug-Resistant Cell Lines and Tumors" *Chem. 21st Century*, Ed. Keinan, Wiley-VCH Verlag, 8-36, 2001.

Danishefsky et al., "Complex Target Oriented Synthesis in the Drug Discovery Process: A Case History in the dEpoB Series" *J. Org. Chem.* 64:8434-8456, 1999.

Danishefsky et al., "Desoxyepothilone B is Curative Against Human Tumor Xenografts that are Refractory to Pacilitaxel" *Proc. Nat. Acad. Sci. USA* 95:15798, 1998.

Danishefsky et al., "En Route to a Plant Scale Synthesis of the Promising Antitumor Agent 12,13- Desocyepothilone B" *Org. Letters* 2:1633-1636, 2000.

Danishefsky et al., "Epothilones: Microtubule Stabilizing Agents with Enhanced Activity Against Multidrug-Resistant Cell Lines and Tumors" Actualites de Chimie Therpaeutique,Vingt-cinqieme serie, Paul Ehrlich Lecture, *Societe de Chimie Therapeutique*, Elsevier, Paris, New York, 25:187-206, 1999.

Danishefsky et al., "Insights into Long-Range Structural Effects on the Stereochemistry of Aldol Condensations: A Practical Total Synthesis of Desoxyepothilone F" *J. Am. Chem. Soc.* 123(22):5249-5259, 2001.

Danishefsky et al., "New Chemical synthesis of the Promising Cancer Chemotherapeutic Agent 12,13-Desoxyepothilone B: Discovery of a Surprising Long-Range Effect on the Diastereoselective of an Aldol Condensation." *J. Am. Chem. Soc.* 121:7050-7062, 1999.

Danishefsky et al., "On the Interactivity of Complex Synthesis and Tumor Pharmacology in the Drug Discovery Process: Total Synthesis and Comparative in Vivo Evaluations of the 15-Aza Epothilones" *J. Org. Chem.* 66(12):4369-4378, 2001.

Danishefsky et al., "On the Total Synthesis and Preliminary Biological Evaluations of 15 (R) and 15 (S) Aza-dEpoB: A Mitsunobu Inversion at C15 in Pre-Epothilone Fragments" *Org. Letters* 2:1637-1639, 2000.

Danishefsky et al., "Remarkable Long Range Effects on the Diastereoface Selectivity in an Aldol Condensation" *Tet. Lett.* 40:2267-2270, 1999.

Danishefsky et al., "Remote Effects in Macrolide Formation Through Ring Forming Olefin Metathesis: An Application to the Synthesis of Fully Active Epothilone Congeners" *J. Am. Chem. Soc.* 119:2733, 1997.

Danishefsky et al., "Structure-Activity Relationships of the Epothilones and the First in Vivo Comparison with Paclitaxel" *Angew. Chem. Int. Ed.* 7:824-826, 1997.

Danishefsky et al., "Subtle Variations in the Long Range Transmission of Stereochemical Information: Matched and Mismatched Aldol Reactions" *Angew. Chem. Int. Ed.* 39:4505-4508, 2000.

Danishefsky et al., "The microtubule-stabilizing agents epothilones A and B and their desoxy-derivatives induce mitotic arrest and apoptosis in human prostate cancer cells" *Prostate Cancer and Prostatic Diseases* 2:41-52, 1999.

Danishefsky et al., "The Synthesis and Evaluation of 12,13-Benzodesoxyepothilone B: a Highly Convergent Route" *Tet. Lett.* 40:6895-6898, 1999.

Danishefsky et al., "The Total Synthesis and Antitumor Activity of 12, 13-Desoxyepothilone F: An Unexpected Solvolysis Problem at C15, Mediated by Remote Substitution at C21" *J. Org. Chem.* 65(20):6525-6533, 2000.

Danishefsky et al., "Total Synthesis of (−)—Epothilone B: An Extension of the Suzuki Coupling Method and Insights into Structure—Activity Relationships of the Epothilones" *Angew. Chem. Int. Ed.* 36:757, 1997.

De Brabander et al., "Towards a Synthesis of Epothilone A" *Synlett.* 3:328, 1998.

De Brabander et al., "Towards a Synthesis of Epothilone A. Rapid Assembly of the C(1)-C(6) and C(7)-C(12) Fragments" *Synlett.* 6:824-826, 1997.

Delbaldo et al., "Nouveaux medicamenets dans le cancer bronchique" La Presse Medicate 31:802-809, 2002.

Denmark et al., "Cyclopropanation with Diazomethane and Bis(Oxazoline) Palladium(II) Complexes" *J. Org. Chem.* 62:3375-3389, 1997.

Duthaler et al., "Enantioselective Aldol Reaction of Tert-Butyl Acetate Using Titanium-Carbohydrate Complexes" *Angew. Chem. Int. Ed. Engl.* 28:495-497, 1989.

End et al., "Synthetic Epothilone Analogs with Modifications in the Northern Hemisphere and the Heterocyclic Side-Chain-Synthesis and Biological Evaluation" *Proc. ECSOC-3, Proc. ECSOC-4*, 1999, 2000, Meeting Date 1999-2000, 1431-1442, Ed: Pombo-Villar, Esteban. Molecular Diversity Preservation International: Basel, Switz. 2000, Doc. No: 134:311010, 2000.

Ermolenko et al., "Synthesis of Epothilones B and D from D-Glucose" *Tet. Lett.* 43:2895-2898, 2002.

Essayan, et al., "Successful Parenteral Desensitization to Paclitaxel", *J. Allergy Clin. Immunol.* 97:42-46, 1996.

Finley et al., "Metathesis vs. Metastasis: The Chemistry and Biology of the Epothilones" *Chem. Ind.* 24:991-996, 1997.

Fletcher et al., "Structure of the Mitogen-Inducible TIS10 Gene and Demonstration That the TIS10-Encoded Protein Is a Functional Prostaglandin G/H Synthase" *J. Biol. Chem.* 267:4338-4344, 1992.

Frykman et al., "Control of Secondary Metabolite Congener Distributions via Modulation of the Dissolved Oxygen Tension" *Biotechnol. Prog.* 18:913-920, 2002.

Furstner et al., "Concise Total Syntheses of Epothilone A and C Based on Alkyne Metathesis" *Chem. Commun.* 12:1057-1059, 2001.

Furstner, "Olefin Metathesis and Beyond", *Angew. Chem. Int. Ed. Engl.* 39:3013-3043, 2000.

Gabriel, "The Chromium-Reformatsky Reaction: Asymmetric Synthesis of the Aldol Fragment of the Cytotoxic Epothilones from 3-(2-Bromoacyl)—2-Oxazolidinones" *Tet. Lett.* 38(8):1363-1366, 1997.

Geng et al., "Design and Synthesis of De Novo Macrocyclic Hybrids as Potential Anticancer Agents" *Abstr. Pap.-Am. Chem. Soc.*, 221$^{st}$, MEDI-130, 2001.

Georg et al., "Studies Toward the Synthesis of Epothilone Affinity Labels" Book of Abstracts, 219$^{th}$ ACS National Meeting, San Francisco, CA, Mar. 26-30, MEDI-075, 2000.

Gerlach et al., "Synthesis of the C(7)-C(17) Segment of Epothilones by a 10-Membered Ring Closing Metathesis Reaction" *Synlett.* 10:1108-1110, 1998.

Gerth et al., "Studies on the Biosynthesis of Epothilones: The Biosynthetic Origin of the Carbon Skeleton" *J. Antibiot.* 53(12):1373-1377, 2000.

Gerth, K. et al., "Epothilone A and B: Antifungal and Cytotoxic Compounds . . . ", *Liebigs Ann.Chem.* 74 & 75, 49-53 (1996).

Gerth. et al., "Studies on the Biosynthesis of Epothilones: the PKS and Epothilone C/D Monooxygenase" *J. Antibiot.*, 54(2):144-148, 2001.

Giannakakou et al., "Paclitaxel-resistant Human Ovarian Cancer Cells Have Mutant β-Tubulins. That Exhibit Impaired Paclitaxel-Driven Polymerization" *J. Biol. Chem.* 272(27):17118-17125, 1997.

Giannakakou, et al., "A Common Pharmacophore for Epothilone and Taxanes: A Molecular Basis for Drug Resistance Conferred by Tubulin Mutations in Human Cancer Cells" *Proc. Natl. Acad. Sci.*, 97(6): 2904-2909, 2000.

Griffin, et al., "Molecular Determinants of Epothilone B Derivative (BMS 247550) and Apo2L/TRAIL-induced Apoptosis of Human Ovarian Cancer Cells", Gynecologic Oncology, 89: 37-47, 2003.

Grubbs, et al., "Ring-Closing Metathesis and Related Processes in Organic Synthesis" *Acc. Chem. Res.* 28: 446-452, 1995.

Gupta, et al., Understanding Tubulin-Taxol Interactions: Mutations That Impart Taxol Binding to Yeast Tubulin PNAS, 100: 5394-6397, 2003.

Haar, et al., "Discodermolide, A Cytotoxic Marine Agent That Stabilizes Microtubules More Potently Than Taxol", *Biochemistry*, 35: 243-250, 1996.

Hamashima, et al., "Highly Enantioselective Cyanosilylation of Aldehydes Catalyzed by a Lewis Acid-Lewis Base Bifunctional Catalyst" *Tetrahedron*, 57(5): 805-814, 2001.

Hardt, et al., "New Natural Epothilones from Sorangium Cellulosum, Strains So ce90/B2 and So ce90/D13: Isolation, Structure Elucidation and SAR Studies" *J. Nat. Prod.*, 64(7): 847-856, 2001.

Harris, et al., "Chemical Synthesis and Biological Studies of the Epothilones—Microtubule Stabilizing Agents with Enhanced Activity Against Multidrug-Resistant Cell Lines and Tumors", *Chemistry for the 21$^{st}$ Century*, 8-36, 2001.

Harris, et al., Complex Target-Oriented Synthesis in the Drug Discovery Process: A Case History in the dEpoB Series *J. Org. Chem.*, 64:8434-8456, 1999.

Hayward, et al. "Total Synthesis of Rapamycin via a Novel Titanium-Mediated Aldol Macrocyclization Reaction", *J. Am. Chem. Soc.*, 115: 9345-9346, 1993.

He, et al., "A Common Pharmacophore for Taxol and the Epothilones Based on the Biological Activity of a Taxane Molecule Lacking a C-13 Side Chain" *Biochemistry*, 39(14): 3972-3978, 2000.

He, et al.. "Novel Molecules that Interact with Microtubules and have Functional Activity Similar to Taxol" *Drug Discovery Today*, 6(22): 1153-1164,2001.

Hindpur, et al., "Total Synthesis of Epothilone A" *Tetrahedron Letters*, 42(42): 7341-7344, 2001.

Hindupur, et al., "Total Synthesis of Epothilone", *Tetrahedron Lett.* 42: 7341-7344, 2000.

Hofle et al., "Epothilone A and B—Novel 16-Membered Macrolides with Cytotoxic Activity: Isolation, Crystal Structure, and Conformation in Solution" *Angew. Chem. Int. Ed. Engl.* 35:1567-1569, 1996.

Holland, et al., "Design, Synthesis and Biological Evaluation of Epothilone Analogs", Book of Abstracts, 215th ACS National Meeting, Dallas, Mar. 29-Apr. 2, ORGN-015.

Holland, J.M., "The Synthesis of a Cyclopropyl Taxane Analog via Sequential Diels-Alder Reactions: the Design and Synthesis of Novel Epothilone Analogs" University of Pennsylvania Order No. DA9953544 From: Diss. Abstr. Int., B2000, 60(12) 6106, 1999.

Inoue, et al., "Design and Synthesis of Taxoid-Epothilone Hybrids", Book of Abstracts, 216th ACS National Meeting, Boston, Aug. 23-27, ORGN-380.

Ivin, "Some Recent Applications of Olefin Metathesis in Organic Synthesis: A Review", *J. Mol. Catal. A: Chem*, 133(1-2): 1998.

Jaenicke, L., "Epothilone from Amphora" *Chem. Unserer Zeit* (German), 34(4): 257, 2000.

Jiang, et al., "Advances in Research on Novel Natural Anticancer Compounds: Epothilones" *Tianran Chanwu Yanjiu Yu Kaifa* (Chinese), 11(3): 77-81, 1999.

Johnson, et al.. "Synthesis, Structure Proof, and Biological Activity of Epothilone Cyclopropanes" *Org. Lett*, 2: 1537-1540, 2000.

Julien, et al., "Isolation and Characterization of the Epothilone Biosynthetic Gene Cluster from Sorangium Cellulosum" *Gene*, 249(1-2): 153-160, 2000.

Kalesse, et al., "The Formal Total Synthesis of Epothilone A" *Eur. J. Org. Chem.*, 11: 2817-2823, 1999.

Koch, et al., Diastereoselective Titanium Enolate Aldol Reaction for the Total Synthesis of Epothilones Organic Letters, 2(22): 3811-3814, 2002.

Kowalski, R.J. et al., "Activities of the Microtubule-stabilizing Agents Epothilones A and B . . . ", *J. of Biol. Chem.* 272:4 2534-2541 (1997).

Krische, et al., "Diastereoselective Cobalt-Catalyzed Aldol and Michael Cycloreductions" *J. Am. Chem. Soc.* 123: 5112-5113, 2001.

Lavelle, et al., "Nouveaux Taxanes et Derives d'Epothilone en Cours d'Etudes Cliniques", *Bull Cancer*, 89(4): 343-350, 2002.

Lee, et al., "BMS-247550: A Novel Epothilone Analog with a Mode of Action Similar to Paclitaxel but Possessing Superior Antitumor Efficacy" *Clin. Cancer Res.*, 7(5): 1429-1437, 2001.

Lee, et al., "Insights into Long-Range Structural Effects on the Stereochemistry of Aldol Condensations: A Practical Total Synthesis of Deoxyepothilone F" *J. Am. Chem. Soc.* 123: 5249-5259, 2001.

Lee, et al., "Synthesis of the C11-C21 and C13-C21 Fragments of Epothilones from D-glucose" *Bull. Korean Chem. Soc.*, 21(12): 1177-1178, 2000.

Lee, et al., "Total Synthesis and Antitumor Activity of 12,13-Desoxyepothilone F: An Unexpected Solvolysis Problem at C15, Mediated by Remote Substitution at C21" *J. Org. Chem.*, 65: 6525-6533, 2000.

Levin, et al., "An Alternative Procedure for the Aluminum-Mediated Conversion of Esters to Amides", *Synth. Commun.* 12: 989, 1982.

Li, et al., "Antimitotic Agents" *Annu. Rep. Med. Chem.*, 34: 139-148, 1999.

Li, et al., "Process Development of the Semisynthesis of a Biologically Active Epothilone Analogue" *Abstracts of Papers, 222nd ACS National Meeting*, Chicago, IL, Aug. 26-30, ORGN-238, 2001.

Li, et al., "Synthesis of a Novel Epothilone B Analog as a Potential Photoaffinity Label" *Abstr. Pap.-Am. Chem. Soc. 221st, MEDI-137*, 2001.

Lichtner, et al., "Subcellular Distribution of Epothilones in Human Tumor Cells" *Proc. Natl. Acad. Sci. U.S.A.*, 98(20): 11743-11748, 2001.

Lin, et al., "Design and Synthesis of Taxoid-Epothilone Hybrids" Book of Abstracts, 216th ACS National Meeting, Boston, Aug. 23-27, ORGN-464.

Lindel, et al., "Eleutherobin, A New Cytotoxin that Mimics Paclitaxel (Taxol) by Stabilizing Microtubules", *J. Am. Chem. Soc.* 119: 8744-8745, 1997.

List, et al., "Proline-Catalyzed Direct Asymmetric Aldol Reactions" *J. Am. Chem. Soc.* 122:2395-2396, 2000.

Liu, et al., "Epoxide Opening with Acetylide for Synthesis of Epothilone A C7-21 Segment", *Tetrahedron Lett.* 39(29): 5261-5264, 1998.

Liu, et al., "Synthesis of the C11-16+C27 Segment of Epothilone A", *Chin. Chem. Lett.* 9(1): 35-38, 1998.

Liu, et al., "Total Synthesis of Epothilone A through Stereospecific Epoxidation of the p-Methoxybenzyl Ether of Epothilone C" *Chem. Eur. J.*, 8(16): 3747-3756, 2002.

Liu, Z.Y. et al., "Chiral Synthesis of the C3-13 Segment of Epothilone A" *Synlett Letters* 1383-84 (1997).

Lythgoe, et al., "Allylic Phosphine Oxides as Precursors of Dienes of Defined Geometry: Synthesis of 3-Deoxyvitamin $D_2$", *Tetrahedron Lett.* 40:3863-3866, 1975.

Lythgoe, et al., "Synthetic Approaches to Vitamin D and its Relatives", *Chem. Soc. Rev.* 449-475, 1981.

Machajewski, et al., "Chemoenzymic Synthesis of Key Epothilone Fragments" *Synthesis (Spec. Iss.)*, 1469-1472, 1999.

Martello, et al., "Taxol and Discodermolide Represent a Synergistic Drug Combination in Human Carcinoma Cell Lines", Clinical Cancer Research, 6: 1978-1987, 1978.

Martello, et al., "Taxol and Discodermolide Represent a Synergistic Drug Combination in Human Carcinoma Cell Lines", *Clinical Cancer Research*, 6: 1978-1987, 2000.

Martin, "How Stable are Epoxides? A Novel Synthesis of Epothilone B" *Angew. Chem. Int. Ed*, 39(3): 581-583, 2000.

Martin, et al.. "The 12,13-diol Cyclization Approach for a Truly Stereocontrolled Total Synthesis of Epothilone B and the Synthesis of a Conformationally Restrained Analog" *Chem. Eur. J*, 42(47): 8373-8377, 2001.

May, et al., "Total Synthesis of (−) Epothilone B", *Chem. Commun.*, 95: 1369-1374, 1998.

McDaid et al., "Validation of the Pharmacodynamics of BMS-247550, an Analogue of Epothilone B, During a Phase I Clinical Study" Clinical Cancer Research 8:2035-2043, 2002.

Meng et al. "Studies toward a Synthesis of Epothilone A: Use of Hydropyran Templates for the Management of Acyclic Stereochemical Relationships" J. Org. Chem. 61:23 7998-8001 (1996).

Meng et al. "Total Synthesis of Epothilones A and B" *J. Am. Chem. Soc.* 119:42 10073-10092 (1997).

Meng et al., "Chapter I: The First Total Syntheses of Epothilones A, B, C and D. Chapter II: The First Total Syntheses of 12-epi-CP-263,114 and 12-epi-CP-225,917" Columbia University Order No. DA9949022 From: Diss. Abstr. Int., B2000, 60(10), 5096 (1999).

Moasser et al., "Farnesyl transferase inhibitors cause enhanced mitotic sensitivity to taxol . . ." *Proc. Natl. Acad. Sci. USA*, 95:1369-1374 (1998).

Molnar, et al., "The Biosynthetic Gene Cluster for the Microtubule-Stabilizing Agents Epothilones A and B from Sorangium Cellulosum So ce90" *Chem. Biol.*, 7(2): 97-109, 2000.

Mooberry, et al., "Laulimalide and Isolaulimalide, New Paclitaxel-Like Microtubule-Stabilizing Agents", *Cancer Res.* 59: 653-680, 1999.

Muhlradt et al., "Epothilone B Stabilizes Microtubuli of Macrophages Like Taxol . . . ", *Cancer Res.* 57, 3344-46 (1997).

Mulzer, "Progress in the Synthesis of Chiral Heterocyclic Natural Products: Epothilone B and Tartrolon B" *J. Heterocycl. Chem.*, 36(6): 1421-1436, 1999.

Mulzer, et al., "Total Syntheses of Epothilones B and D" *J. Org. Chem.*, 65(22); 7456-7467, 2000.

Mulzer, et al.,"Epothilone B and its Derivatives as Novel Antitumor Drugs: Total and Partial Synthesis and Biological Evaluation" *Monatsh. Chem.*, 131(3): 205-238, 2000.

Mulzer, et al.. "Easy Access to the Epothilone Family-Synthesis of Epothilone B", *Tetrahedron Letters*, 39(47): 8633-8636, 1998.

Mulzer, J. et al., "Synthesis of the C(1)-C(9) Segment of the Cytotoxic Macrolides Epothilon A and B", *Tetrahedron Letters* 37:51, 9179-9182 (1996).

Nagaoka, et al., "Further Synthetic Studies on Rifamycin S", *Tetrahedron*, 37: 3873-3888, 1981.

Nahm, et al., "N-Methoxy-N-Methylamides as Effective Acylating Agents", *Tetrahedron Lett.* 22: 3815-3818, 1981.

Nakamura, S., "Total Synthesis of Antitumor Antibiotic Epothilone Having Same Mechanism of Action with Taxol", *Kagaku (Kyoto)*, (In Japanese) 52(7): 70-71, 1997.

Newman, et al., "Antitumor Efficacy of 26-Fluoroepothilone B Against Human Prostate Cancer Xenografts" *Cancer Chemother. Pharmacol.*, 48(4): 319-326, 2001.

Nicolaou et al. "Synthesis and Biological Properties of C12,13-Cyclopropyl-Epothilone A and Related Epothilones" *Chem. Biol*, 5(7): 365-372, 1998.

Nicolaou, et al. "Chemical Synthesis and Biological Evaluation of cis- and trans-12,13-cyclopropyl and 12,13-cyclobutyl Epothilones and Related Pyridine Side Chain Analogues" *J. Am. Chem. Soc.*, 123(38): 9313-9323, 2001.

Nicolaou, et al., "Chemical Biology of Epothilones", *Angew. Chem. Int. Ed.*, 37: 2014-2045, 1998.

Nicolaou, et al., "Chemical Synthesis and Biological Properties of Pyridine Epothilones" *Chem. Biol.* 7(8): 593-599, 2000.

Nicolaou, et al., "Chemistry and Biology of Taxol", *Angew. Chem. Int. Ed. Engl.* 33: 15-44, 1994.

Nicolaou, et al., "Chemistry, Biology and Medicine of Selected Tubulin Polymerizing Agents" *Pure Appl. Chem.*, 71(6): 989-997, 1999.

Nicolaou, et al., "Recent Developments in the Chemistry, Biology and Medicine of the Epothilones" *Chem. Commun.*, 17:1523-1535, 2001.

Nicolaou, et al., "Ring-Closing Metathesis in the Synthesis of Epothilones and Polyether Natural Products" *Top. Organomet. Chem. 1 (Alkene Metathesis in Organic Synthesis)*1: 73-104, 1998.

Nicolaou, et al., "Synthesis and Biological Evaluation of 12, 13-cyclopropyl and 12,13-cyclobutyl Epothilones" *ChemBioChem (Angew. Chem. Int. Ed. Engl.)*, 2(1): 69-75, 2001.

Nicolaou, et al., "Synthesis of 16-desmethylepothilone B: Improved Methodology for the Rapid, Highly Selective and Convergent Construction of Epothilone B and Analogs" *Chem. Commun.*, 6:519-520, 1999.

Nicolaou, et al., "Synthesis of Epothilones: A and B in Solid and Solution Phase", *Nature*, 390: 100, 1997.

Nicolaou, et al., "Total Synthesis of 16-Desmethylepothilone B, Epothilone B10, Epothilone F, and Related Side Chain Modified Epothilone B Analogues", *Chem. Eur. J.*, 6(15): 2783-2800, 2000.

Nicolaou, et al., "Total Synthesis of Epothilone E and Related Side-Chain Modified Analogues via a Stille Coupling Based Strategy" *Bioorg. Med. Chem.*, 7(5):665-697, 1999.

Nicolaou, et al., Chemie and Biologie der Epothilone, *Agnew. Chem.*, 110: 2120-2153, 1998.

Nicolaou, et al., Intellectual Screening of Natural Products for Drugs, *Farumashia*, 33(12): 1339-1345, 1997.

Nicolaou, K.C. et al. "Total Synthesis of Epothilone A and B via a Macrolactonization-Based Strategy", *J. Am. Chem. Soc.* 119: 7974-7991 (1997).

Nicolaou, K.C. et al. "Total Synthesis of Epothilone E and Analogues with Modified Side Chains through the Stille Coupling Reaction" *Angew. Chem. Int. Ed.*, 37: 84-87 (1998).

Nicolaou, K.C. et al., "An Approach to Epothilones Based on Olefin Metathesis" *Angew,Chem. Int. Ed. EngL* 35:20 2399-2401 (1996).

Nicolaou, K.C. et al., "An Approach to Epothilones Based on Olefin Metathesis" *Angew. Chem. Int. Ed.* 35:20 2399-2401 (1996).

Nicolaou, K.C. et al., "Probing the Riga Size of Epothilone: Total Synthesis of [14]-, [15]-,[17]- , . . . " *Angew. Chem. 1st. Ed.* 37:1/2, 81-87 (1998).

Nicolaou, K.C. et al., "Synthesis of Epothilones A and B in solid and solution phase", *Nature* 387:15 268-272, 238-239 (1997).

Nicolaou, K.C. et al., "The Olefin Metathesis Approach to Epothilone A and Its Analogues" *J. Am. Chem. Soc.* 119: 7960-7973 (1997).

Nicolaou, K.C. et al., "Total Synthesis of 26-Hydroxy-Epothilone B and Related Analogs via a Macrolactonization Based Strategy" *Tetrahedron* 54: 7127-7166 (1998).

Nicolaou, K.C. et al., "Total Synthesis of 26•-hydroxyepothilone B and related analogues", *Chem. Commun.* 2343-2344 (1997).

Nicolaou, K.C. et al., "Total Synthesis of Epothilone A: The Macrolactonization Approach", *Angew Chem. Int. Ed. EngL*, (1997).

Nicolaou, K.C. et al., "Total Synthesis of Oxazole-and Cyclopropane-Containing Epothilone A Analogues . . . ", *Chem. Eur. J.* 3:12 1957-1970 (1997).

Nicolaou, K.C. et al., "Total Synthesis of Oxazole-and Cyclopropane-Containing Epothilone B Analogues . . . ", *Chem. Eur. J.* 3:12 1971-1986 (1997).

Nicolaou, K.C. et al., "Variation der RinggrOPe von Epothilonen-Totalsyntheses von [14]-,[15]-,[17]-, . . . " *Angew. Chem.* 110:1/2 85-92 (1998).

Nicolaou, K.C. et al., "Designed Epothilones: Combinatorial Synthesis, Tubulin Assembly . . . " *Agnew Chem. Inst. Ed. EngL* 36:19 2097-2103 (1997).

Njardarson, et al., "Discovery of Potent Cell Migration Inhibitors Through Total Synthesis: Lessons from Structure—Activity Studies of (+)- Migrastatin", *J. Am. Chem. Soc.* 126:1038-1040, 2004.

Njardarson, et al., Application of hitherto unexplored macrocyclization strategies in the epothilone series: novel epothilone analogs by total synthesis, *Chem. Commun.*, 2759-2761, 2002.

Noyori, et al., "Asymmetric Hydrogenation of β-Keto Carboxylic Esters. A Practical, Purely Chemical Access to β-Hydroxy Esters in High Enantiomeric Purity" *J. Am. Chem. Soc.* 109: 5856-5859, 1987.

Ojima, et al., A Common Pharamcophore for Cytotoxic Natural Products that Stabilize Microtubules *Proc. Natl. Acad. Sci. U.S.A.*, 96: 4256-4261, 1999.

Ojima, et al., "Enantiopure Fluorine-Containing Taxoids: Potent Anticancer Agents and Versatile Probes for Biomedical Problems", *J. Fluorine Chem.* 97:3-10, 1999.

Ojima, et al., "New-Generation Taxoids and Hybrids of Microtubule-Stabilizing Anticancer Agents" *Book of Abstracts, 219th ACS National Meeting*, San Francisco, CA, Mar. 26-30, ORGN-245, 2000.

Panicker et al., "An unusual Reversal of Stereoselectivity in a Boron Mediated Aldol Reaction: Enantioselective Synthesis of the C1-C6 Segment of the Epothilones" *Tetrahedron*, 56(40): 7859-7868, 2000.

Paterson et al., "Stereocontrolled Aldol Additions to α-Methylene-β-Alkoxy Aldehydes: Application to the Synthesis of a $C_{13}$-$C_{25}$ Segment of Bafilomycin $A_1$" *Tetrahedron Lett.* 36:175-178, 1995.

Petrache et al., "The Role of the Microtubules in Tumor Necrosis Factor-a-Induced Endothelial Cell Permeability" *Am. J. Respir. Cell Mol. Biol.* 28:574-581, 2003.

Pettet et al., "Isolation and Structure of the Cancer Cell Growth Inhibitor Dictyostatin 1", *J. Chem. Soc. Chem. Commun.* 1111-1112, 1994.

Pradella et al., "Characterisation, Genome Size and Genetic Manipulation of the Myxobacterium Sorangium Cellulosum So ce56" Archives of Microbiology 1-17, 2002.

Pryor et al., "The Microtubule Stabilizing Agent Laulimalide Does Not Bind in the Taxoid Site, Kills Cells Resistant to Paclitaxel and Epothilones, and May Not Require Its Epoxide Moiety for Activity" Biochemistry 41:9109-9115, 2002.

Quitschalle et al., "Improved Synthesis of the Northern Hemisphere of Epothilone A by a Sharpless Asymmetric Dihydroxylation" *Tetrahedron Letters*. 40(44):7765-7768, 1999.

Regentin et al., "Development of a Cost Effective Epothilone D Process in *Myxococcus xanthus*" *Abstr. Pap-Am. Chem. Soc.* $221^{st}$, BIOT-061, 2001.

Regentin et al., "Nutrient Regulation of Epothilone Biosynthesis in Heterologous and Native Production Strains" Appl. Microbiol. Biotechnol. 61:451-455, 2003.

Regueiro-Ren et al., "Synthesis and Biological Activity of Novel Epothilone Aziridines" *Org. Lett.* 3(17): 2693-2696, 2001.

Regueiro-Ren et al., SAR and pH Stability of Cyano-Substituted Epothilones, Organic Letters, 4(22): 3815-3818, 2002.

Rivkin et al., "On the Introduction of a Trifluoromethyl Substituent in the Epothilone Setting: Chemical Issues Related to Ring Forming Olefin Metathesis and Earliest Biological Findings" *Organic Letters*, 4(23):4081-4084, 2002.

Rivkin et al., "Total Syntheses of [17]- and [18] Dehydrodesoxyepothilones B via a Consise Ring-Closing Metathesis-Based Strategy: Correlation of Ring Size with Biological Activity in the Epothilone Series" *J. Org. Chem.*, 67:7737-7740, 2002.

Rivkin, et al., "Complex Target-Oriented Total Synthesis in the Drug Discovery Process: The Discovery of a Highly Promising Family of Second Generation Epothilones", *J. Am. Chem. Soc.*, 125:2899-2901, 2003.

Rothermel, et al., "EPO906 (Epothilone B): A Promising Novel Microtubule Stabilizer", *Seminars in Oncology*, 30(3): 51-55, 2003.

Roush et al., "Acyclic Diastereoslective Synthesis Using Tartrate Ester Modified Crotylboronates. Double Asymmetric Reactions with α-Methyl Chiral Aldehydes and Synthesis of the C(19)-C(29) Segment of Rifamycin S" *J. Am. Chem. Soc.* 112:6348-6359, 1990.

Santi et al., "An Approach for Obtaining Perfect Hybridization Probes for Unknown Polyketide Synthase Genes: A Search for the Epothilone Gene Cluster" *Gene*, 247(1-2): 97-102, 2000.

Sawada et al., "Enantioselective Total Synthesis of Epothilone A Using Multifunctional Asymmetric Catalysis" *Angew. Chem. Int. Ed.* 39(1):209-213, 2000.

Sawada et al., "Enantioselective Total Synthesis of Epothilones A and B Using Multifunctional Asymmetric Catalysis" *J. Am. Chem. Soc.* 122(43):10521-10532, 2000.

Schiff et al., "Promotion of Microtubule Assembly in vitro by Taxol" *Nature*, 277:665-667, 1979.

Schinzer et al., "New and Convenient Synthesis of (R) and (S) of 2-methyl-3-oxa-5-(tert-butyldiphenylsilyloxy)methylpentanoate and 2-methyl-3-oxa-5-(tert-butyldimethylsiloxy)methylpentanoate" *Phosphorus, Sulfur Silicon Relat. Elem.*, 158:187-199, 2000.

Schinzer et al., "Synthesis and Biological Evaluation of Aza-Epothilones" *Angew. Chem. Int. Ed. ChemBiochem*, 1(1): 67-70, 2000.

Schinzer et al., "Synthesis of Epothilones. Stereoselective Routes to Epothilone B" *Synlett*, 8:861-864, 1998.

Schinzer et al., "Total Synthesis of (−)-epothilone A" *Chem.-Eur. J.*, 5(9):2483-2491, 1999.

Schinzer et al., "Total Synthesis of (−)-epothilone B" *Chem.-Eur. J.*, 5(9):2492-2500, 1999.

Schinzer, D. et al., "Studies Toward the Total Synthesis of Epothilones: . . . ", *Chem. Eur. J.*2:11 1477-1488 (1996).

Schinzer, D. et al., "Total Synthesis of 0-Epothilone A", *Angew. Chem. Int. Ed. Engl.* 36:5 523-524 (199'1).

Schneider et al., "Utilization of Alternate Substrates by the First Three Modules of the Epothilone Synthetase Assembly Line" *J. Am. Chem. Soc.* 124:11272-11273, 2002.

Schnizer, et al., "Synthesis and Biological Evaluation of Aza-Epothilones", Chembiochem, 1(1): 67-70, 2000.

Scholl et al., "Increased Ring Closing Metathesis Activity of Ruthenium-Based Olefin Metathesis Catalysts Coordinated with Imidazolin-2-Ylidene Ligands", *Tetrahedron Lett.* 40:2247-2250, 1999.

Scholl, et al., "Increased Ring Closing Metathesis Activity of Ruthenium-Based Olefin Metathesis Catalysts Coordinated with bnidazolin-2-Ylidene Ligands" *Tetrahedron Lett.* 40:2247, 1999.

Schrock, "Olefin Metathesis by Well-Defined Complexes of Molybdenum and Tungsten" *Top. Organomet. Chem.* 1:1-36, 1998.

Scudiero et al., "Evaluation of a Soluble Tetrazolium/Formazan Assay for Cell Growth and Drug Sensitivity in Culture Using Human and Other Tumor Cell Lines", *Cancer Res.* 48:4827-4833, 1988.

Sefkow et al.,"Derivatization of the C12-C13 Functional Groups of Epothilones A, B, and C" *Bioorg. Med. Chem.* 8:3031-3036, 1998.

Sefkow et al., "Oxidative and Reductive Transformations of Epothilone A" *Bioorg. Med. Chem.* 8(21):3025-3030, 1998.

Sefkow et al., "Substitutions at the Thiazole Moiety of Epothilone" *Heterocycles*, 48(12):2485-2488, 1998.

Seiden, M., "Ovarian Cancer", *The Oncologist*, 6: 327-332, 2001.

Shibasaki et al., "Multifunctional Asymmetric Catalysis" *Chem. Pharm. Bull.*, 49(5):511-524, 2001.

Shioji et al., "Synthesis of C1-C6 Fragment for Epothilone A via Lipase-Catalyzed Optical Resolution" *Synth. Commun.*, 31(23):3569-3575, 2001.

Sinha et al., "Regioselective Synthesis of Fluoro Aldols. Studies Toward Fluro Epothilones Syntheses via Antibody Catalysis" *Tetrahedron Letters*, 41(43):8243-8246, 2000.

Sinha et al., "Sets of Aldolase Antibodies with Antipodal Reactivities. Formal Synthesis of Epothilone E by Large Scale Antibody-Catalyzed Resolution of Thiazole Aldol" *Org. Lett.*, 1(10):1623-1626, 1999.

Sinha et al., "Synthesis of Epothilone Analogues by Antibody-Catalyzed Resolution of Thiazole Aldol Synthons on a Multigram Scale. Biological Consequences of C-13 Alkylation of Epothilones" *Chem. Bio. Chem.* , 2(9):656-665, 2001.

Sinha, et al., "Catalytic Antibody Route to the Naturally Occurring Epothilones: Total Synthesis of Epothilones A-F" *Chem. Eur. J.* 7(8):1691-1702, 2001.

Sinha, et al., "The Antibody Catalysis Route to the Total Synthesis of Epothilones" *Proc. Natl. Acad. Sci.* 95(25):14603-14608, 1998.

Skehan et al., "New Colorimetric Cytotoxicity Assay for Anticancer-Drug Screening" Journal of the National Cancer Institute, 82:1107-1112, 1990.

Smart, "Fluorine Substituent Effects (on bioactivity)" Journal of Fluorine Chemistry, 109:3-11, 2001.

Stachel et al., "Chemo- and Stereoselective Epoxidation of 12,13-Desoxyepothilone B using 2,2'-dimethyldioxirane" *Tetrahedron Lett.*, 42(39):6785-6787, 2001.

Stachel et al., "On the Interactivity of Complex Synthesis and Tumor Pharmacology in the Drug Discovery Process: Total Synthesis and Comparative in Vivo Evaluations of the 15-Aza Epothilones" *J. Org. Chem.* 66:4369-4378, 2001.

Stachel et al., "The Epothilones, Eleutherobins, and Related Types of Molecules" *Curr. Pharm. Des.* 7(13):1277-1290, 2001.

Still, et al., "Stereoselective Synthesis of 1,3-Diol Derivatives and Application to the Ansa Bridge of Rifamycin S" *J. Am. Chem. Soc.* 105: 2487-2489, 1983.

Su et al., "Structure-Activity Relationships of the Epothilones and the First In Vivo Comparison with Paclitaxel" *Angew. Chem. Int. Ed. Engl.* 36:2093-2096, 1997.

Su et al., "Total Synthesis of (-) Epothilone B: An Extension of the Suzuki Coupling Method and Insights into Structure-Activity Relationships of the Epothilones", *Angew. Chem. Int. Ed. Engl.* 36:757-759, 1997.

Sun et al. "Stereoselective Total Synthesis of Epthilones by the Metathesis Approach involving C9-C10 Bond Formation" *Angew. Chem. Int. Ed.* 8:1381-1383, (Need Year).

Tamao, et al., "Selective Carbon-Carbon Bond Formation by Cross-Coupling of Grignard Reagents with Organic Halides. Catalysis by Nickel-Phospine Complexes" *J. Am. Chem Soc.* 94: 4374-4379, 1972.

Tang et al., "Cloning and Expression of the Epothilone Gene Cluster" *Science*, 287:640-642, 2000.

Tang et al., "Generation of Novel Epothilone Analogs with Cytotoxic Activity by Biotransformation" The Journal of Antibiotics, 56:16-23, 2003.

Tanimori et al., "Easy Access to Both Enantiomers of C7-C12 Segment of Epothilones" *Synth. Commun.* 29(24): 4353-4360, 1999.

Tanimori et al., "Simple Synthesis of Both Enantiomers of the C7-C12 Segment of Epothilones" *Biosci. Biotechnol. Biochem*, 62(12):2428-2430, 1998.

Taylor et al., "Catalytic Diastereoselective Reductive Aldol Reaction: Optimization of Interdependent Reaction Variables by Arrayed Catalyst Evaluation" *J. Am. Chem. Soc.* 121:12202-12203, 1999.

Taylor et al., "Conformational Properties of Epothilone" *J. Org. Chem.* 64(19):7224-7228, 1999.

Taylor et al., "The Conformational Properties of Epothilone"—Erratum *J. Org. Chem.*, 65(17):5449, 2000.

Taylor et al., "Total Synthesis of Epothilones B and D" *Org. Lett.* 3(14):2221-2224, 2001.

Taylor, "A Formal Total Synthesis of Epothilone A: Enantioselective Preparation of the C1-C6 and C7-C12 Fragments" *J. Org. Chem.* 63(25):9580-9583, 1998.

Taylor, R.E., et al., "Towards the Synthesis of Epothilone A: Enantioselective Preparation . . . " *Tetrahedron Letters* 38:12 2061 2064 (1997).

Toh et al., "Studies on a Convergent Route to Side-Chain Analogues of Vitamin D: 25-Hydroxy-23-Oxavitamin $D_3$" *J. Org. Chem.* 48:1414-1417, 1983.

Trnka, et al., "The Development of $L_2X_2Ru=CHR$ Olefin Methathesis Catalysts: An Organometallic Success Story," *Acc. Chem. Res.* 34:18-31, 2001.

Tsuji et al., "Alterations in Cellular Adhesion and Apoptosis in Epithelial Cells Overexpressing Prostaglandin Endoperoxide Synthase 2", *Cell*, 3:493, 1995.

Valluri et al., "Total Synthesis of Epothilone B" *Org. Lett.* , 3(23):3607-3609, 2001.

Victory et al., "Relative Stereochemistry and Solution Conformation of the Novel Paclitaxel-Like Antimitotic Agent Epothilone A" *Bioorganic & Medicinal Chemistry Letters* 6(7):893-898, 1996.

Vite, et al., "Epothilones A and B: Springboards for Semisynthesis of Promising Antimitotic Agents" *Book of Abstracts, 219th ACS National Meeting*, San Francisco, CA, Mar. 26-30, ORGN-286, 2000.

Von Angerer, "Tubulin as a Target for Anticancer Drugs" *Curr. Opin. Drug Discovery Dev.* 3(5):575-584, 2000.

Walsh, "Enzymatic Assembly of Hybrid Polyketide/Nonribosomal Peptide Natural Products" *Abstracts of Papers, 222nd ACS National Meeting*, Chicago, IL, Aug. 26-30, BIOL-126, 2001.

Wartmann et al., "The Biology and Medicinal Chemistry of Epothilones" *Curr. Med. Chem.* 2:123-148, 2002.

Wessjohann et al., "Synthesis of Natural-Product-Based Compound Libraries" *Curr. Opin. Chem. Biol.* 4:303-309, 2000.

Wessjohann et al., "Synthetic Access to Epothilones-Natural Products with Extraordinary Anticancer Activity" *Org. Synth. Highlights IV Ed: Schmalz, H., Wiley-VCH Verlab GmbH*: Weinheim Germany, 251-267, 2000.

Wessjohann, "Epothilones: Promising Natural products with Taxol-Like Activity" *Angew. Chem. Int. Ed. Engl.* 36(7):715-718, 1997.

White et al. "Synthesis, Conformational Analysis, and Bioassay of 9,10-didehydroepothilone D" *Organic Letters* 4:995-997, 2002.

White et al., "Total Synthesis of Epothilone B, Epothilone D, and cis- and trans-9,10-Dehydroepothilone D" *J. Am. Chem. Soc.*, 123(23):5407-5413, 2001.

White et al., Total Synthesis of Epothilone B, Epothilone D, and cis-and trans-9, 10-Dehydroepothilone D, *J. Am. Chem. Soc.*, 125:3190, 2003, Additions and Corrections.

White, et al., "A Highly Stereoselective Synthesis of Epothilone B" *J. Org. Chem.*, 64(3):684-685, 1998.

White, et al., "Improved Synthesis of Epothilone B Employing Alkylation of an Alkyne for Assembly of Subunits" *Org. Lett.*, 1(9):1431-1434, 1999.

White, et al., "Synthetic Approach Towards the Total Synthesis of Epothilone B" *Book of Abstracts, 216th ACS National Meeting*, Boston, Aug. 23-27, ORGN-041.

White, et al., "Two Coupling Strategies for a Stereoselective Synthesis of Epothilone B" *Book of Abstracts, 219th ACS National Meeting*, San Francisco, CA, Mar. 26-30, ORGN-813, 2000.

Winkler, et al., "A Model for the Taxol (Paclitaxel) Epothilone Pharmacophore", *Bioorg., Med. Chem. Letter*, 6: 2963-2966, 1996.

Winkler, et al., "Design and Synthesis of Constrained Epothilone Analogs: The Efficient Synthesis of Eleven-Membered Rings by Olefin Metathesis" *Tetrahedron*, 55(27): 8199-8214, 1999.

Winssinger, et al., "Epothilones and Sarcodictyins: Rrom Combinatorial Libraries to Designed Analogs" *Book of Abstracts, 219th ACS National Meeting*, San Francisco, CA, Mar. 26-30, ORGN-289, 2000.

Wittmann, et al., Flavopiridol Down-Regulates Antiapoptotic Proteins and Sensitizes Human Breast Cancer Cells to Epothilone B-induced Apoptosis, Cancer Research, 63: 93-99, 2003.

Wolff, A., "Epothilone A Induces Apoptosis in Neuroblastoma Cells with Multiple Mechanisms of Drug Resistance", *Int. J. Oncol.*, 11(1):123-126, 1997.

Woltering, et al., Development of a Novel in Vitro Human Tissue-Based Angiogenesis Assay to Evaluate the Effect of Antiangiogenic Drugs, Annals of Surgery, 237: 790-800, 2003.

Wu et al. "Subtle Variations in the Long-Range Transmission of Stereochemical Information: Matched and Mismatched Aldol Reactions" Angew. Chem. Int. Ed. 39(24):4505-4508 (2000).

Yamaguchi, et al., "Epothilone B Analogue (BMS-247550)—Mediated Cytotoxicity Through Induction of Bax Conformational Change in Human Breast Cancer Cells", *Cancer Research*, 62: 466-471, 2002.

Yang, et al., Total Synthesis of Epothilone A: The Olefin Metathesis Approach: *Angew. Chem. Int. Ed.*, 36: 166-168, 1997.

Yoshimura et al., "Synthesis ad Conformational Analysis of (E)-9,10-Dehydroepothilone B: A Suggestive Link between the Chemistry and Biology of Epothilones", *Angew. Chem. Int. Ed.* 42:2518-2521, 2003.

Zhou, et al., Brominated Derivatives of Noscapine Are Potent Microtubule-Interfering Agents That Perturb Mitosis and Inhibit Cell Proliferation, Molecular Pharmacology, 63:799-807, 2003.

Zhu, et al., "Methodology Based on Chiral Silanes in the Synthesis of Polypropionate-Derived Natural Products-Total Synthesis of Epothilone A" *Eur. J. Org. Chem.*, 9: 1701-1714, 2001.

Zhu, et al., "Studies Toward the Total Synthesis of Epothilone A" Book of Abstracts, 216th ACS National Meeting, Boston, Aug. 23-27, ORGN-660.

Zhu, et al., "Total Synthesis of Epothilone A" *Org. Lett.*, 2(17): 2575-2578, 2000.

Zhu, et al., "Enzymatic Resolution of Thiazole-Containing Vinyl Carbinols. Synthesis of the C12-C21 Fragment of the Epothilones" *Tetrahedron Lett.*, 41(12):1863-1866, 2000.

Berge et al., "Pharmaceutical Salts" *J. Pharmaceutical Sciences* 66(1):1-19, 1977.

Chou et al., "The synthesis, discovery, and development of a highly promising class of microtubule stabilization agents: Curative effects of desoxyepothilones B and F against human tumor xenografts in nude mice" *Proc. Natl. Acad. Sci. U.S.A.* 98(14):8113-8118, 2001.

Curran, "The Design and Application of Free Radical Chain Reactions in Organic Synthesis. Part 1" *The Design and Application of Free Radical Chain Reactions in Organic Synthesis* 417-439, 1988.

Curran, "The Design and Application of Free Radical Chain Reactions in Organic Synthesis. Part 2" *The Design and Application of Free Radical Chain Reactions in Organic Synthesis* 489-513, 1988.

Keck and Yates, "Carbon-Carbon Bond Formation via the Reaction of Trialkylallylstannanes with Organic Halides" *J. Am. Chem. Soc.* 104:5829-5831 (1982).

Kowalski et al., "Comparison of Novel Microtubule Polymerizing Agents, Discodermolide and Epothilone A/B, with Taxol" *Mol. Biology of the Cell* 6:2137, 1995.

IC$_{50}$ values for the new Epothilones against CCRF-CEM cell growth

| | IC$_{50}$ (µM) for | | |
|---|---|---|---|
| | CCRF-CEM | CCRF-CEM/VBL | CCRF-CEM/Taxol |
| Compound | Potency Rank | Rank | Rank |
| dEpoB (EpoD) | 0.0038 ⟨0.0048 / 0.0036 / 0.0030⟩ (7) | 0.013 ⟨0.0115 / 0.014$_{[3.9x]}$⟩$_{[3.4x]}$ (5) | 0038 ⟨0.0031 / 0.0057$_{[1.6x]}$⟩ (4) |
| EpoB (Toxic) | 0.00048 (1) | 0.0026$_{[5.4x]}$ (1) | 0.0011$_{[2.3x]}$ (1) |
| dEpoF | 0.0015 | | |
| 10,11-didehydro-dEpoB (Epo-490) | 0.0160 (11) | 0.078$_{[4.8]}$ (10) | 0.032$_{[2x]}$ (13) |
| 26-methyl-dEpoB | 0.040 (13) | 0.123$_{[3.1x]}$ (12) | 0.077$_{[1.9x]}$ (12) |
| 4-des-me-EpoB | 0.00081 (3) | 0.0078$_{[9.6x]}$ (4) | 0.017$_{[2.1x]}$ (9) |
| 11-OH (cis)EpoD | 0.0029 (5) | 0.077$_{[26.6x]}$ (9) | 0.0091$_{[3.1x]}$ (7) |
| 11-α-F-dEpoB | 0.0285 (12) | 0.147$_{[5.2x]}$ (13) | 0.0550$_{[1.9x]}$ (10) |
| 11-β-F-dEpoB | 0.0980 (14) | 0.230$_{[2.3x]}$ (14) | 0.138$_{[1.4x]}$ (14) |
| 19-oxazole EpoD | 0.0054 (9) | 0.045$_{[8.3x]}$ (8) | 0.0017$_{[1.2x]}$ (3) |
| 19-oxazole EpoB (Toxic) | 0.00034 (7) | 0.0057$_{[16.8x]}$ (3) | 0.0057$_{[1.6x]}$ (6) |
| 19-oxazole Epo490 | 0.0077 (10) | 0.0227$_{[2.9x]}$ (7) | 0.0130$_{[1.7x]}$ (8) |

FIG. 1A

| Compound | IC$_{50}$ (μM) for | | | | | |
|---|---|---|---|---|---|---|
| | CCRF-CEM | Potency Rank | CCRF-CEM/VBL | Rank | CCRF-CEM/Taxol | Rank |
| 9,10-deH-[16]dEpoB (Iso-490) | 0.0009 (0.0005 / 0.0014) | (4) | 0.0042 (0.0020 / 0.0065) [4.7x] [4.6x] | (2) | 0.0012 (0.0006 / 0.0017) [1.3x] [1.2x] | (2) |
| 26-F$_3$-9,10-deH-[16]dEpoB | 0.0035 | (6) | 0.0210 [5.7x] | (6) | 0.0057 [1.6x] | (5) |
| 26-F$_3$-dEpoB | 0.0041 | (8) | 0.080 [19.5x] | (11) | 0.018 [4.4x] | (10) |
| Taxol | 0.0018 (0.0014 / 0.0021) | | 2.30 [1095x] | | 0.058 (0.0272 / 0.089) [320x] [42x] | |
| Vinblastine | 0.0020 (0.0036 / 0.00045) | | 0.379 (0.444 / 0.313) [190x] [695x] | | 0.018 [40x] | |
| Iso-490-dEpoF | 0.00060 | | | | | |
| Iso-490-dEpo-MeKetone | 24.99 | | | | | | aCell growth inhibition was measured by XTT tetrazonium assay after 72-hr incubation for cell growth, as described previously (1). IC$_{50}$ values were determined from dose-effect relationship at six or seven concentrations of each drug, by using a computer program (2,3) as described earlier (4).

FIG. 1B

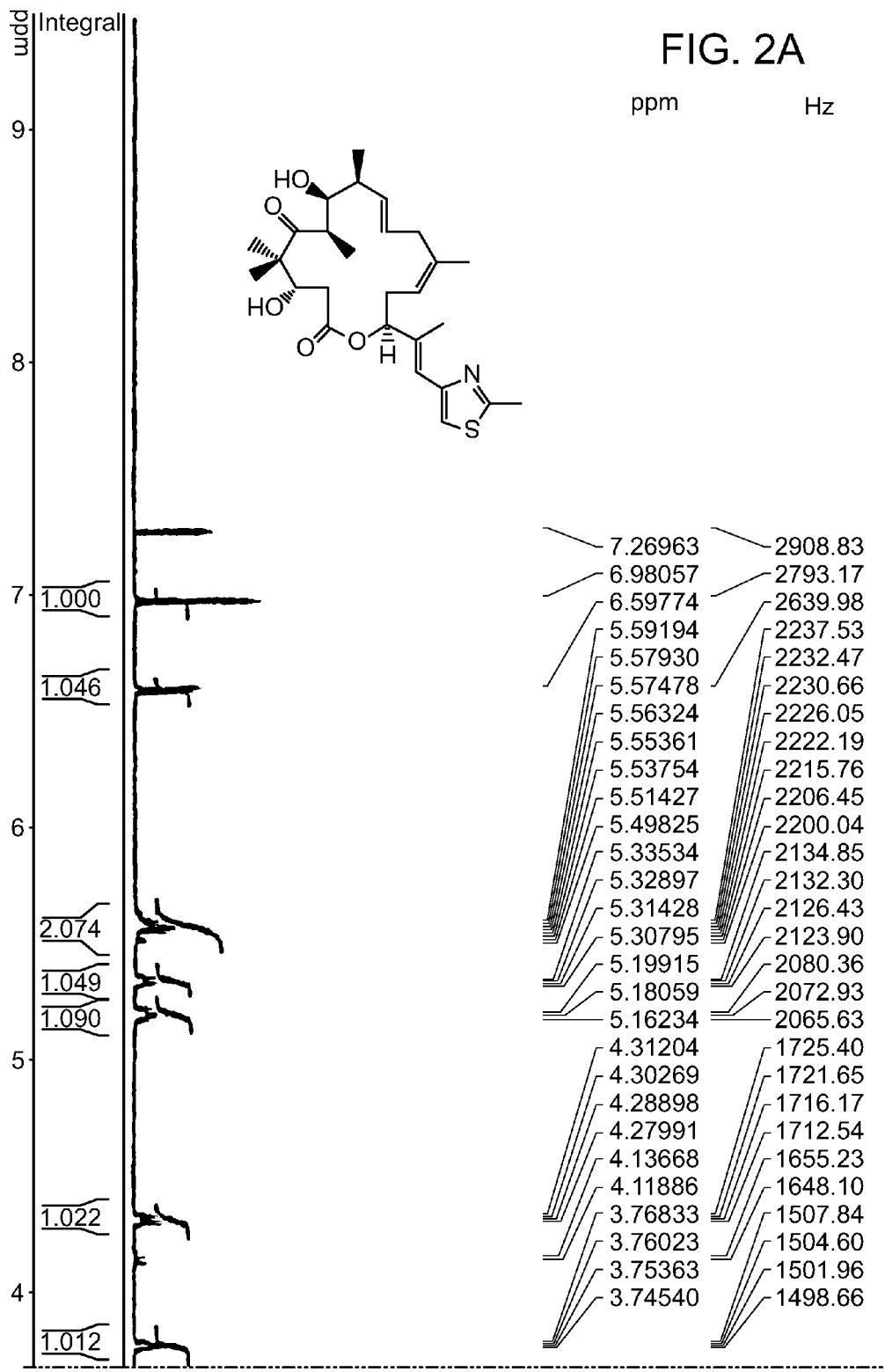

1. Macro-Stille Strategy
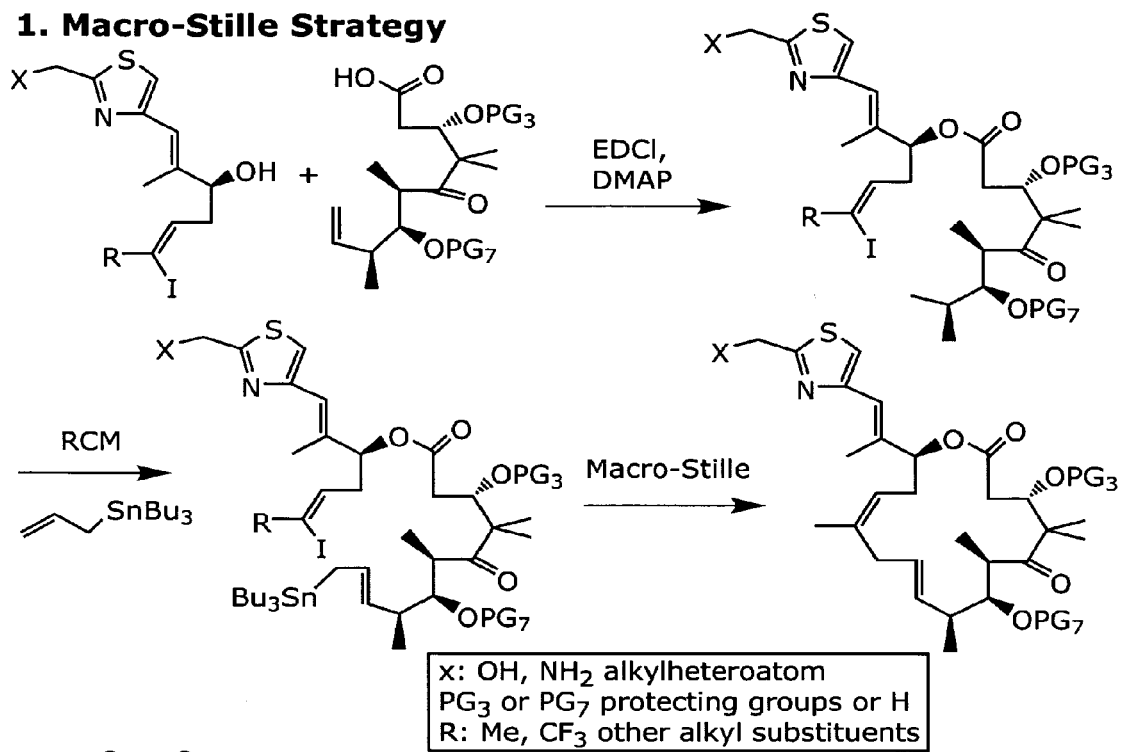
2. sp³-sp³ Coupling Strategy
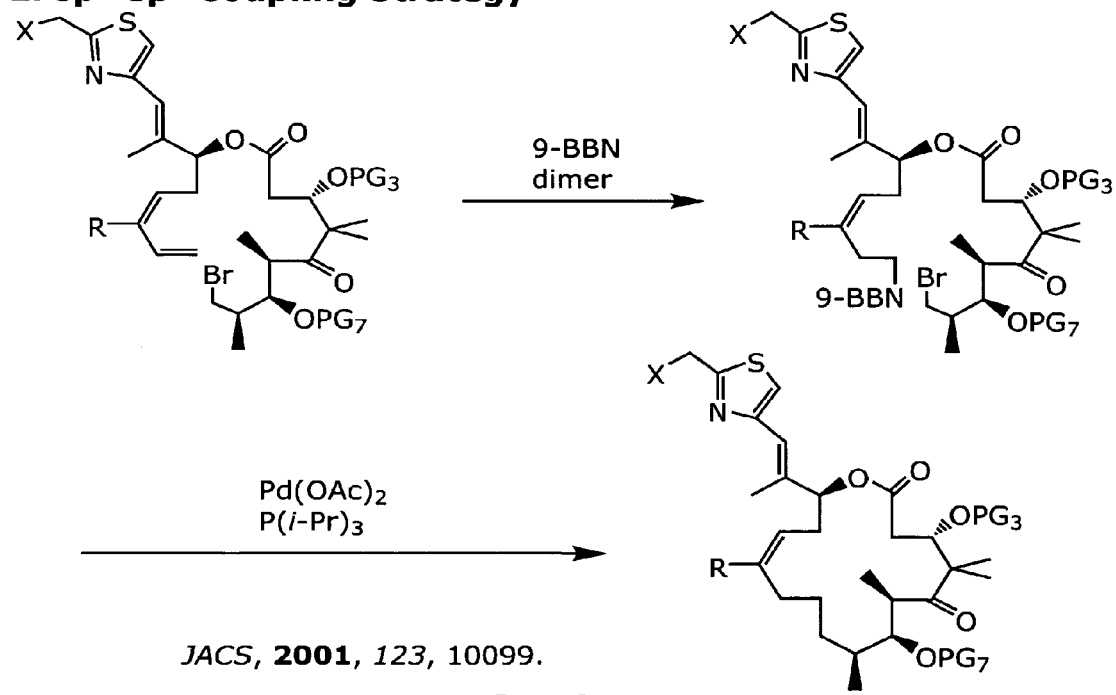
*JACS*, 2001, *123*, 10099.
FIG. 6A

3. β-Suzuki Coupling
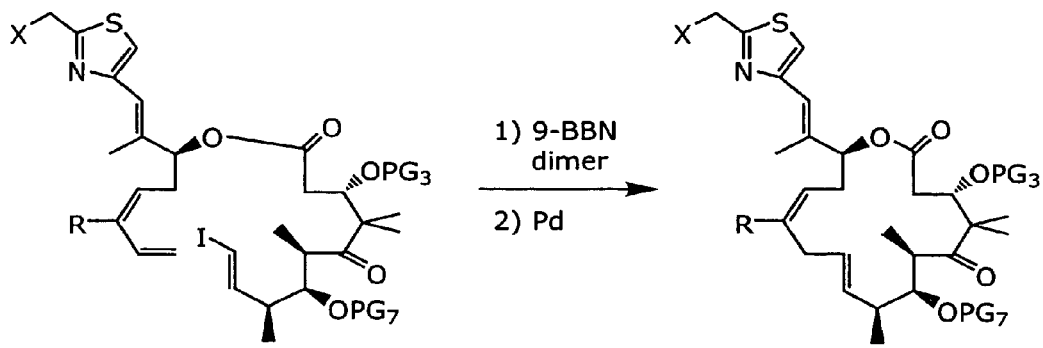
4. Julia Olefination Strategy
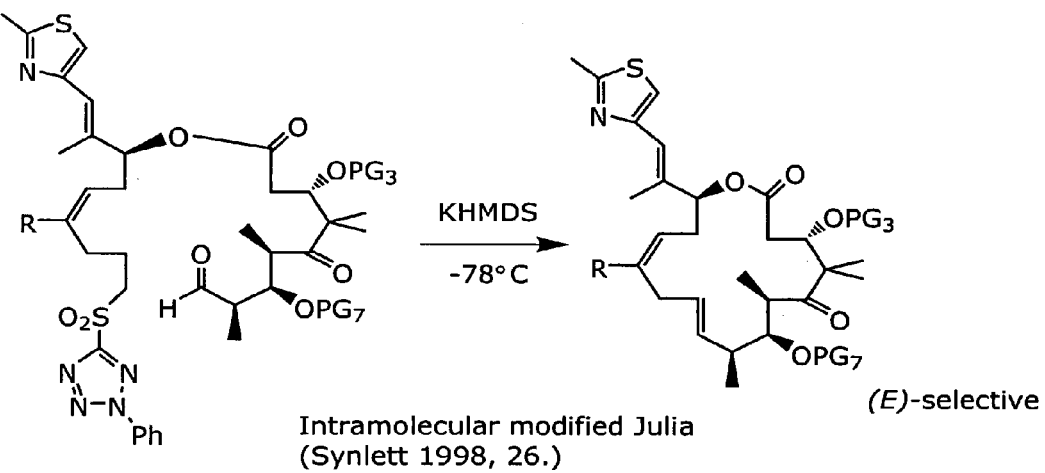
Intramolecular modified Julia
(Synlett 1998, 26.)
5. Wadsworth-Emmons Strategy
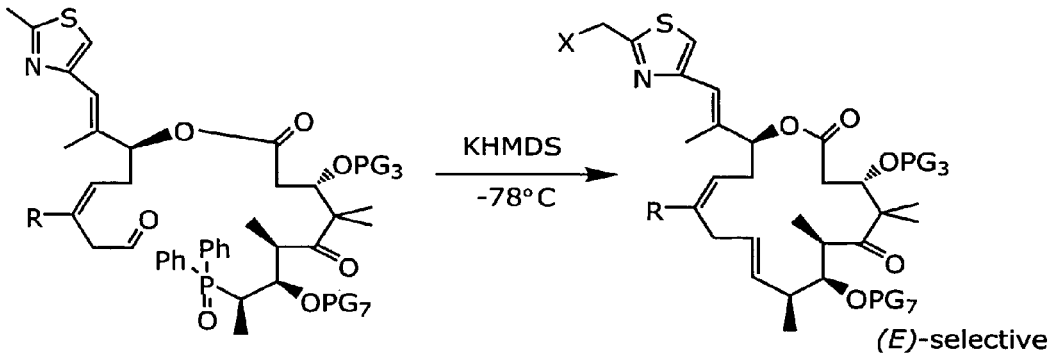
FIG. 6B

6. Macro-Reformatosky Strategy
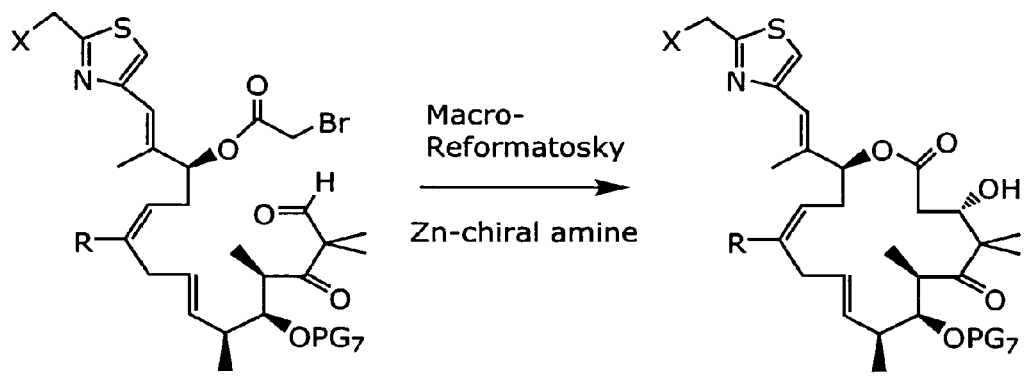
7. McMurry Coupling Strategy
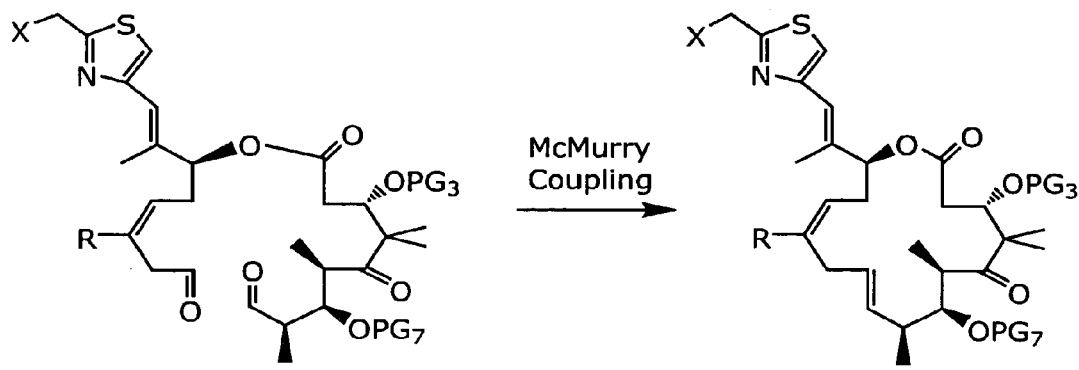
FIG. 6C Potency for the New Epothilones Against Tumor Cell Growth in Vitro[a] and Therapeutic Index[b]

| Compound | IC$_{50}$ (µM) for | | | | | Relative Cytotoxicity in Vitro (Rank Order)[d] | Relative Therapeutic Index against Mice Xenograft at MTD[e] |
|---|---|---|---|---|---|---|---|
| | Human T-cell Lymphoblastic Leukemia Sublines | | | Human Lung Carcinoma A549 | Human Lung Carcinoma HCT-116 | | |
| | CCRF-CEM | CCRF-CEM/ VBL | CCRF-CEM/ Taxol | | | | |
| dEpoB (EpoD, MSK-D10, KOS-862) (MSK NSC-703147) | 0.0056 ±0.0028 | 0.016 ±0.003 [2.9x] [c] | 0.0085 ±0.0055 [1.5x] | 0.0039 ±0.0004 | 0.0068 ±0.0032 | 7 | ++++ |
| dEpoF (MSK-D60) | 0.0015 ±0.0001 | 0.0456 [30.4x] | 0.0035 [2.3x] | 0.012 ±0.004 | 0.0041 | 6 | ++++ |
| EpoB (MSK-E08) (Epo906 Novartis) | 0.00053 ±0.00017 | 0.0032 ±0.0012 [6.05x] | 0.0011 ±0.00008 [2.1x] | 0.0013 | 0.00039 | 2 | +++ |
| 15-Aza-EpoB (MSK-E61) (BMS-247550) | 0.0021 | 2.99 [1423x] | 0.171 [81.4x] | 0.0075 | 0.0023 | 10 | ++ |
| 9,10-dehydro-dEpoB (MSK-D88) | 0.0009 ±0.0004 | 0.0042 ±0.0022 [4.7x] | 0.0012 ±0.0006 [1.3x] | 0.00089 ±0.00064 | 0.00094 ±0.00055 | 4 | ++ |
| 9,10-dehydro-dEpoF (MSK-D93) | 0.00051 ±0.00009 | 0.0106 [20.8] | 0.00073 [1.4x] | 0.00091 ±0.0006 | 0.00055 ±0.0007 | 3 | ND[f] |
| 9,10-dehydro-dEpoB (MSK-E95) | 0.00023 ±0.00002 | 0.00032 [1.4x] | 0.00042 [1.8x] | 0.00026 ±0.00004 | 0.00014 ±0.00001 | 1 | ++ |

FIG. 11A

Potency for the New Epothilones Against Tumor Cell Growth in Vitro[a] and Therapeutic Index

| Compound | IC$_{50}$ (μM) for | | | | | Relative Cytotoxicity in Vitro (Rank Order) | Relative Therapeutic Index against Mice Xenograft at MTD |
|---|---|---|---|---|---|---|---|
| | Human T-cell Lymphoblastic Leukemia Sublines | | | Human Lung Carcinoma A549 | Human Lung Carcinoma HCT-116 | | |
| | CCRF-CEM | CCRF-CEM/ VBL | CCRF-CEM/ Taxol | | | | |
| 26-F$_3$-9,10-dehydro-dEpoB (MSK-D89) | 0.0035 ±0.0005 | 0.0210 [5.7x] | 0.0057 [1.6x] | 0.0037 ±0.0024 | 0.0036 ±0.0010 | 5 | +++++ |
| 26-F$_3$-dEpoB (MSK-D91) | 0.0041 ±0.00009 | 0.080 [19.5x] | 0.018 [4.4x] | 0.019 | 0.012 | 11 | ND |
| Paclitaxel (Taxol®) | 0.0018 ±0.0005 | 3.22 ±0.92 [1789x] | 0.079 ±0.029 [43.9x] | 0.0031 | 0.0035 | 8 | ++++ |
| Vinblastine (Velban®) | 0.00054 ±0.00009 | 0.389 ±0.074 [720x] | 0.0196 ±0.0111 [36.3x] | 0.0081 | 0.0094 | 9 | ++++ |

[a] Cell growth inhibition for leukemic cells and solid tumor cells were measured by XTT tetrazonium assay and by sulforhodemine B (SRB) method, respectively, after 72-hr incubation for cell growth, as described previously (1,2). IC$_{50}$ values were determined from dose-effect relationship at six or seven concentrations of each drug, by using a computer program (3,4) as described earlier (5).
[b] The therapeutic experiments for epothilones against human tumor xenografts in nude mice, such as MX-1, were described (in 6 and 7).

FIG. 11B

[c] The numbers in brackets are fold of resistance based on the $IC_{50}$ ratio when compared with the corresponding parent cell lines. CCRF-CEM/VBL and CCRF-CEM/Taxol are the CCRF-CEM leukemic cells resistant to vinblastine and paclitaxel, 720-fold and 44-fold, respectively.

[d] Cytotoxicity in vitro rank order (CRO) is determined by: i) The potency of cell growth inhibition for each compound for a given cell line is assigned a rank order in a "column" of the Table. Different cell lines have different columns. ii) The rank orders for each compound for different cell lines form a "row" in the Table. The rank orders for each row are summed. iii) CROs are determined and ranked from the lowest sum to the highest sum for a series of compounds to form a column for overalll ranks.

[e] Graded therapeutic index (TI) at MTD( maximal tolerated dose):

+ Tumor growth suppressed 25-50%.
++ Tumor growth suppressed 50-100%.
+++ Tumor shrinkage but no tumor disappearance.
++++ Tumor disappearance in some or all nude mice with slow body weight recovery and/or with relapse in some mice.
+++++ Tumor disappeared in all nude mice, body weight rapidly recovered and/or without relapse.

[f] Not Determined

FIG. 11C

Therapeutic effect of dEpoB, Paclitaxel and F$_3$-deH-dEpoB against MX-1 xenograft in nude mice in terms of doses body weight loss and regains and tumor disappearance and relapses[a]

| Drug | Dosage (mg/kg) | Changes of body weight (%) | | Tumor free after Q2Dx6 6hr-iv Infusion | Tumor reappeared on day 10 after stopping administration |
|---|---|---|---|---|---|
| | | On day 4 after stopping administration | On day 8 after stopping administration | | |
| dEpoB | 30 | -25.3±2.1 | -9.1±4.1 | 10/10 | 5/10 |
| Paclitaxel | 20 | -23.9±3.7 | -8.7±0.7 | 7/7 | 3/7 |
| F$_3$-deH-dEpoB | 20 | -22.4±0.6 | -7.3±0.7 | 4/4 | 0/4[b] |
| | 30 | -27.1±2.7 | ±17.4±5.5 | 4/4 | 0/4[c] |

[a] Human mammary carcinoma MX-1 xenograft tissue 50 mg was implanted S.C. on Day 0. The treatment, Q2Dx6 6hr-i.v. infusion was started on Day 8 and stopped on Day 18.

[b] Detectable tumor reappearance in 2/4 on 27th day after stopping treatment. No further tumor reappearance during 26th–64th day after stopping treatment.

[c] No tumor reappearance during 64 days after stopping treatment. Estimated tumor cell kill was over 99.99999% assuming the tumor doubling time of 2.5 days.

FIG. 12

IC$_{50}$ values for the new Epothilones against CCRF-CEM cell growth

| Compound | IC$_{50}$ (µM) for CCRF-CEM | CCRF-CEM/VBL | CCRF-CEM/Taxol |
|---|---|---|---|
| dEpoB (EpoD) | 0.0036±0.0002 | 0.016±0.003$_{[4.4x]}$ | 0.0046±0.0002$_{[1.3x]}$ |
| dEpoF | 0.0015±0.0001 | 0.0456$_{[30.4x]}$ | 0.0035$_{[2.3x]}$ |
| EpoB | 0.00062±0.00013 | 0.0037±0.0011$_{[5.9x]}$ | 0.0011±0.0001$_{[1.8x]}$ |
| 26-methyl-dEpoB | 0.040 | 0.123$_{[3.1x]}$ | 0.077$_{[1.9x]}$ |
| 11-α-F-dEpoB | 0.0285 | 0.147$_{[5.2x]}$ | 0.0550$_{[1.9x]}$ |
| 11-β-F-dEpoB | 0.0980 | 0.230$_{[2.3x]}$ | 0.138$_{[1.4x]}$ |
| 19-oxazole-10,11-dehydro-dEpoB | 0.0077 | 0.0227$_{[2.9x]}$ | 0.0130$_{[1.7x]}$ |
| 9,10-deH-[16]dEpoB | 0.0009±0.0004 | 0.0042±0.0022$_{[4.7x]}$ | 0.0012±0.0006$_{[1.3x]}$ |
| 9,10-deH-[16]dEpoF | 0.00051±0.00009 | 0.0106$_{[20.8x]}$ | 0.00073$_{[1.4x]}$ |
| 9,10-deH-[16]EpoB | 0.00023±0.00002 | 0.0032$_{[1.4x]}$ | 0.00042$_{[1.8x]}$ |
| 12,13-epi-9,10-deH-EpoB | 0.0134±0.0032 | 0.0959$_{[3.1x]}$ | 0.0802$_{[2.6x]}$ |
| 12,13-epi-EpoB | 0.0830±0.0001 | 0.4519$_{[5.4x]}$ | 0.1507$_{[1.8x]}$ |
| 9,10-deH-dEpo-Me-ketone | 5.02 | ------ | ------ |
| 26-F$_3$-9,10-deH-[16]dEpoB | 0.0035 | 0.0210$_{[5.7x]}$ | 0.0057$_{[1.6x]}$ |
| 26-F$_3$-dEpoB | 0.0041 | 0.080$_{[19.5x]}$ | 0.018$_{[4.4x]}$ |
| Taxol | 0.0016±0.0005 | 2.30$_{[1438x]}$ | 0.058±0.001$_{[36x]}$ |
| Vinblastine | 0.00045 | 0.418±0.076$_{[929x]}$ | 0.026±0.008$_{[58x]}$ |

FIG. 31

Metabolic Stability of Epothilones (Experiments in progress)

| Compound | In vitro $t_{1/2}$ in | | | |
|---|---|---|---|---|
| | Mouse plasma | Dog plasma | Human plasma | Human liver prep |
| dEpoB(EpoD) | 31 min | >8 hr | >8 hr | 60 min |
| 26-F$_3$-9,10-deH-dEpoB | 150 min | ---- | ---- | 180 min |
| 26-F$_3$-dEpoB(MDR) | 68 min | ---- | ---- | 105 min |
| 26-methyl-dEpoB | 50 min | >8 hr | ---- | ---- |
| 9,10-deH-dEpoB | 90 min | ---- | ---- | 150 min |

FIG. 32

Therapeutic effect of epothilone compounds against human tumor xenografts in mice with 6hr-iv infusion.

| Compound | Dose & Schedule | Xenograft model | Therapeutic effect | | Toxicity | | Date |
|---|---|---|---|---|---|---|---|
| | | | % tumor volume reduction | Proportion of tumor disappearance | % body weight change | Proportion of mice dead | |
| dEpoB (#10) | 30mg/kg, Q2Dx5 d10-18 | MX-1 | 99.4% (d26) | 4/5 (d26) | (control -0.3%) +3.9% (d26) | 0/5 (d26) | 7/6/01 -8/20/01 |
| dEpoB (#10) | 30mg/kg, Q2Dx5x2 d8-16 then d20-22 | MX-1 | 99.9% (d24) 100% (d28) | 2/4 (d24) 4/4 (d28) | -14.6% (d24) -0.3% (d28) | 0/4 (d28) | 6/28/02 -7/28/02 |
| Epo[17]-10,11-deH-dEpoB (#70) | 50mg/kg, Q2Dx3 then 80mg/kg, Q2Dx1 then 100mg/kg, Q2Dx1 d10-14, d16, d18 | MX-1 | 11.3% (d22) | 0/3 (d22) | (control +2%, d22) +2.1% (d22) | 0/3 (d22) | 12/7/01 -12/29/01 |
| Epo[18]-10,11-deH-dEpoB (#76) | 80mg/kg, Q2Dx5 d10-18 | MX-1 | 13.2% (d24) | 0/3 (d24) | (control +4.7%, d24) -4.4% (d24) | 0/3 (d24) | 12/16/01 -1/09/02 |
| 27-F$_3$-EpoD[17] (#78) | 60mg/kg, Q2Dx3 then 80mg/kg, Q2Dx2 d10-14, d16-18 | MX-1 | 4.8% (d20) | 0/4 (d20) | (control -6.6%, d20) -7.4% (d20) | 0/4 (d20) | 1/28/02 -2/05/02 |

FIG. 33A

| Compound | Dose & Schedule | Xenograft model | Therapeutic effect | | Toxicity | | Date |
|---|---|---|---|---|---|---|---|
| | | | % tumor volume reduction | Proportion of tumor disap-pearance | % body weight change | Proportion of mice dead | |
| 26-Me-EpoD (#25) | 50mg/kg, Q2Dx5, x1 d12-20, d24 | MX-1 | 65.7% (d26) | 0/2 (d26) | (control +3.8%, d26) +1.7% (d26) | 0/2 (d28) | 7/3/02 -7/19/02 |
| 19-Oxazole-10,11-deH-dEpoB (#84) | 30mg/kg, Q2Dx7 d22-34 | HCT-116 | 43.2% (d44) | 0/3 (d44) | (control -14%, d44) -18% (d44) | 0/3 (d44) | 8/9/02 |
| | 40mg/kg, Q2Dx7 d22-34 | | 70.3% (d44) | 0/3 (d44) | -18% (d44) | 0/3 (d44) | -9/02/02 |

FIG. 33B

In vitro microtubule assembly

| | MT assembly (37°C, %) |
|---|---|
| Control | 0 |
| EpoB | 100 |
| dEpoB | 117 |
| 9,10-dehydro-[16]dEpoB | 108 |
| 26-tri-F-9,10-dehydro-[16]dEpoB | 106 |
| 26-tri-F-[16]dEpoB | 84 |
| 21-hydroxy-9,10-dehydro-[16]dEpoB | 88 |

Cytotoxicity assay

| | A549 (IC50, nM) | A549 EpoB40 (IC50, nM) |
|---|---|---|
| EpoB | 1.94 | 55.44 |
| dEpoB | 11.6 | >500 |
| 9,10-dehydro-[16]dEpoB | 1.88 | 122.78 |
| 26-tri-F-9,10-dehydro-[16]dEpoB | 5.98 | 431.50 |
| 26-tri-F-[16]dEpoB | 44.2 | >500 |
| 21-hydroxy-9,10-dehydro-[16]dEpoB | 3.59 | 244.02 |

FIG. 41

Potency for the Epothilones Against Tumor Cell Growth in Vitro[a] and Relative Therapeutic Index[b]

| Compound | IC$_{50}$ (µM) for | | | Human Lung Carcinoma A549 | Human Lung Carcinoma HCT-116 | Relative Therapeutic Index against Mice Xenograft at MTD[d] |
|---|---|---|---|---|---|---|
| | Human T-cell Lymphoblastic Leukemia Sublines | | | | | |
| | CCRF-CEM | CCRF-CEM/ VBL | CCRF-CEM/ Taxol | | | |
| dEpoB | 0.0056 ±0.0028 | 0.016 ±0.003$_{[3.9x]}$[c] | 0.0085 ±0.0055$_{[1.5x]}$ | 0.0039 ±0.0004 | 0.0068 ±0.0032 | ++++ |
| dEpoF | 0.0015 ±0.0001 | 0.055 ±0.09$_{[36x]}$ | 0.0066 ±0.0031$_{[4.4x]}$ | 0.012 ±0.004 | 0.0034 ±0.0006 | ++++ |
| EpoB | 0.00053 ±0.00017 | 0.0032 ±0.0012$_{[6.05x]}$ | 0.0011 ±0.00008$_{[2.1x]}$ | 0.0008 ±0.0005 | 0.00038 ±0.00001 | +++ |
| Aza-EpoB | 0.0024 ±0.0003 | 2.08 ±0.92$_{[867x]}$$_{[1423x]}$ | 0.103 ±0.068$_{[43x]}$ | 0.0040 ±0.0035 | 0.0014 ±0.00009 | ++ |
| deH-dEpoB | 0.0009 ±0.0004 | 0.0042 ±0.0022$_{[4.7x]}$ | 0.0012 ±0.0006$_{[1.3x]}$ | 0.00089 ±0.00064 | 0.00094 ±0.00055 | ++++ |
| deH-dEpoF | 0.00051 ±0.00009 | 0.021 ±0.010$_{[41x]}$ | 0.0017 ±0.0010$_{[3.3x]}$ | 0.00091 ±0.00006 | 0.00056 ±0.00006 | +++ |
| deH-EpoB | 0.00023 ±0.00002 | 0.00096 ±0.00064$_{[4.2x]}$ | 0.00041 ±0.00001$_{[1.8x]}$ | 0.00026 ±0.00004 | 0.00014 ±0.00001 | ++++ |

FIG. 52A

Potency for the Epothilones Against Tumor Cell Growth in Vitro[a] and Relative Therapeutic Index[b]

| Compound | IC$_{50}$ (μM) for | | | | | Relative Therapeutic Index against Mice Xenograft at MTD[d] |
|---|---|---|---|---|---|---|
| | Human T-cell Lymphoblastic Leukemia Sublines | | | Human Lung Carcinoma A549 | Human Lung Carcinoma HCT-116 | |
| | CCRF-CEM | CCRF-CEM/ VBL | CCRF-CEM/ Taxol | | | |
| F$_3$-deH-dEpoB | 0.0032 ±0.0003 | 0.023 ±0.002 [7.2x] | 0.0047 ±0.0010 [1.5x] | 0.0037 ±0.0024 | 0.0056 ±0.0010 | +++++ |
| F$_3$-deH-dEpoF | 0.00089 | 0.038 [43x] | 0.0058 [6.5x] | | | |
| F$_3$-dEpoB | 0.0093 ±0.0052 | 0.085 ±0.005 [9.1x] | 0.018 ±0.001 [1.9x] | 0.015 ±0.004 | 0.012 ±0.001 | ND[e] |
| Paclitaxel | 0.0018 ±0.0005 | 3.22 ±0.92 [1789x] | 0.079 ±0.029 [43.9x] | 0.0029 ±0.0003 | 0.0026 ±0.0009 | ++++ |
| Vinblastine | 0.00054 ±0.00009 | 0.389 ±0.074 [720x] | 0.0196 ±0.0111 [36.3x] | 0.0099 ±0.0018 | 0.0087 ±0.0007 | ++++ |

[a] Cell growth inhibition for leukemic cells and solid tumor cells were measured by XTT tetrazonium assay and by sulforhodemine B (SRB) method, respectively, after 72-hr incubation for cell growth, as described previously (1,2). IC$_{50}$ values were determined from dose-effect relationship at six or seven concentrations of each drug, by using a computer program (3,4) as described earlier (5).
[b] The therapeutic experiments for epothilones against human tumor xenografts in nude mice, such as MX-1, were described (in 6 and 7).

FIG. 52B c The numbers in brackets are fold of resistance based on the $IC_{50}$ ratio when compared with the corresponding parent cell lines. CCRF-CEM/VBL and CCRF-CEM/Taxol are the CCRF-CEM leukemic cells resistant to vinblastine and paclitaxel, 720-fold and 44-fold, respectively.

d Graded therapeutic index (TI) at MTD (maximal tolerated dose):
+     Tumor growth suppressed 25-50%.
++    Tumor growth suppressed 50-100%.
+++   Tumor shrinkage but no tumor disappearance.
++++  Tumor disappearance in some or all nude mice with slow body weight recovery and/or with relapse in some mice.
+++++ Tumor disappeared in all nude mice, body weight rapidly recovered and/or without relapse.

e Not Determined

FIG. 52C

SYNTHESIS OF EPOTHILONES, INTERMEDIATES THERETO AND ANALOGUES THEREOF

PRIORITY INFORMATION

The present application is a continuation of and claims priority under 35 U.S.C. §120 to application U.S. Ser. No. 10/435,408, filed May 9, 2003, now issued as U.S. Pat. No. 7,649,006; which is a continuation-in-part of and claims priority under 35 U.S.C. §120 to application U.S. Ser. No. 10/402,004, filed Mar. 28, 2003, now issued as U.S. Pat. No. 6,921,769; and also claims priority under 35 U.S.C. §119(e) to provisional applications U.S. Ser. No. 60/405,823, filed Aug. 23, 2002, entitled "Synthesis of Epothilones, Intermediates Thereto and Analogues Thereof"; U.S. Ser. No. 60/408,589, filed Sep. 6, 2002, entitled "Synthesis of Epothilones, Intermediates Thereto and Analogues Thereof"; U.S. Ser. No. 60/423,129, filed Nov. 1, 2002, entitled "Synthesis of Epothilones, Intermediates Thereto and Analogues Thereof"; and U.S. Ser. No. 60/456,159, filed Mar. 20, 2003, entitled "Synthesis of Epothilones, Intermediates Thereto and Analogues Thereof"; the entire contents of each of which are incorporated herein by reference.

GOVERNMENT SUPPORT

This invention was supported by grant 5 R37CA028824-25 from the National Institutes of Health. The United States government has certain rights in this invention.

BACKGROUND OF THE INVENTION

Epothilones A and B (2a and 2b, Scheme 1) are naturally occurring cytotoxic macrolides that were isolated from a cellulose degrading mycobacterium, *Sorangium cellulosum* (Höfle et al. *Angew. Chem., Int. Ed. Engl.* 1996, 35, 1567 and *J. Antibiot.* 1996, 49, 560; each of which is incorporated herein by reference). Despite their vastly different structures, epothilones A and B share the same mechanism of action as paclitaxel (Taxol®) which involves growth inhibition of tumor cells by tubulin polymerization and stabilization of microtubule assemblies (Bollag et al. *Cancer Res.* 1995, 55, 2325; incorporated by reference). In spite of its unquestioned clinical value as a front-line chemotherapeutic agent, Taxol® is far from an ideal drug. Its marginal water solubility necessitates recourse to formulation vehicles such as Cremophores that pose their own risks and management issues (Essayan et al. *J. Allergy Clin. Immunol.* 1996, 97, 42; incorporated herein by reference). Moreover, Taxol® is vulnerable to deactivation through multiple drug resistance (MDR) (Giannakakou et al. *J. Biol. Chem.* 1997, 272, 17118; incorporated herein by reference). However, it has also been demonstrated that epothilones A and B retain remarkable potency against MDR tumor cells (Kowalski et al. *Mol. Biol. Cell* 1995, 6, 2137; incorporated herein by reference). Additionally, the increased water solubility in comparison to paclitaxel may be useful for the formulability of epothilones. While the naturally occurring compound, epothilone B (2b, EpoB, in Scheme 1), is a potent member of the epothilone family of natural products, it unfortunately possesses, at least in xenograft mice, a worrisomely narrow therapeutic index (Su et al. *Angew. Chem. Int. Ed. Engl.* 1997, 36, 1093; Harris et al. *J. Org. Chem.* 1999, 64, 8434; each of which is incorporated herein by reference).

Scheme 1: Taxoids and Epothilones

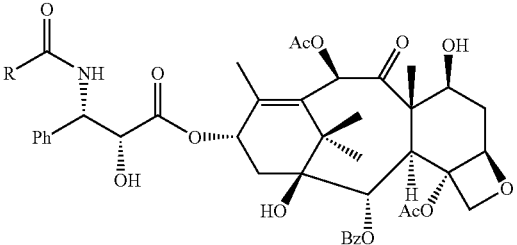

1a R = Ph, Paclitaxel (aTxol)
1b R = t-Bu, Docetaxel (Taxotere)

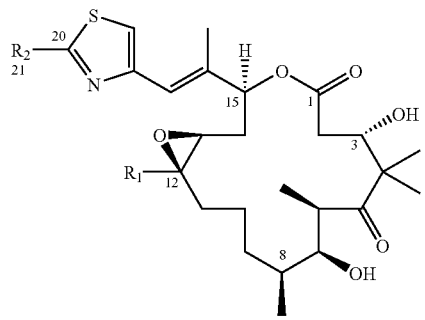

2a $R_1$ = H, $R_2$ = $CH_3$, Epothilone A (EpoA)
2b $R_1$ = $CH_3$, $R_2$ = $CH_3$, Epothilone B (EpoB)
2c $R_1$ = H, $R_2$ = $CH_2OH$, Epothilone E (EpoE)
2d $R_1$ = $CH_3$, $R_2$ = $CH_2OH$, Epothilone F (EpoF)

Given the limited therapeutic index of EpoB, other epothilone analogues, in particular the 12,13-desoxyepothilones, were investigated for their ability to provide an improved therapeutic profile (see, U.S. Pat. Nos. 6,242,469, 6,284,781, 6,300,355, 6,369,234, 6,204,388, 6,316,630; each of which is incorporated herein by reference). In vivo experiments conducted on various mouse models demonstrated that 12,13-desoxyepothilone B (3b, dEpoB in Scheme 2) possesses therapeutic potential against various sensitive and resistant human tumors in mice xenografts (Chou et al. *Proc. Natl. Acad. Sci. U.S.A.* 1998, 95, 9642 and 15798; incorporated herein by reference). Recently, the therapeutic superiority of these desoxyepothilones over other anticancer agents has been conclusively demonstrated by thorough comparative studies (Chou et al. *Proc. Natl. Acad. Sci. U.S.A.* 2001, 98, 8113; incorporated herein by reference). Due to its impressive in vivo profile, dEpoB has been advanced through toxicology evaluations in dogs, and is now2 in human trials as an anticancer drug.

Scheme 2. Various Desoxyepothilone Analogues

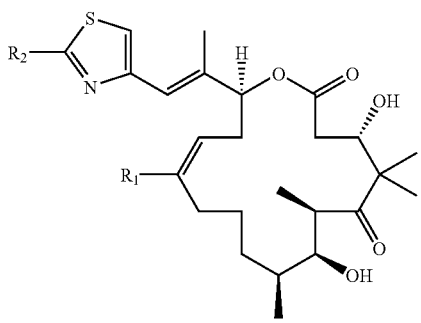

3a R$_1$ = H, R$_2$ = CH$_3$, Desoxyepothilone A (dEpoA)
3b R$_1$ = CH$_3$, R$_2$ = CH$_3$, Desoxyepothilone B (dEpoB)
3c R$_1$ = H, R$_2$ = CH$_2$OH, Desoxyepothilone E (dEpoE)
3d R$_1$ = CH$_3$, R$_2$ = CH$_2$OH, Desoxyepothilone F (dEpoF)
3e R$_1$ = H, R$_2$ = NH$_2$, Desmethylamino-dEpoA (dadEpoA)
3f R$_1$ = CH$_3$, R$_2$ = NH$_2$, Desmethylamino-dEpoB (dadEpoB)
3g R$_1$ = CH$_2$F, R$_2$ = CH$_3$, 26-Fluoro-dEpoB
3h R$_1$ = CF$_3$, R$_2$ = CH$_3$, 26-TRifluoro-dEpoB

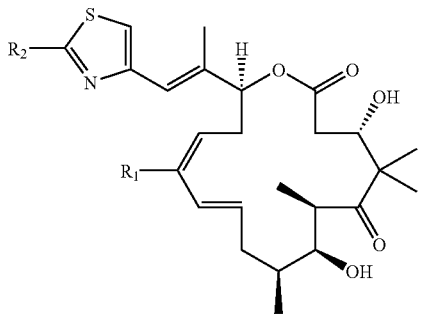

4a R$_1$ = H, R$_2$ = CH$_3$, Dehydro-dEpoA (ddEpoA)
4b R$_1$ = CH$_3$, R$_2$ = CH$_3$, Dehdro-dEpoB (ddEpoB)
4c R$_1$ = H, R$_2$ = CH$_2$OH, Dehydro-dEpoE (ddEpoE)
4d R$_1$ = CH$_3$, R$_2$ = CH$_2$OH, Dehydro-dEpoF (ddEpoF)
4e R$_1$ = H, R$_2$ = NH$_2$, Desmethylamino-ddEpoA
4f R$_1$ = CH$_3$, R$_2$ = NH$_2$, Desmethylamino-ddEpoB
4g R$_1$ = CH$_2$F, R$_2$ = CH$_3$, 26-Fluoro-ddEpoB
4h R$_1$ = CF$_3$, R$_2$ = CH$_3$, 26-TRifluoro-ddEpoB

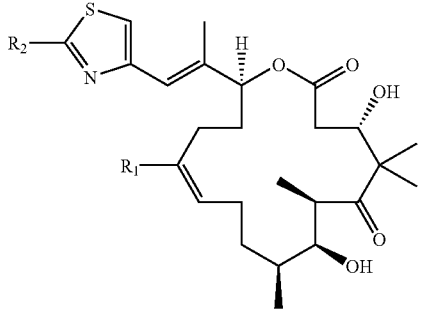

5a R$_1$ = H, R$_2$ = CH$_3$, iso-dEpoA
5b R$_1$ = CH$_3$, R$_2$ = CH$_3$, iso-dEpoB
5c R$_1$ = H, R$_2$ = CH$_2$OH, iso-dEpoE
5d R$_1$ = CH$_3$, R$_2$ = CH$_2$OH, iso-dEpoF (ddEpoF)
5e R$_1$ = H, R$_2$ = NH$_2$, Desmethylamino-iso-dEpoA
5f R$_1$ = CH$_3$, R$_2$ = NH$_2$, Desmethylamino-iso-dEpoB In light of the promising therapeutic utility of the 12,13-desoxyepothilones, it would be desirable to investigate additional analogues as well as additional synthetic methodologies for the synthesis of existing epothilones, desoxyepothilones, and analogues thereof, as well as novel analogues thereof. In particular, given the interest in the therapeutic utility of this class of compounds, it would also be desirable to develop methodologies capable of providing significant quantities of any epothilones or desoxyepothilones previously described, or those described herein, for clinical trials and for large-scale preparation.

DESCRIPTION OF THE DRAWINGS

FIG. 1 is a table of IC$_{50}$ values of epothilones against CCRF-CEM cell growth.

FIG. 11 shows the potencies of various epothilone analogues against tumor cell growth in vitro and therapeutic index, as compared to paclitaxel and vinblastine.

FIG. 12 is a table summarizing the effect of dEpoB, Taxol, and 26-triF-9,10-deH-dEpoB against MX-1 xenograft in nude mice.

FIG. 31 is table with IC50 values for epothilone analogues against CCRF-CEM cell growth.

FIG. 32 shows the metabolic stability of epothione analogues in vitro and in vivo.

FIG. 33 is table detailing the therapeutic effects of various epothilone analogues against human tumor xenografts in mice with 6 hour iv infusion.

FIG. 41 are tables describing the effect of various epothilone analogues on in vitro microtubule polymerization at 37° C. in the absence of GTP (A) and the cytotoxicity of various epothilone analogs in the human lung cell line A549 (B).

FIG. 52 is a table comparing the potency of various epothilone analogs with respect to inhibition of tumor growth in vitro and relative therapeutic index.

DEFINITIONS

Figure 2B:
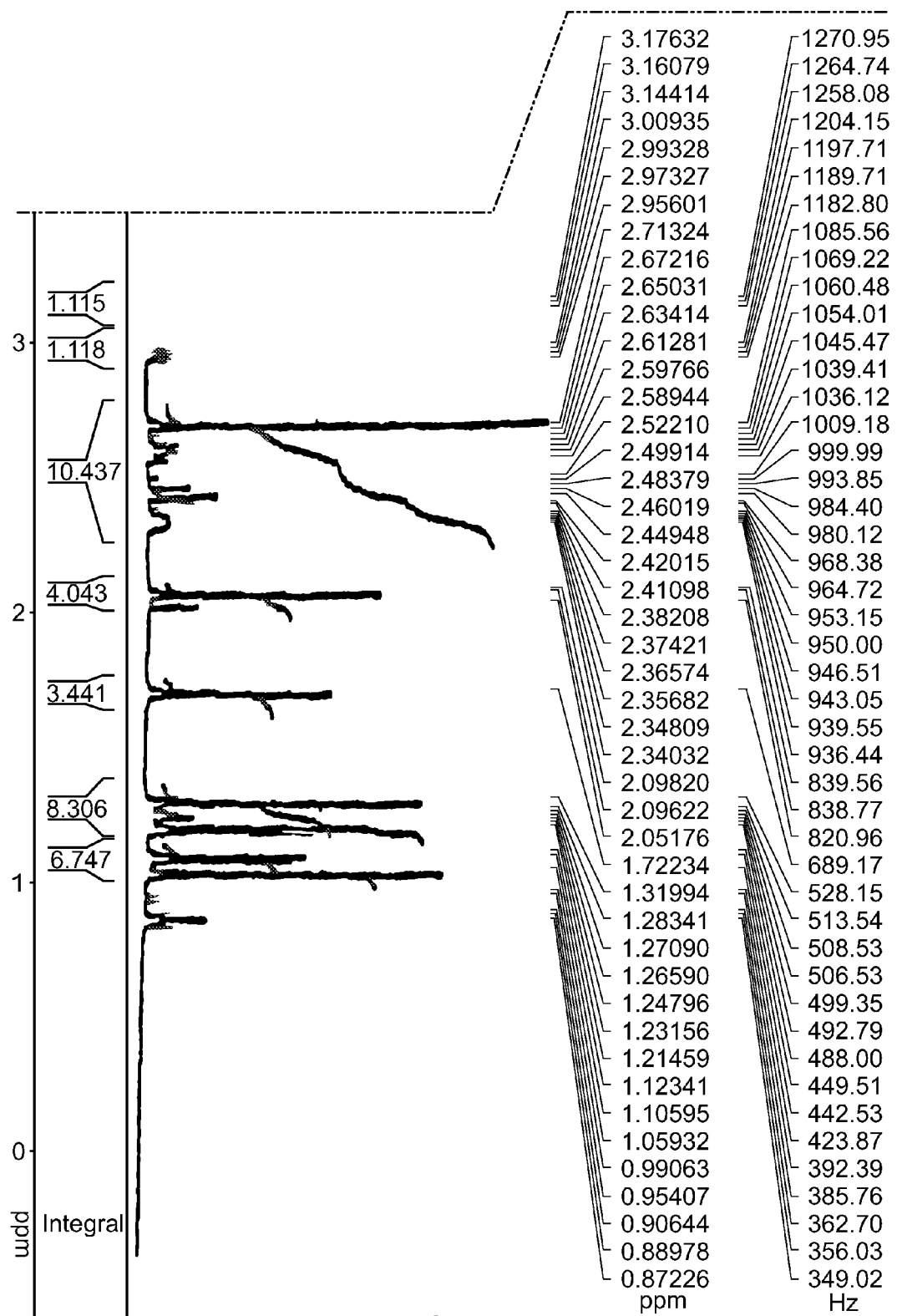
FIG. 2 is a $^1$H NMR spectrum of trans-9,10-dehydro-12,13-desoxyEpoB.
Figure 3A:
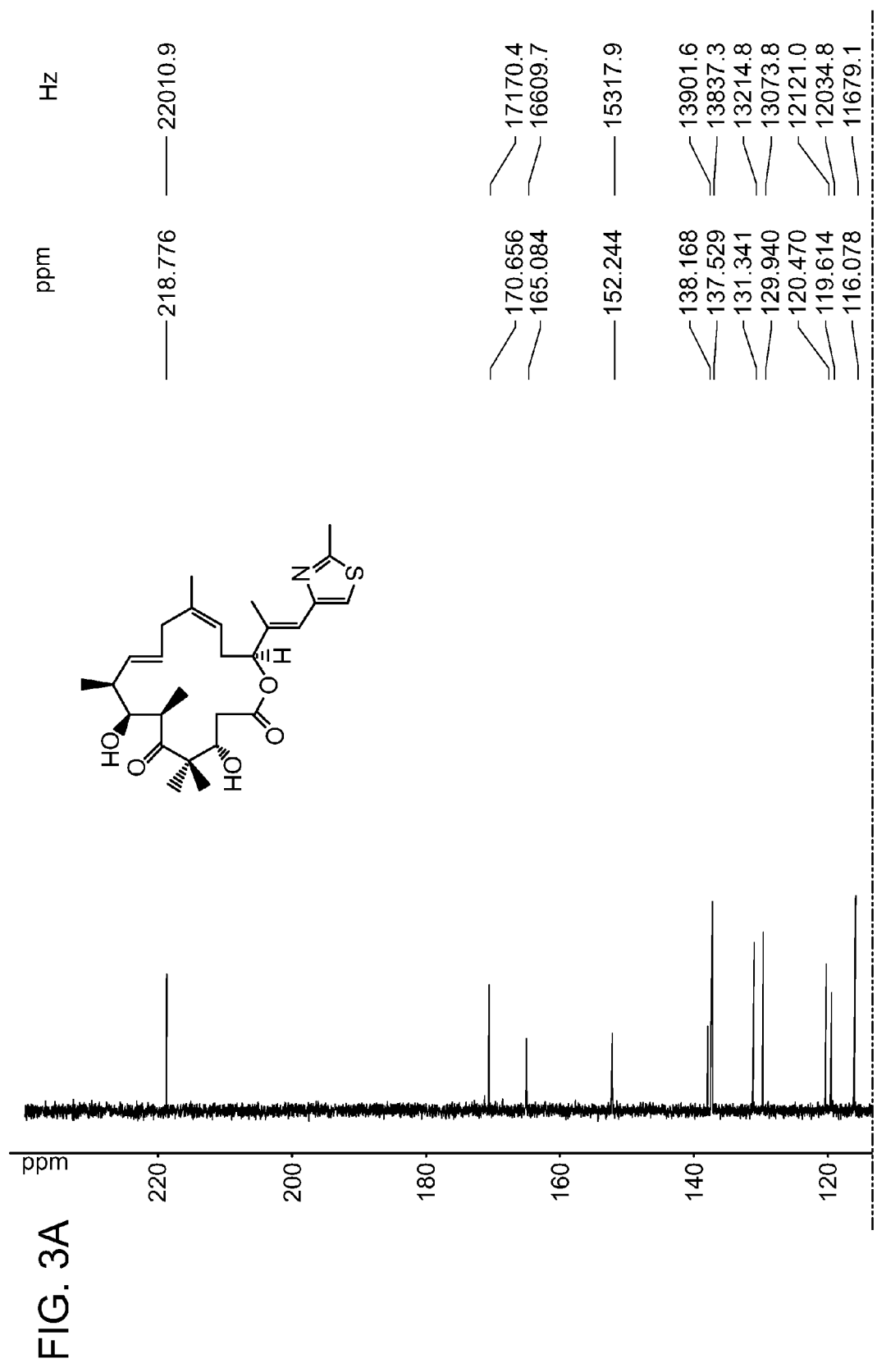
FIG. 3 is a $^{13}$C NMR spectrum of trans-9,10-dehydro-12,13-desoxyEpoB.
Figure 3B:
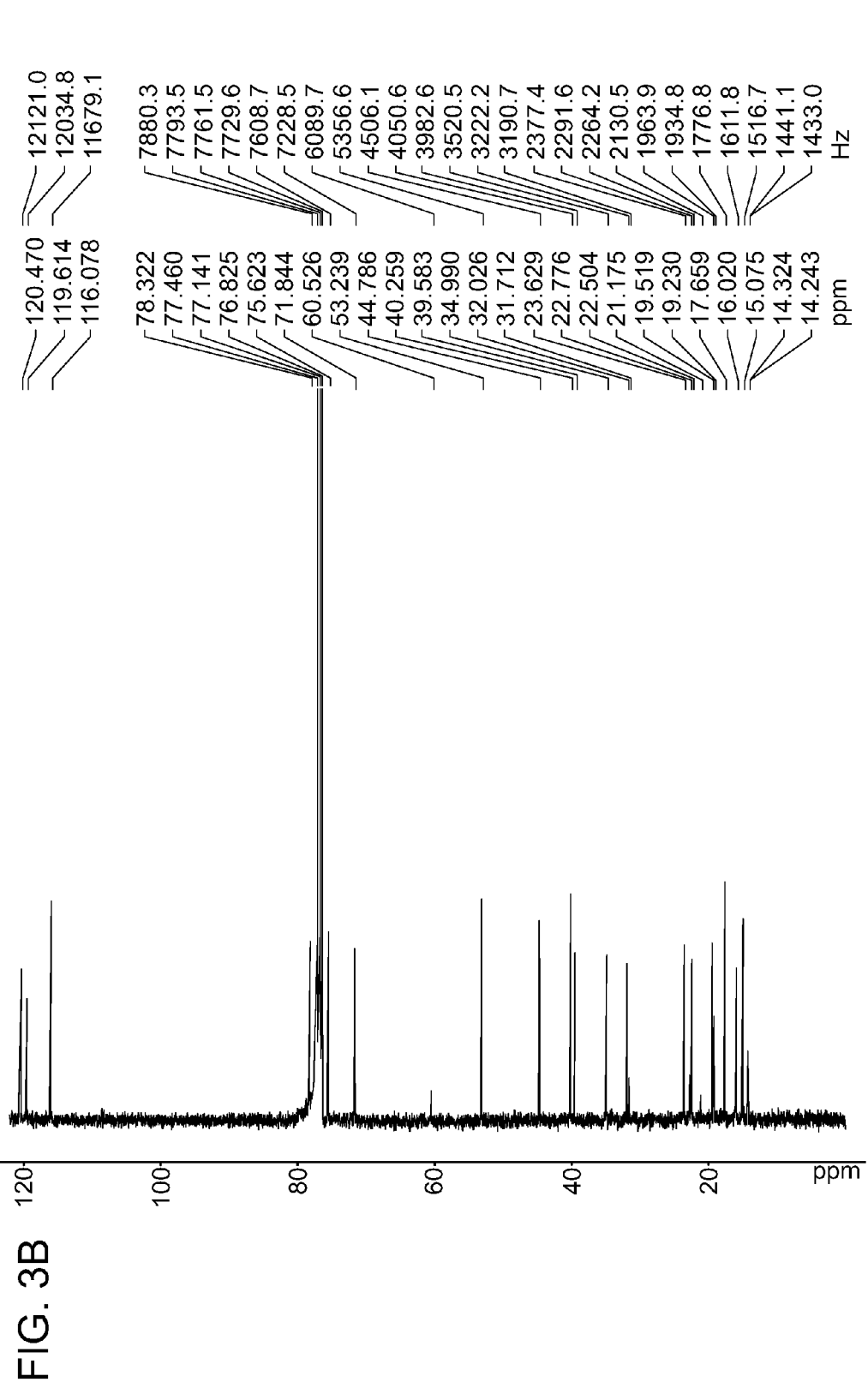
Figure 4:
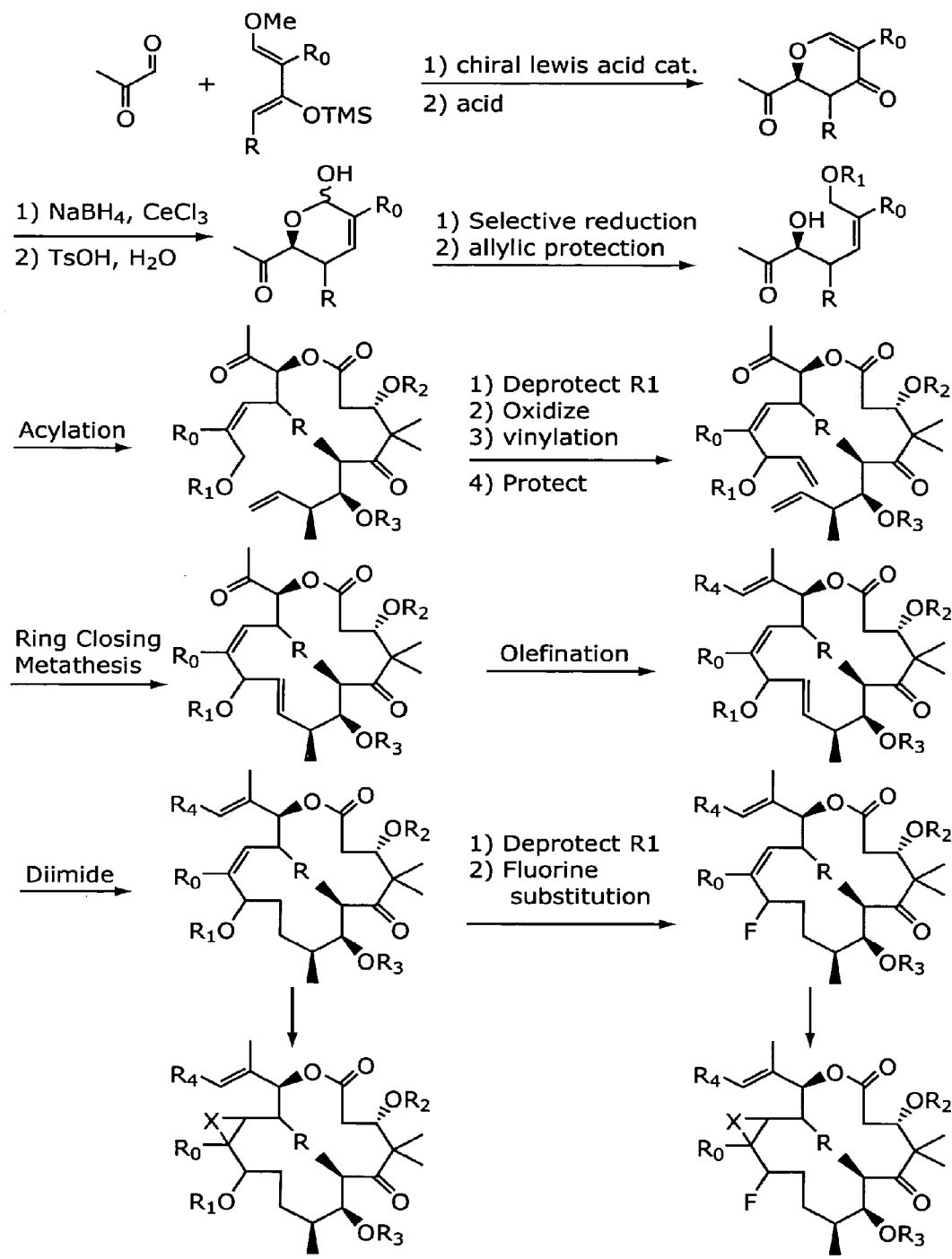
FIG. 4 shows a scheme for synthesis of 11-R and 14-R epothilones using LACDAC-ring closing olefin methathesis, and illustrates certain substitutions available with synthetic strategies that pass through a 9,10-dehydro epothilone.
Figure 5A:
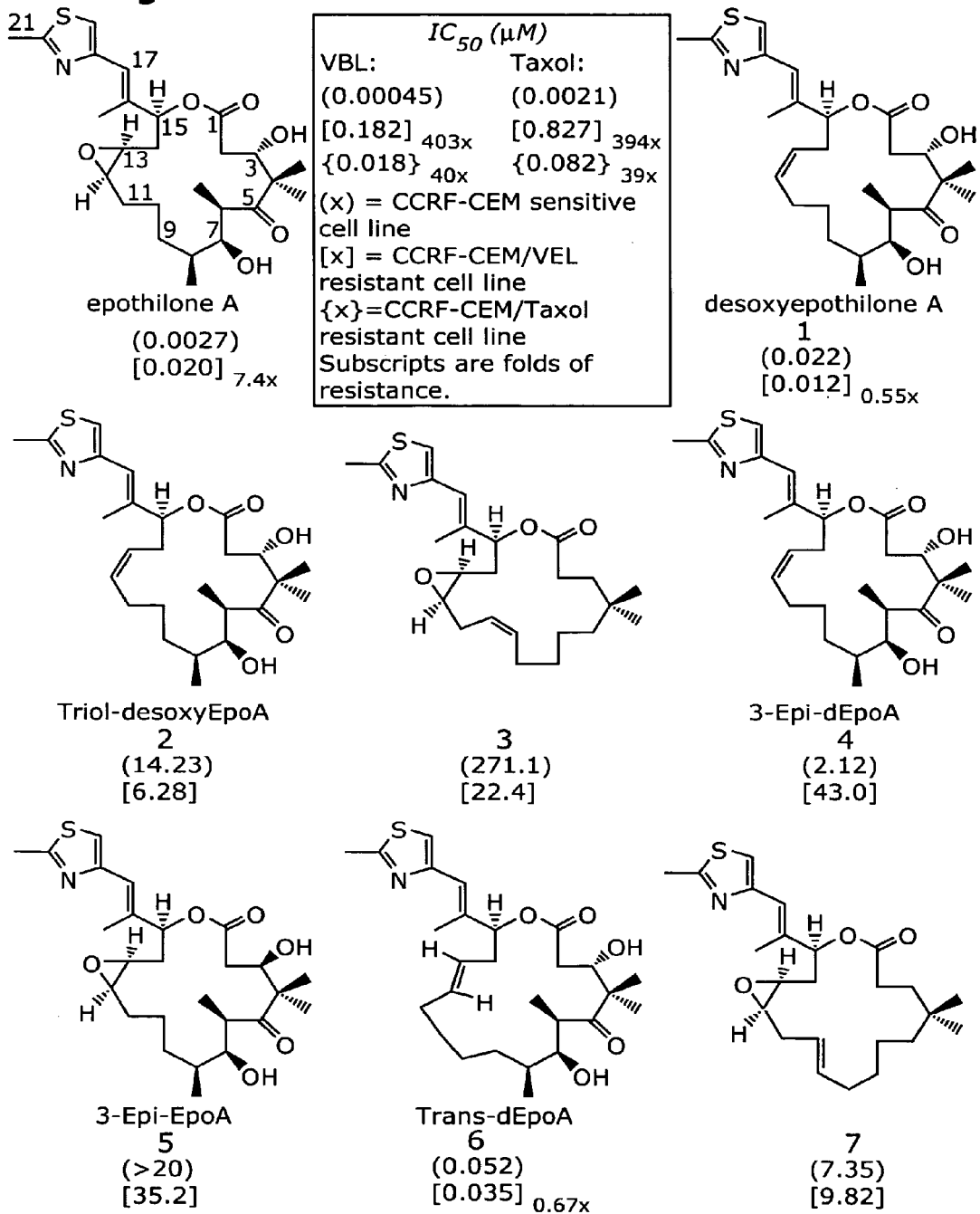
FIG. 5 presents relative cytotoxicity data against human leukemic cells in vitro for a variety of epothilone compounds and derivatives including certain 9,10-dehydro compounds (e.g., compound 7 in FIG. 5A and compound 89 in FIG. 5B).
Figure 5B:
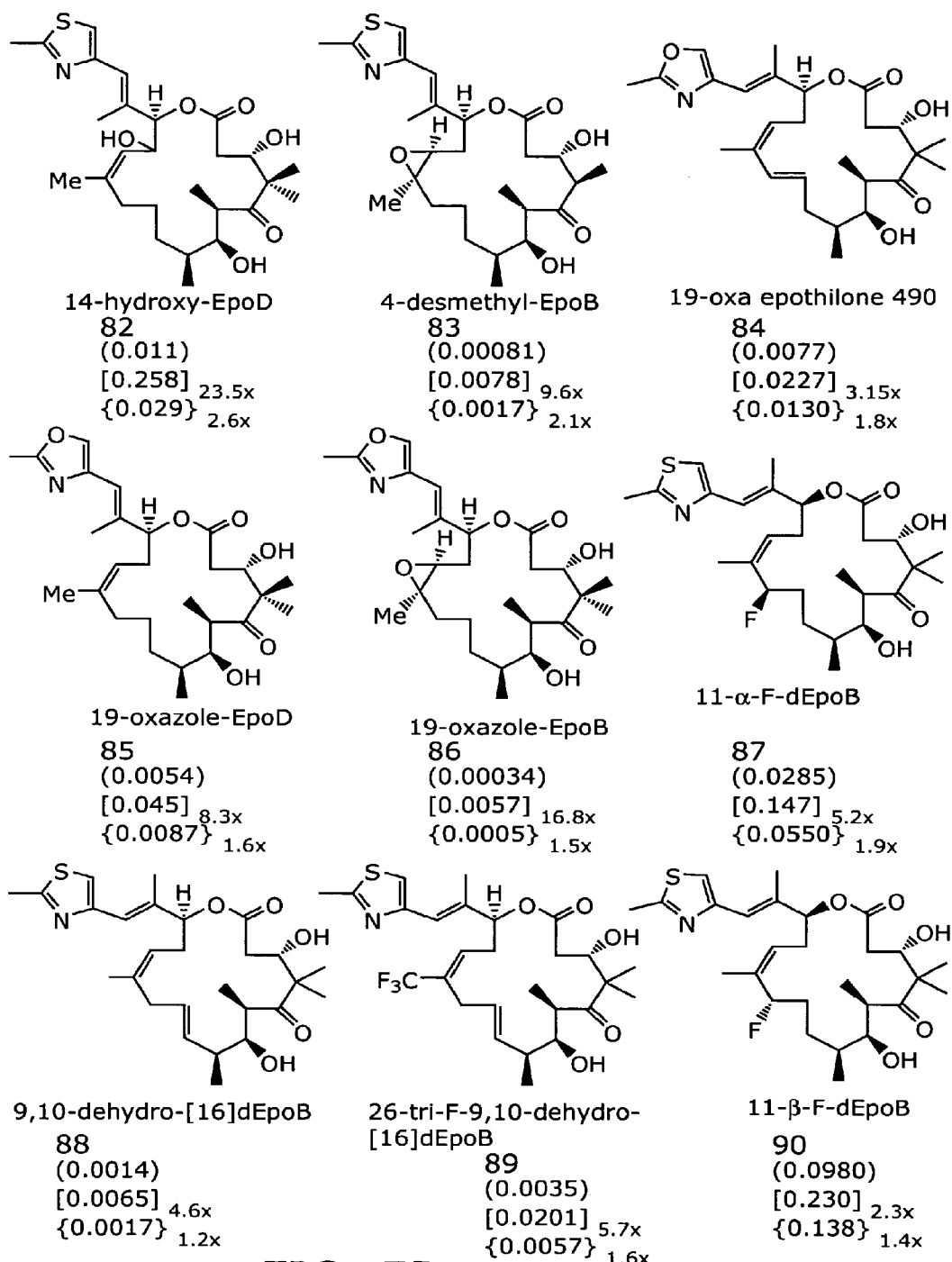
Figure 6D:
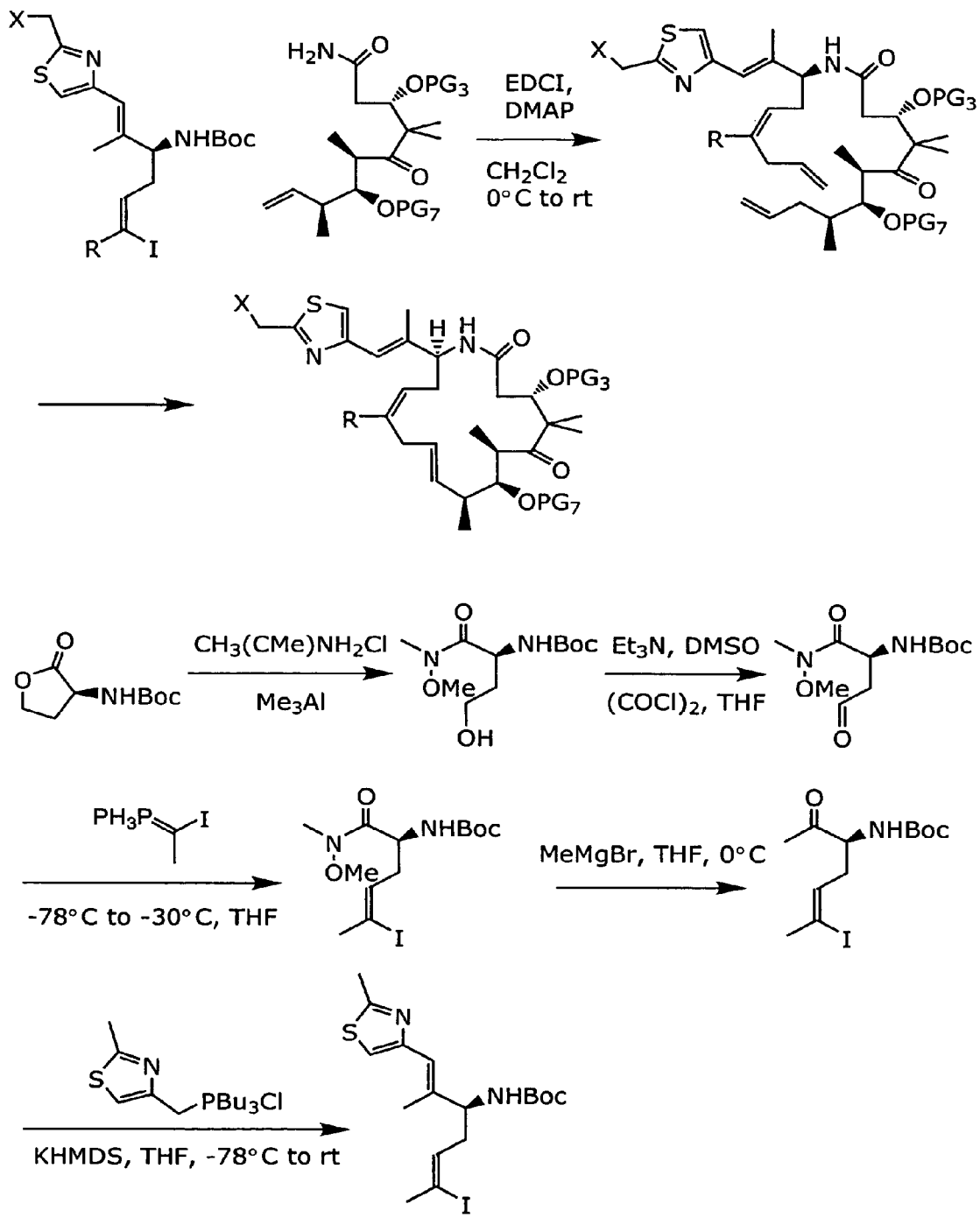
FIG. 6 depicts alternative synthetic strategies for preparing 9,10-dehydro epothilone analogs.
Figure 7:
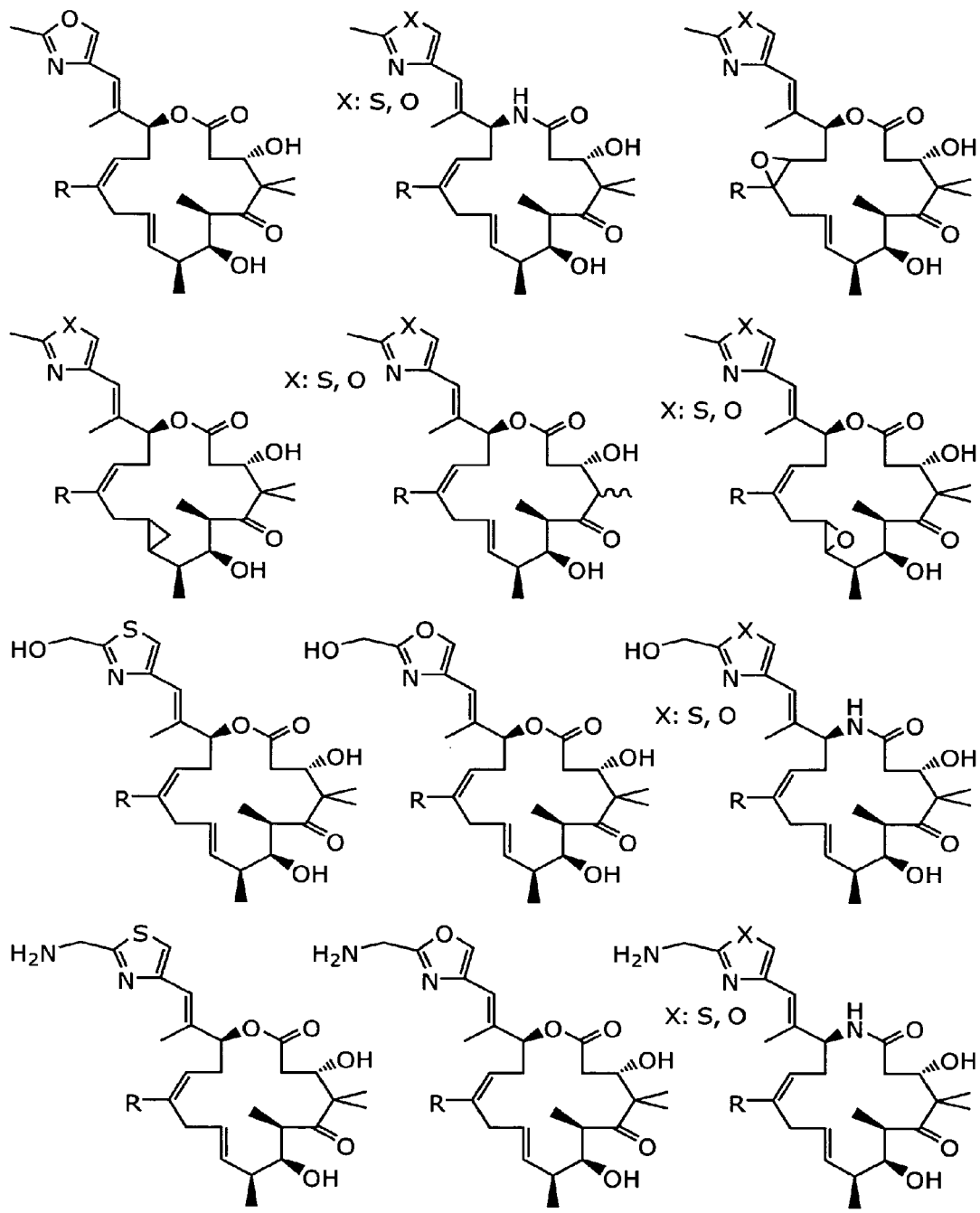
FIG. 7 shows analogs of 9,10-dehydro-12,13-desoxy EpoB.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1-20 alipathic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Labeled": As used herein, the term "labeled" is intended to mean that a compound has at least one element, isotope or chemical compound attached to enable the detection of the compound. In general, labels fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens; and c) colored or fluorescent dyes. It will be appreciated that the labels may be incorporated into the compound at any position that does not interfere with the biological activity or characteristic of the compound that is being detected. In certain embodiments of the invention, photoaffinity labeling is utilized for the direct elucidation of intermolecular interactions in biological systems (e.g., to probe the epothilone binding site in a tubulin dimer). A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Polymer": The term "polymer", as used herein, refers to a composition comprising chains that may be open, closed, linear, branched or cross-linked of repeating units (monomers) that may be the same or different. It will be appreciated that in certain embodiments the term polymer refers to biopolymers, which, as used herein, is intended to refer to polymeric materials found in nature or based upon those materials found in nature, including, but not limited to nucleic acids, peptides, and mimetics thereof. In certain other embodiments, the term polymer refers to synthetic polymers, such as biodegradable polymers or other polymeric materials. It will be appreciated that polymeric solid supports are also encompassed by the polymers of the present invention. Inventive compounds can be attached to polymeric supports and thus certain synthetic modifications can be conducted on the solid phase. As used herein, the term "solid support" is meant to include, but is not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N—N'-bis-acryloylethylenediamine, and glass particles coated with a hydrophobic polymer. One of ordinary skill in the art will realize that the choice of particular solid support will be limited by the compatability of the support with the reaction chemistry being utilized. An exemplary solid support is a Tentagel amino resin, a composite of 1) a polystyrene bead crosslinked with divinylbenzene and 2) PEG (polyethylene glycol). Tentagel is a particularly useful solid support because it provides a versatile support for use in on-bead or off-bead assays, and it also undergoes excellent swelling in solvents ranging from toluene to water.

DESCRIPTION OF CERTAIN EMBODIMENTS OF THE INVENTION

In recognition of the need to develop novel and effective cancer therapies, the present invention provides novel synthetic methodologies enabling access to macrocycles having a broad range of biological and pharmacological activity, as well as novel compounds with such activity, novel therapeutic compositions, and methods of using these compounds and compositions.

In certain embodiments, the inventive compounds are useful in the treatment of cancer. Certain compounds of the invention exhibit cytotoxic or growth inhibitory effects on cancer cells lines, exhibit an ability to polymerize tubulin and stabilize microtubule assemblies, and/or lead to shrinkage or diappearance of tumors in cancer cell xenograft models. In certain embodiments, the compounds may have reduced or minimal side effects including toxicity to vital organs, nausea, vomiting, diarrhea, allopecia, weight loss, weight gain, liver toxicity, skin disorders, etc. The compounds may also be easier to formulate due to increased water solubility, decreased toxicity, increased therapeutic range, increased efficacy, etc.

General Description of Compounds of the Invention

Compounds of the invention include compounds of the general formula (0) and (0') as further defined below:

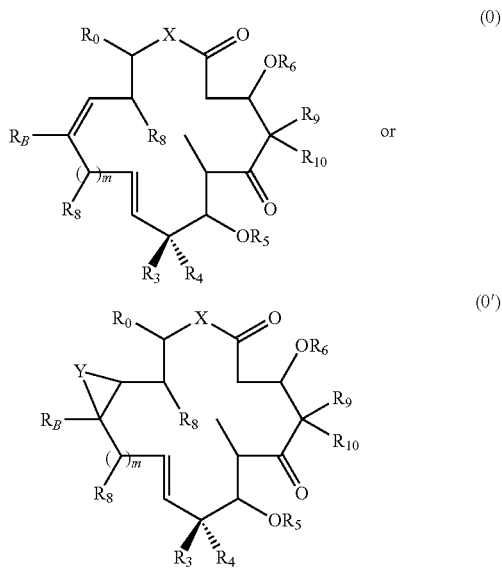

wherein R$_0$ is a substituted or unsubstituted aryl, heteroaryl, arylalkyl, arylalkenyl, arylalkynyl, heteroarylalkyl, heteroarylalkenyl, or heteroarylalkynyl moiety; in certain embodiments, R$_0$ is a arylalkyl, arylalkenyl, heteroarylalkyl, or heteroarylalkenyl moiety; in other embodiments, R$_0$ is a heteroarylalkenyl moiety; in certain embodiments, R$_0$ is a heteroarylalkyl moiety; in other embodiments, $R_0$ is a 5-7 membered aryl or heteroaryl moiety; in yet other embodiments, $R_0$ is an 8-12 membered bicyclic aryl or heteroaryl moiety; in still other embodiments, $R_0$ is a bicyclic moiety wherein a phenyl ring is fused to a heteroaryl or aryl moiety; in other embodiments, $R_0$ is a bicyclic moiety wherein a phenyl ring is fused to a thiazole, oxazole, or imidazole moiety; in yet other embodiments, $R_0$ is a substituted or unsubstituted phenyl moiety;

$R_3$ and $R_4$ are each independently hydrogen; or substituted or unsubstituted, linear or branched, cyclic or acyclic aliphatic, heteroaliphatic, aryl, heteroaryl, arylalkyl, or heteroarylalkyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_3$ and $R_4$ are each independently hydrogen, fluorine, or lower alkyl; in other embodiments, $R_3$ and $R_4$ are each independently hydrogen or methyl; in still other embodiments, $R_3$ is methyl, and $R_4$ is hydrogen;

$R_5$ and $R_6$ are each independently hydrogen or a protecting group; in certain embodiments, $R_5$ and $R_6$ are both hydrogen;

X is O, S, $C(R_7)_2$, or $NR_7$, wherein each occurrence of $R_7$ is independently hydrogen or lower alkyl; in certain embodiments, X is O; in other embodiments, X is NH;

Y is O, S, NH, $C(R_7)_2$, $CH_2$, $N(R_7)$, or NH, wherein each occurrence of $R_7$ is independently hydrogen or lower alkyl; in certain embodiments, Y is O; in other embodiments, Y is NH; in yet other embodiments, Y is $CH_2$;

each $R_8$ is independently hydrogen; halogen, hydroxy, alkoxy, amino, dialkylamino, alkylamino, fluoro, cyano, or substituted or unsubstituted, linear or branched, cyclic or acyclic aliphatic, heteroaliphatic, aryl, heteroaryl, arylalkyl, arylalkenyl, arylalkynyl, or heteroarylalkyl, heteroarylalkenyl, heteroarylalkynyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_8$ is hydrogen; in other embodiments, $R_8$ is hydroxy; in yet other embodiments, $R_8$ is fluorine; in still other embodiments, $R_8$ is lower alkyl such as methyl; in other embodiments $R_8$ is —$CF_3$, —$CF_2H$, or —$CFH_2$; in other embodiments, $R_8$ is perfluorinated or fluorinated alkyl group; in yet other embodiments, $R_8$ is halogenated or perhalogenated alkyl group;

$R_9$ and $R_{10}$ are each independently hydrogen; or substituted or unsubstituted, linear or branched, cyclic or acyclic aliphatic, heteroaliphatic, aryl, heteroaryl, aryl, arylalkyl, arylalkenyl, arylalkynyl, heteroarylalkyl, heteroarylalkenyl, or heteroarylalkynyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, one of $R_9$ and $R_{10}$ is methyl; in other embodiments, both $R_9$ and $R_{10}$ are methyl; in yet other embodiments, one of $R_9$ and $R_{10}$ is methyl, and the other is hydrogen; in other embodiments, both $R_9$ and $R_{10}$ are hydrogen;

$R_B$ is, independently for each occurrence, hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —N$(R_{B'})_2$; —$C(O)OR_{B'}$; —$C(O)R_{B'}$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; in certain embodiments, $R_B$ is hydrogen,

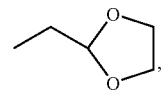

number methyl, ethyl, propyl, butyl, pentyl, hexyl, cyclopropyl, cyclobutyl, cyclopentyl, or cyclohexyl, each unsubstituted or optionally substituted with one or more occurrences of halogen, —OH, —$OR_{B'}$, $NH_2$, or $N(R_{B'})_2$, or any combination thereof, wherein each occurrence of $R_{B'}$ is independently hydrogen, alkyl, aryl, or a protecting group, in other embodiments, $R_B$ is hydrogen, methyl, or ethyl, in still other embodiments, $R_B$ is methyl, in other embodiments, —$CY_3$, —$CHY_2$, —$CH_2Y$, where Y is F, Br, Cl, I, $OR_{B'}$, $NHR_{B'}$, $N(R_{B'})_2$, or $SR_{B'}$; in yet other embodiments, $R_B$ is —$CF_3$, —$CH_2F$, or $CHF_2$; in other embodiments, $R_B$ is perfluorinated or fluorinated alkyl group; in yet other embodiments, $R_B$ is halogenated or perhalogenated alkyl group;

each occurrence of $R_{B'}$ is independently hydrogen; a protecting group; a linear or branched, substituted or unsubstituted, cyclic or acyclic, aliphatic, heteroalliphatic, aryl, heteroaryl, arylalkyl, arylalkenyl, arylalkynyl, heteroarylalkyl, heteroarylalkenyl, or heteroarylalkynyl moiety;

m is 1, 2, 3, or 4, m is 1 or 2 in certain embodiments, m is 1 in other embodiments; and pharmaceutically acceptable derivatives thereof.

The compounds of the invention include compounds of the general formula (I) or (I') as further defined below:

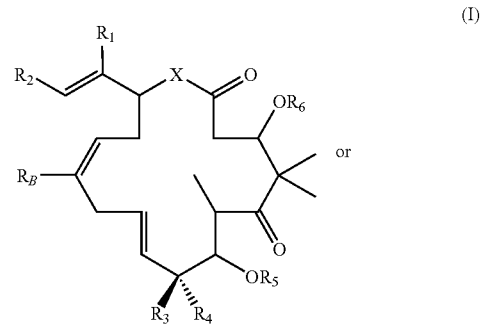

(I)

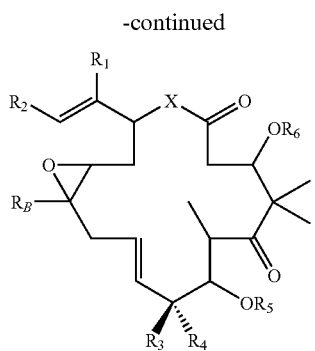

(I″)

wherein $R_1$ is hydrogen or lower alkyl; in certain embodiments, $R_1$ is methyl; in certain embodiments, $R_1$ is —$CF_3$, —$CF_2H$, or $CH_2F$; in other embodiments, $R_1$ is perfluorinated or fluorinated alkyl group; in yet other embodiments, $R_1$ is halogenated or perhalogenated alkyl group;

$R_2$ is a substituted or unsubstituted aryl, heteroaryl, arylalkyl, or heteroarylalkyl moiety; in certain embodiments, $R_2$ is substituted or unsubstituted oxazole; in other embodiments, $R_2$ is substituted or unsubstituted thiazole;

$R_3$ and $R_4$ are each independently hydrogen; or substituted or unsubstituted, linear or branched, cyclic or acyclic aliphatic, heteroaliphatic, aryl, heteroaryl, arylalkyl, or heteroarylalkyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_3$ and $R_4$ are each independently hydrogen, fluorine, or lower alkyl; in other embodiments, $R_3$ and $R_4$ are each independently hydrogen or methyl; in still other embodiments, $R_3$ is methyl, and $R_4$ is hydrogen;

$R_5$ and $R_6$ are each independently hydrogen or a protecting group; in certain embodiments, $R_5$ and $R_6$ are both hydrogen;

X is O, S, C($R_7$)$_2$, or N$R_7$, wherein each occurrence of $R_7$ is independently hydrogen or lower alkyl; in certain embodiments, X is O; in other embodiments, X is NH;

$R_B$ is, independently for each occurrence, hydrogen; halogen; —$OR_{B'}$; —$SR_{B'}$; —$N(R_{B'})_2$; $C(O)OR_{B'}$; —$C(O)R_{B'}$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; in certain embodiments, $R_B$ is hydrogen,

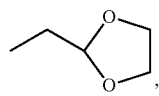

methyl, ethyl, propyl, butyl, pentyl, hexyl, cyclopropyl, cyclobutyl, cyclopentyl, or cyclohexyl, each unsubstituted or optionally substituted with one or more occurrences of halogen, —OH, —$OR_{B'}$, $NH_2$, or $N(R_{B'})_2$, or any combination thereof, wherein each occurrence of $R_{B'}$ is independently hydrogen, alkyl, aryl, or a protecting group, in other embodiments, $R_B$ is hydrogen, methyl, or ethyl, in still other embodiments, $R_B$ is methyl, in yet other embodiments, $R_B$ is —$CF_3$, —$CH_2F$, or $CHF_2$; and pharmaceutically acceptable derivatives thereof.

In certain embodiments, the compounds of the invention include compounds of the general formula (II) or (II') with the stereochemistry defined as shown:

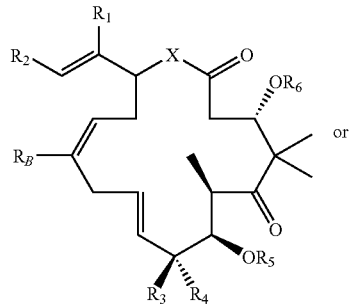

(II)

or

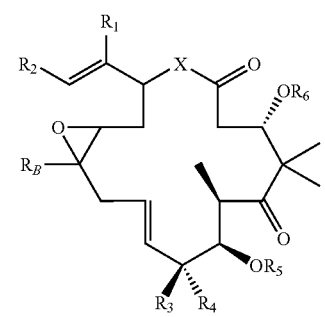

(II')

wherein X, $R_1$, $R_2$, $R_3$, $R_4$, $R_5$, $R_6$, $R_B$, and X are as defined above.

In certain embodiments, X is O. In other embodiments, X is NH. In other embodiments, X is $CH_2$.

In some embodiments, $R_2$ is a substituted or unsubstituted thiazole. In certain embodiments, $R_2$ is 2-methyl-thiazo-4-yl. In other embodiments, $R_2$ is 2-hydroxylmethyl-thiazo-4-yl. In yet other embodiments, $R_2$ is 2-aminomethyl-thiazo-4-yl. In other embodiments, $R_2$ is 2-thiolmethyl-thiazo-4-yl.

In certain embodiments $R_2$ is a substituted or unsubstituted oxazole. In certain embodiments, $R_2$ is 2-methyl-oxazo-4-yl. In other embodiments, $R_2$ is 2-hydroxylmethyl-oxazo-4-yl. In yet other embodiments, $R_2$ is 2-aminomethyl-oxazo-4-yl. In other embodiments, $R_2$ is 2-thiolmethyl-oxazo-4-yl.

In certain embodiments, $R_B$ is hydrogen, methyl, ethyl, —$CF_3$, —$CH_2F$, —$CF_2H$. In certain embodiments, $R_B$ is methyl. In yet other embodiments, $R_B$ is —$CF_3$. In certain embodiments, $R_B$ is hydrogen. In other embodiments, $R_B$ is ethyl.

Certain preferred compounds include, for example:
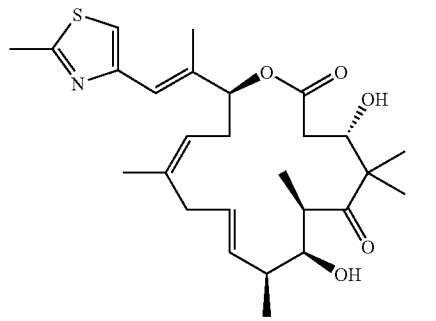
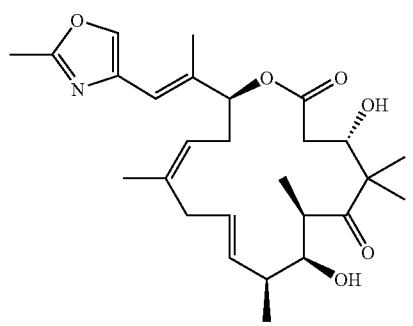
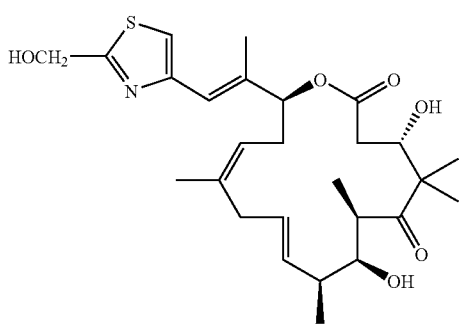
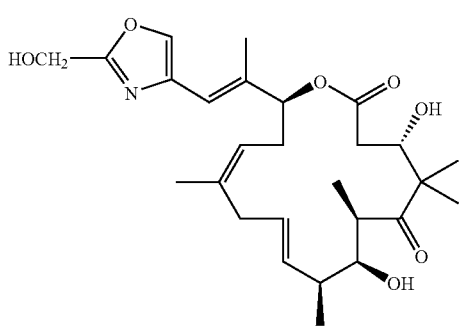
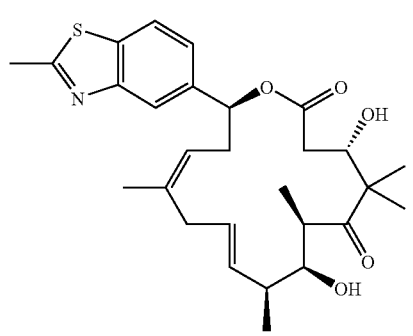
-continued
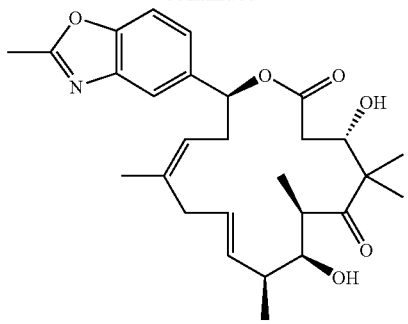
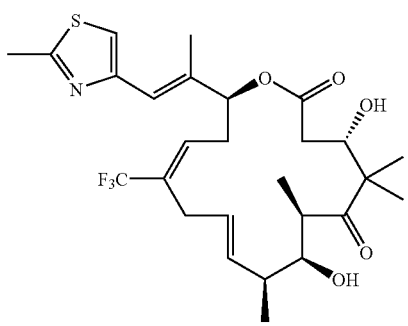
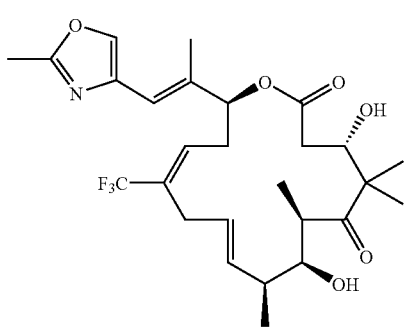
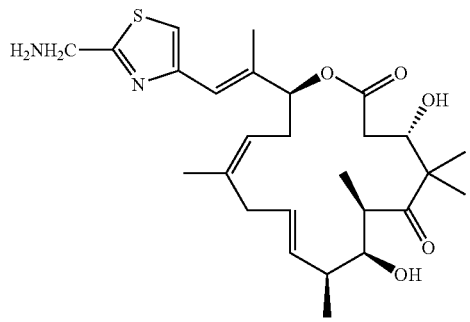
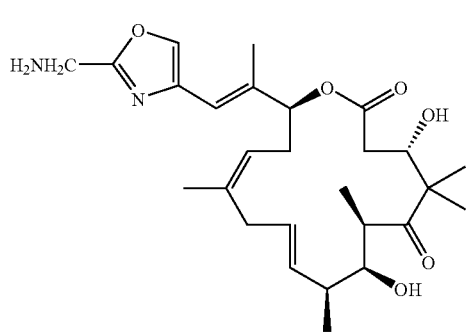

-continued
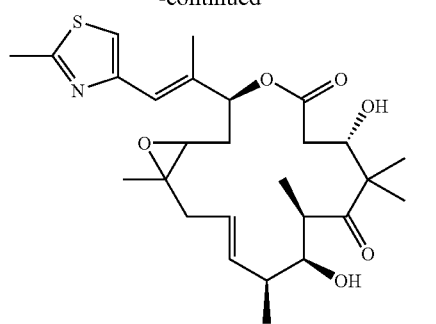
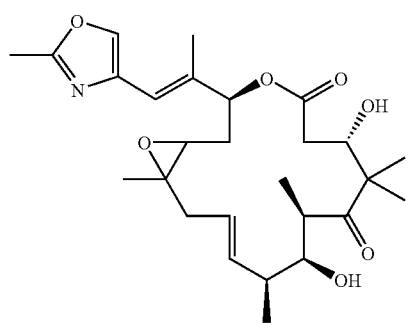
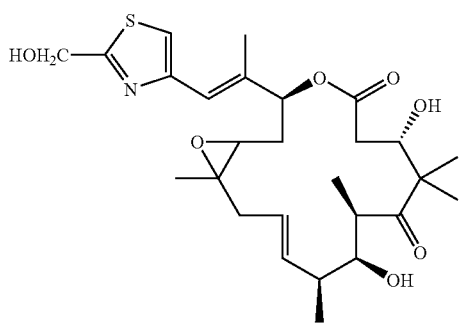
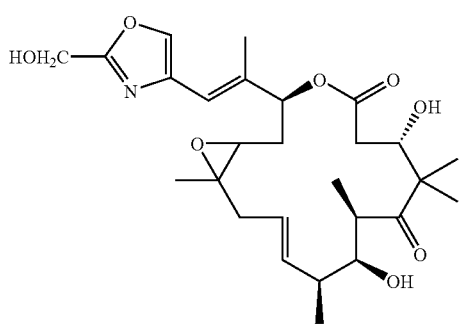
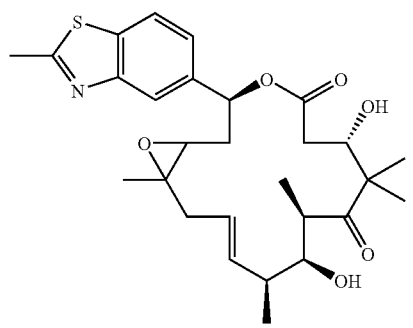
-continued
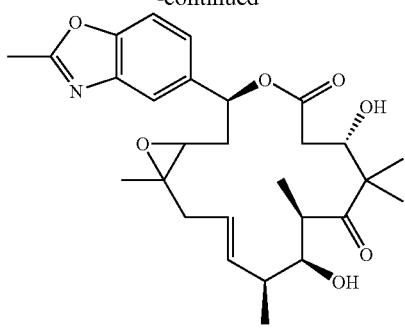
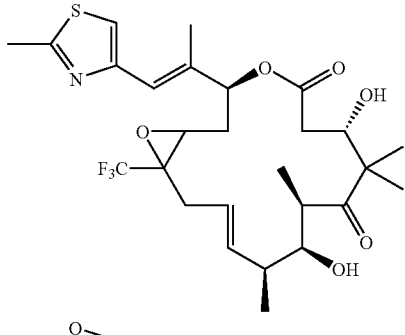
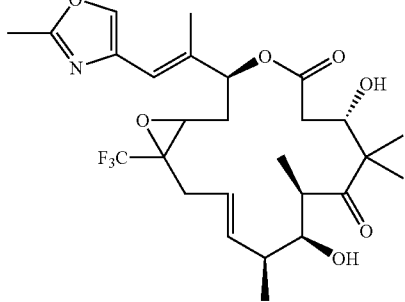
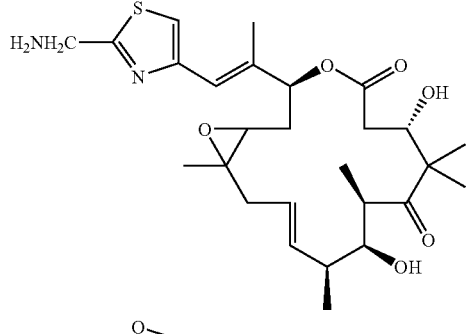
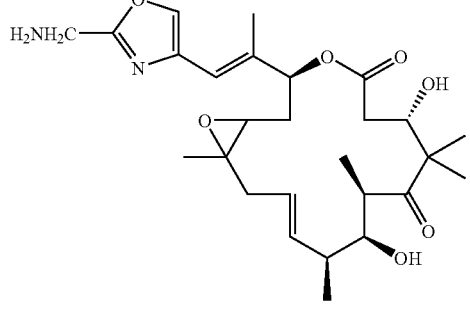
Compounds of this invention include those specifically set forth above and described herein, and are illustrated in part by the various classes, subgenera and species disclosed elsewhere herein.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixtures of stereoisomers or diastereomers are provided.

It will be appreciated that some of the foregoing classes and subclasses of compounds can exist in various isomeric forms. The invention encompasses the compounds as individual isomers substantially free of other isomers and alternatively, as mixtures of various isomers, e.g., racemic mixtures of stereoisomers. Additionally, the invention encompasses both (Z) and (E) double bond isomers unless otherwise specifically designated. Thus, compounds of the invention generally depicted in structure (0), (0'), (I), (I'), (II), and (II') encompass those structures in which double bonds are (Z) or (E). In certain preferred embodiments, the double bond at the C12-C13 position is in the cis or Z configuration. In some embodiments, the double bond at the C9-C10 position is in the trans or E configuration. In still other embodiments, the double bond at the C12-C13 position is in the cis or Z configuration, and the double bond at the C9-C10 position is in the trans or E configuration. The invention also encompasses tautomers of specific compounds as described above.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester that is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Compounds of this invention which are of particular interest include those which:

- exhibit cytotoxic or growth inhibitory effect on cancer cell lines maintained in vitro or in animal studies using a scientifically acceptable cancer cell xenograft model;
- exhibit an ability to polymerize tubulin and stabilize microtubule assemblies;
- exhibit minimal levels of toxicity to vital organs;
- lead to tumor disappearance in scientifically acceptable cancer cell xenograft models;
- lead to tumor shrinkage in scientifically acceptable cancer cell xenograft models;
- lead to tumor disappearance in scientifically acceptable cancer cell xenograt models and no recurrence of the tumor after stopping treatment;
- exhibit transient and reversible body weight decreases in scientifically acceptable cancer cell xenograft models;
- exhibit enhanced water solubility over epothilones A, B, C or D, or paclitaxel, or additionally or alternatively exhibit sufficient solubility to be formulated in an aqueous medium; and/or
- exhibit a therapeutic profile (e.g., optimum safety and curative effect) that is superior to that of epothilone B, epothilone D, or paclitaxel.

A variety of epothilone analogs as described supra have been prepared, characterized, and tested as exemplified herein. 9,10-dehydro-epothilone analogs have been found to be useful in the treatment of cancer, and in particular compounds have been prepared and found to possess one or more of the desired characteristics listed above.

Synthetic Methodology

The synthesis of certain epothilones, desoxyepothilones and analogues thereof have been previously described (see, U.S. Pat. Nos. 6,242,469, 6,284,781, 6,300,355, 6,204,388, 6,316,630, and 6,369,234; U.S. patent application Ser. Nos. 09/797,027, 09/796,959, and 10/236,135; and PCT Publication Nos. WO 99/01124, WO 99/43653, and WO 01/64650, the entire contents of which are hereby incorporated by reference). In recognition of the need for improved or additional synthetic methodologies to efficiently generate epothilones, desoxyepothilones and analogues thereof in large quantities, the present invention provides an efficient and modular route for the synthesis of epothilones, desoxyepothilones and analogues thereof. Although the synthesis of certain exemplary compounds is described in the Exemplification herein, it will be appreciated that this methodology is generally applicable to the generation of analogues and conjugates as discussed above for each of the classes and subclasses described herein.

In particular, the 9,10-dehydroepothilone compounds of the present invention may be prepared in a variety of ways using synthetic methodologies useful in the synthesis of epothilones. In certain embodiments, the compounds are prepared using a convergent synthetic route. For example, the epothilone may be synthesized by preparing two or three intermediates which are brought together to yield the desired compound. In one embodiment, one of the intermediates is an acyl portion containing carbons 1-9, and another intermediate contains carbons 10-15 and may also contain the thiazole side chain. These two roughly equal portions of the epothilone may be brought together first using an esterification reaction between C-1 and an oxygen off C-15. The macrocycle may then be closed using a carbon-carbon coupling reaction such as a Suzuki coupling or ring closing metathesis reaction. In one embodiment, the final ring closing step is accomplished using a ring closing metathesis reaction to form the 9,10-double bond and close the macrocycle. The ring closing metathesis reaction is accomplished using an organometallic catalyst such as the Grubbs catalyst as shown in Scheme 8 below. In certain embodiments, the 9,10-double bond is reduced or oxidized, or the 9,10-double bond may be further functionalized to prepare additional epothilone derivatives.

In other embodiments, the final ring closing step is accomplished using a ring closing metathesis reaction to form the 12,13-double bond and close the macrocycle. In certain embodiments, the 12,13-double bond is reduced or oxidized. In other embodiments, a macroaldolization or macrolactonization reaction is used to form the macrocycle.

Certain exemplary syntheses of the compounds of the invention are provided in the Figures and in the Examples. As would be appreciated by one of ordinary skill in the art, a variety of analogs and derivatives may be prepared using the synthetic procedures described herein. For example, one could accomplish many of the synthetic steps with different protecting groups or different substituents on the 16-membered ring.

Pharmaceutical Compositions

This invention also provides a pharmaceutical preparation comprising at least one of the compounds as described above and herein, or a pharmaceutically acceptable derivative thereof, which compounds are capable of inhibiting the growth of or killing cancer cells, and, in certain embodiments of special interest are capable of inhibiting the growth of or killing multidrug resistant cancer cells. In certain embodiments, the pharmaceutical preparation also comprises as solubilizing or emulsifying agent such as Cremophor (polyoxyl 35 castor oil) or Solutol (polyethylene glycol 660 12-hydroxystearate).

As discussed above, the present invention provides novel compounds having antitumor and antiproliferative activity, and thus the inventive compounds are useful for the treatment of cancer. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents. In certain other embodiments, the additional therapeutic agent is an anticancer agent, as discussed in more detail herein.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method for inhibiting tumor growth and/or tumor metastasis. In certain embodiments of special interest, the invention provides a method of treating cancers by inhibiting tumor growth and/or tumor metastasis for tumors multidrug resistant cancer cells. The method involves the administration of a therapeutically effective amount of the compound or a pharmaceutically acceptable derivative thereof to a subject (including, but not limited to a human or animal) in need of it. In certain embodiments, specifically for treating cancers comprising multidrug resistant cancer cells, the therapeutically effective amount is an amount sufficient to kill or inhibit the growth of multidrug resistant cancer cell lines. In certain embodiments, the inventive compounds are useful for the treatment of solid tumors.

The compounds and pharmaceutical compositions of the present invention may be used in treating or preventing any disease or conditions including proliferative diseases (e.g., cancer), autoimmune diseases (e.g., rheumatoid arthritis), and infections (e.g., bacterial, fungal, etc.). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered parenterally.

In yet another aspect, according to the methods of treatment of the present invention, tumor cells are killed, or their growth is inhibited by contacting the tumor cells with an inventive compound or composition, as described herein. Thus, in still another aspect of the invention, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments of the invention, the inventive compounds as described herein are formulated by conjugating with water soluble chelators, or water soluble polymers such as polyethylene glycol as poly (1-glutamic acid), or poly (1-aspartic acid), as described in U.S. Pat. No. 5,977,163, the entire contents of which are hereby incorporated by reference. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may delivered as delivered every other day, every third day, every week, every two weeks, every three weeks, or every four weeks. In certain embodiments, the desired dosage may be delivered using multiple administrations (e.g., two, three, four, five, six, seven, eight, nine, or ten administrations).

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, brain cancer, skin cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells). In certain embodiments, the inventive anticancer agents are active against cancers which are resistant to other known anti-neoplastic agents or which have been found not to respond clinically to other known anti-neoplastic agents. In other embodiments, the inventive anticancer agents are active against cancer which are resistant to other anti-neoplastic microtubule-stabilizing agents (e.g., paclitaxel).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

EXEMPLIFICATION

Example 1

Synthesis of 9,10-dehydro-12,13-desoxy-epothilones

This Example describes the synthesis of trans-9,10-dehydro-12,13-desoxyepothilone B, 26-trifluoro-trans-9,10-dehydro-12,13-desoxyepothilone B, 26-trifluoro-12,13-desoxyepothilone B, and 12,13-desoxyepothilone B and biological testing of these compounds.

Fluorinated derivatives of epothilones were prepared and tested given the enhanced pharmacokinetics and chemotherapeutic indices of other medicinal agents with fluorine substitutions (Ojima, I.; Inoue, T.; Chakravarty, S.; *J. Fluorine Chem.* 1999, 97; Newman, R. A.; Yang, J.; Finlay, M. R. V.; Cabral, F., Vourloumis, D.; Stephens, L. C.; Troncoso, P.; Wu, X.; Logothetis, C. J.; Nicolaou, K. C.; Navone, N. M. *Cancer Chemother. Pharmacol.* 2001, 48, 319-326; each of which is incorporated herein by reference).

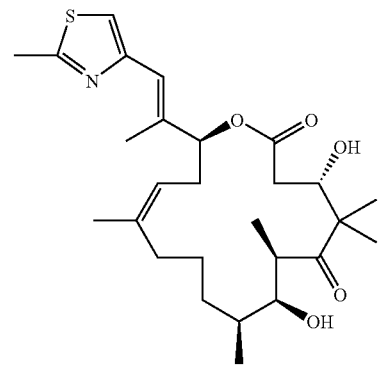

1 [16]dEpoB

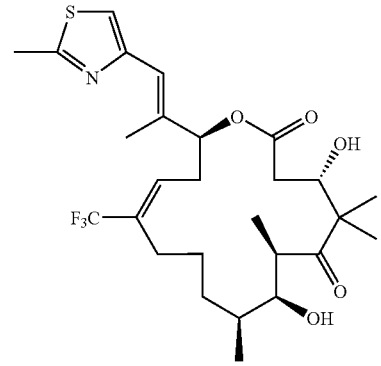

2 26-F$_3$-[16]dEpoB

To reach compound 2, we sought to take advantage of a highly convergent route recently reported from our laboratory for the synthesis of epothilone 490 (6, dehydrodeoxy Epo B) en route to dEpoB (1, Scheme 1) (Biswas, K.; Lin, H.; Njardarson, J. T.; Chappell, M. D., Chou, T. C., Guan, Y.; Tong, W. P., He, L.; Horwitz, S. B., Danishefsky, S. J. *J. Am. Chem. Soc.* 2002, 124 (33); 9825-9832; Rivkin, A.; Njardarson, J. T.; Biswas, K; Chou, T. C.; Danishefsky, S. J. *J. Org. Chem.* 2002, 67, 7737-7740; each of which is incorporated herein by reference). In that synthesis, we introduced a flanking vinyl group to compound 4 via a stereospecific Stille coupling of a vinyl iodide precursor 3 with tri-n-butylvinylstannane. Ring closing metathesis followed by deprotection led to 6, which was then transformed to dEpoB (1) via a regioselective diimide reduction.

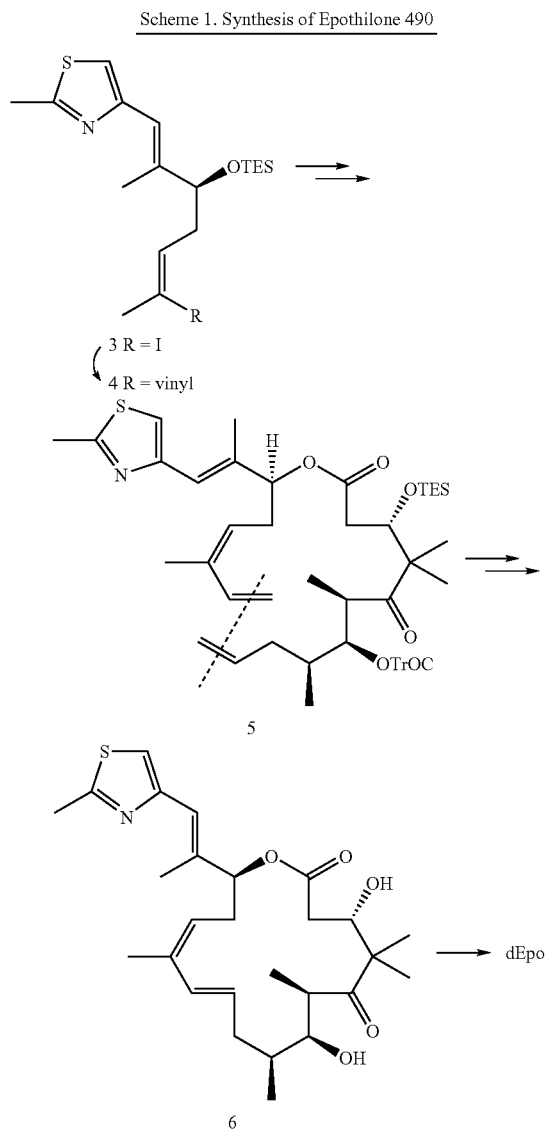

Scheme 1. Synthesis of Epothilone 490

Attention was first directed to the synthesis of 15 (Scheme 2). Alkylation of the previously reported lithium enolate of 7 (Chappell, M. D.; Stachel, S. J.; Lee, C. B.; Danishefsky, S. J. Org. Lett. 2000, 2(11), 1633-1636; incorporated herein by reference) with iodide 8 (synthesized from the known alcohol 16 using TMSI in methylene chloride) afforded 9 in 78% yield and high diastereoselectivity (>25:1 de). Compound 9 was advanced in three steps to 10 as shown. Attempts to accomplish addition of methylmagnesium bromide to the Weinreb amide linkage of 10 failed. The breakdown of this reaction was attributed to the presence of the iodoalkene linkage. However we could accomplish our goal by changing the order of these two C—C bond forming steps. Thus, reaction of 10 with vinyltributyltin under Stille conditions could then be followed by addition of methyl Grignard reagent to give the desired ketone 11. Condensation of ketone 11 with phosphine oxide 12, followed by deprotection of the triethylsilyl ether, afforded fragment 13 in good yield. Esterification of the resulting 13 with C1-C10 acid fragment 14 (Biswas, K.; Lin, H.; Njardarson, J. T.; Chappell, M. D., Chou, T. C., Guan, Y.; Tong, W. P.; He, L.; Horwitz, S. B., Danishefsky, S. J. J. Am. Chem. Soc. 2002, 124 (33); 9825-9832; Rivkin, A.; Njardarson, J. T.; Biswas, K; Chou, T. C.; Danishefsky, S. J. J. Org. Chem. 2002, 67, 7737-7740; incorporated herein by reference), provided the desired 15, in 75% yield (Scheme 2).

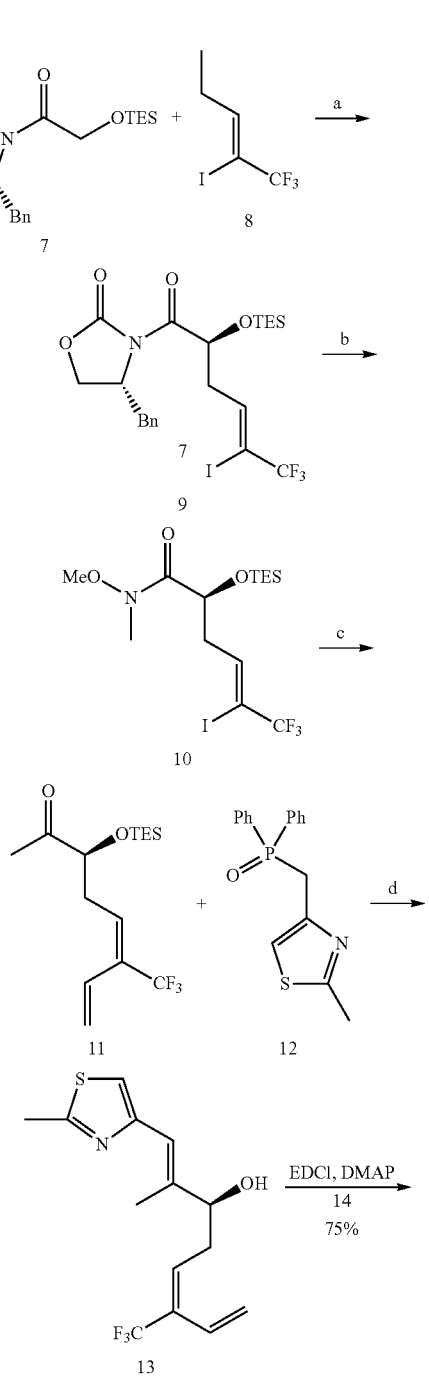

Scheme 2. Synthesis of the RCM precursor 15

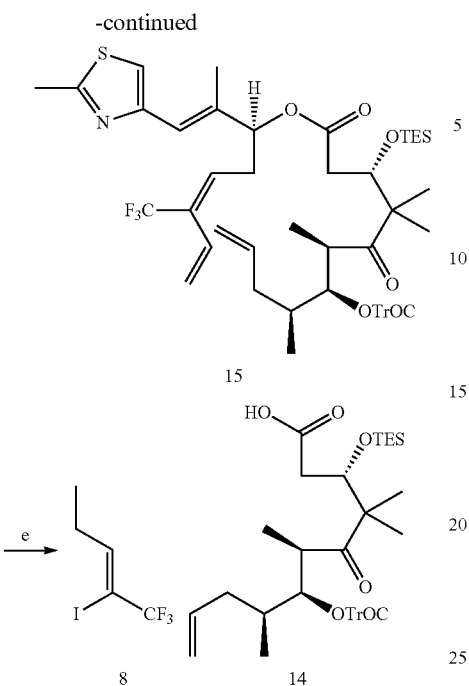

(a) LHMDS, -78° C., 78%; (b) i) HOAc: THF: H₂O (3:1:1);
ii) CH₃ONHCH₃, AlMe₃; iii) TESCl, imidazole, DMF, 79%
overall; (c) i) Vinyltributyltin, Pd(dba), DMF, 80° C., 3 h
43%; ii) MeMgBr, 0° C., 94%; (d) i) n-BuLi, THF, -78° C.,
30 min., ii) 12, -78° C. to rt, 81%; iii) HOAc: THF: H₂O
(3:1:1), 94%; (e) TMSI, CH₂Cl₂, 0° C., 92%

Unfortunately, attempts to carry out the ring-closing metathesis reaction of 15 using the second generation Grubbs catalyst (Reviews: Grubbs, R. H.; Miller, S. J.; Fu, G. C. *Acc. Chem. Res.* 1995, 28, 446; Trnka, T. M.; Grubbs, R. H. *Acc. Chem. Res.* 2001, 34, 18; *Alkene Metathesis in Organic Chemistry* Ed.: Fürstner, A.; Springer, Berlin, 1998; Fürstner, A. *Angew. Chem. Int. Ed. Engl.* 2000, 39, 3012; Schrock, R. R. Top. *Organomet. Chem.* 1998, 1, 1; each of which is incorporated herein by reference) in methylene chloride led primarily to apparent dimerization of the starting material (Equation 1). Given the fact that the RCM works quite well in the related setting of 5→6, we naturally attributed the failure in the case of 15 to the presence of the trifluoromethyl group at $C_{12}$.

It was conjectured that the detrimental impact of the resident 26-trifluoro substitutent on the desired reaction, might be alleviated by adding a carbon spacer between the RCM reaction center and the trifluoromethyl group. Accordingly, we undertook a synthesis of 19 (Equation 2) via the ring-closing metathesis of 18, which would present the trifluoromethyl group in the context of a 17-membered ring containing a shipped (1,4)-diene.

The synthesis program directed to 19 commenced with the preparation of compound 21, which corresponds to the O-alkyl sector of our proposed RCM substrate (Scheme 3). We began with allylation of 10, this time under radical reaction conditions as shown (Keck, G. E.; Yates, J. B. *J. Am. Chem. Soc.* 1982, 104, 5829; review: Curran, D. P. *Synthesis*

1988, Part 1, pp 417-439; Part 2, pp. 489; each of which is incorporated herein by reference). This conversion was followed by reaction of the alkylated product with methyl magnesium bromide, thus affording the required ketone 20. Condensation of this compound with phosphine oxide 12, followed by deprotection of the triethylsilyl ether function provided 21 in good yield.

Scheme 3. Synthesis of the alcohol fragment 21

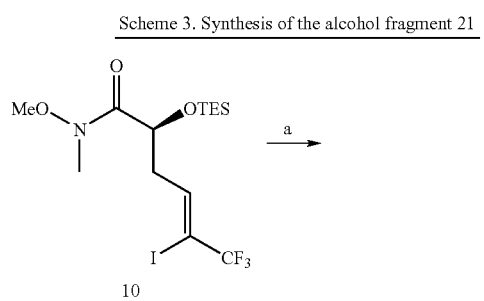

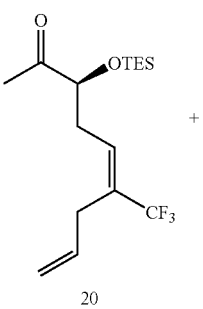

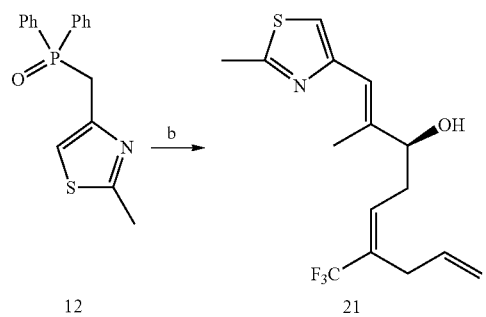

(a) i) Allyltributyltin, AIBN, Benzene, 80° C., 3 h 74%; ii) MeMgBr, 0° C., 93%; (b) i) 12, n-BuLi, THF, -78° C., 30 min., ii) 20, -78° C. to rt, 85%; iii) HOAc: THF: $H_2O$ (3:1:1), 98%; (c) TMSI, $CH_2Cl_2$, 0° C., 92%

Esterification of 21 with the C1-C10 acid fragment 14, provided the proposed RCM precursor 18 in 75% yield (Scheme 4). Happily in this case, the ring-closing metathesis reaction of 18 could be accomplished using the second generation Grubbs catalyst in methylene chloride. As in the case of the conversion of 5→6, the reaction provided exclusively the trans isomer 22 in 57% yield.[6] Finally, reductive cleavage of the trichloro ethoxycarbonyl protecting group with zinc and acetic acid, followed by deprotection of the TES ether with HF-pyridine, provided the desired 19 containing a trifluoromethyl function at $C_{12}$, albeit in the context of the 17-membered ring series.

Scheme 4. Synthesis 27-$F_3$-ddEpoB (19)

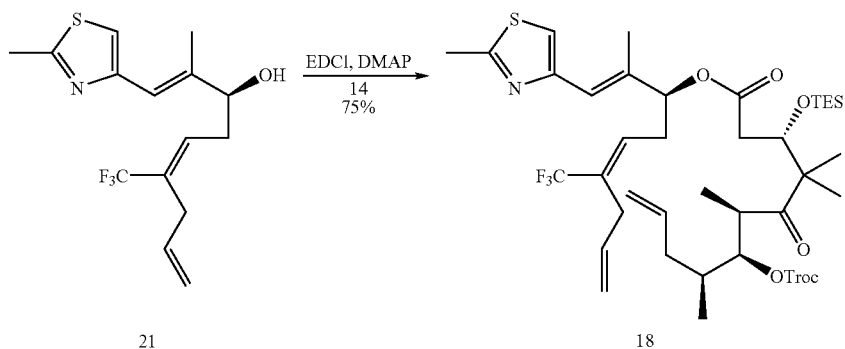

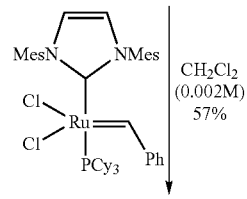

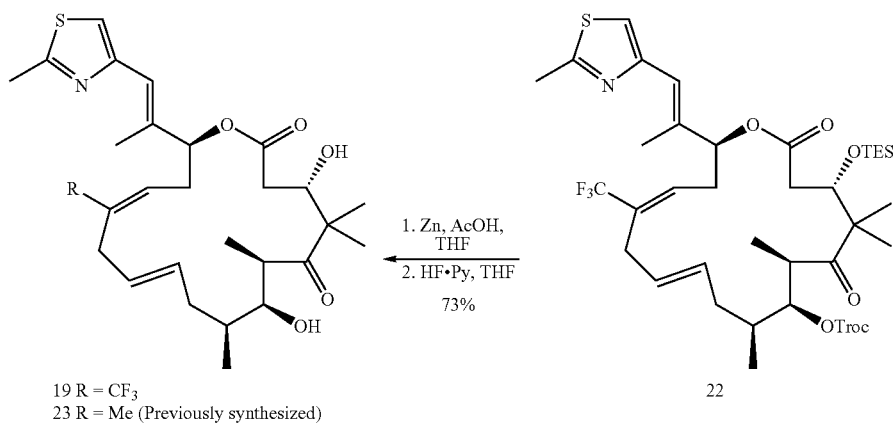

19 R = CF₃
23 R = Me (Previously synthesized)

22

Synthetic 19 was evaluated as to its cytotoxic activity. As shown in Table 1 below, direct comparison of the previously reported [17]ddEpoB (23) with 27-F₃-[17]ddEpoB (19) indicated that the new perfluorinated compound possessed a comparably high cytotoxic potency.

TABLE 1

In vitro Cytotoxicities (IC$_{50}$) with tumor cell lines[a]

| Compound | CCRF-CEM (IC$_{50}$ (μM)[a]) | CCRF-CEM/VBL (IC$_{50}$ (μM)[a]) |
|---|---|---|
| 27-F₃-[17]ddEpoB (19) | 0.068 | 0.191 |
| [17]ddEpoB (23) | 0.040 | 0.126 |
| [16]ddEpoB (6) | 0.020 | 0.068 |

[a]XTT assay following 72 h inhibition. CCRF-CEM is a human T-cell acute lymphoblastic leukemia cell line. The CCRF-CEM/$_{VBL100}$, CCRF-CEM/$_{VM1}$ and CCRF-CEM/$_{Taxol}$ cell lines all overexpress P-glycoprotein and display a multidrug resistance phenotype to MDR associated oncolytics (Ojima, I.; Inoue, T.; Chakravarty, S.; *J. Fluorine Chem.* 1999, 97; Newman, R. A.; Yang, J.; Finlay, M. R. V.; Cabral, F., Vourloumis, D.; Stephens, L. C.; Troncoso, P.; Wu, X.; Logothetis, C. J.; Nicolaou, K. C.; Navone, N. M. *Cancer Chemother. Pharmacol.* 2001, 48, 319-326; each of which is incorporated herein by reference).

Though the trifluoromethyl isosteric substitution had little effect on the gross cytotoxic activity, preliminary data from metabolic degradation studies in mouse plasma showed 19 to be notably more stable than is the parent 23. Exposure of epothilones 19 and 23 to nude mouse and human plasma led to degradation of 23 within 30 minutes, while epothilone 19 remained mostly intact. Since pharmokinetic issues are likely to be critical in the actual use of any epothilone agent as a drug, we take this finding to be quite encouraging.

We reasoned that the synthesis of 26-F₃-dEpoB (2) could be accomplished via a highly convergent strategy, related to that employed in the synthesis of 27-F₃-[17]ddEpoB (19). Accordingly, fragments of similar complexity would serve as key building blocks (Scheme 5). We envisioned that the acyl sector 25, could serve as the polypropionate domain and the alkyl sector 21 or 24 would be prepared as previously described in the introduction. The union of the two fragments 21(24) and 25 would be initiated through an esterification and consumated via a subsequent ring-closing metathesis. Finally, cleavage of the protecting groups would provide the desired analogs 28 and 29. Chemoselective reduction of the 9,10-olefin of 28 and 29 would furnish dEpoB (1) and the desired 26-F₃-12,13-desoxyEpoB (2).

Scheme 5

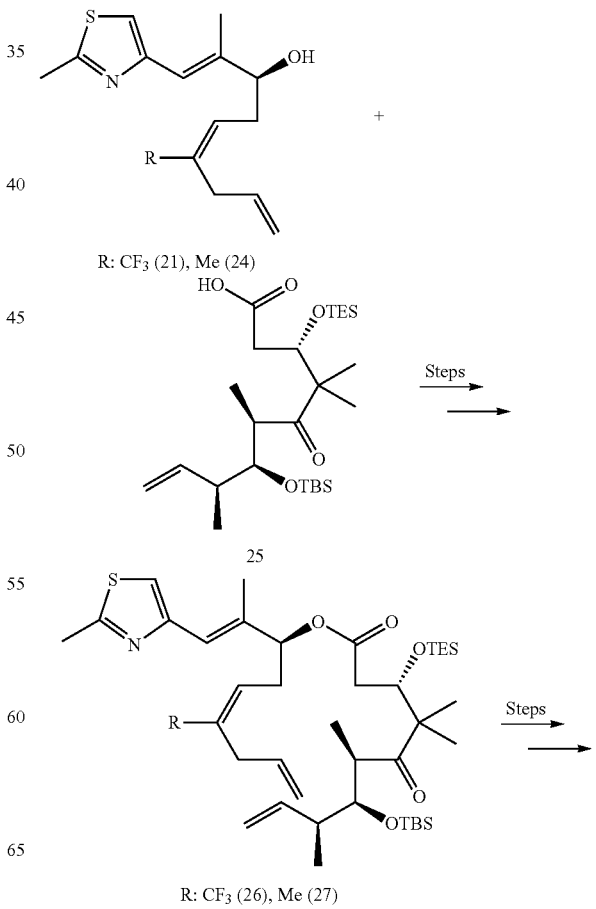

R: CF₃ (21), Me (24)

25

R: CF₃ (26), Me (27)

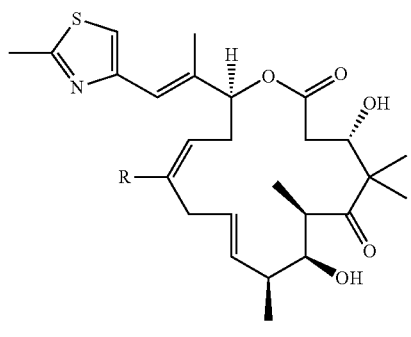

trans-9,10-dehydro-12,13-desoxyEpoB (28)
26-F₃-trans-9,10-dehydro-12,13-desoxyEpoB (29)

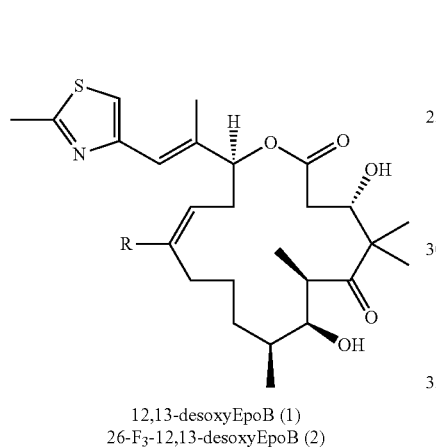

12,13-desoxyEpoB (1)
26-F₃-12,13-desoxyEpoB (2)

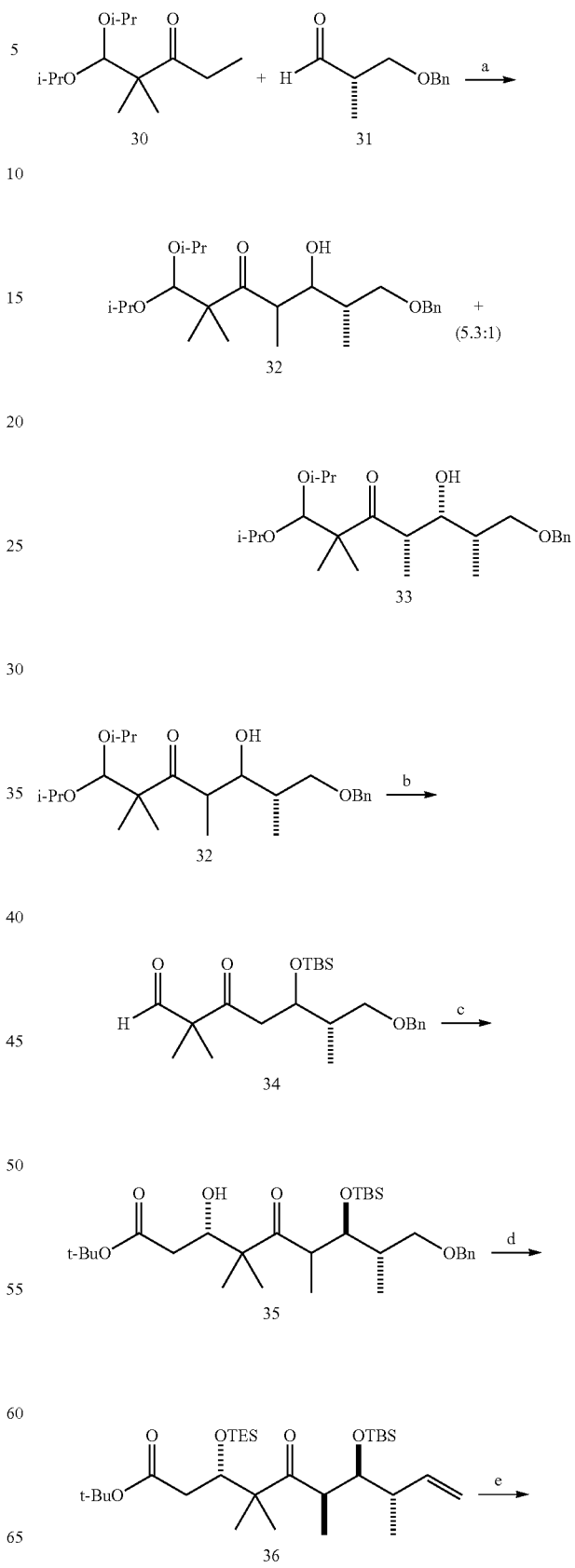

The synthesis of 1 and 2 commenced with the preparation of acyl sector 25. Ketone 30, previously reported, was subjected to an aldol reaction with the readily available aldehyde 31. Upon deprotonation and reaction of "lithio" 30 with 31, smooth condensation gave rise to a 5.3:1 mixture of aldol products 32 and 33. The major diastereoisomer 32 was easily separated by flash chromatography and protected as a TBS silyl ether. Hydrolysis of the diisopropyl acetal group under acid catalysis gave keto aldehyde 34, setting the stage for the second aldol reaction. Following the previously practiced "titano" tert-butyl ester method, with the new aldehyde 34 as the coupling partner, the desired aldol product 35 was obtained in high diastereoselectivity (dr>20:1) and yield (86%). Protection of the C3 alcohol of 35 with a TES silyl group was followed by deprotection of the benzyl ether. Oxidation of the resultant primary hydroxy provided the corresponding aldehyde, which was then converted to a terminal olefin via a Wittig reaction to provide 36 in high yield. Finally, hydrolysis of the t-butyl ester of 36 with TESOTf provided the acyl sector 25 (82%) along with side-product 37 (14%), which was converted to acyl sector 38 in high yield. Spectral and chromatographic properties of 38 were identical to previously obtained material from other programs in Dr. Sinha's laboratories (Scripps).

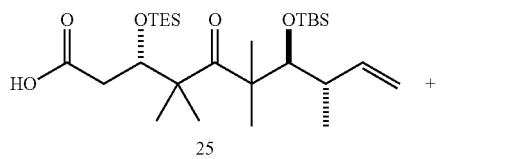

25

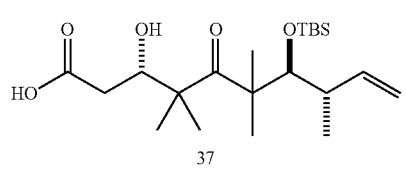

37

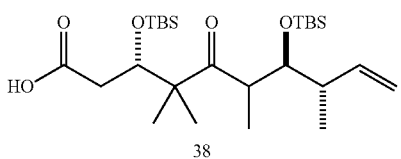

38

Reagents and Conditions: (a) LDA, THF, -90° C., 79%; (b) (i) TBSOTf, 2,6-lutidine CH$_2$Cl$_2$, -40 to -20° C., 97%, (ii) 2)p-TsOH·H$_2$O (cat.) THF—H$_2$O (4:1), 64° C., 86%; (c)t-butyl acetate, LDA, chiral-Ti complex, Et$_2$O, -78° C., 92%, (dr = >20:1); (d) (i) TESCl, imidazole, DMF, 0° C. to rt, 99%, (ii) H$_2$, Pd/C (10%), EtOH, 83%, (iii) TPAP, NMO, CH$_2$Cl$_2$, 93%, (iv) MePPh$_3$I, n-BuLi, THF, -78 to -5° C, 78%; (e) TESOTf, 2,6-lutidine, CH$_2$Cl$_2$, 0° C. to rt 82%; (f) (i) TBSOTf, 2,6-lutidine, CH$_2$Cl$_2$, 0° C. to rt, (ii) sat. NaHCO$_3$ (aq.), MeOH, THF, rt, 99%.
Esterfication of the allylic alcohols 21 and 24 with C$_1$-C$_9$ acid fragment 25 provided the corresponding RCM cyclization precursors 26 and 27, respectively (Scheme 7).

Scheme 7.

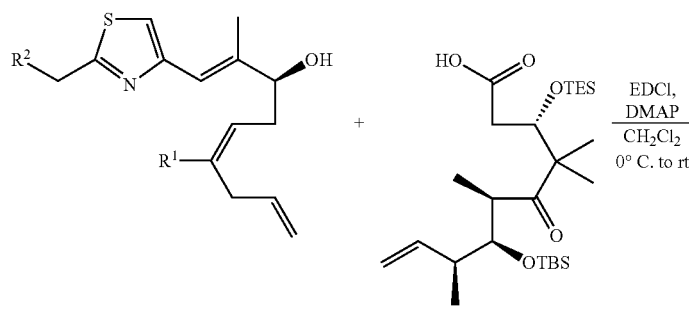

21 (R$^1$ = Me, R$^2$ = H), 24 (R$^1$ = CF$_3$, R$^2$ = H),
53 (R$^1$ = Me, R$^2$ = OTBS)

25

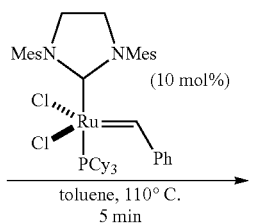

toluene, 110° C.
5 min

R$^1$ = Me, R$^2$ = H, (26, 79%)
R$^1$ = CF$_3$, R$^2$ = H (27, 70%)
R$^1$ = Me, R$^2$ = OTBS (54, 92% from ester)

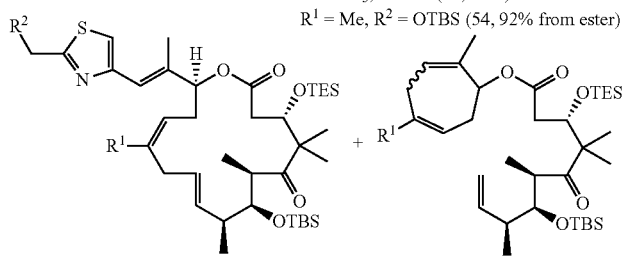

HF-Pyridine, THF (1:3) 0° C. to rt 39a (R$^1$ = Me, R$^2$ = H, 38%), 39b (R$^1$ = Me, R$^2$ = H, 62%)
40a (R$^1$ = CF$_3$, R$^2$ = H, 22%), 40b (R$^1$ = CF$_3$, R$^2$ = H, 60%)
55 (R$^1$ = Me, R$^2$ = OTBS, 27%), 56 (R$^1$ = Me, R$^2$ = OTBS, 57%)

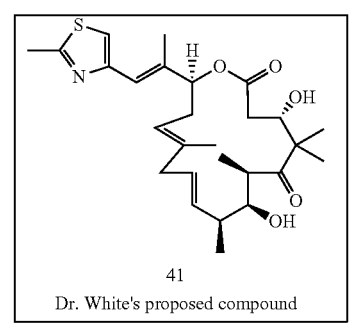

41
Dr. White's proposed compound

-continued

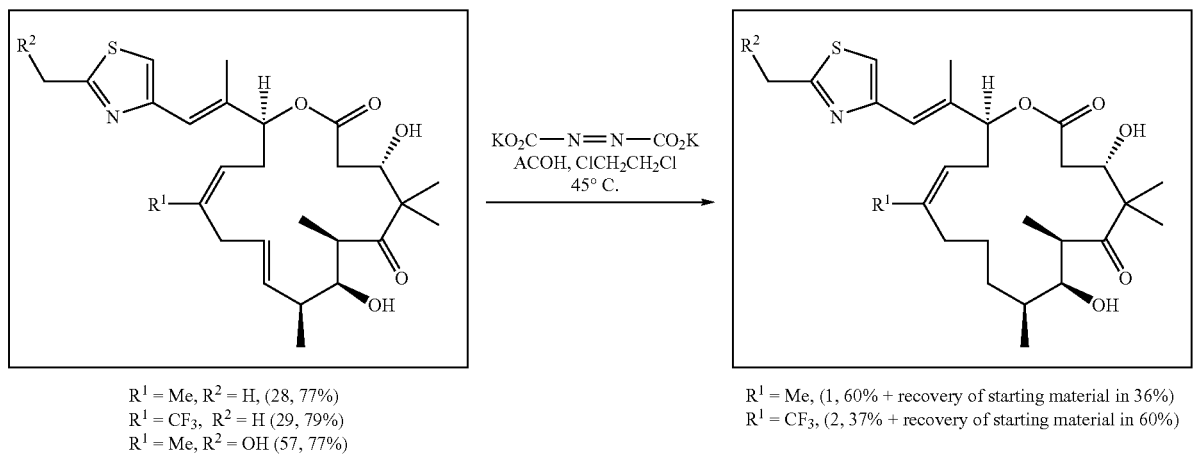

$R^1$ = Me, $R^2$ = H, (28, 77%)
$R^1$ = $CF_3$, $R^2$ = H (29, 79%)
$R^1$ = Me, $R^2$ = OH (57, 77%)

$R^1$ = Me, (1, 60% + recovery of starting material in 36%)
$R^1$ = $CF_3$, (2, 37% + recovery of starting material in 60%)

The ring-closing metathesis reactions 26, 27 and 54 were then carried out using the second generation Grubbs catalyst in toluene, which provided, as in our earlier study, exclusively the trans isomer 39a, 40a, and 55 along with the corresponding side products 39b, 40b, and 56. Finally, deprotection of silyl ethers with HF-pyridine led to the desired compounds 28, 29, and 57. Spectral and chromatographic properties of 28 were not identical to previously obtained material from the epothilone program in Dr. James D. White's laboratories (Oregon State University). We believe that Dr. James D. White thought he had synthesized 28, however inadvertently made the 12,13E isomer 41, which would explain the poor biological activity he obtained. Consequently, we are the first ones to have synthesized 28 and tested this compound for its antitumor activity.

The fully synthetic 28, 29, and 2 have been evaluated against a variety of cell types to determine their antitumor potential. As shown in table 2, all three compounds exhibited high cytotoxic activity against a variety of sensitive and resistant tumor cell lines. Direct comparison of 28 with the previously reported dEpoB (1) indicates that the new compound possesses nearly three times more potency.

TABLE 2

In vitro Cytotoxicities ($IC_{50}$) with tumor cell lines[a].

| Tumor Cell Lines | $IC_{50}$ (µM)[a] | | | |
|---|---|---|---|---|
| | 28 | 29 | dEpoB (1) | 57 |
| CCRF-CEM | 0.0014 | 0.0035 | 0.0036 | 0.00051 |
| CCRF-CEM/$VBL_{100}$ | 0.0065 | 0.0210 | 0.014 | 0.0106 |
| CCRF-CEM/Taxol | 0.0017 | 0.0057 | 0.0057 | 0.00073 |

[a]XTT assay following 72 h inhibition. CCRF-CEM is a human T-cell acute lymphoblastic leukemia cell line. The CCRF-CEM/$_{VBL100}$, CCRF-CEM/$_{VM1}$ and CCRF- CEM/$_{Taxol}$ cell lines all overexpress P-glycoprotein and display a multidrug resistance phenotype to MDR associated oncolytics (Prié, G.; Thibonnet, J.; Abarbri, M.; Duchêne, A.; Parrain, J. Synlett 1998, 839; incorporated herein by reference).

To improve the overall yield of our synthesis of 28, 29, and 2, we decided to carry out the RCM reaction in the absense of the thiazole substituted olefin and in so doing avoid the formation of the undesired side product 39b and 40b. Deprotection of the silyl ether of the previously reported 42 and 20 provided hydroxyketones 43 and 44. Esterification of the resultant hydroxyketones 43 and 44 with $C_1$-$C_9$ acid fragment 25 provided the corresponding RCM cyclization precursors 45 and 46, respectively (Scheme 8). The ring-closing metathesis reaction of 45 and 46 was then carried out using the second generation Grubbs catalyst in toluene, which provided, as in our earlier study, exclusively the trans isomer 47 and 48 in high yields. Installation of the thiazole moiety gave 39a, 40a, and 55 in high yield. Deprotection of the two silyl ethers with HF-pyridine led to 28 and 29. Finally, selective reduction of the C9-C10 olefin afforded the corresponding epothilones 1 and 2. The structure of 28 was rigorously corroborated by its high yielding conversion to 1. The total synthesis of 1 has been very substantially simplified relative to previously practiced routes. Thus the use of the readily available 31, obtained from the chiral pool, is certainly a large improvement relative to reliance on (S)-2-methyl-4-pentenal whose synthesis requires intervening chiral auxilliaries.

Scheme 8
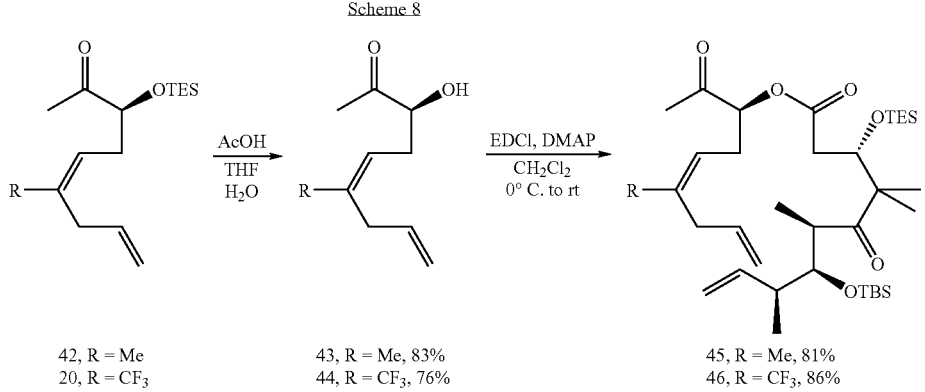
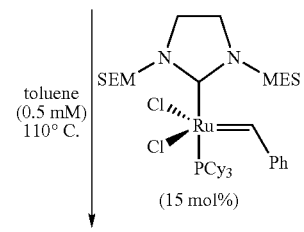
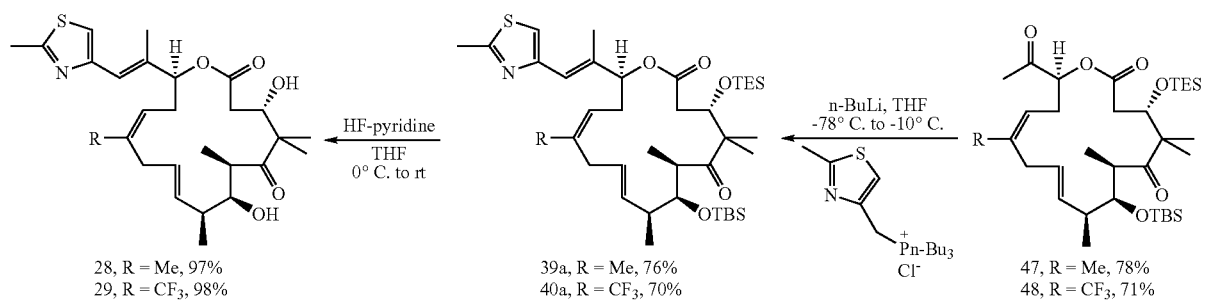
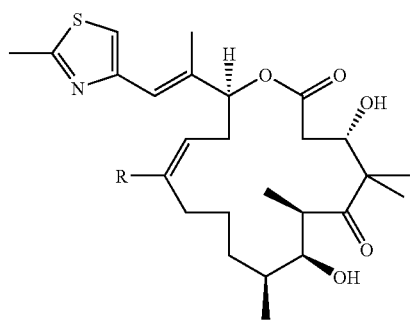

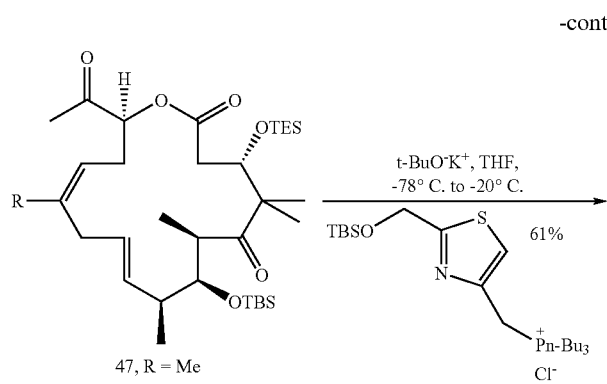

47, R = Me t-BuO⁻K⁺, THF,
-78° C. to -20° C.

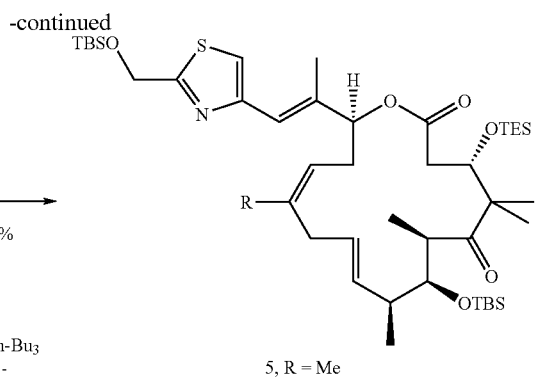

61%

5, R = Me

With compound 28 of rigorously proven structure in hand, we were surprised to find that its spectral properties were not congruent with those previously reported for a compound presumed to be the same entity. The actual structure of the compound previously assigned as 28 has now been re-evaluated and will be disclosed in short order.[13] However it is clear in retrospect that 28 had not been previously prepared and, in fact the whole family of (E)-9,10-dehydroepothilones reported here is a new genus.

Examination of synthetic analogs (2, 28 and 29), in cell culture settings, revealed stronger inhibitory effects on various sensitive and MDR tumor cell lines than are exhibited by our clinical entry dEpoB (1) (Table 3). We note that Epo 3 (28) is the first 12,13-desoxyepothilone compound that possess substantially improved cytotoxicity relative to that of dEpoB (1).

TABLE 3

In vitro Cytotoxicities (IC$_{50}$) with Tumor Cell Lines[a]

| Compound | CCRF-CEM(C) (μM) | C/VBL$_{100}$ (μM) | C/Taxol (μM) |
| --- | --- | --- | --- |
| Epo 1 (1, dEpoB) | 0.0036 | 0.016 | 0.0046 |
| Epo 2 (2) | 0.0041 | 0.080 | 0.018 |
| Epo 3 (28) | 0.0009 | 0.0042 | 0.0012 |
| Epo 4 (29) | 0.0035 | 0.0210 | 0.0057 |

[a]XTT assay following 72 h inhibition. CCRF-CEM is a human T-cell acute lymphoblastic leukemia cell line. The CCRF-CEM/VBL$_{100}$ cell line is resistant to vinblastine and CCRF-CEM/Taxol to taxol.

Figure 9:
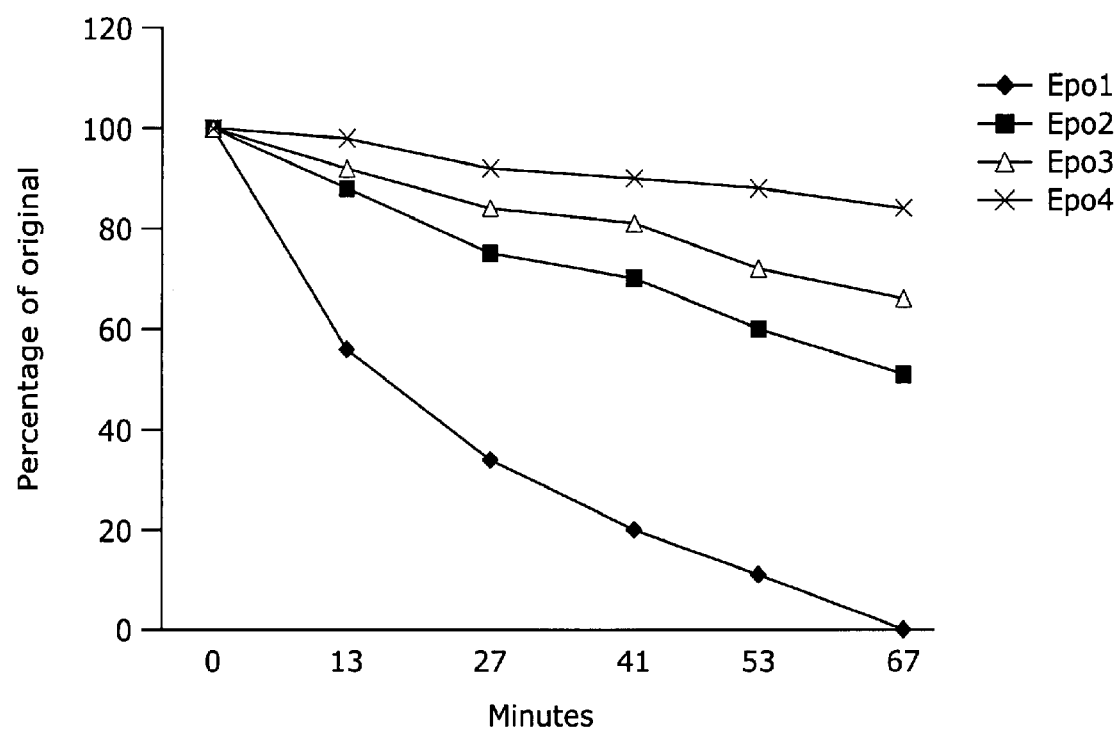
FIG. 9 shows the stability of epothilone analogs in murine plasma. Epo 1 is 12,13-desoxyEpoB, Epo 2 is 26-F$_3$-12,13-desoxyEpoB, Epo 3 is (E)-9,10-dehydro-12,13-desoxyEpoB, and Epo 4 is 26-F$_3$-(E)-9,10-dehydro-12,13-desoxyEpoB.
Figure 10:
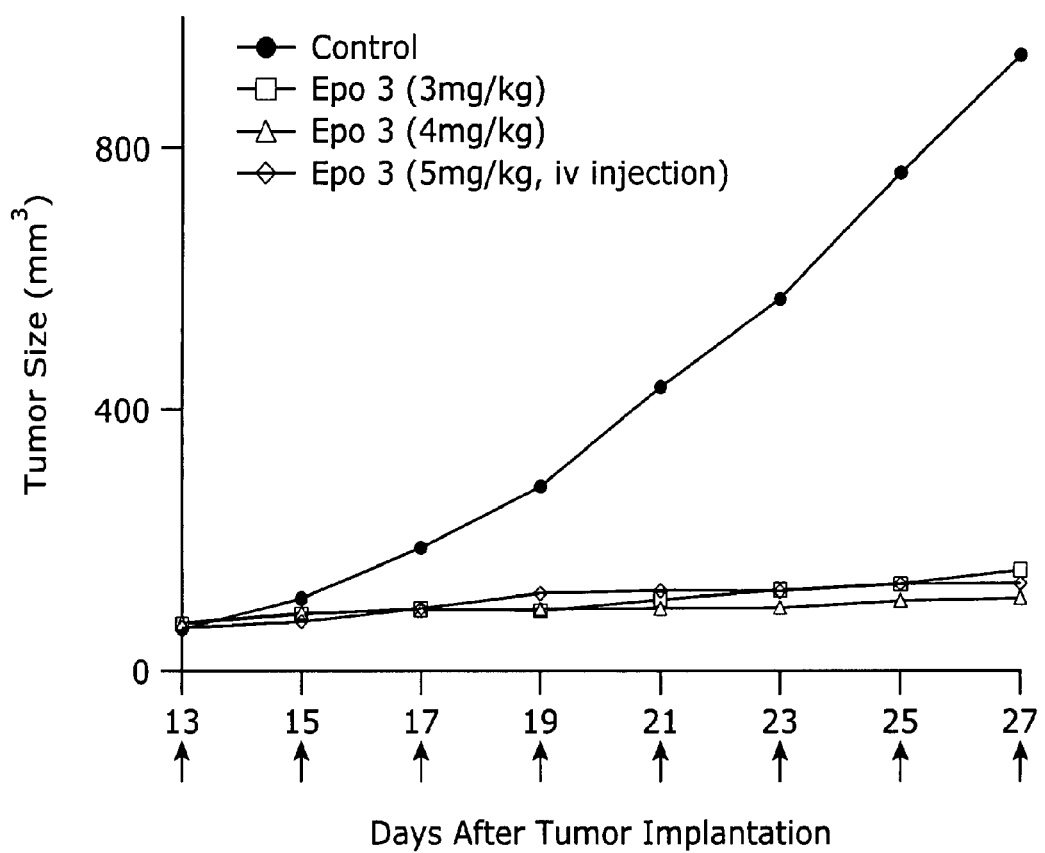
FIG. 10 depicts the therapeutic effect of epothilone analogs in nude mice bearing HCT-116 xenograft (iv infusion, Q2Dx7, n=3). Arrows indicate drug administration.
Figure 13:
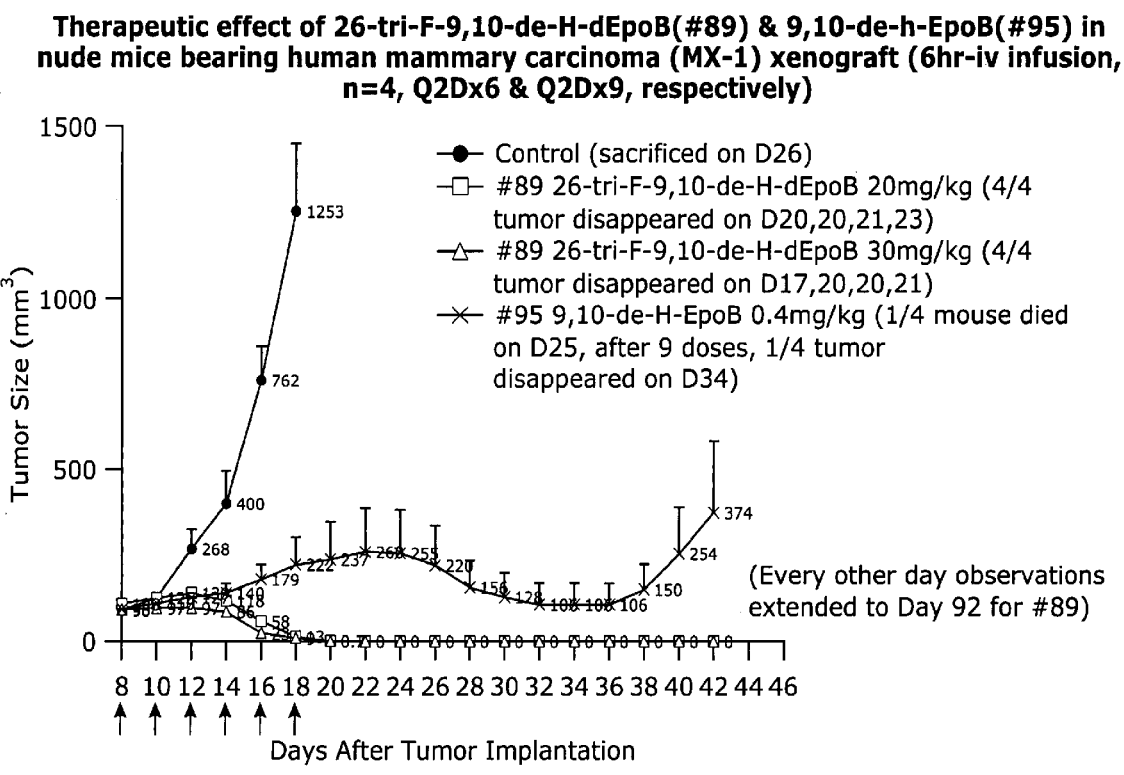
FIG. 13 shows the effect of 26-trifluoro-9,10-dehydro-dEpoB and 9,10-dehydro-EpoB on tumor size in nude mice bearing MX-1 xenografts.
Figure 14:
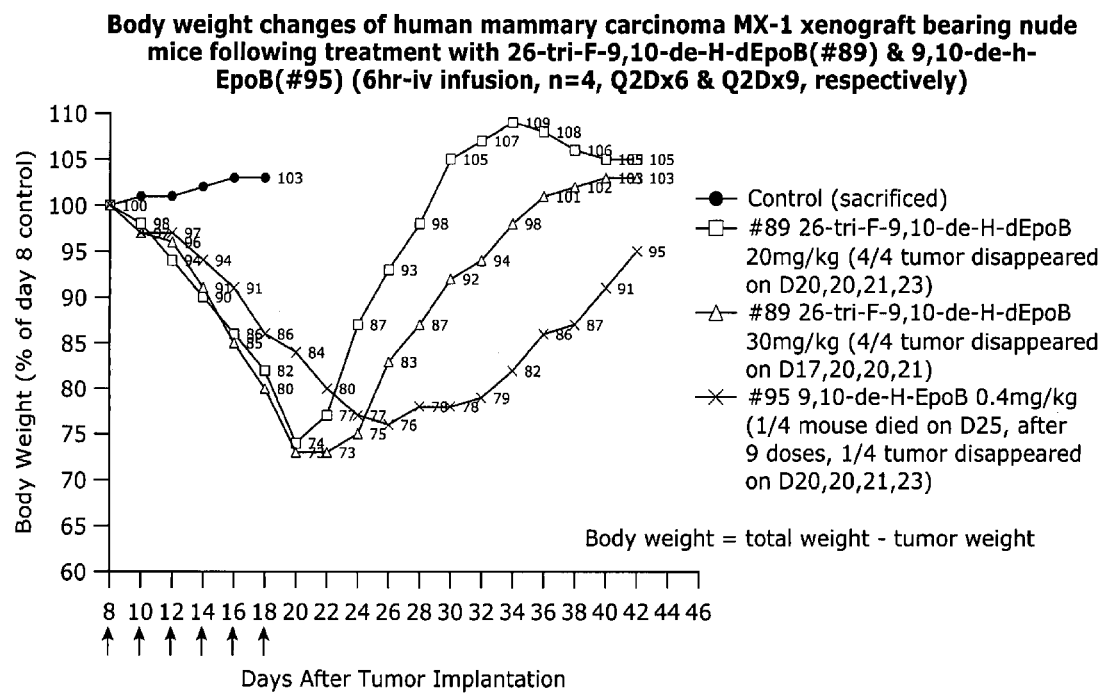
FIG. 14 shows body weight changes of nude mice bearing human mammary carcinoma tumor MX-1 xenograft following treatment with 26-trifluoro-9,10-dehydro-dEpoB and 9,10-dehydro-EpoB.

The impressive cell growth inhibition exhibited by epothilones 2, 28 and 29 (Epo 2-4) across a range of various drug-resistant tumors prompted determination of the blood plasma stability of these new (E)-9,10 congeners. For instance the recently described (E)-10,11-dehydro-dEpoB (of case 1 with a CH$_3$ group at C12) exhibits very poor plasma stability with respect to lactone opening. It is this plasma instability which has stifled advancement of (E)-10,11-dehydro-dEpoB. By contrast, on exposure of 2, 28 and 29 (Epo 2-4) to murine plasma, we observed a much slower drug degradation as compared to dEpoB (1) by a factor of seven. This stability constitutes a substantial advance from a drug availability perspective relative to dEpoB (FIG. 9). The combination of the cytotoxicity and plasma stability data encouraged us to synthesize substantial amounts of 28 (Epo 3) in order to determine its in vivo efficacy, in nude mice bearing human tumor xenografts. The direct and high quality total synthesis described above allowed us to indulge these interests. Epothilone 28 (Epo 3) demonstrated a markedly improved potency in inhibiting on the growth of implanted tumors, relative to dEpoB. The improved potency and plasma stability allows very substantial reduction of drug dosing (an order of magnitude) in the context of xenografts of 28 (Epo 3).

In our early studies we had found that epothilone B, by way of the 12,13 epoxide, is significantly more cytotoxic than is its 12,13-desoxy analog (dEpoB). However, from the perspective of therapeutic index, the desoxy compound seemed to us to be more much promising. More recently, we reported the total synthesis of (E)-9,10-dehydro-12,13-desoxyepothilone B (28) using a stereoselective ring closing metathesis. We showed that the incorporation of E-9,10 unsaturation in the context of the usual Z-12,13 olefin (see compound 1) results in a great increase in in vitro potency. More to the point, this is translatable to an in vivo setting in xenografts mice. Moreover, compound 28 enjoys major pharmaceutical advantages relative to dEpoB (1). This allowed for the reduction of the dosing levels for 28 relative to 1 in xenograft experiments to be reduced by an order of magnitude.

Accordingly, we wondered if the incorporation of C9-C10 olefin in epothilone B (51, EpoB) would alter its biological profile in the same direction.

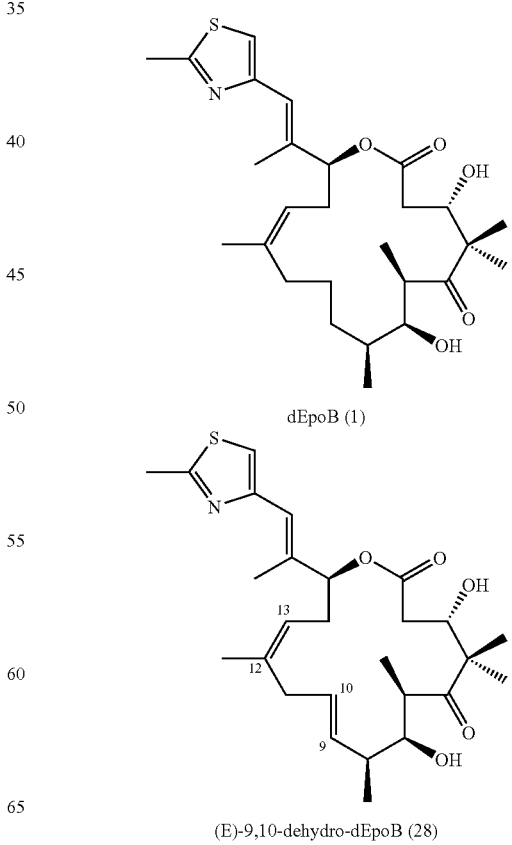

dEpoB (1)

(E)-9,10-dehydro-dEpoB (28)

49

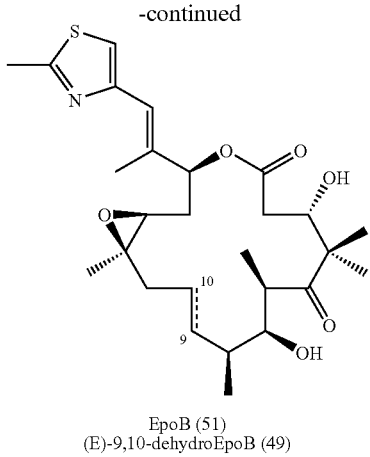

EpoB (51)
(E)-9,10-dehydroEpoB (49)

50

Epoxidation of 28 with 2,2'-dimethydroxirane (DMDO) proceeded with high chemoselectively at the more substituted C12-C13 olefin to give an 87% yield of a 1:2.6 ratio of the (E)-9,10-dehydroepothilone B (49) and its diastereomer (50). The stereochemistry of the epoxides was determined by selective diimide reduction of the C9-C10 double bonds. Examination of the spectral properties of these products revealed the minor product (49) to be dEpoB. The preference for α-epoxidation in the case of 28 stands in striking contrast to the highly stereoselective epoxidation of dEpoB, which occurs from the β face leading to EpoB (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073; incorporated herein by reference).

Scheme 9

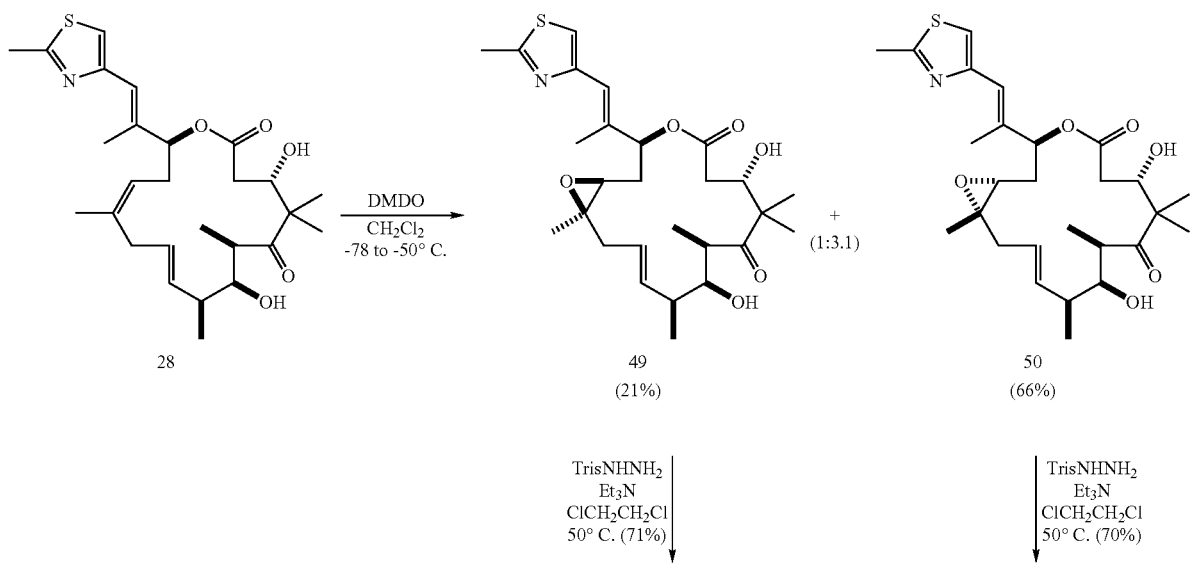

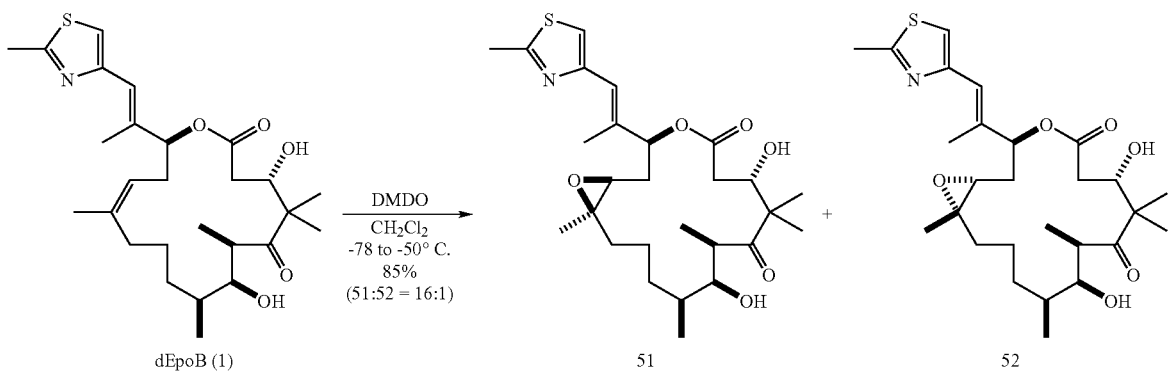

Figure 15:
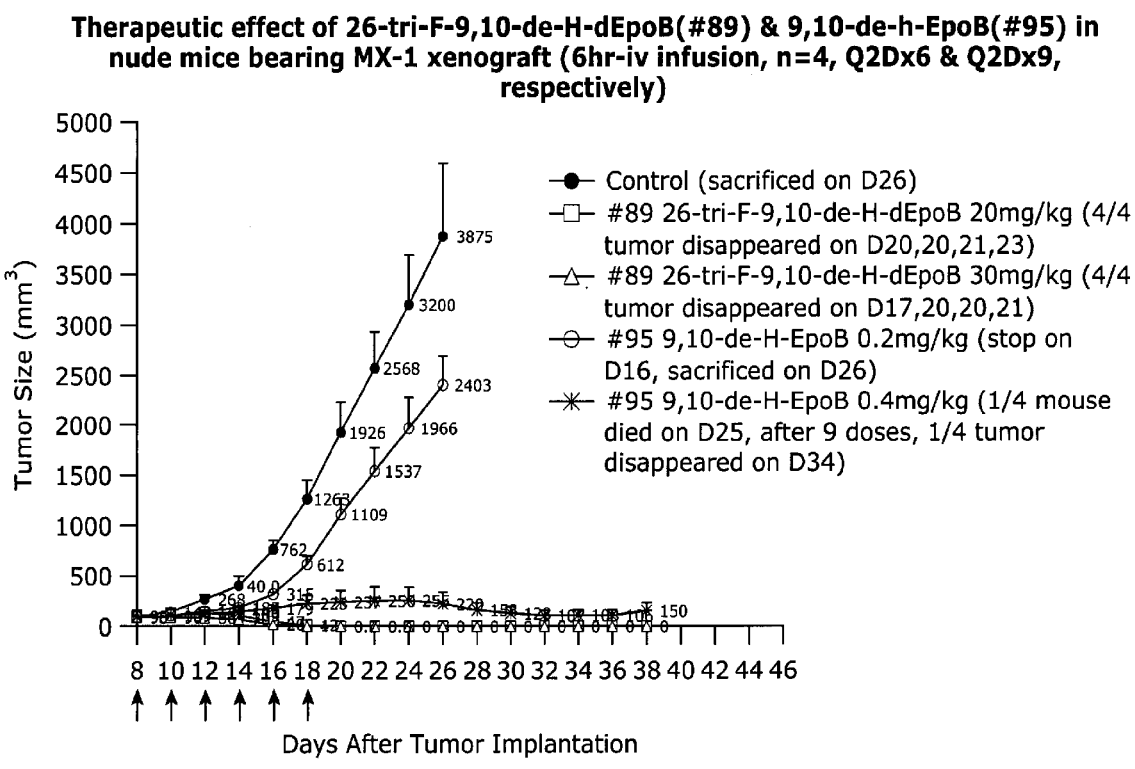
FIG. 15 shows the therapeutic effect of 26-trifluoro-9,10-dehydro-dEpoB and 9,10-dehydroEpoB on tumor size in nude mice bearing MX-1 xenografts.
Figure 16:
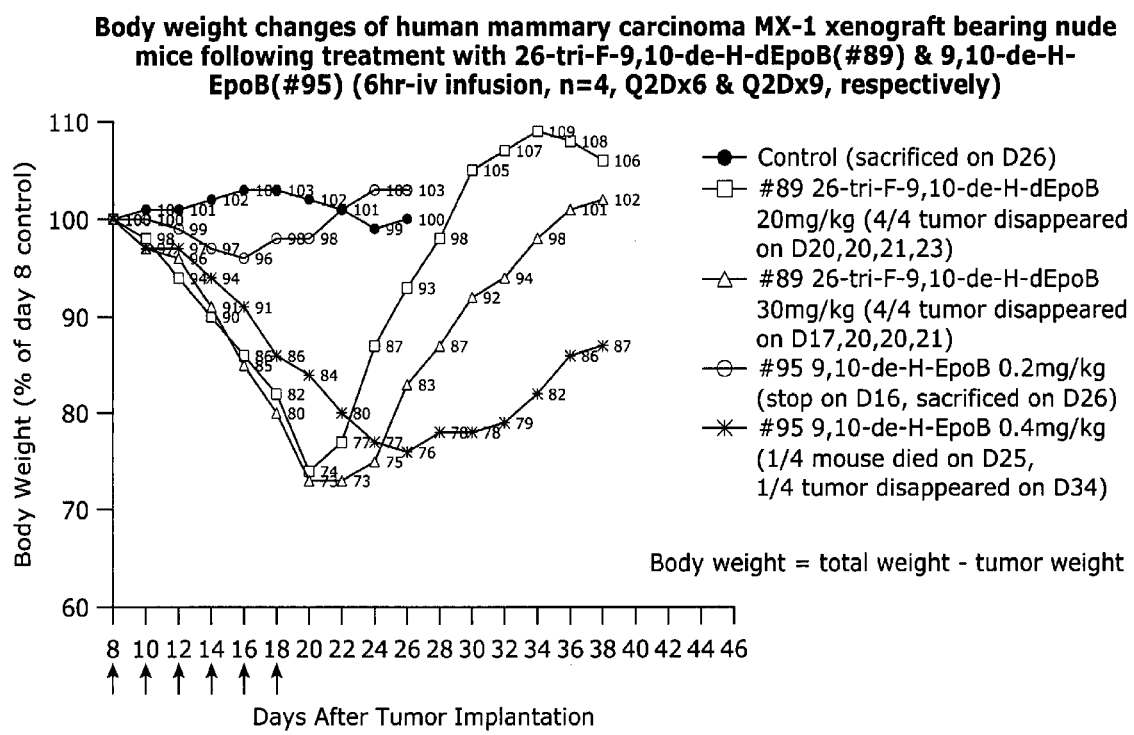
FIG. 16 shows body weight changes of nude mice bearing human mammary carcinoma tumor MX-1 xenograft following treatment with 26-trifluoro-9,10-dehydro-dEpoB and 9,10-dehydro-EpoB.
Figure 17:
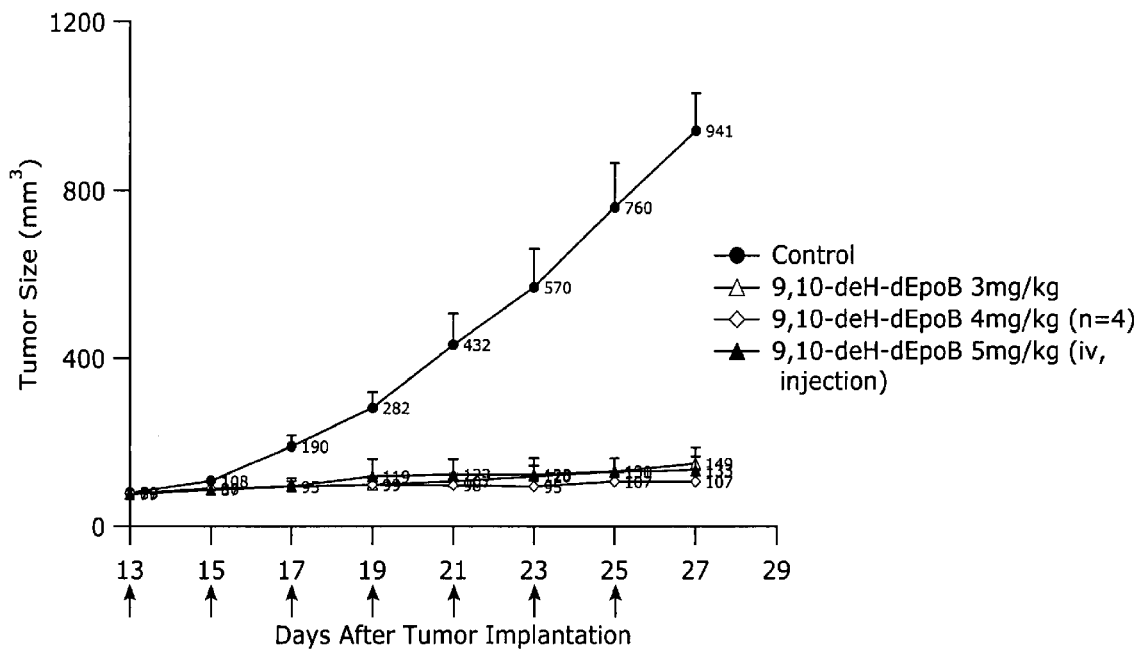
FIG. 17 shows the effect of 9,10-dehydro-dEpoB on tumor size in nude mice bearing HCT-116 xenografts.
Figure 18:
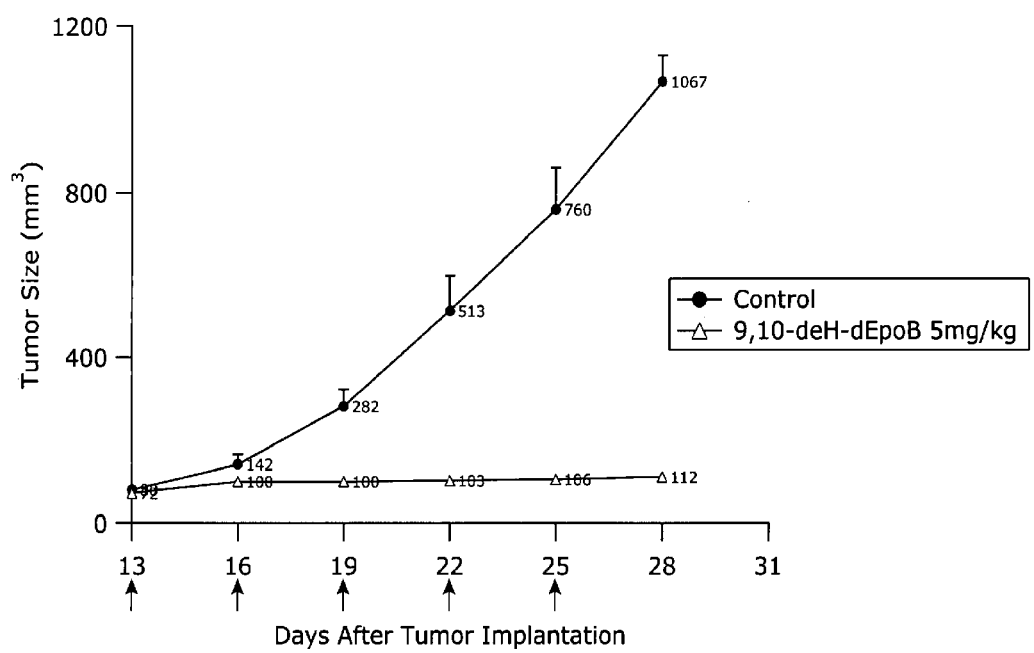
FIG. 18 shows the effect of 9,10-dehydro-dEpoB on tumor size in nude mice bearing human colon carcinoma HCT-116 xenografts.
Figure 19:
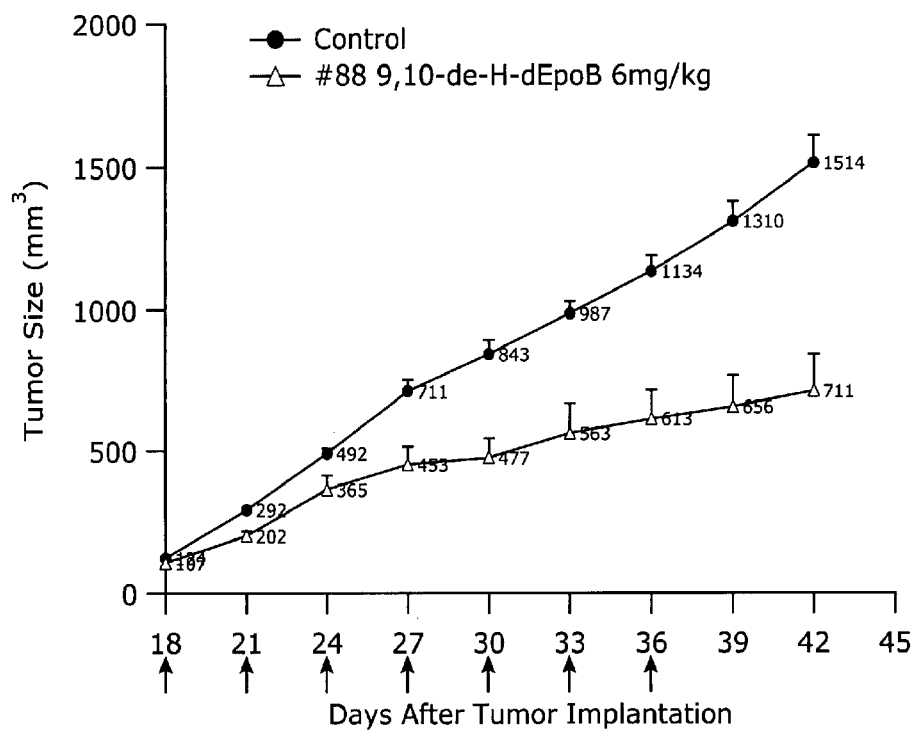
FIG. 19 shows the effect of 9,10-dehydro-dEpoB on tumor size in nude mice bearing A549/Taxol xenografts.
Figure 20:
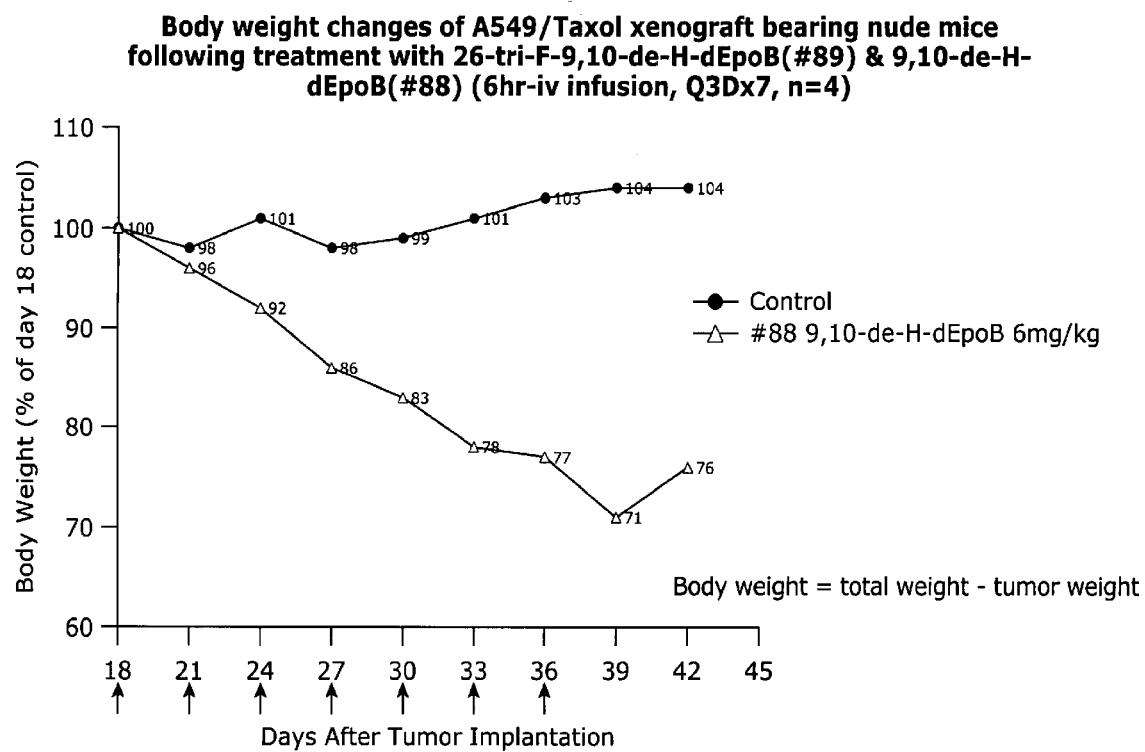
FIG. 20 shows changes in body weight of nude mice bearing A549/Taxol xenograft treated with 26-trifluoro-9,10-dehydro-dEpoB and 9,10-dehydro-dEpoB.
Figure 21:
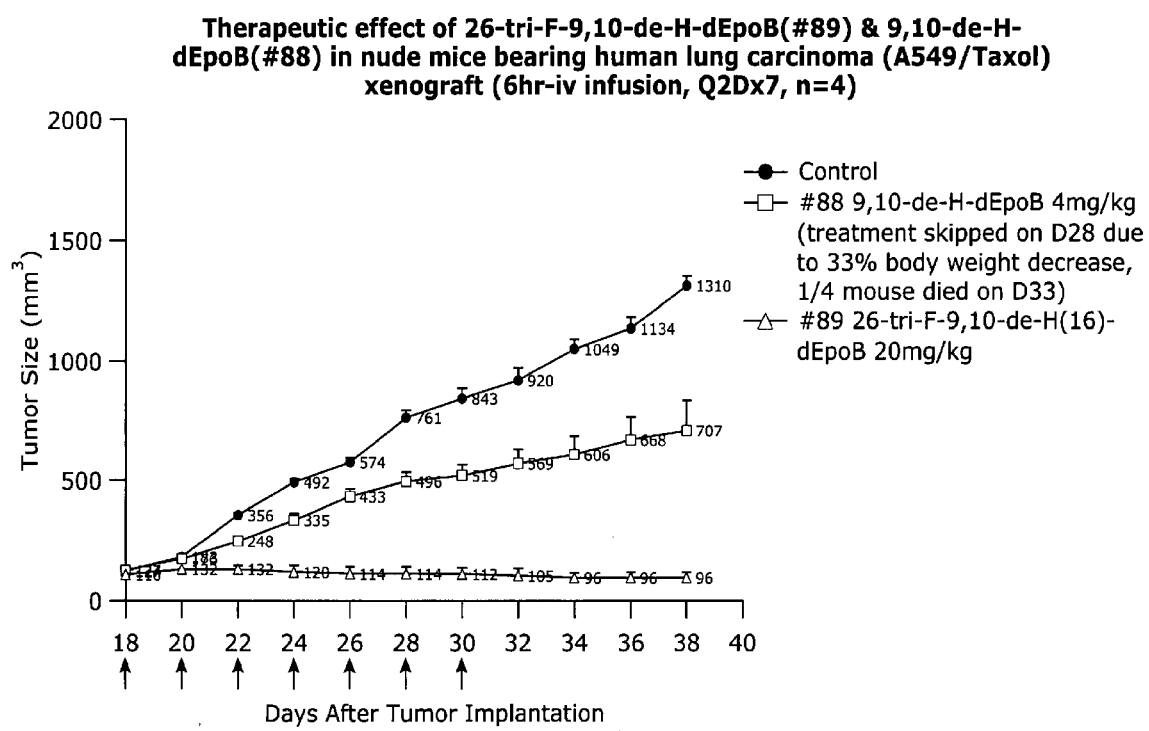
FIG. 21 shows the effect of 26-trifluoro-9,10-dehydro-dEpoB and 9,10-dehydro-dEpoB on tumor size in nude mice bearing A549/Taxol xenografts.
Figure 22:
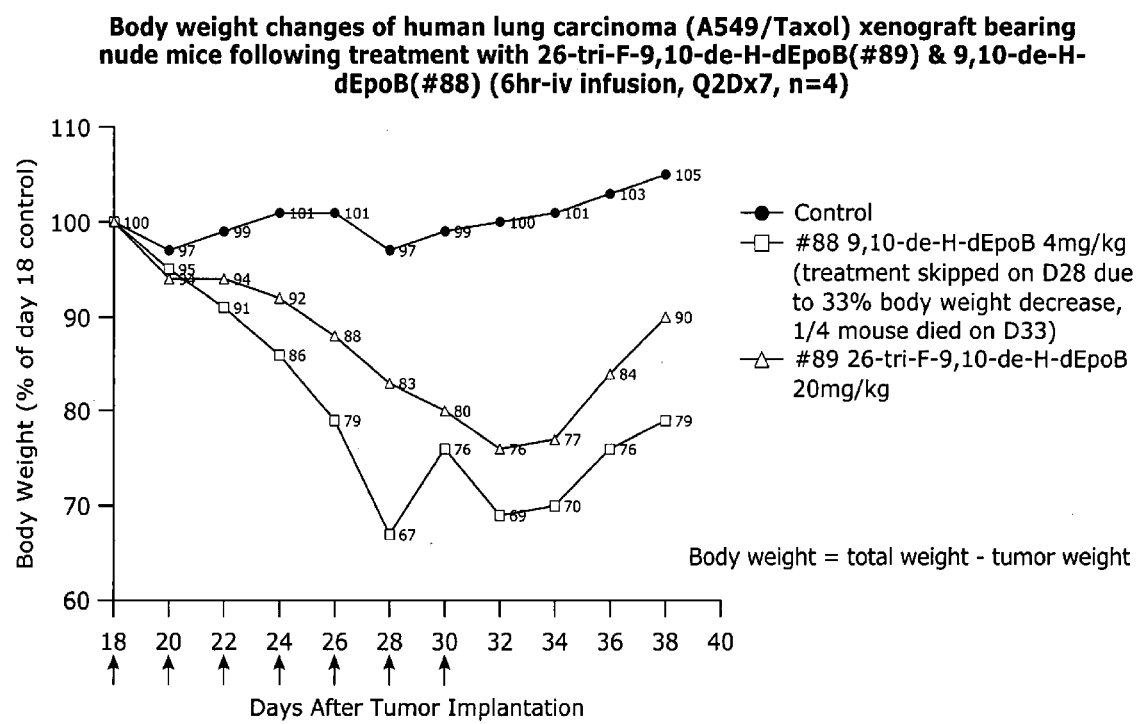
FIG. 22 shows changes in body weight of nude mice bearing A549/Taxol xenografts treated with 26-trifluoro-9,10-dehydro-dEpoB and 9,10-dehydro-dEpoB.
Figure 23:
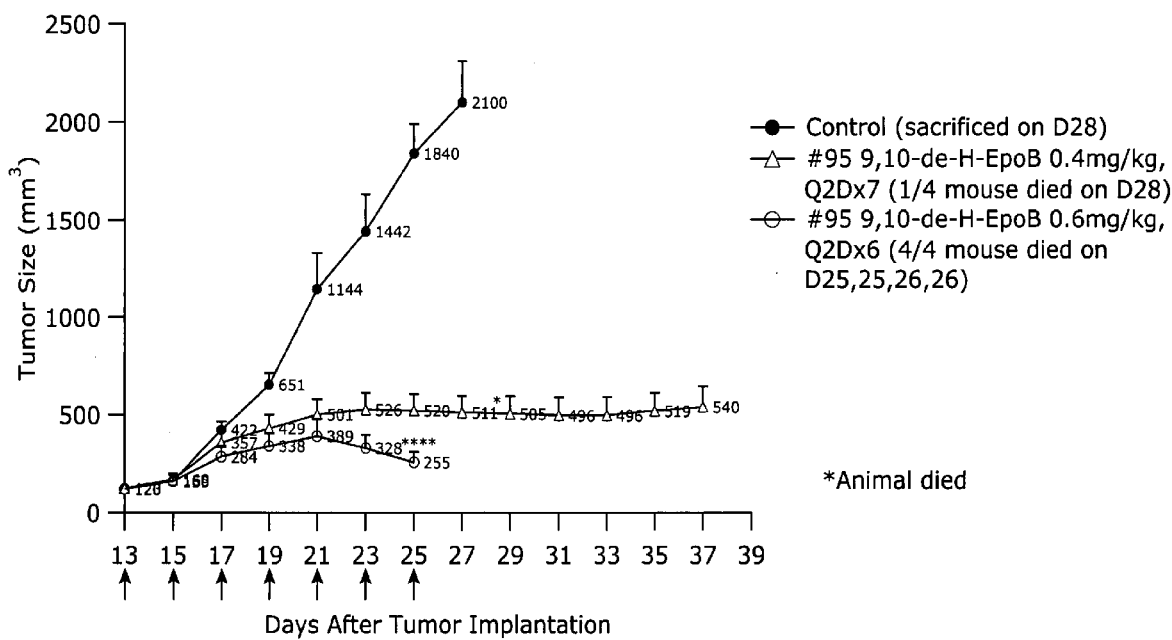
FIG. 23 shows the effect of 9,10-dehydro-EpoB on tumor size in nude mice bearing human colon carcinoma HCT-116 tumor xenografts.
Figure 24:
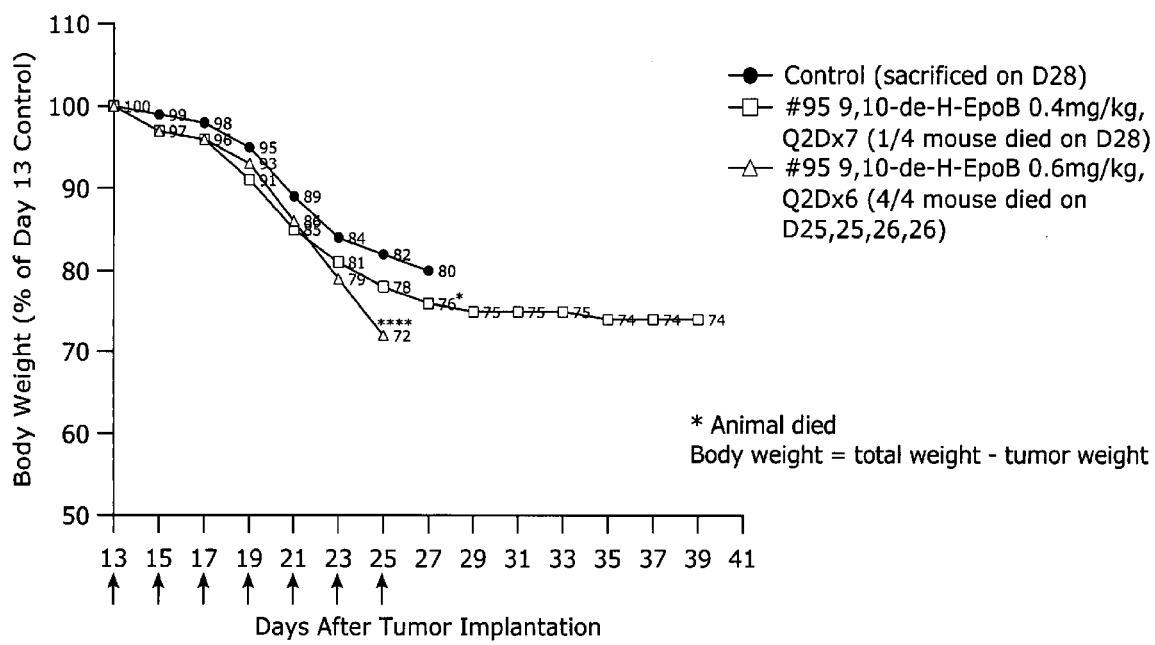
FIG. 24 shows changes in body weight of nude mice bearing human colon carcinoma HCT-116 tumor xenograft following treatment with 9,10-dehydro-EpoB.
Figure 25:
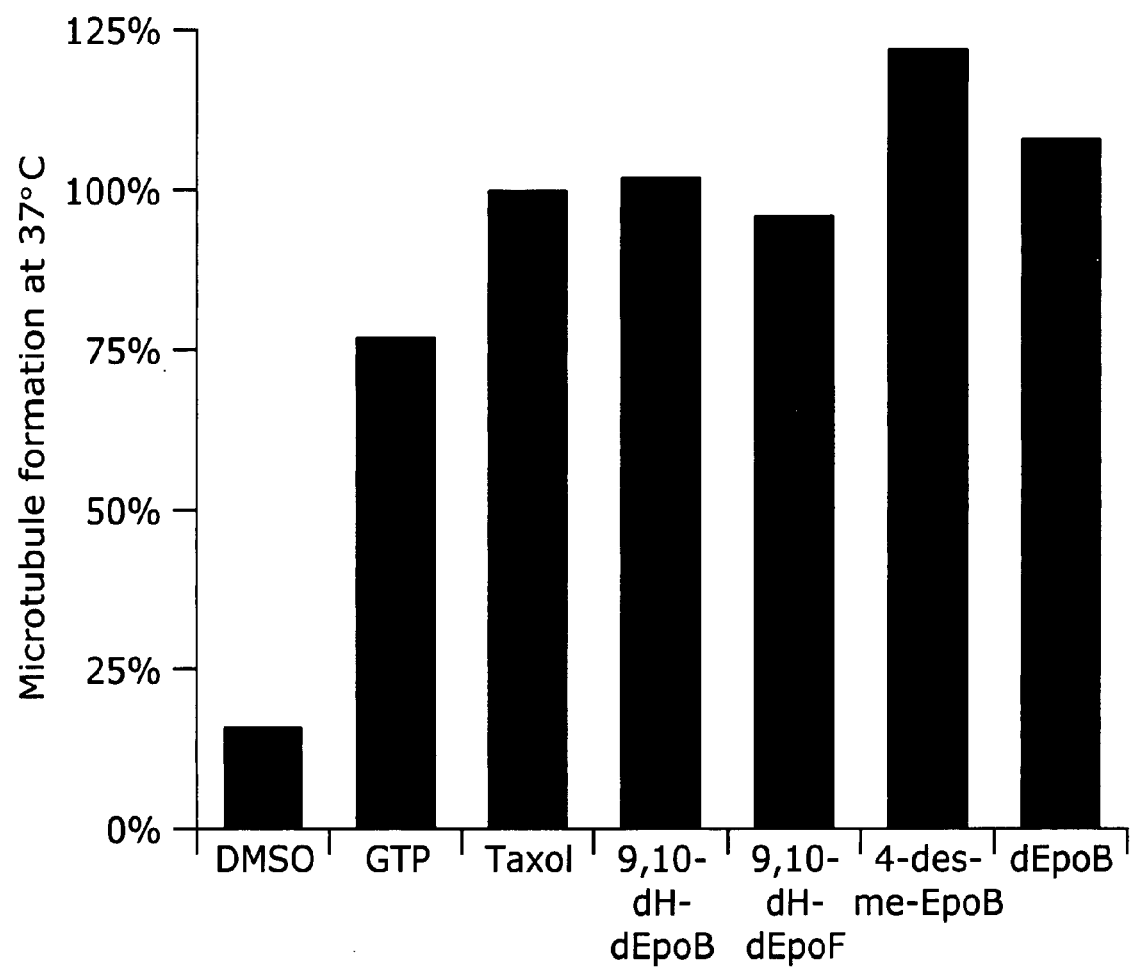
FIG. 25 shows microtubule formation from tubulin in the presence of various epothilone analogues at 37° C.
Figure 26:
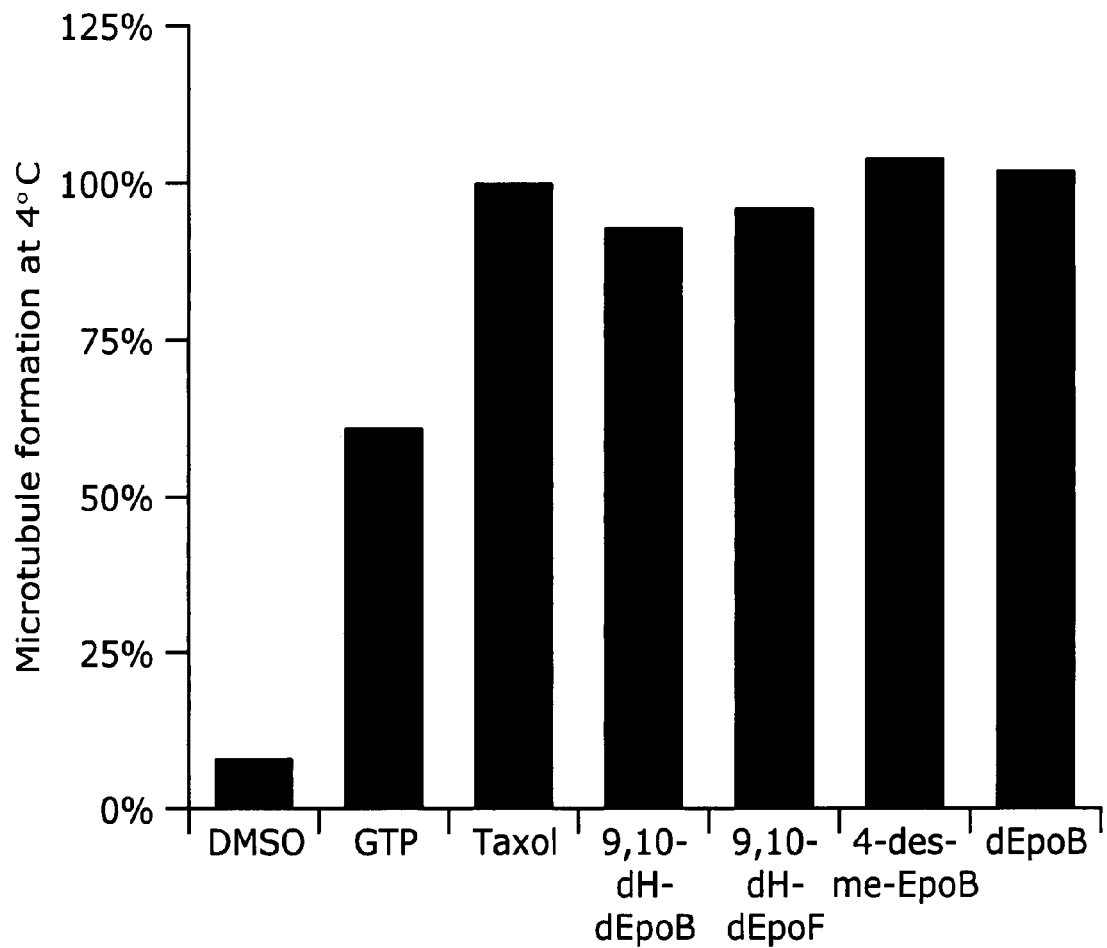
FIG. 26 shows microtubule formation from tubulin in the presence of various epothilone analogues at 4° C.
Figure 27:
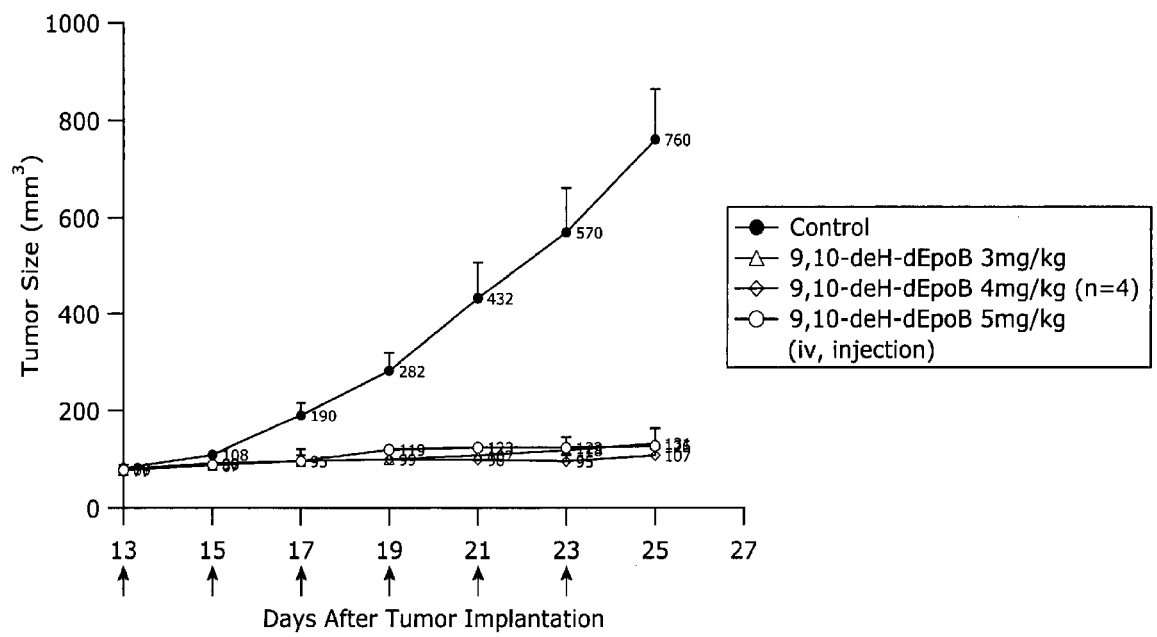
FIG. 27 shows the effect of 9,10-dehydro-dEpoB and dEpoB on tumor size in nude mice bearing HCT-116 xenografts.
Figure 28:
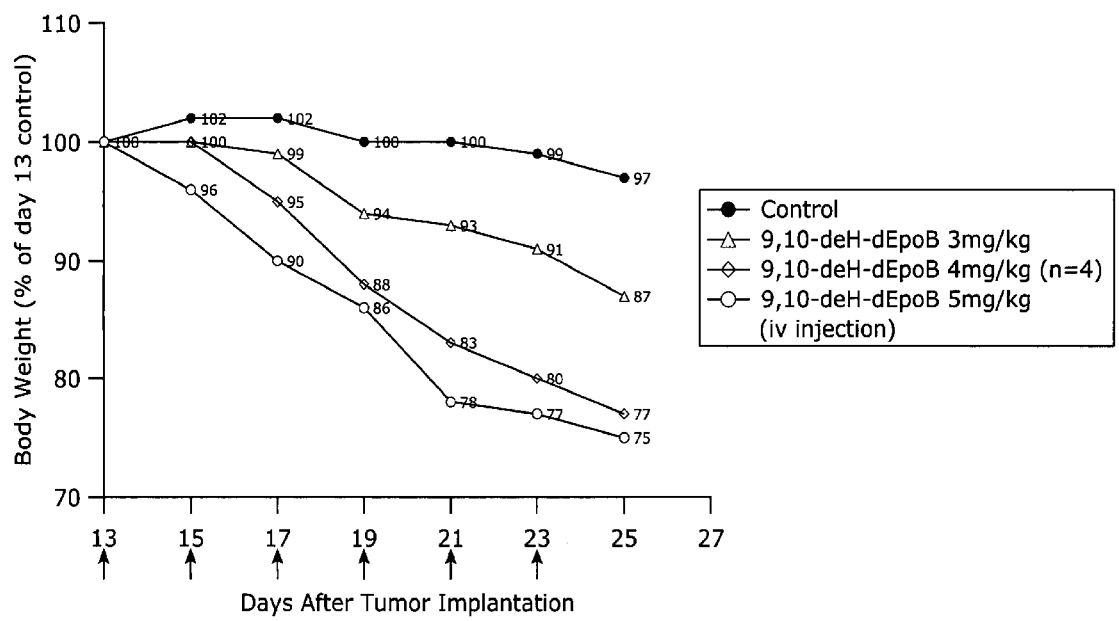
FIG. 28 shows changes in body weight of nude mice bearing HCT-116 xenografts after treatment with 9,10-dehydro-dEpoB and dEpoB.
Figure 29:
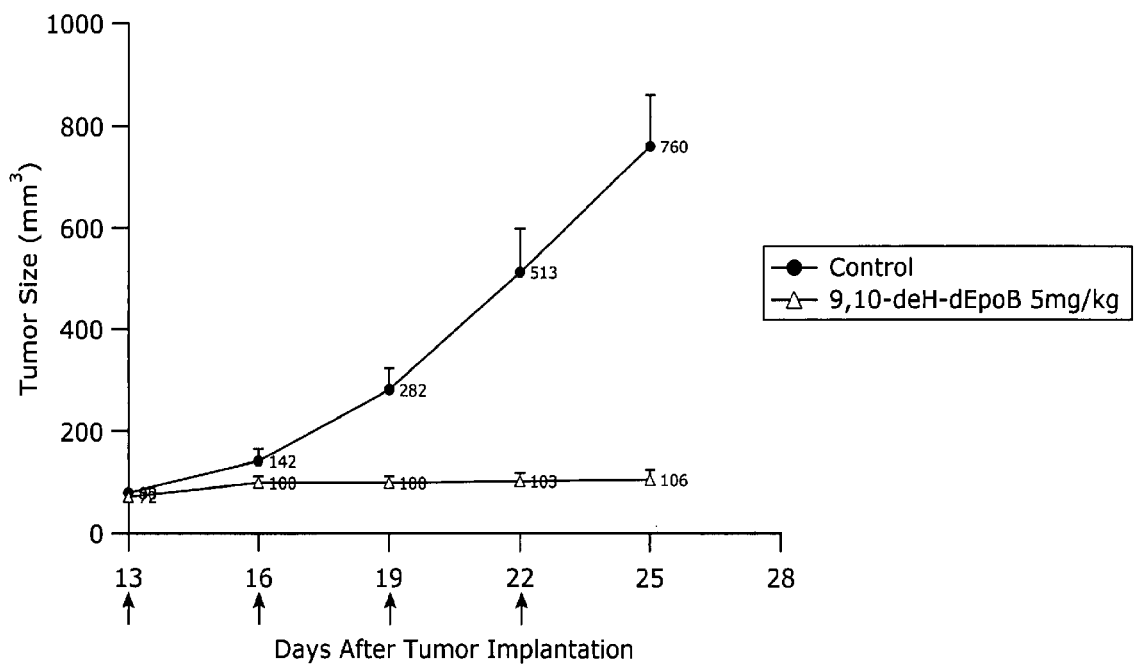
FIG. 29 shows the effect of 9,10-dehydro-dEpoB on tumor size in nude mice bearing human colon carcinoma HCT-116 xenografts.
Figure 30:
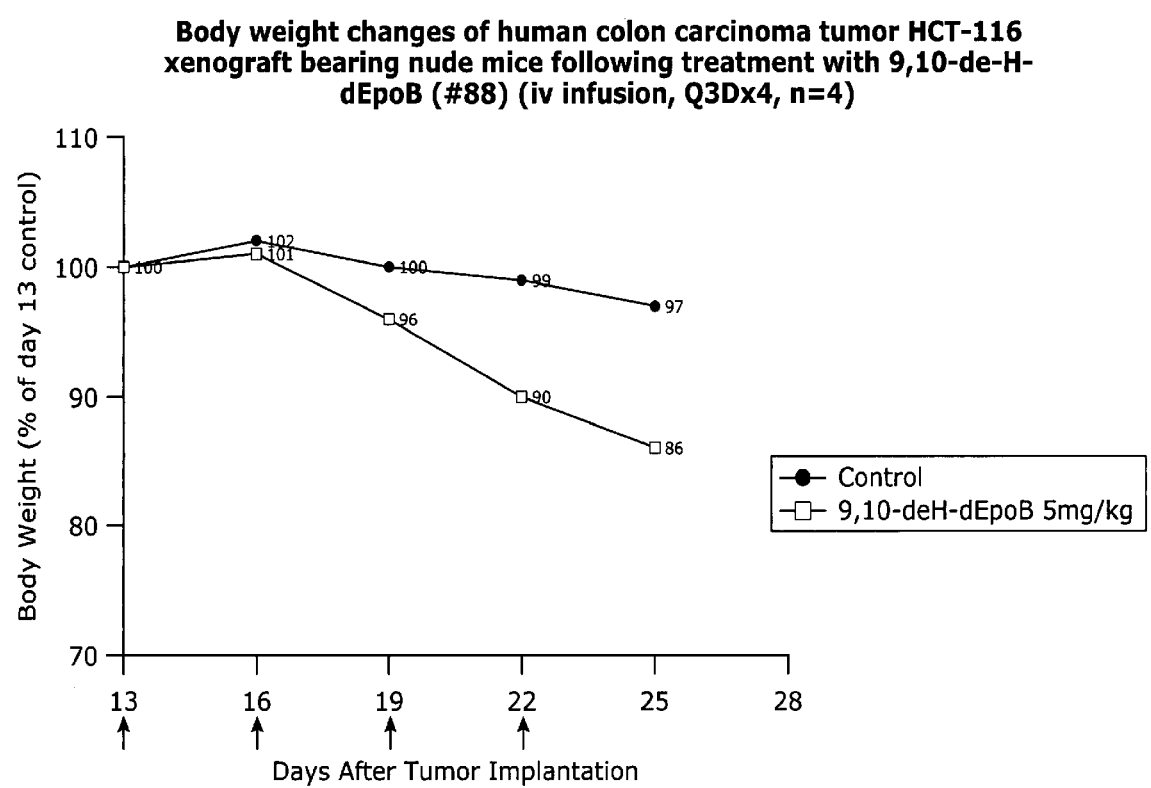
FIG. 30 shows changes in body weight of nude mice bearing human colon carcinoma tumor HCT-116 xenografts following treatment with 9,10-dehydro-dEpoB (5 mg/kg, iv infusion, X3Dx4).
Figure 34:
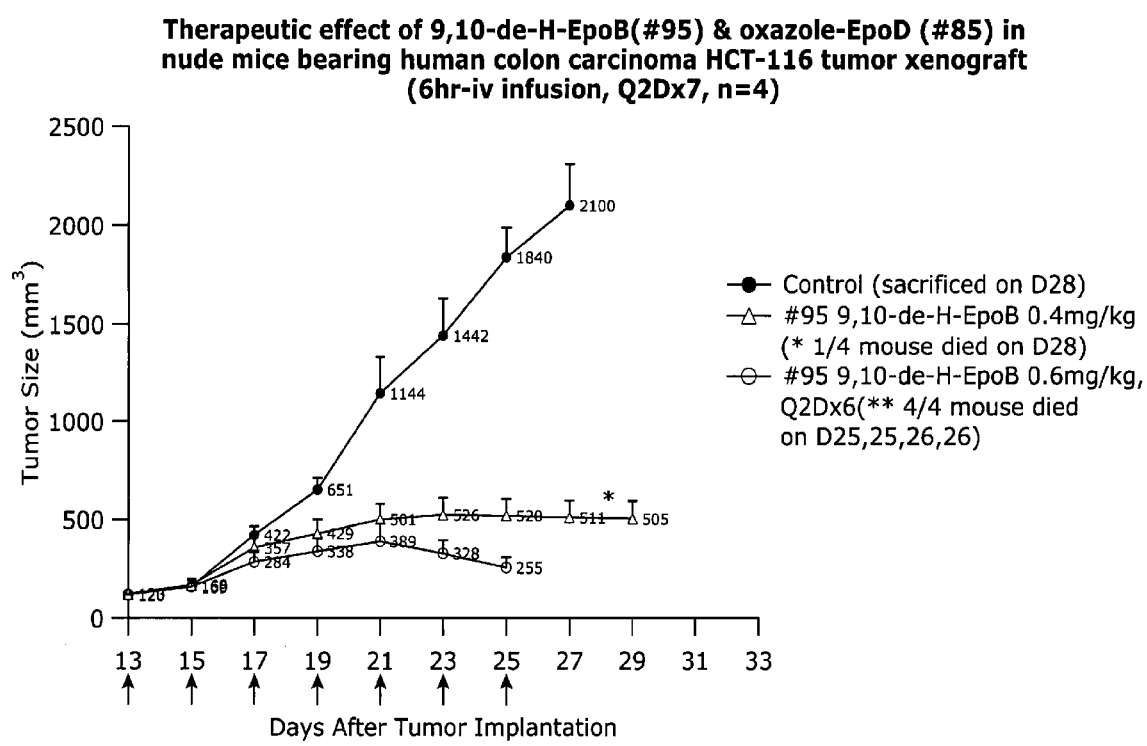
FIG. 34 shows the effect of 9,10-dehydro-EpoB and oxazole-EpoD on tumor size in nude mice bearing human colon carcinoma HCT-116 tumor xenograft (6 hour iv infusion, Q2Dx7).
Figure 35:
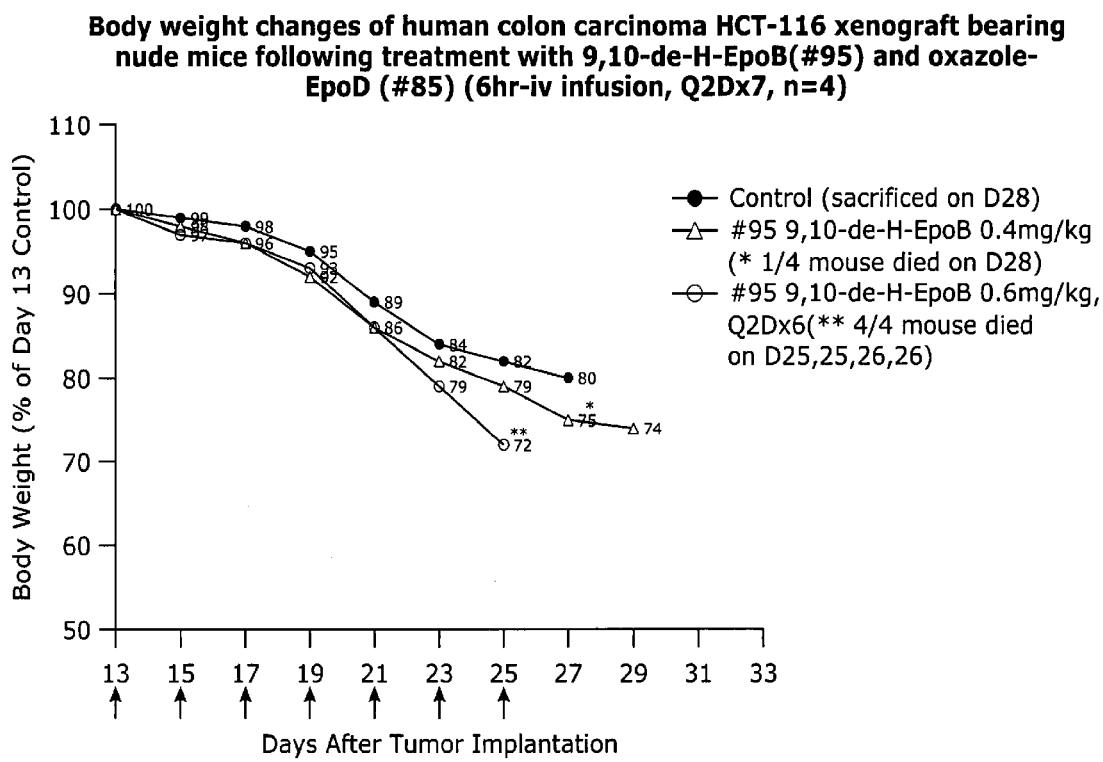
FIG. 35 shows changes in body weight of nude mice bearing human colon carcinoma HCT-116 tumor xenografts following treatment with 9,10-dehydro-EpoB and oxazole-EpoD (6 hour infusion, Q2Dx7).
Figure 36:
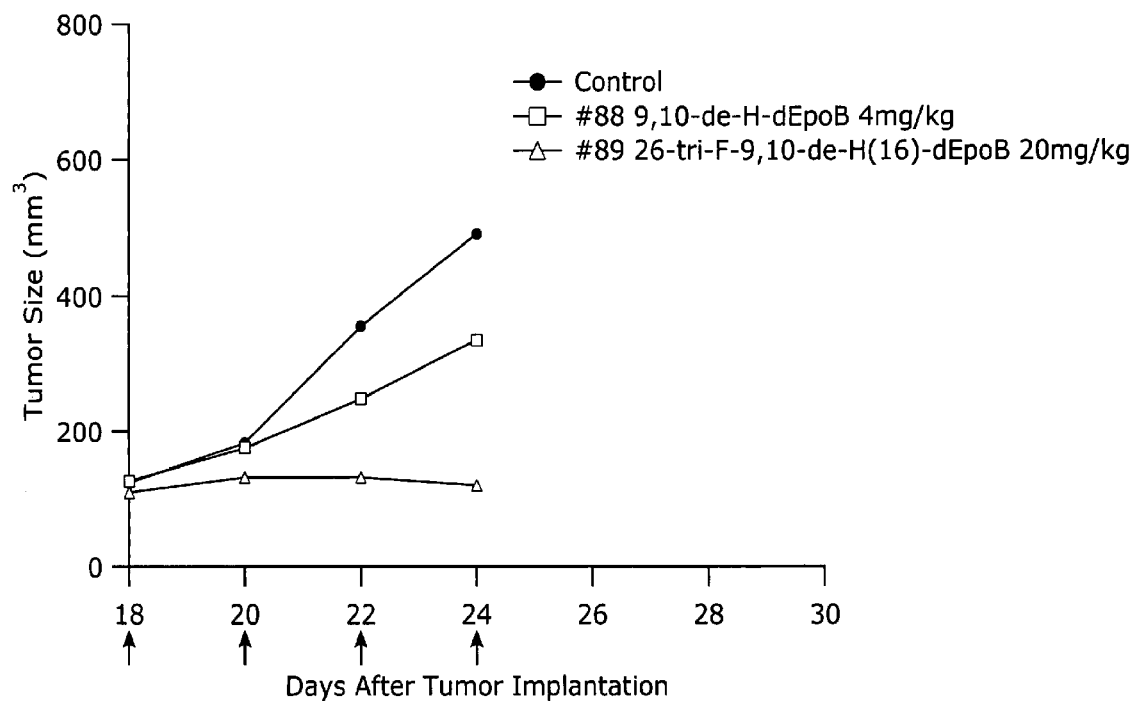
FIG. 36 shows the effect of 26-trifluoro-9,10-dehydro-dEpoB and 9,10-dehydro-dEpoB on tumor size in nude mice bearing A549/Taxol xenografts (6 hour iv infusion, Q2Dx4).
Figure 37:
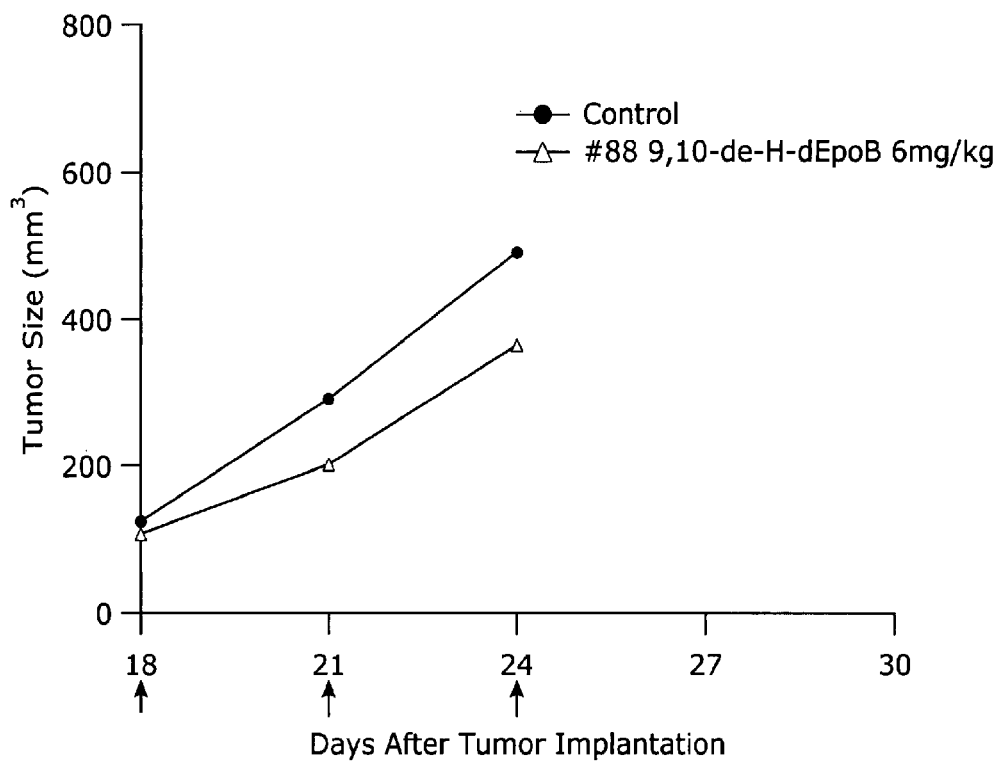
FIG. 37 shows the effect of 9,10-dehydro-dEpoB on tumor size in nude mice bearing A549/Taxol xenografts (6 hour iv infusion, Q3Dx3).
Figure 38:
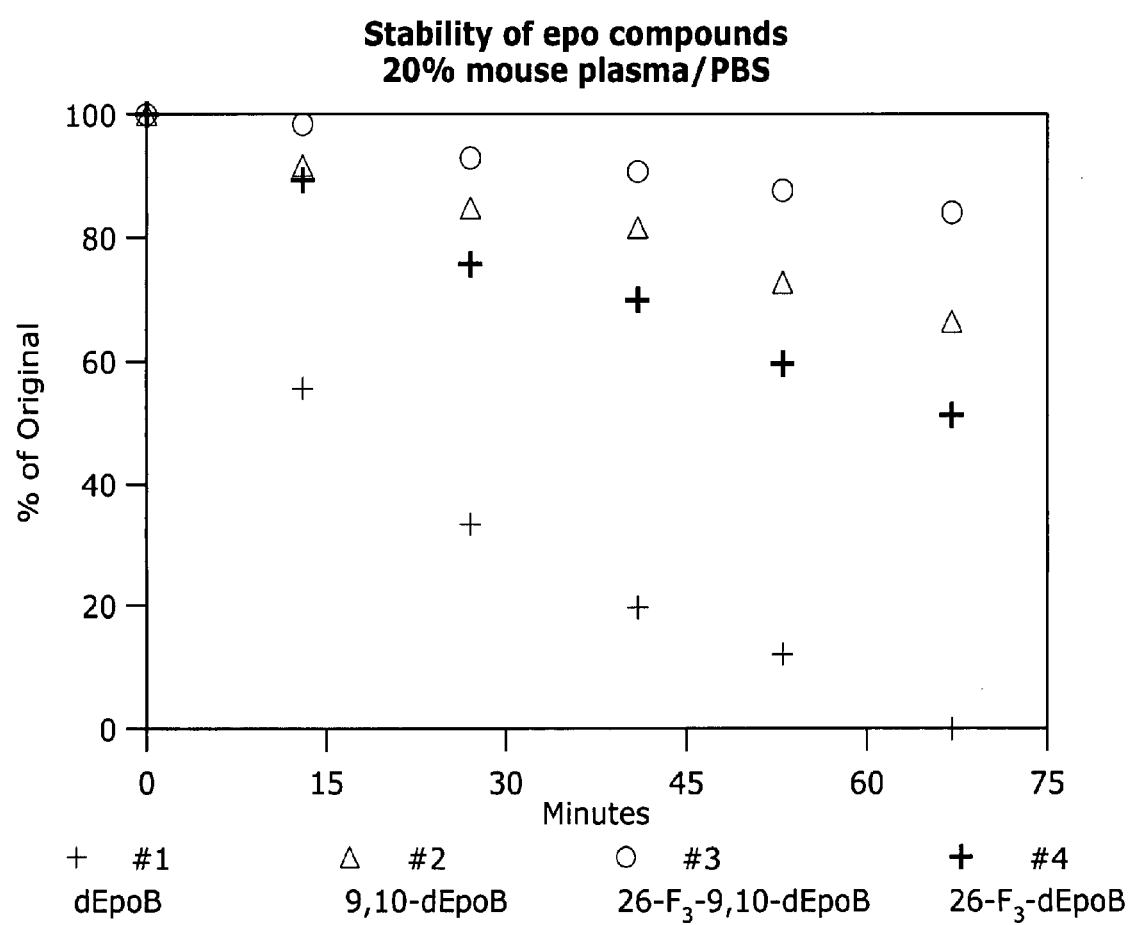
FIG. 38 shows the stability of epothilone analogues in 20% mouse plasma/PBS.
Figure 39:
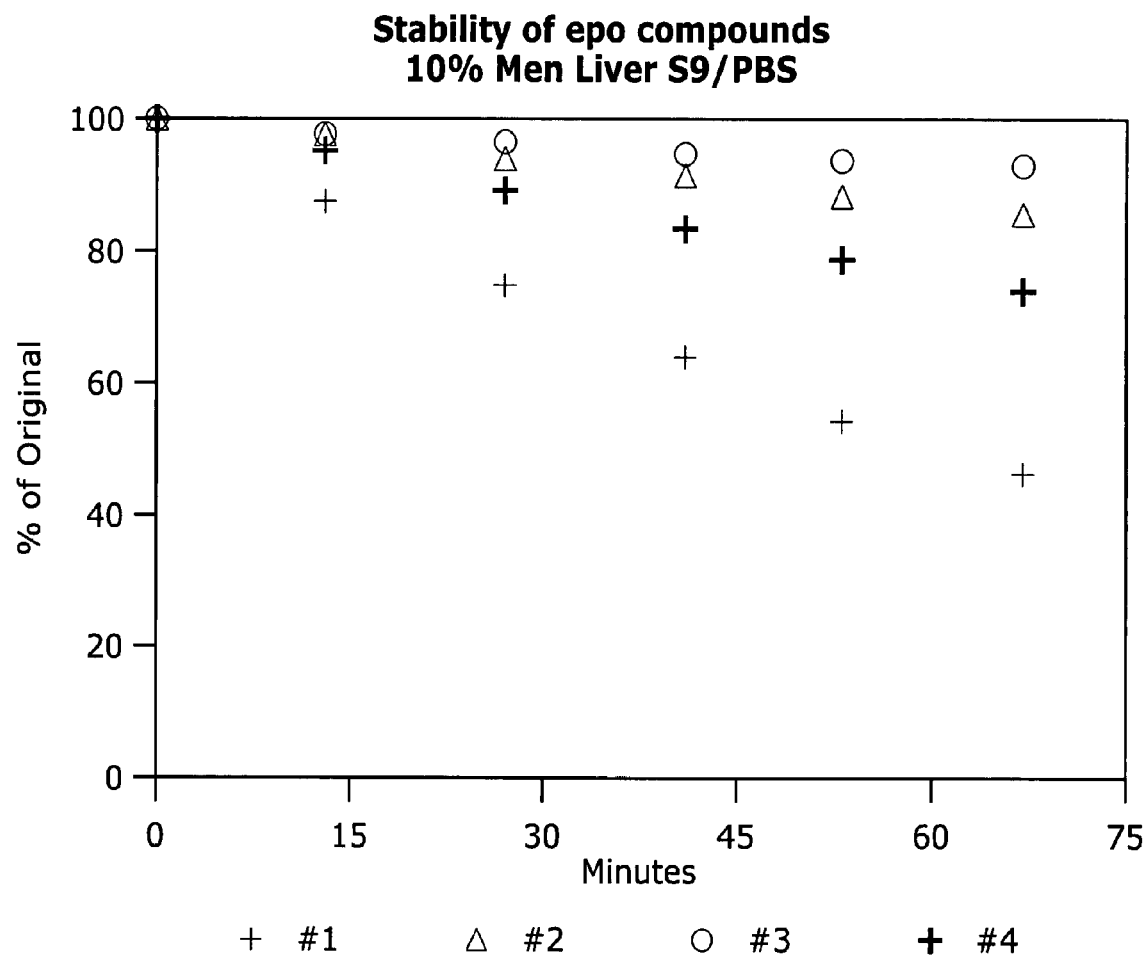
FIG. 39 shows the stability of epothilone analogues in 10% Men Liver S9/PBS.
Figure 40:
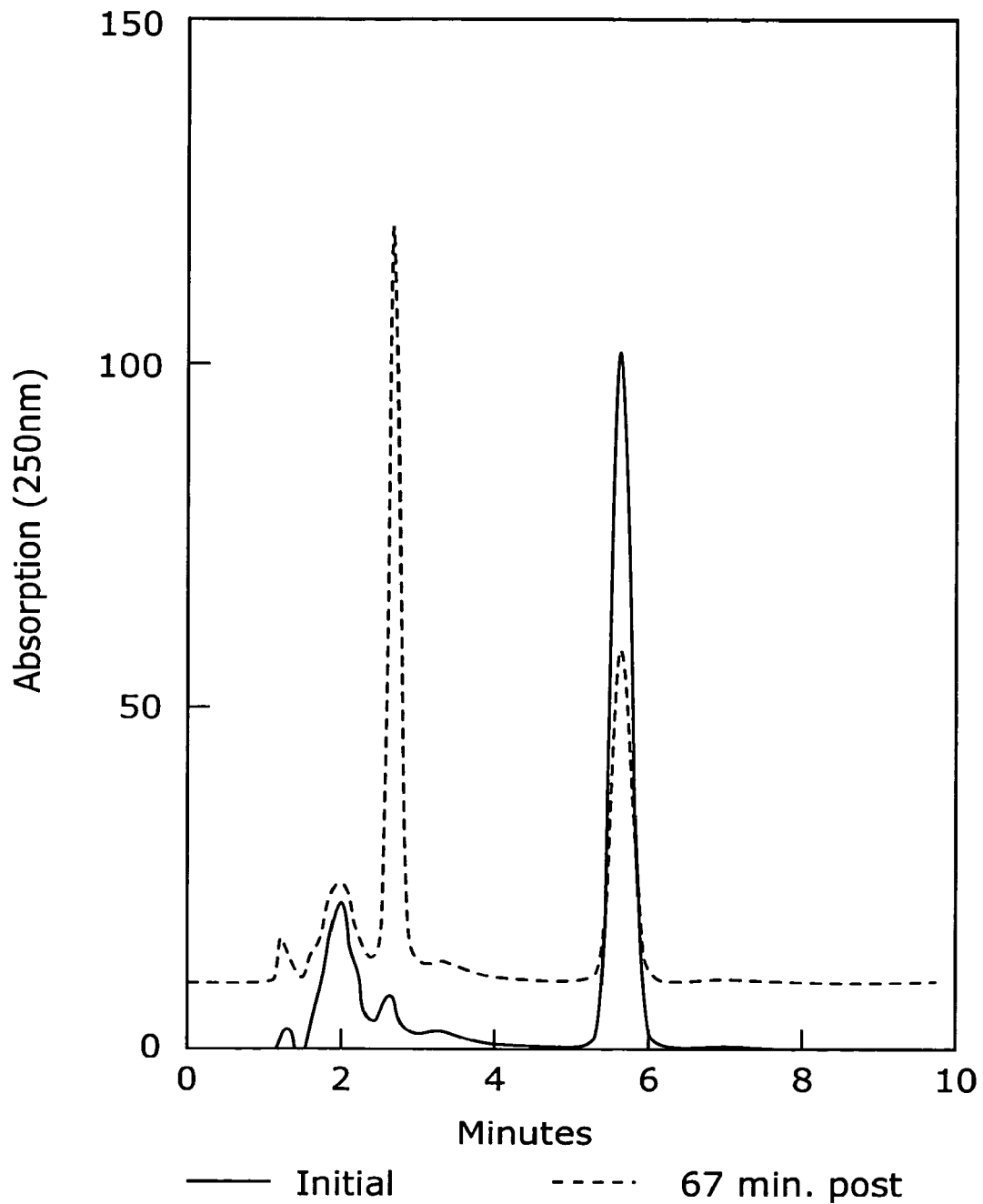
FIG. 40 shows EpoD stability chromatogram in 10% Men Liver S9/PBS.
Figure 42:
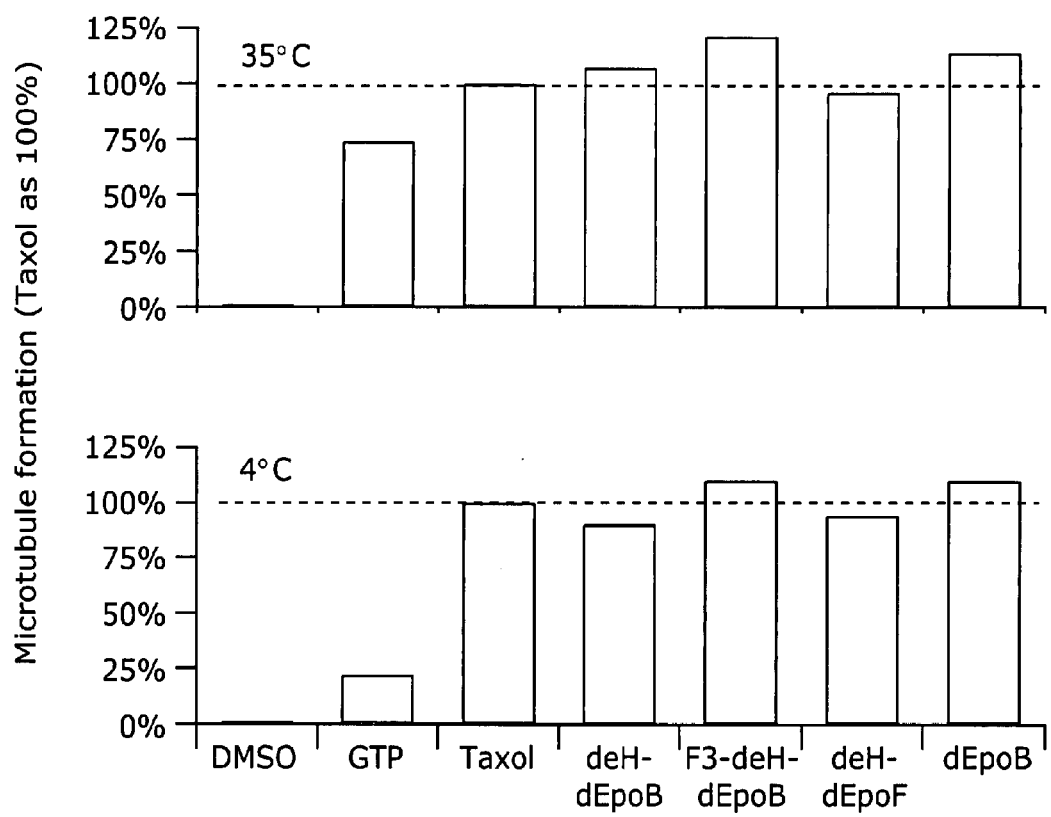
FIG. 42 shows the stabilization of microtubule formation by epothilones at 35° C. and 4° C.
Figure 43:
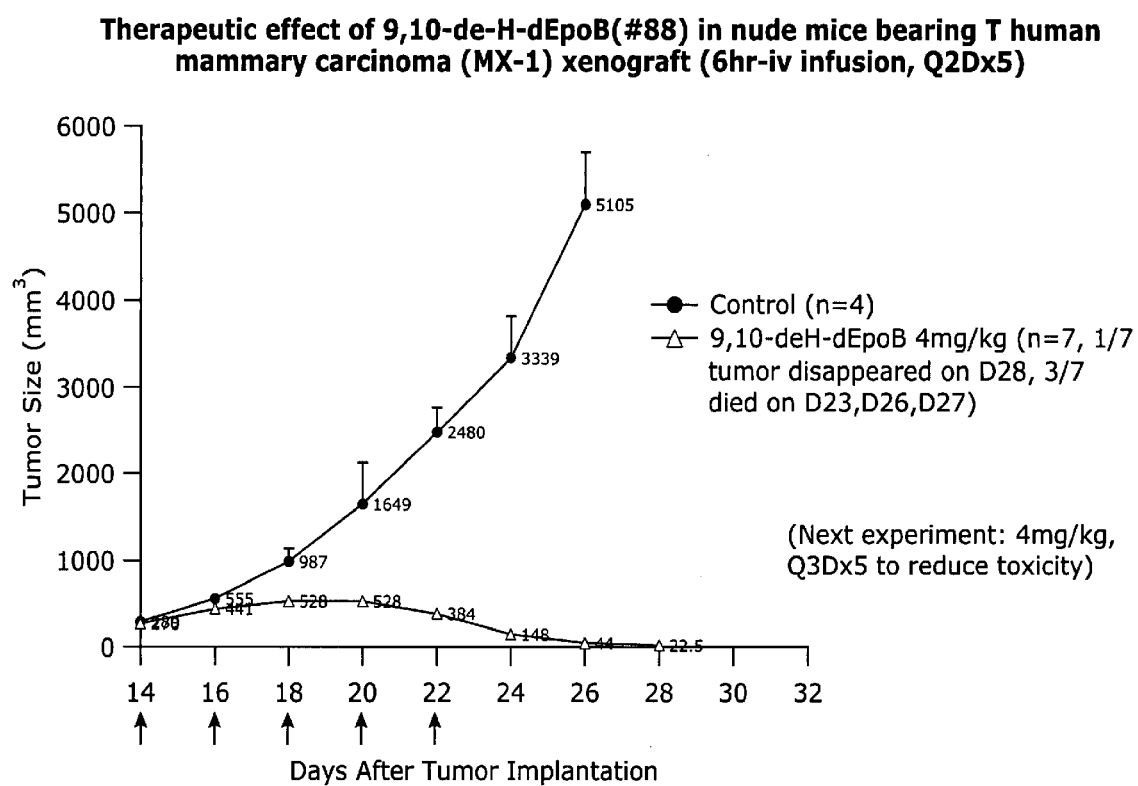
FIG. 43 shows the therapeutic effect of 9,10-dehydro-dEpoB in nude mice bearing T human mammary carcinoma (MX-1) xenograft (6 hour infusion, Q2Dx8).
Figure 44:
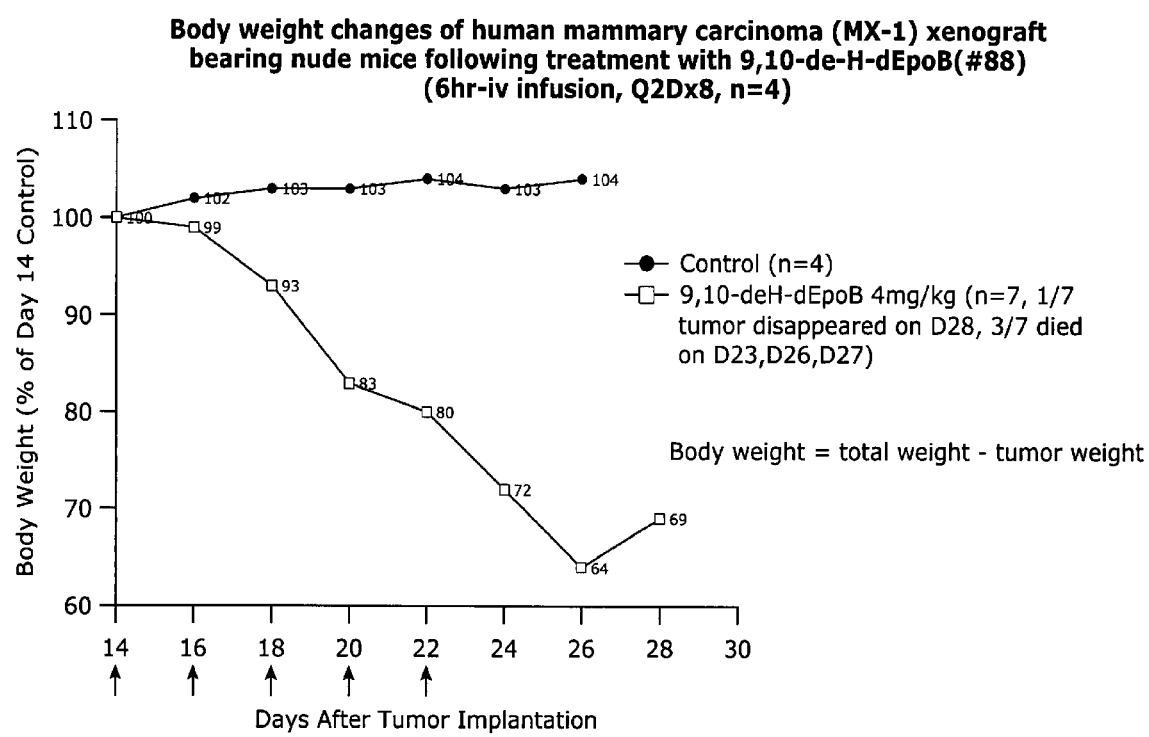
FIG. 44 shows the change in body weight of nude mice bearing human mammary carcinoma (MX-1) xenograft following treatment with 9,10-dehydro-dEpoB (6 hour infusion, Q2Dx8, n=4).
Figure 45:
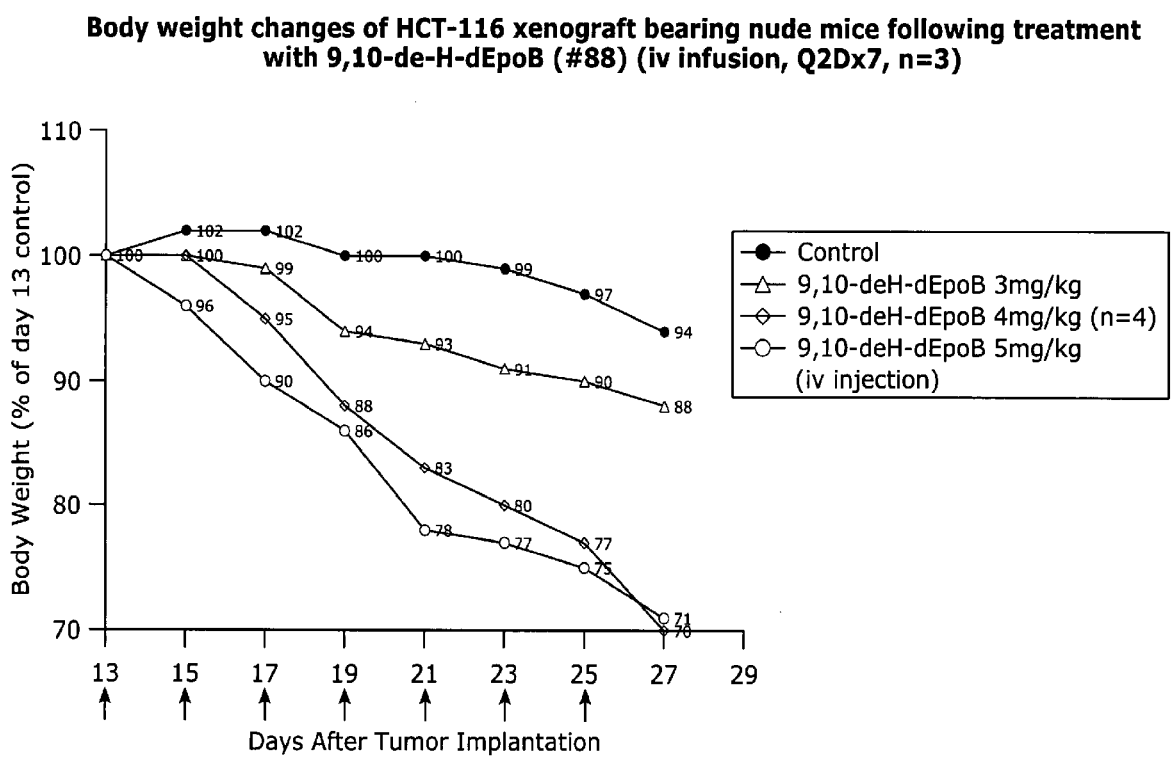
FIG. 45 shows the change in body weight of nude mice bearing HCT-116 xenograft following treatment with 9,10-dehydro-dEpoB (iv infusion, Q2Dx7).
Figure 46:
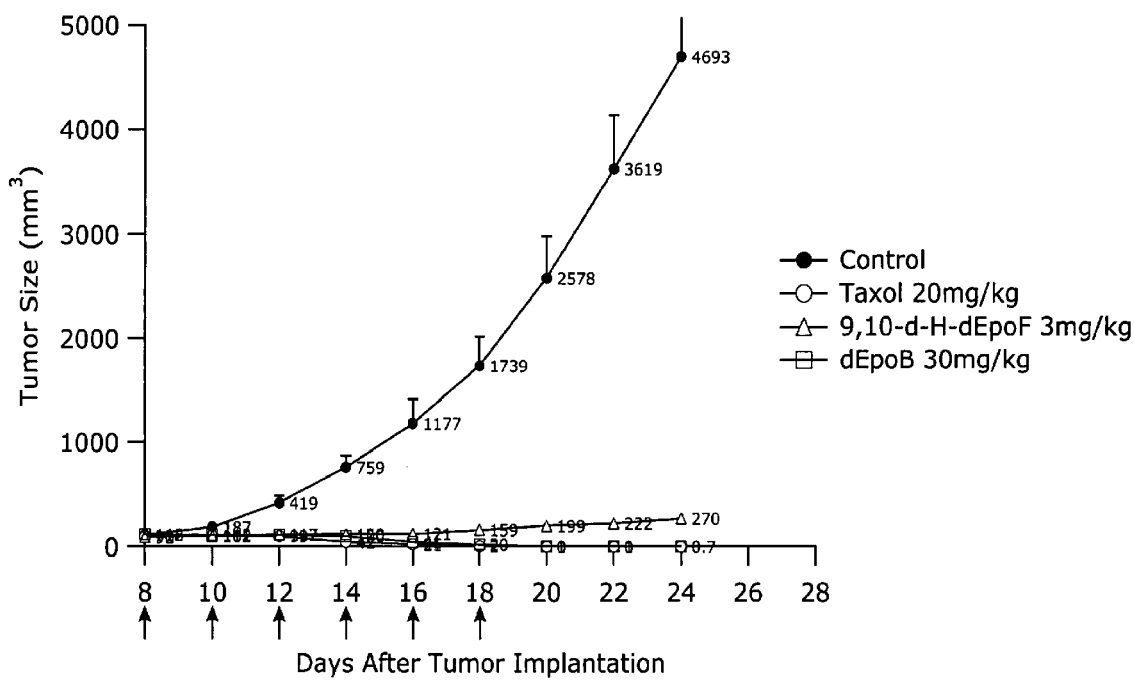
FIG. 46 shows the therapeutic effect of 9,10-dehydro-dEpoF, dEpoB, and Taxol on tumor size in nude mice bearing human mammary carcinoma (MX-1) tumor xenograft (6 hour iv infusion, Q2Dx6).
Figure 47:
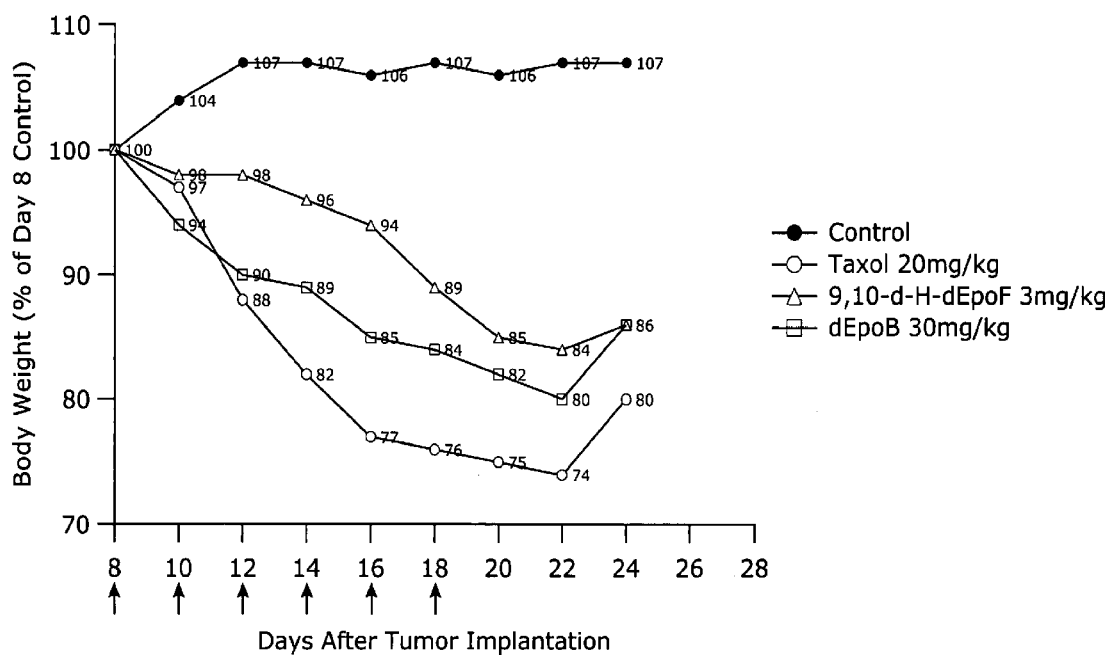
FIG. 47 shows the changes in body weight of nude mice bearing human mammary carcinoma (MX-1) tumor xenograft following treatment with 9,10-dehydro-dEpoF, dEpoB, and Taxol (6 hour infusion, Q2Dx6).
Figure 48:
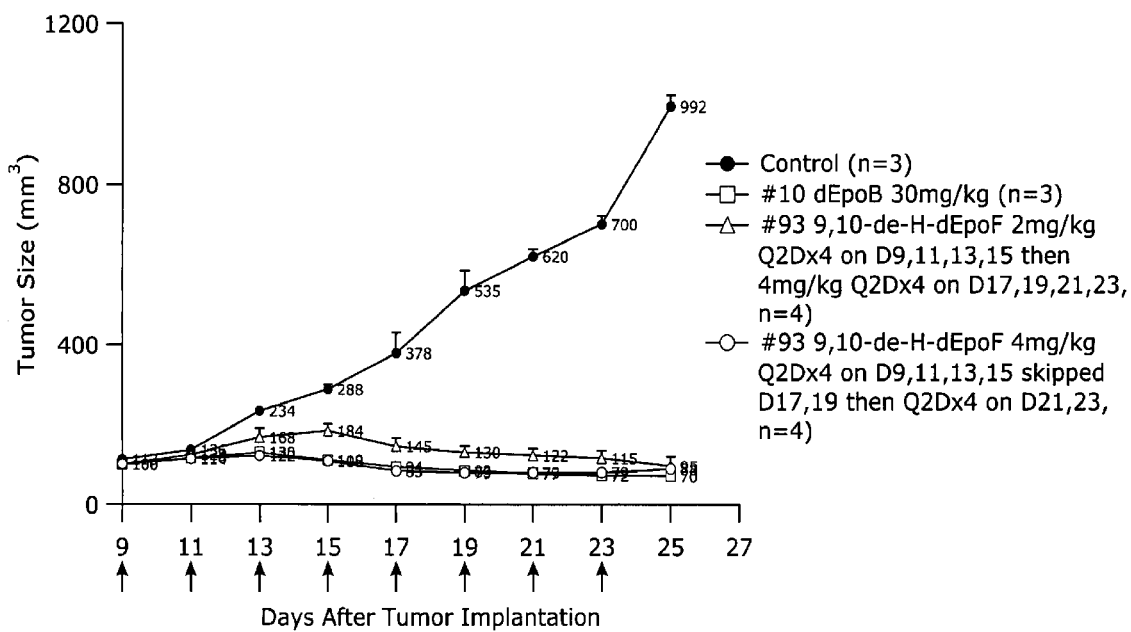
FIG. 48 shows the therapeutic effect of 9,10-dehydro-dEpoF and dEpoB in nude mice bearing human colon carcinoma HCT-116 xenograft (6 hour infusion, Q2Dx8).
Figure 49:
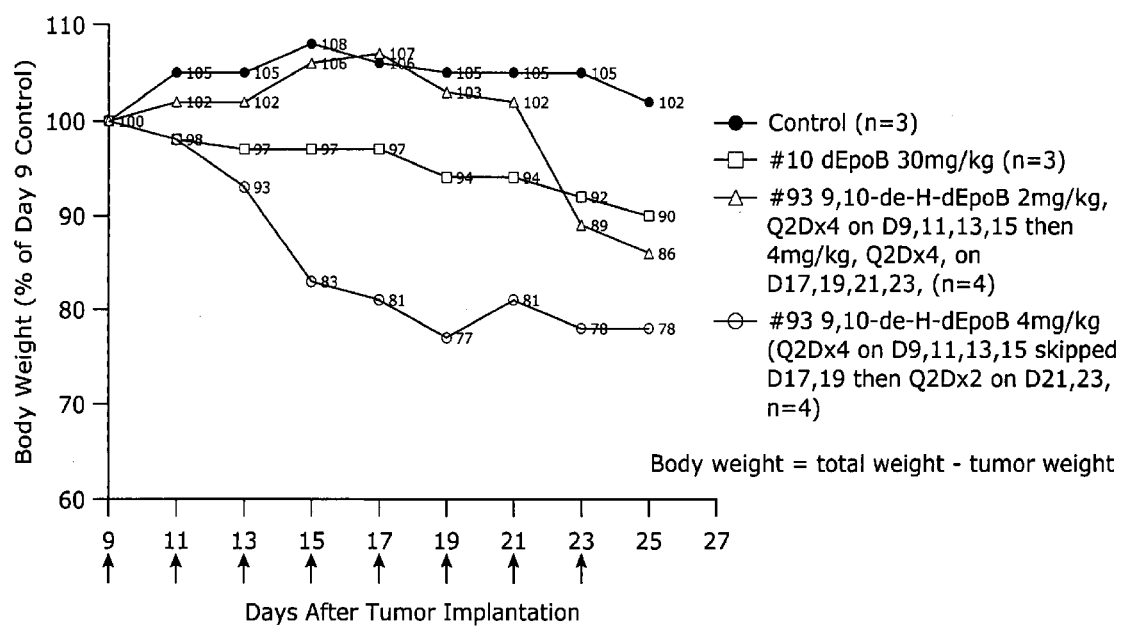
FIG. 49 shows the changes in body weight of nude mice bearing HCT-116 xenograft following treatment with 9,10-dehydro-dEpoF and dEpoB (6 hour infusion, Q2Dx8).
Figure 50:
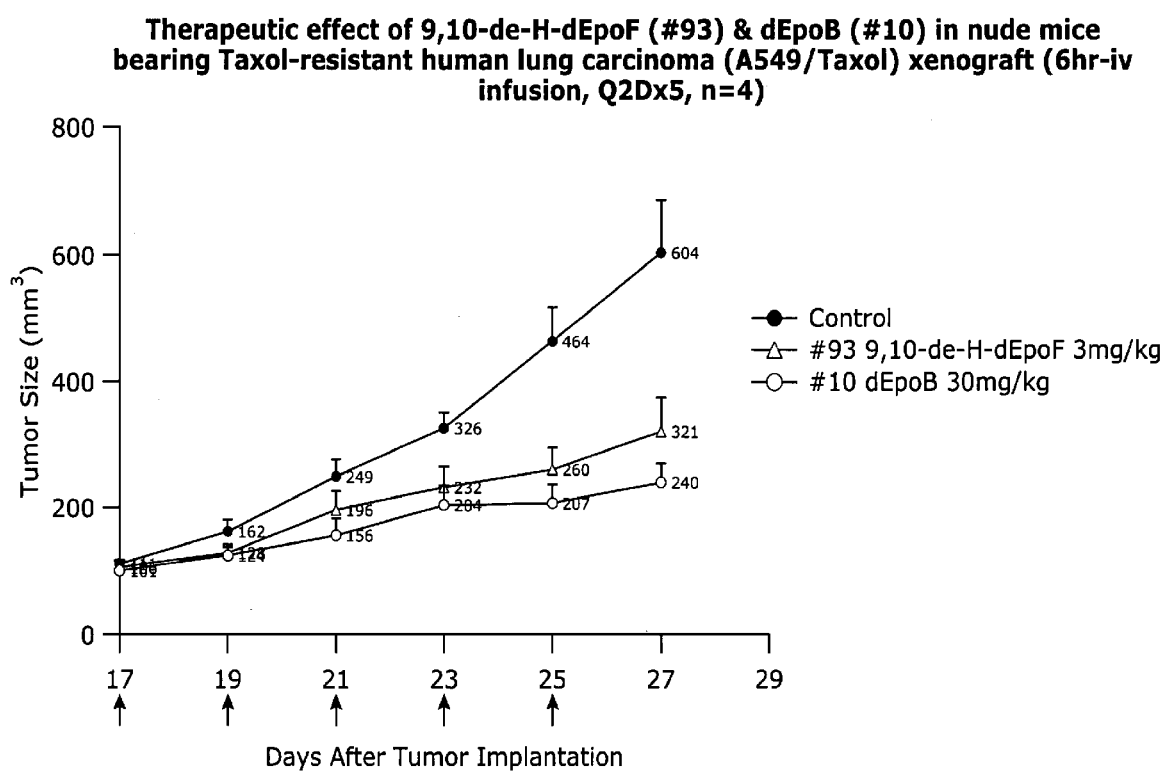
FIG. 50 shows the therapeutic effect of 9,10-dehydro-dEpoF and dEpoB in nude mice bearing Taxol-resistant human lung carcinoma (A549/Taxol) xenograft (6 hour infusion, Q2Dx5).
Figure 51:
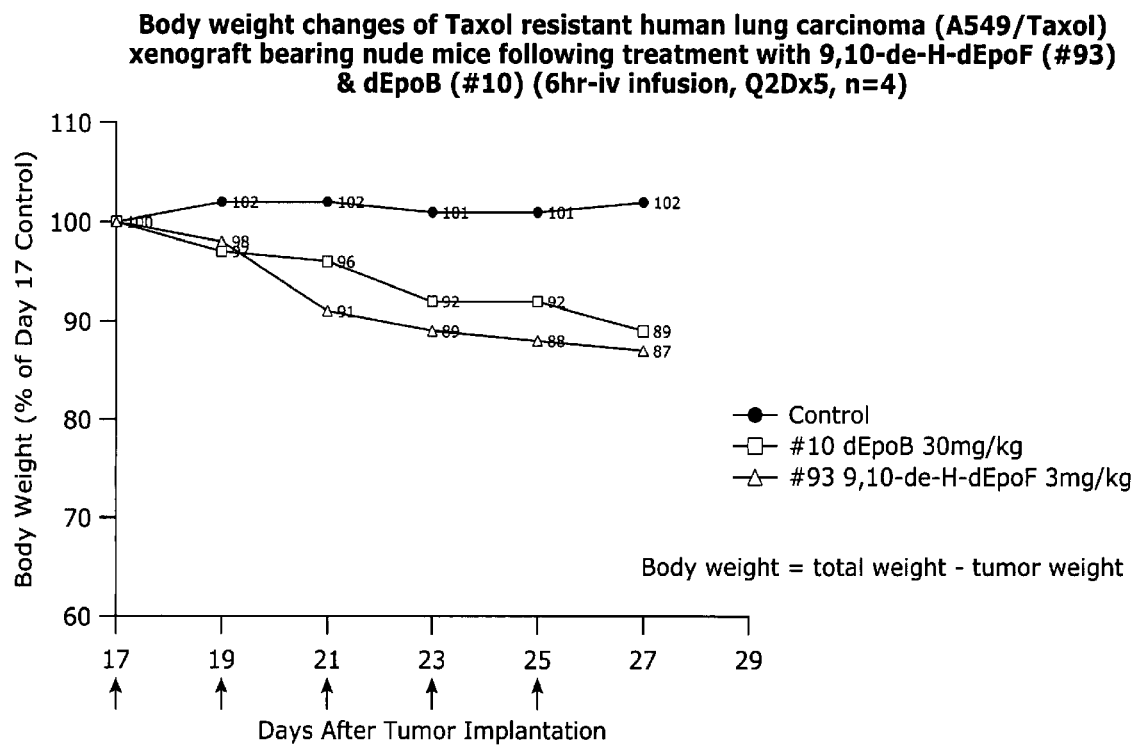
FIG. 51 shows changes in body weight of nude mice bearing Taxol-resistant human lung carcinoma (A549/Taxol) xenograft following treatment with 9,10-dehydro-dEpoF and dEpoB (6 hour infusion, Q2Dx5).

(E)-9,10-dehydroepothilone B (51) was evaluated against a variety of cell types to determine their antitumor potential. As shown in Table 4, (E)-9,10-dehydroepothiloneB (49) exhibits high cytotoxic activity against a variety of sensitive and resistant tumor cell lines. Direct comparison of 49 and EpoB (51) indicates this new analog possesses nearly 3-fold more potency than EpoB (51) making it one of the most potent epothilone analogs reported to date. Interestingly, α-epoxide series (50, 52) displayed a much lower activity than EpoB (51). FIG. 15 shows the findings for in vivo studies of compound 49.

TABLE 4

In vitro cytotoxicities (IC$_{50}$) with tumor cell lines[a]

| compound | CCRF-CEM | CCRF-CEM/VBL | CCRF-CEM/Taxol |
|---|---|---|---|
| 1 (dEpoB) | 0.0036 | 0.016 | 0.0046 |
| 28 | 0.0009 | 0.0042 | 0.0012 |
| 51 (EpoB) | 0.00062 | 0.0037 | 0.0011 |
| 49 | 0.00023 | 0.00032 | 0.00042 |
| 50 | 0.0134 | 0.0959 | 0.0802 |
| 52 | 0.083 | 0.4519 | 0.1507 |

[a]XTT assay following 72 h inhibition. CCRF-CEM is a human T-cell acute lymphoblastic leukemia cell line. The CCRF-CEM/VBL and CCRF-CEM/Taxol cell lines all overexpress P-glycoprotein and display a multidrug resistance phenotype to MDR-associated oncolytics.

In summary, delineated above is a powerful stereoselective total synthesis of 28 (Epo 3) and, following site-selective diimide reduction, dEpoB (1) itself. The described herein strategy was then straightforwardly applied to the preparation of the corresponding trifluoro analogs 2 and 29 (Epo 4). Furthermore, epoxidation of 28 provided 49 and 50, which upon site-selective diimide reduction gave Epothilone B(51) and 52. The data reported above point to the emergence of a most promising new family of anticancer drugs appropriate for further evaluation en route to then possible advancement to a human clinical setting. Furthermore the new synthesis strategy comprises a significant practical improvement in the total synthesis of dEpoB and Epothilone B. Parenthetically the study serves to underscore the potential applicability of target directed total synthesis, even in a multi step setting, in the quest for new substances of material clinical benefit.

EXPERIMENTALS

General Methods: Reagents obtained from commercial suppliers were used without further purification unless otherwise noted. The following solvents were obtained from a dry solvent system (passed through a prepacked column of alumina) and used without further drying: tetrahydrofuran, methylene chloride, diethyl ether, benzene, and toluene. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced to CDCl$_3$ (7.27 ppm for $^1$H and 77.0 ppm for $^{13}$C). Infrared spectra (IR) were obtained on a Perkin-Elmer FT-IR model 1600 spectrometer. Optical rotations were obtained on a JASCO model DIP-370 digital polarimeter at 22±2° C. Analytical thin-layer chromatography was performed on E. Merck silica gel 60 F254 plates. Compounds which were not UV active were visualized by dipping the plates in a ceric ammonium molybdate or para-anisaldehyde solution and heating. Silica gel chromatography was performed using the indicated solvent on Davisil® (grade 1740, type 60A, 170-400 mesh) silica gel.

Acronyms and Abbreviations

TES, triethylsilyl; TBS, Dimethyltertbutylsilyl; EDCI, 1-ethyl-3-(3-dimethylaminopropyl)carbodiimide; HF-PY, hydrogen fluoride in pyridine; DMAP, 4-N,N-dimethylaminopyridine; DCM, dichloromethane; DMF, N,N-dimethylformamide; THF, tetrahydrofuran.

Experimental

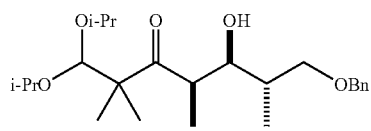

32

Compound 32: To a solution of freshly prepared LDA (11.6 mmol) in THF (25 mmol) was added dropwise a solution of ketone 30 (2.40 g, 10.4 mmol) in THF (6.8 mL) at −78° C. After stifling at −40° C. for 0.5 h, the mixture was cooled to −90° C. A solution of aldehyde 31 (1.38 g, 7.72 mmol) in THF (6.8 mL) was added dropwise. After stifling at −90° C. for 35 min, the reaction was quenched with sat. aq. NH$_4$Cl (15 mL) and extracted with EtOAc (50 mL×3). The combined organic extracts were dried over Na$_2$SO$_4$ and concentrated. Purification by flash column chromatography (SiO$_2$, hexane/EtOAc=15:1 to 12:1) gave 32 (2.09 g, 66%) and isomer 33 (0.39 g, 12%) both as yellow oils. 32: $[\alpha]_D^{25}$ 13.1 (c 1.22, CHCl$_3$); IR (film) v 3494, 2972, 2932, 1708, 1454, 1380, 1329, 1120, 1038, 998, 734 cm$^{-1}$; $^1$H NMR (400 MHz, CDCl$_3$) δ 0.98 (3H, d, J=6.9 Hz), 1.06 (3H, d, J=6.9 Hz), 1.10 (3H, d, J=6.1 Hz), 1.14 (3H, d, J=6.9 Hz), 1.15 (3H, s), 1.17 (3H, d, J=6.2 Hz), 1.18 (3H, s), 1.20 (3H, d, J=6.2 Hz), 1.81-1.92 (1H, m), 3.33 (1H, qd, J=7.0, 2.2. Hz), 3.51 (1H, dd, J=8.9, 6.3 Hz), 3.64 (1H, d, J=1.8 Hz), 3.66-3.71 (2H, m), 3.78-3.86 (2H, m), 4.51 (1H, d, J=12.0 Hz), 4.54 (1H, d, J=12.0 Hz), 4.58 (1H, s), 7.25-7.35 (5H, m); $^{13}$C NMR (100 MHz, CDCl$_3$) δ 10.0, 14.3, 20.5, 21.3, 21.9, 22.5, 23.5, 23.6, 36.4, 42.1, 54.1, 69.8, 71.2, 72.8, 73.3, 73.4, 103.8, 127.6, 127.7 (2C), 128.5 (2C), 138.9, 221.6; LRMS (ESI) calcd for C$_{24}$H$_{40}$O$_5$Na [M+Na$^+$] 431.3, found 431.4.

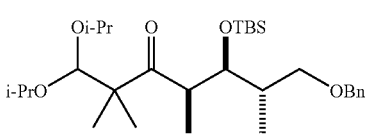

32a

Compound 32a (not shown): To a cooled (−40° C.) solution of alcohol 32 (1.01 g, 2.47 mmol) and 2,6-lutidine (691 μL, 5.93 mmol) was added TBSOTf (681 μL, 3.00 mmol), and the mixture was warmed to −20° C. over 3.5 h. The reaction was quenched with sat. aq. NaHCO$_3$ (10 mL). After extraction with hexane (50 mL×3), the combined organic extracts were dried over Na$_2$SO$_4$ and concentrated. Purification by flash column chromatography (SiO$_2$, hexane/EtOAc=50:1) gave 32a (1.25 g, 2.39 mmol, 97%) as a colorless oil; $[\alpha]_D^{25}$±19.7 (c 0.58, CHCl$_3$); IR (film) v 2966, 2931, 1696, 1455, 1378, 1320, 1255, 1091, 1044, 991, 873, 838, 773 cm$^{-1}$; $^1$H NMR (400 MHz, CDCl$_3$) δ 0.08 (6H, s), 0.89 (9H, s), 0.99 (3H, d, J=7.0 Hz), 1.04 (3H, d, J=7.0 Hz), 1.07 (3H, d, J=7.0 Hz), 1.07 (3H, s), 1.14 (3H, d, J=6.1 Hz), 1.17 (3H, s), 1.17 (3H, d, J=6.0 Hz), 1.20 (3H, d, J=6.2 Hz), 1.76-1.85 (1H, m), 3.21

(1H, dd, J=9.2, 7.3 Hz), 3.32 (1H, quint, J=7.4 Hz), 3.62 (1H, dd, J=9.2, 5.7 Hz), 3.78-3.85 (2H, m), 3.87 (1H, dd, J=7.7, 2.0 Hz), 4.46 (1H, d, J=12.1 Hz), 4.50 (1H, d, J=12.1 Hz), 4.73 (1H, s), 7.24-7.37 (5H, m); $^{13}$C NMR (100 MHz, CDCl$_3$) δ −3.6, −3.3, 15.6, 16.8, 18.7, 18.8, 21.8, 22.1, 22.5, 23.5, 23.7, 26.4 (3C), 39.0, 46.2, 54.0, 69.7, 70.9, 72.1, 73.4, 76.7, 103.1, 127.6, 127.8 (2C), 128.5 (2C), 139.0, 218.9; LRMS (ESI) calcd for C$_{30}$H$_{54}$O$_5$SiNa [M+Na$^+$] 545.4, found 545.4.

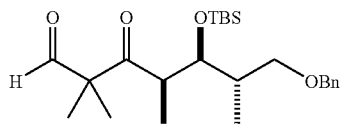

Compound 34: The mixture of 32a (3.03 g, 5.79 mmol) and p-TsOH.H$_2$O (286 mg) in aqueous THF (64 mL, THF/H$_2$O=4:1) was heated under reflux for 6.5 h. The reaction mixture was cooled to rt and poured into sat. aq. NaHCO$_3$ (25 mL). After extraction with EtOAc (100 mL+50 mL×2), the combined organic layers were washed with brine, dried over Na$_2$SO$_4$ and concentrated. Purification by flash column chromatography (SiO$_2$, hexane/EtOAc=50:1 to 30:1) gave 34 (2.37 g, 5.64 mmol, 98%) as a colorless oil: [α]$_D^{25}$ −25.8 (c 0.515, CHCl$_3$); IR (film) ν 2955, 2931, 1731, 1696, 1455, 1360, 1255, 1091, 1026, 873, 826, 767 cm$^{-1}$; $^1$H NMR (400 MHz, CDCl$_3$) δ 0.06 (3H, s), 0.07 (3H, s), 0.90 (9H, s), 0.95 (3H, d, J=7.1 Hz), 1.03 (3H, d, J=7.0 Hz), 1.28 (3H, s), 1.33 (3H, s), 1.73-1.82 (1H, m), 3.16 (1H, dd, J=9.2, 6.1 Hz), 3.28 (1H, quint, J=7.3 Hz), 3.55 (1H, dd, J=9.2, 6.7 Hz), 3.91 (1H, dd, J=7.8, 2.1 Hz), 4.46 (2H, s), 7.27-7.36 (5H, m), 9.58 (1H, s); $^{13}$C NMR (100 MHz, CDCl$_3$) δ −3.6, −3.5, 15.7, 16.3, 18.6, 19.8, 20.1, 26.3 (3C), 39.1, 47.0, 61.1, 71.9, 73.4, 75.8, 127.7, 128.0 (2C), 128.5 (2C), 138.6, 201.3, 213.3; LRMS (ESI) calcd for C$_{24}$H$_{40}$O$_4$SiNa [M+Na$^+$] 443.3, found 443.2.

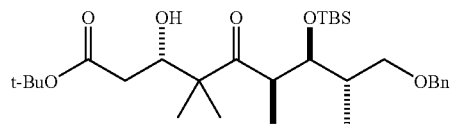

Compound 35: To a solution of freshly prepared LDA (18 mL of a 0.5 M solution in Et$_2$O, 9.0 mmol) in Et$_2$O (20 mL) was added t-butyl acetate (1.16 mL, 8.61 mmol) at −78° C. After stirring for 50 min, CpTiCl(OR)$_2$ (100 mL of a 0.1 M solution in Et$_2$O, 10.0 mmol) was added dropwise over 65 min via syringe pump. After stirring for 20 min, the reaction mixture was warmed to −30° C., stirred for 50 min, and re-cooled to −78° C. A solution of 34 (2.42 g, 5.75 mmol) in Et$_2$O (9 mL) was added dropwise over 10 min, and the resulting mixture was stirred at −78° C. After stirred for 2 h, the reaction was quenched with aqueous THF (5 M H$_2$O, 37 mL) and stirred at rt for 2 h. After addition of water (40 mL), the mixture was stirred for further 1 h. The precipitate formed was filtered off by Celite (Et$_2$O rinse), and the filtrate was washed with water (40 mL). The aqueous layer was extracted with Et$_2$O (100 mL×2) and the combined organic layers were washed with brine (40 mL), dried over Na$_2$SO$_4$ and concentrated. Purification by flash column chromatography (SiO$_2$, hexane/EtOAc=10:1) gave 35 (2.65 g, 4.94 mmol, 86%) as a pale yellow oil; [α]$_D^{25}$ −20.3 (c 1.0, CHCl$_3$); IR (film) ν 3523, 2957, 2930, 2856, 1732, 1700, 1472, 1368, 1252, 1152, 1091, 1042, 986, 834, 774 cm$^{-1}$; $^1$H NMR (400 MHz, CDCl$_3$) δ 0.07 (3H, s), 0.07 (3H, s), 0.90 (9H, s), 0.99 (3H, d, J=7.0 Hz), 1.07 (3H, d, J=7.0 Hz), 1.10 (3H, s), 1.14 (3H, s), 1.47 (9H, s), 1.77-1.83 (1H, m), 2.26 (1H, dd, J=16.0, 10.0 Hz), 2.34 (1H, dd, J=15.9, 2.7 Hz), 3.23 (1H, dd, J=9.2, 7.1 Hz), 3.35 (1H, d, J=2.7 Hz, —OH), 3.36 (1H, quint, J=7.0 Hz), 3.61 (1H, dd, J=9.2, 5.9 Hz), 3.88 (1H, dd, J=7.6, 2.0 Hz), 4.17 (1H, dt, J=10.0, 2.7 Hz), 4.48 (2H, s), 7.27-7.36 (5H, m); $^{13}$C NMR (100 MHz, CDCl$_3$) δ −3.5, −3.4, 16.3, 16.7, 18.7, 20.1, 21.6, 26.4 (3C), 28.3 (3C), 38.0, 39.1, 45.8, 51.8, 72.2, 72.9, 73.5, 76.7, 81.4, 127.7, 128.0 (2C), 128.5 (2C), 138.8, 172.7, 219.6; LRMS (ESI) calcd for C$_{30}$H$_{52}$O$_6$SiNa [M+Na$^+$] 559.3, found 559.4.

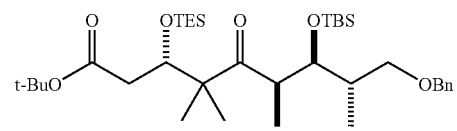

Compound 35a (Not Shown): To a mixture of alcohol 35 (10.2 g, 18.9 mmol) and imidazole (2.70 g, 39.7 mmol) in DMF (25 mL) was added TESCl (3.3 mL, 19.8 mmol) at 0° C., and the mixture was stirred at rt for 2 h. The reaction was quenched with sat. aq. NaHCO$_3$ (50 mL). After extraction with hexane (500 mL+120 mL×2), the combined organic extracts were washed successively water (30 mL×2) and brine (30 mL), dried over Na$_2$SO$_4$ and concentrated. Purification by flash column chromatography (SiO$_2$, hexane/EtOAc=40:1) gave 35a (12.1 g, 18.5 mmol, 98%) as a colorless oil: [α]$_D^{25}$ −38.0 (c 0.46, CHCl$_3$); IR (film) ν 2955, 2877, 1733, 1697, 1456, 1367, 1298, 1251, 1155, 1099, 988, 835, 742 cm$^{-1}$; $^1$H NMR (400 MHz, CDCl$_3$) δ 0.05 (6H, s), 0.57-0.68 (6H, m), 0.89 (9H, s), 0.95 (9H, t, J=7.9 Hz), 0.99 (3H, d, J=7.0 Hz), 1.02 (3H, d, J=6.8 Hz), 1.04 (3H, s), 1.18 (3H, s), 1.45 (9H, s), 1.70-1.79 (1H, m), 2.16 (1H, dd, J=17.0, 7.0 Hz), 2.40 (1H, dd, J=17.0, 3.1 Hz), 3.22 (1H, dd, J=9.1, 7.5 Hz), 3.31 (1H, quint, J=6.9 Hz), 3.61 (1H, dd, J=9.1, 5.4 Hz), 3.83 (1H, dd, J=7.3, 2.3 Hz), 4.30 (1H, dd, J=6.9, 3.1 Hz), 4.48 (2H, s), 7.27-7.36 (5H, m); $^{13}$C NMR (100 MHz, CDCl$_3$) δ −3.5, −3.4, 5.3 (3C), 7.3 (3C), 15.3, 16.9, 18.7, 20.1, 23.4, 26.4 (3C), 28.3 (3C), 39.1, 41.1, 46.2, 53.4, 72.2, 73.4, 74.3, 76.7, 80.6, 127.6, 127.9 (2C), 128.5 (2C), 138.9, 171.5, 218.4; LRMS (ESI) calcd for C$_{36}$H$_{66}$O$_6$Si$_2$Na [M+Na$^+$] 673.4, found 673.5.

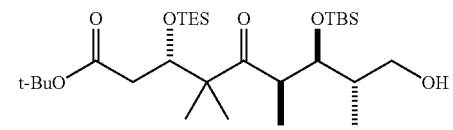

Compound 35b (Not Shown): To a stirred solution of 35a (242.5 mg, 0.373 mmol) in EtOH (5.7 mL) was added Pd/C (10% wt, 24.2 mg) and the mixture was stirred under an atmosphere of H$_2$. After stirred for 30 min, the mixture was filtered through a pad of Celite, which was rinsed with EtOH. The filtrate was concentrated and purified by flash column chromatography (SiO$_2$, hexane/EtOAc=10:1) gave 35b (172.6 mg, 0.308 mmol, 83%) as a colorless oil; [α]$_D^{25}$ −16.1 (c 0.62, CHCl$_3$); IR (film) ν 3543, 2956, 1732, 1696, 1472, 1368, 1299, 1252, 1155, 1100, 988, 837, 775, 742 cm$^{-1}$; $^1$H NMR (400 MHz, CDCl$_3$) δ 0.10 (3H, s), 0.12 (3H, s), 0.60-

0.68 (6H, m), 0.93 (9H, s), 0.96 (9H, t, J=8.0 Hz), 0.99 (3H, d, J=7.1 Hz), 1.10 (3H, d, J=6.9 Hz), 1.14 (3H, s), 1.20 (3H, s), 1.45 (9H, s), 1.46-1.55 (1H, m), 2.21 (1H, dd, J=17.2, 7.1 Hz), 2.39 (1H, dd, J=17.2, 2.8 Hz), 2.54 (1H, t, J=5.8 Hz, —OH), 3.30 (1H, quint, J=6.9 Hz), 3.58 (1H, dt, J=11.5, 5.5 Hz), 3.66 (1H, dt, J=11.3, 5.4 Hz), 3.92 (1H, dd, J=8.0, 2.1 Hz), 4.32 (1H, dd, J=7.1, 2.9 Hz); $^{13}$C NMR (100 MHz, CDCl$_3$) δ −3.6, −3.5, 5.3 (3C), 7.2 (3C), 16.0, 16.1, 18.6, 20.0, 23.4, 26.4 (3C), 28.3 (3C), 40.0, 40.9, 46.9, 53.7, 64.8, 73.3, 78.1, 80.9, 171.7, 218.5; LRMS (ESI) calcd for C$_{29}$H$_{60}$O$_6$Si$_2$Na [M+Na$^+$] 583.4, found 583.5.

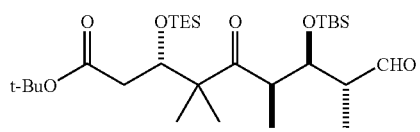

35c

Compound 35c (Not shown): To a stirred mixture of alcohol 35b (644.1 mg, 1.15 mmol) and powdered MS4A (1.14 g) in CH$_2$Cl$_2$ (22 mL) were added NMO (403.5 mg, 3.44 mmol) followed by TPAP (28.2 mg, 80.4 μmol). After stirred at rt for 48 min, the mixture was filtered through a silica gel column (hexane/Et$_2$O=5:1) gave 35c (610.1 mg, 1.09 mmol, 95%) as a colorless oil; [α]$_D^{25}$ −69.6 (c 0.25, CHCl$_3$); IR (film) ν 2955, 2878, 1732, 1696, 1472, 1368, 1253, 1155, 1097, 989, 837 cm$^{-1}$; $^1$H NMR (400 MHz, CDCl$_3$) δ 0.09 (3H, s), 0.10 (3H, s), 0.59-0.68 (6H, m), 0.89 (9H, s), 0.95 (9H, t, J=8.0 Hz), 1.08 (3H, s), 1.11 (3H, d, J=6.9 Hz), 1.14 (3H, d, J=7.1 Hz), 1.24 (3H, s), 1.45 (9H, s), 2.19 (1H, dd, J=17.0, 6.7 Hz), 2.33 (1H, qt, J=7.1, 2.2 Hz), 2.41 (1H, dd, J=17.0, 3.3 Hz), 3.28 (1H, quint, J=7.5 Hz), 4.07 (1H, dd, J=7.9, 2.2 Hz), 4.32 (1H, dd, J=6.7, 3.2 Hz), 9.74 (1H, d, J=2.0 Hz); $^{13}$C NMR (100 MHz, CDCl$_3$) δ −3.8, −3.5, 5.3 (3C), 7.2 (3C), 12.6, 15.6, 18.5, 20.5, 23.3, 26.2 (3C), 28.3 (3C), 41.1, 46.9, 51.1, 53.5, 74.0, 76.5, 80.7, 171.1, 204.3, 218.0; LRMS (ESI) calcd for C$_{29}$H$_{58}$O$_6$Si$_2$Na [M+Na$^+$] 581.3, found 581.3.

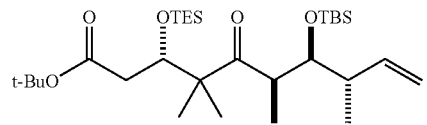

36

Compound 36: MePPh$_3$I (197.4 mg, 0.488 mmol) in THF (4.0 mL) was treated with n-BuLi (287 μL of a 1.6 M solution in hexane, 0.460 mmol) at 0° C. After stirred at 0° C. for 0.5 h, the resulting suspension was cooled to −78° C. and a solution of aldehyde 35c (160.6 mg, 0.2873 mmol) was added. The mixture was allowed to warm to −5° C. over 4 h. The reaction was quenched with sat. aq. NH$_4$Cl (5 mL) and extracted with Et$_2$O (20 mL×3). The combined organic extracts were washed with brine (10 mL), dried over Na$_2$SO$_4$, and concentrated. The residue was purified by flash column chromatography (SiO$_2$, hexane/Et$_2$O=20:1) gave 36 (125.3 mg, 0.225 mmol, 78%) as a colorless oil; [α]$_D^{25}$ −33.6 (c 0.250, CHCl$_3$); IR (film) ν 2956, 2878, 1733, 1696, 1472, 1367, 1299, 1253, 1156, 1100, 988, 837, 774 cm$^{-1}$; $^1$H NMR (400 MHz, CDCl$_3$) δ 0.08 (3H, s), 0.08 (3H, s), 0.60-0.68 (6H, m), 0.93 (9H, s), 0.96 (9H, t, J=8.0 Hz), 1.04 (6H, d, J=7.0 Hz), 1.09 (3H, s), 1.20 (3H, s), 1.45 (9H, s), 2.08-2.15 (1H, m), 2.29 (1H, dd, J=17.0, 7.0 Hz), 2.41 (1H, dd, J=17.0, 3.1 Hz), 3.08 (1H, quint, J=7.0 Hz), 3.84 (1H, dd, J=7.0, 2.1 Hz), 4.32 (1H, dd, J=7.0, 3.1 Hz), 5.02 (1H, dd, J=17.9, 1.0 Hz), 5.06 (1H, dd, J=10.5, 1.0 Hz), 5.93 (1H, ddd, J=17.9, 10.5, 7.7 Hz); $^{13}$C NMR (100 MHz, CDCl$_3$) δ −3.6, −3.3, 5.4 (3C), 7.2 (3C), 15.2, 18.7, 19.0, 20.2, 23.6, 26.4 (3C), 28.3 (3C), 41.1, 43.8, 46.4, 53.5, 73.9, 76.6, 80.6, 115.5, 140.2, 171.5, 218.5; LRMS (ESI) calcd for C$_{30}$H$_{60}$O$_5$Si$_2$Na [M+Na$^+$] 579.4, found 579.4.

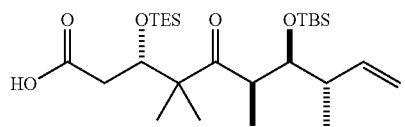

25

Compound 25: To a solution of t-butyl ester 36 (1.79 g, 3.21 mmol) and 2,6-lutidine (1.5 mL, 12.8 mmol) in CH$_2$Cl$_2$ (21 mL) was added TESOTf (1.45 mL, 6.42 mmol) at 0° C. After stirred at 0° C. for 20 min, the mixture was stirred at rt for 3 h. The mixture was diluted with Et$_2$O (300 mL), washed with successively 5% aq. KHSO$_4$ (30 mL×2) and brine (40 mL), dried over Na$_2$SO$_4$, and concentrated. The residue was dried under high vacuum to give silylester (2.31 g). The crude silylester (2.31 g) was dissolved in aqueous THF (35 mL, THF/H$_2$O=6:1) and treated with sat. aq. NaHCO$_3$ (5 mL). After stirred at rt for 20 min, the resulting suspension was diluted with Et$_2$O (300 mL) and acidified with aqueous 5% KHSO$_4$ (30 mL). After layers were separated, the aqueous layer was extracted with Et$_2$O (60 mL) and the combined organic layers were washed with brine (30 mL×2), dried over Na$_2$SO$_4$ and concentrated. The residue was dried under high vacuum to give crude acid 25 (1.89 g, contaminated with TESOH) as a colorless oil, which was used for next reaction without further purification. Purified for characterization by flash column chromatography over silica gel eluting with hexane/EtOAc=4/1.

[α]$_D^{25}$ −30.7 (c 0.985, CHCl$_3$); IR (film) ν 2956, 2936, 2879, 1712, 1472, 1417, 1303, 1253, 1107, 1046, 1003, 988, 872, 837, 775, 741 cm$^{-1}$; $^1$H NMR (400 MHz, CDCl$_3$) δ 0.08 (3H, s), 0.09 (3H, s), 0.59-0.67 (6H, m), 0.93 (9H, s), 0.96 (9H, t, J=8.1 Hz), 1.05 (3H, d, J=7.0 Hz), 1.05 (3H, d, J=7.0 Hz), 1.20 (3H, s), 1.21 (3H, s), 2.06-2.13 (1H, m), 2.34 (1H, dd, J=16.4, 7.4 Hz), 2.50 (1H, dd, J=16.4, 3.0 Hz), 3.06 (1H, quint, J=7.3 Hz), 3.87 (1H, dd, J=7.5, 1.8 Hz), 4.40 (1H, dd, J=7.3, 2.9 Hz), 5.01 (1H, dd, J=18.0, 0.9 Hz), 5.07 (1H, dd, J=10.4, 1.2 Hz), 5.93 (1H, ddd, J=18.0, 10.4, 7.8 Hz); $^{13}$C NMR (100 MHz, CDCl$_3$) δ −3.6, −3.3, 5.3 (3C), 7.1 (3C), 15.6, 18.7, 19.1, 19.2, 24.1, 26.4 (3C), 39.8, 43.6, 46.4, 53.5, 73.7, 76.6, 115.6, 140.0, 177.9, 218.7; LRMS (ESI) calcd for C$_{26}$H$_{52}$O$_5$Si$_2$Na [M+Na$^+$] 523.3, found 522.9.

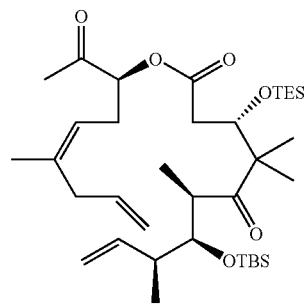

45

Compound 45: The 3-O-TES-6-O-TBS protected acid 25 was dried through azeotropic distillation from benzene. Freshly dried alcohol 43 (200 mg, 1.19 mmol) is dissolved in DCM (10 mL) and cooled to 0° C., at which point solid DMAP (167 mg, 1.37 mmol) and solid EDCI (261 mg, 1.37 mmol) are added. After stirring the reaction mixture at 0° C. for 15 min, a solution of acid 25 (425 mg, 0.85 mmol) in DCM (2 mL) is added dropwise. The cooling bath is removed and stifling continued for another 2 hours. The crude reaction mixture is diluted with DCM (10 mL) and stripped onto silica and purified using silica gel chromatography employing 10% EtOAC/Hexanes as the eluent yielding ester 45 (380 mg, 81% yield, two steps, starting from 36) as a clear oil: $[\alpha]_D$–15.1 (c 1.2, CDCl$_3$); IR (neat) 2955, 2932, 2877, 1743, 1732, 1694, 1474, 1461, 1417, 1380, 1360, 1295, 1252, 1169, 1094, 1043, 988.3, 912.9, 871.4, 836.5, 774.8, 741.6 cm$^{-1}$; $^1$H NMR (500 MHz, CDCl$_3$) 0.08 (3H, s), 0.08 (3H, s), 0.60-0.68 (6H, m), 0.93 (9H, s), 0.95 (9H, t, J=8.0 Hz), 1.04 (3H, d, J=6.9 Hz), 1.05 (3H, d, J=6.9 Hz), 1.10 (3H, s), 1.25 (3H, s), 1.69 (3H, s), 2.08-2.15 (2H, m), 2.16 (3H, s), 2.38 (1H, dd, J=17.0, 7.0 Hz), 2.48 (2H, t, J=6.5 Hz), 2.57 (1H, dd, J=17.0, 2.7 Hz), 2.71-2.76 (2H, m), 3.07 (1H, quint, J=7.0 Hz), 3.83 (1H, d, J=7.2 Hz), 4.36 (1H, dd, J=7.0, 2.7 Hz), 4.97-5.07 (4H, m), 5.19 (1H, t, J=7.0), 5.73 (1H, td, J=15.4, 5.9 Hz), 5.92 (1H, td, J=15.7, 8.0 Hz); $^{13}$C NMR (500 MHz, CDCl$_3$) δ 218.4, 205.4, 172.1, 140.1, 137.4, 135.4, 119.1, 115.8, 115.6, 78.7, 76.5, 73.9, 53.3, 46.3, 43.7, 39.6, 36.6, 29.2, 26.7, 26.4, 23.8, 23.7, 19.9, 18.9, 18.7, 15.4, 7.06, 5.30, –3.29, –3.62; LRMS (ESI) calcd for C$_{36}$H$_{66}$O$_6$Si$_2$Na [M+Na$^+$] 673.4, found 673.5.

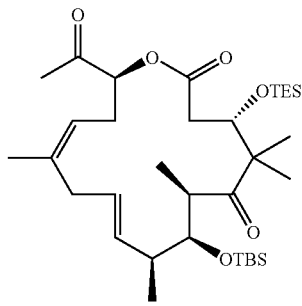

47

Compound 47: To a solution of compound 45 (20 mg, 0.031 mmol) in dry toluene (60 mL) at reflux was added in one portion a solution of tricyclohexylphosphine[1,3-bis(2,4,6-trimethylphenyl)-4,5-dihydroimidazol-2-ylidene][benzylidene]ruthenium (IV) dichloride (5.2 mg, 0.0061 mmol) in dry toulene (2 mL) and heated for 10 minutes. The reaction mixture was cooled immediately in ice bath and stripped onto silica and purified using silica gel chromatography employing 4-10% EtOAc/pentane gradient as the eluent to furnish compound 47 (15 mg, 78% yield) as an oil: [α] –28.6 (c 1.2, CHCl$_3$); IR (neat) 2955, 2933, 2878, 1745, 1731, 1695, 1471, 1462, 1380, 1361, 1251, 1159, 1104, 1080, 1019, 985.0, 876.1, 835.5, 774.7, 743.1, 670.1 cm$^{-1}$; $^1$H NMR (500 MHz, CDCl$_3$) 0.07 (3H, s), 0.10 (3H, s), 0.59-0.68 (6H, m), 0.91 (9H, t, J=8.0 Hz), 0.93 (9H, s), 1.04 (3H, d, J=7.0 Hz), 1.10 (3H, s), 1.11 (3H, d, J=7.0 Hz), 1.17 (3H, s), 1.71 (3H, s), 2.21 (3H, s), 2.27-2.32 (1H), 2.38 (1H, dd, J=14.6, 6.8 Hz), 2.51-2.61 (2H, m), 2.57 (1H, dd, J=15.5, 3.3 Hz), 2.93-3.1 (3H, m), 3.94 (1H, d, J=8.5 Hz), 4.28 (1H, dd, J=8.6, 3.0 Hz), 5.04 (1H, dd, J=8.7, 2.4), 5.16 (1H, t, J=7.5), 5.73 (1H, tdd, J=12.8, 9.94, 6.9 Hz), 5.92 (1H, ddd, J=18.0, 10.3, 7.8 Hz); $^{13}$C NMR (125 MHz, CDCl$_3$) δ 215.9, 204.8, 171.3, 140.0, 132.7, 129.2, 118.6, 79.1, 78.2, 75.4, 54.0, 48.2, 41.7, 40.3, 35.0, 29.2, 26.6, 26.5, 23.5, 22.8, 20.6, 18.8, 17.5, 14.3, 7.19, 5.53, –3.36; LRMS (ESI) calcd. for C$_{34}$H$_{62}$O$_6$Si$_2$ 645.4, found 645.4 (M+Na$^+$).

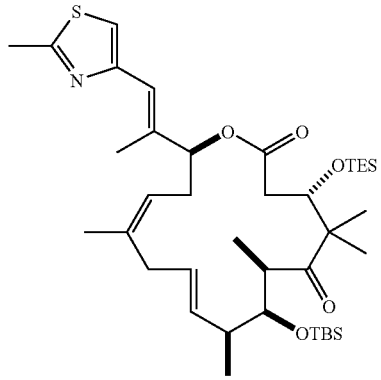

39a

Compound 39a: To a solution of Wittig reagent (19.1 mg, 54.7 μmol) in THF (0.4 mL) was added KHMDS (109 μL of a 0.5 M solution in toluene, 54.7 μmol) at 0° C. The mixture was stirred at 0° C. for 0.5 h and then cooled to –78° C. To the mixture was added dropwise a solution of ketone 47 (5.7 mg, 9.12 μmol) in THF (0.3 mL), and the resulting mixture was allowed to warm to –20° C. over 1.5 h. The reaction was quenched with sat. aq. NH$_4$Cl (2 mL) and extracted with EtOAc (7 mL×3). The combined organic layers were dried over Na$_2$SO$_4$ and concentrated. The residue was purified by flash column chromatography (SiO$_2$, hexane/Et$_2$O=10:1) gave 5.6 mg of inseparable olefin mixture (E/Z=9:1). The mixture was purified by preparative TLC (hexane/Et$_2$O=4:1) gave pure 39a (5.0 mg, 6.96 μmol, 76%) as a colorless oil; $[\alpha]_D^{25}$–41.5 (c 0.715, CHCl$_3$); IR (film) ν 2955, 2884, 1737, 1690, 1467, 1378, 1249, 1179, 1102, 1014, 979, 879, 826, 773 cm$^{-1}$; $^1$H NMR (400 MHz, CDCl$_3$) δ 0.08 (3H, s), 0.12 (3H, s), 0.57 (6H, q, J=7.8 Hz), 0.89 (9H, t, J=8.0 Hz), 0.93 (9H, s), 1.04 (3H, s), 1.06 (3H, d, J=7.1 Hz), 1.12 (3H, s), 1.17 (3H, d, J=7.1 Hz), 1.68 (3H, s), 2.15 (3H, d, J=0.8 Hz), 2.14-2.27 (2H, m), 2.45 (1H, dd, J=14.0, 4.8 Hz), 2.50 (1H, dd, J=14.9, 3.2 Hz), 2.64-2.74 (2H, m), 2.72 (3H, s), 3.02 (1H, quint, J=7.0 Hz), 3.10 (1H, dd, J=14.4, 7.3 Hz), 3.96 (1H, d, J=8.7 Hz), 4.43 (1H, dd, J=8.3, 2.9 Hz), 5.22 (1H, dd, J=9.8, 5.7 Hz), 5.33-5.42 (2H, m), 5.69 (1H, dd, J=15.8, 8.2 Hz), 6.57 (1H, s), 6.96 (1H, s); $^{13}$C NMR (100 MHz, CDCl$_3$) δ –3.3, –3.2, 5.6 (3C), 7.1 (3C), 15.0, 17.2, 18.8, 19.4, 21.4, 21.7, 23.8, 24.3, 26.5 (3C), 33.2, 35.6, 41.3, 41.8, 48.2, 54.0, 74.4, 77.4, 79.3, 116.4, 120.5, 121.0, 129.3, 132.1, 137.8, 138.0, 152.7, 164.8, 170.7, 216.8; LRMS (ESI) calcd for C$_{39}$H$_{68}$NO$_5$SSi$_2$ [M+H$^+$] 718.4, found 718.3.

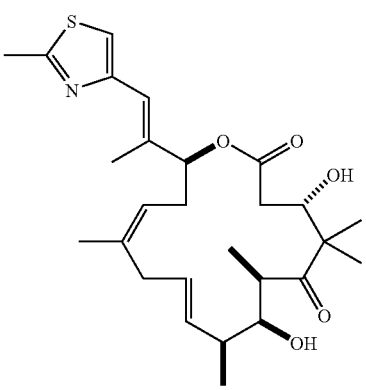

28

Compound 28 (Epo 3): To a solution of 39a (298.8 mg, 0.416 mmol) in THF (6.5 mL) in a plastic tube was added HF.pyridine (3.2 mL) at 0° C., and the mixture was stirred at rt for 3 h. The reaction was quenched with dropwise addition of TMSOMe (30 mL) at 0° C. After concentrated and dried under high vacuum, the residue was purified by flash column chromatography (SiO$_2$, hexane/EtOAc=1:1) gave 28 (196.6 mg, 0.402 mmol, 97%) as a white solid; [α]$_D^{25}$ −96.6 (c 0.235, CHCl$_3$); IR (film) ν 3502, 2970, 2927, 1733, 1685, 1506, 1456, 1375, 1251, 1152, 1040, 977 cm$^{-1}$; $^1$H NMR (400 MHz, CDCl$_3$) δ 1.06 (3H, s), 1.11 (3H, d, J=7.0 Hz), 1.22 (3H, d, J=6.8 Hz), 1.28 (3H, s), 1.72 (3H, s), 2.10 (3H, s), 2.31-2.40 (2H, m), 2.43 (1H, dd, J=16.0, 3.7 Hz), 2.49 (1H, dd, J=16.0, 9.2 Hz), 2.55-2.68 (2H, m), 2.71 (3H, s), 2.98 (1H, dd, J=14.4, 6.4 Hz), 3.16 (1H, quint, J=6.2 Hz), 3.76 (1H, dd, J=5.9, 3.2 Hz), 4.30 (1H, dd, J=9.2, 3.7 Hz), 5.18 (1H, brt, J=7.3 Hz), 5.32 (1H, dd, J=8.4, 2.5 Hz), 5.63 (1H, dd, J=15.7, 6.4 Hz), 5.60 (1H, ddd, J=15.7, 6.9, 5.1 Hz), 6.60 (1H, s), 6.98 (1H, s); $^{13}$C NMR (100 MHz, CDCl$_3$) δ 15.1, 16.0, 17.7, 19.2, 19.5, 22.5, 23.6, 32.0, 35.0, 39.6, 40.3, 44.8, 53.3, 71.8, 75.6, 78.3, 116.1, 119.6, 120.5, 129.9, 131.3, 137.5, 138.2, 152.2, 165.0, 170.7, 218.8; LRMS (ESI) calcd for C$_{27}$H$_{40}$NO$_5$S [M+H$^+$] 490.3, found 490.2.

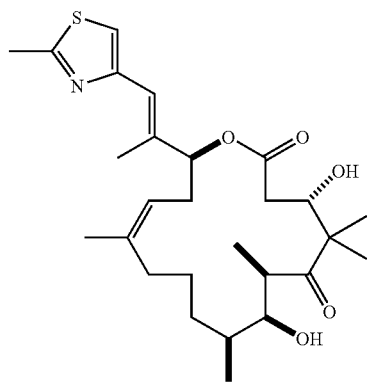

1 dEpoB (1, Epo 1): To a solution of 28 (1.2 mg, 2.5 μmol) and TrisNHNH$_2$ (29.3 mg, 98 μmol) in ClCH$_2$CH$_2$Cl (0.7 mL) at 50° C. was added Et$_3$N (13.7 μL, 98 μmol). The reaction was monitored by HPTLC (hexane/EtOAc/CH$_2$Cl$_2$=1/1/2). After stirred for 7 h, the mixture was cooled to rt, diluted with EtOAc and filtered through a pad of silica gel, which was rinsed with EtOAc. After concentrated, the residue was purified by preparative TLC (hexane/EtOAc/CH$_2$Cl$_2$=1/1/2) gave 1 (1.1 mg, 2.2 μmol, 91%) as a white solid.

The spectral data of 1 was identical to those reported of dEpoB.

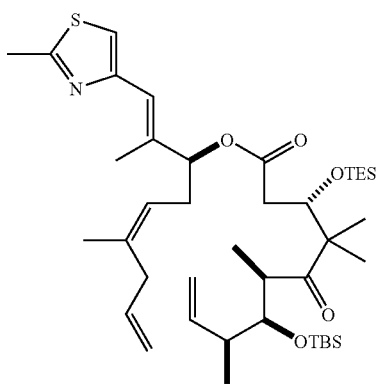

27

Compound 27: Acid 25 and alcohol 24 were azeotroped with dry benzene (5 mL×2) and dried under high vacuum before reaction. To a solution of alcohol 24 (639 mg, 2.63 mmol) in CH$_2$Cl$_2$ (13 mL) were added EDCI (576 mg, 3.09 mmol) and DMAP (366 mg, 3.09 mmol) at 0° C. To the mixture was added a solution of acid 25 (1.11 g, as 1.88 mmol) in CH$_2$Cl$_2$ (5 mL+2 mL rinse) dropwise over 16 min at 0° C. After stirred at 0° C. for 1.5 h, the mixture was stirred at rt for 3.5 h. After concentrated, the residue was purified by flash column chromatography (SiO$_2$, hexane/EtOAc=30:1 to 20:1) gave 27 (1.20 g, 1.61 mmol, 86% from t-butyl ester) as a colorless oil;

[α]$_D^{24}$ −25.1 (c 1.30, CHCl$_3$); IR (film) ν 2955, 2925, 2872, 1732, 1696, 1461, 1378, 1290, 1243, 1173, 1091, 985, 873, 773 cm$^{-1}$; $^1$H NMR (400 MHz, CDCl$_3$) δ 0.06 (3H, s), 0.06 (3H, s), 0.58-0.66 (6H, m), 0.92 (9H, s), 0.95 (9H, t, J=8.0 Hz), 1.02 (3H, d, J=6.5 Hz), 1.03 (3H, d, J=6.5 Hz), 1.07 (3H, s), 1.21 (3H, s), 1.67 (3H, s), 2.07 (3H, s), 2.05-2.12 (1H, m), 2.30 (1H, dd, J=16.9, 7.5 Hz), 2.39 (1H, dt, J=14.8, 6.7 Hz), 2.49 (1H, dd, J=17.0, 3.0 Hz), 2.50 (1H, dt, J=14.8, 6.7 Hz), 2.70 (3H, s), 2.74-2.30 (2H, m), 3.07 (1H, dd, J=7.0 Hz), 3.83 (1H, dd, J=7.1, 2.0 Hz), 4.35 (1H, dd, J=7.4, 2.8 Hz), 4.98-5.07 (4H, m), 5.16 (1H, brt, J=7.0 Hz), 5.23 (1H, t, J=6.9 Hz), 5.74 (1H, ddt, J=16.7, 10.2, 6.5 Hz), 5.91 (1H, ddd, J=17.8, 10.5, 7.8 Hz), 6.50 (1H, s), 6.95 (1H, s); $^{13}$C NMR (100 MHz, CDCl$_3$) δ −3.7, −3.3, 5.3 (3C), 7.2 (3C), 14.8, 15.2, 18.7, 18.9, 19.4, 20.3, 23.6, 23.7, 26.4 (3C), 31.7, 36.7, 40.1, 43.8, 46.4, 53.3, 74.2, 76.5, 79.6, 115.5, 115.6, 116.5, 120.5, 121.3, 135.8, 136.1, 137.4, 140.2, 152.9, 164.7, 171.5, 218.4; LRMS (ESI) calcd for C$_{41}$H$_{71}$NO$_5$SSi$_2$ [M+Na$^+$] 768.5, found 768.5.

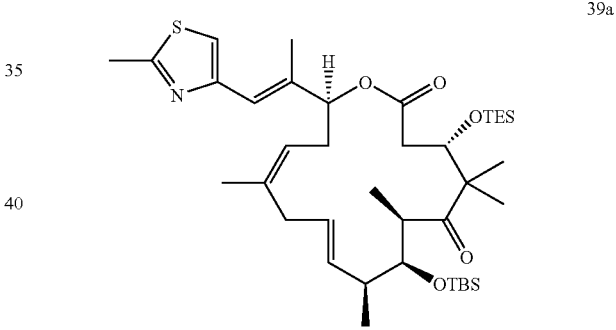

39a

Compound 39a: A solution of 27 (26.9 mg, 36.1 μmol) in toluene (70 mL) was heated to reflux and treated with a solution of Grubbs' catalyst (3.1 mg, 3.61 μmol) in toluene (2 mL). The mixture was stirred for 25 min, cooled to 0° C., filtered through a pad of silica gel, which was rinsed with hexane/EtOAc=2/1. The combine filtrate was concentrated and purified by flash column chromatography (SiO$_2$, hexane/Et$_2$O=40:1 to 5:1) gave 39a (9.9 mg, 13.8 μmol, 38%) as a colorless oil;

[α]$_D^{25}$ −41.5 (c 0.715, CHCl$_3$); IR (film) ν 2955, 2884, 1737, 1690, 1467, 1378, 1249, 1179, 1102, 1014, 979, 879, 826, 773 cm$^{-1}$; $^1$H NMR (400 MHz, CDCl$_3$) δ 0.08 (3H, s), 0.12 (3H, s), 0.57 (6H, q, J=7.8 Hz), 0.89 (9H, t, J=8.0 Hz), 0.93 (9H, s), 1.04 (3H, s), 1.06 (3H, d, J=7.1 Hz), 1.12 (3H, s), 1.17 (3H, d, J=7.1 Hz), 1.68 (3H, s), 2.15 (3H, d, J=0.8 Hz), 2.14-2.27 (2H, m), 2.45 (1H, dd, J=14.0, 4.8 Hz), 2.50 (1H, dd, J=14.9, 3.2 Hz), 2.64-2.74 (2H, m), 2.72 (3H, s), 3.02 (1H, quint, J=7.0 Hz), 3.10 (1H, dd, J=14.4, 7.3 Hz), 3.96 (1H, d, J=8.7 Hz), 4.43 (1H, dd, J=8.3, 2.9 Hz), 5.22 (1H, dd, J=9.8, 5.7 Hz), 5.33-5.42 (2H, m), 5.69 (1H, dd, J=15.8, 8.2 Hz), 6.57 (1H, s), 6.96 (1H, s); $^{13}$C NMR (100 MHz, CDCl$_3$) δ −3.3, −3.2, 5.6 (3C), 7.1 (3C), 15.0, 17.2, 18.8, 19.4, 21.4, 21.7, 23.8, 24.3, 26.5 (3C), 33.2, 35.6, 41.3, 41.8, 48.2, 54.0, 74.4, 77.4, 79.3, 116.4, 120.5, 121.0, 129.3, 132.1, 137.8, 138.0, 152.7, 164.8, 170.7, 216.8; LRMS (ESI) calcd for $C_{39}H_{68}NO_5SSi_2$ [M+H$^+$] 718.4, found 718.3.

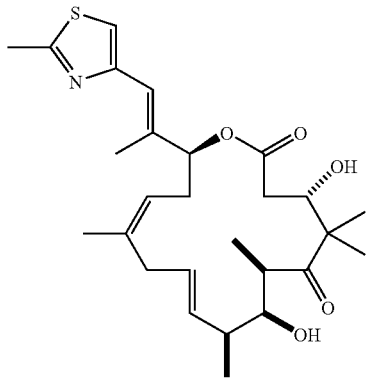

28

Compound 28: To a solution of 39a (298.8 mg, 0.416 mmol) in THF (6.5 mL) in a plastic tube was added HF.pyridine (3.2 mL) at 0° C., and the mixture was stirred at rt for 3 h. The reaction was quenched with dropwise addition of TMSOMe (30 mL) at 0° C. and the mixture was stirred at rt for 3 h. After concentrated and dried under high vacuum, the residue was purified by flash column chromatography (SiO$_2$, hexane/EtOAc=1:1) gave 28 (196.6 mg, 0.402 mmol, 97%) as a white solid;

$[\alpha]_D^{25}$ –96.6 (c 0.235, CHCl$_3$); IR (film) ν 3502, 2970, 2927, 1733, 1685, 1506, 1456, 1375, 1251, 1152, 1040, 977 cm$^{-1}$; $^1$H NMR (400 MHz, CDCl$_3$) δ 1.06 (3H, s), 1.11 (3H, d, J=7.0 Hz), 1.22 (3H, d, J=6.8 Hz), 1.28 (3H, s), 1.72 (3H, s), 2.10 (3H, s), 2.31-2.40 (2H, m), 2.43 (1H, dd, J=16.0, 3.7 Hz), 2.49 (1H, dd, J=16.0, 9.2 Hz), 2.55-2.68 (2H, m), 2.71 (3H, s), 2.98 (1H, dd, J=14.4, 6.4 Hz), 3.16 (1H, quint, J=6.2 Hz), 3.76 (1H, dd, J=5.9, 3.2 Hz), 4.30 (1H, dd, J=9.2, 3.7 Hz), 5.18 (1H, brt, J=7.3 Hz), 5.32 (1H, dd, J=8.4, 2.5 Hz), 5.63 (1H, dd, J=15.7, 6.4 Hz), 5.60 (1H, ddd, J=15.7, 6.9, 5.1 Hz), 6.60 (1H, s), 6.98 (1H, s); $^{13}$C NMR (100 MHz, CDCl$_3$) δ 15.1, 16.0, 17.7, 19.2, 19.5, 22.5, 23.6, 32.0, 35.0, 39.6, 40.3, 44.8, 53.3, 71.8, 75.6, 78.3, 116.1, 119.6, 120.5, 129.9, 131.3, 137.5, 138.2, 152.2, 165.0, 170.7, 218.8; LRMS (ESI) calcd for $C_{27}H_{40}NO_5S$ [M+H$^+$] 490.3, found 490.2.

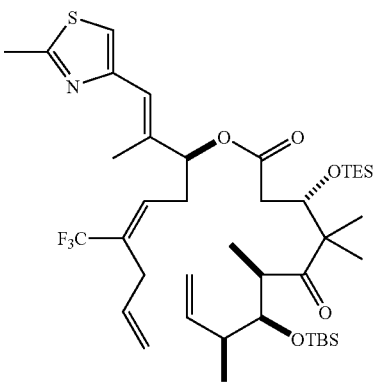

26

Compound 26: Acid 25 and alcohol 21 were azeotroped with dry benzene (5 mL×2) and dried under high vacuum before reaction. To a solution of alcohol 21 (240 mg, 0.756 mmol) in CH$_2$Cl$_2$ (5 mL) were added EDCI (192.7 mg, 1.01 mmol) and DMAP (122.8 mg, 1.01 mmol) at 0° C. To the mixture was added a solution of acid 25 (314.6 mg, 0.628 mmol) in CH$_2$Cl$_2$ (2 mL+1 mL rinse) dropwise over 15 min at 0° C. After stirred at 0° C. for 2 h, the mixture was stirred at rt for 2 h. After concentrated, the residue was purified by flash column chromatography (SiO$_2$, hexane/EtOAc=20:1 to 15:1) gave 26 (340.1 mg, 0.425 mmol, 68% based on acid) as a colorless oil;

$[\alpha]_D^{24}$ –27.5/0.28, CHCl$_3$); IR (film) ν 2956, 2878, 1740, 1692, 1472, 1378, 1317, 1253, 1174, 1118, 988, 915, 872, 837, 775 cm$^{-1}$; $^1$H NMR (400 MHz, CDCl$_3$) δ 0.06 (6H, s), 0.57-0.65 (6H, m), 0.92 (9H, s), 0.94 (9H, t, J=7.9 Hz), 1.02 (3H, d, J=6.9 Hz), 1.03 (3H, d, J=6.8 Hz), 1.07 (3H, s), 1.22 (3H, s), 2.07-2.10 (1H, m), 2.09 (3H, s), 2.31 (1H, dd, J=16.9, 7.3 Hz), 2.51 (1H, dd, J=16.8, 3.0 Hz), 2.49-2.65 (2H, m), 2.71 (3H, s), 2.96-2.99 (2H, m), 3.06 (1H, quint, J=7.1 Hz), 3.83 (1H, dd, J=7.3, 2.1 Hz), 4.35 (1H, dd, J=7.2, 3.0 Hz), 4.98-5.12 (4H, m), 5.30 (1H, t, J=6.7 Hz), 5.76 (1H, ddt, J=16.7, 10.2, 6.2 Hz), 5.92 (1H, ddd, J=17.8, 9.9, 7.8 Hz), 6.19 (1H, t, J=7.0 Hz), 6.51 (1H, s), 6.97 (1H, s); LRMS (ESI) calcd for $C_{41}H_{68}F_3NO_5SSi_2Na$ [M+Na$^+$] 822.4, found 822.4.

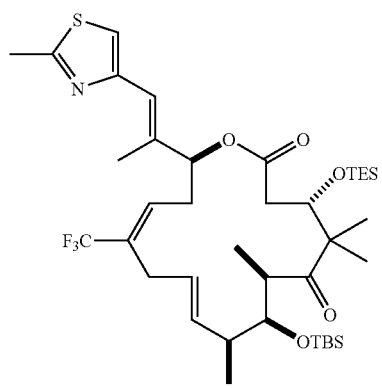

40a

Compound 40a (via RCM of 26): A solution of 26 (57.6 mg, 72.0 μmol) in toluene (142 mL) was heated to reflux and treated with a solution of Grubbs' catalyst (6.1 mg, 7.20 μmol) in toluene (2 mL). The mixture was stirred for 28 min, cooled to 0° C., filtered through a pad of silica gel, which was rinsed with hexane/EtOAc=2/1 (300 mL). The combine filtrate was concentrated and purified by flash column chromatography (SiO$_2$, hexane/Et$_2$O=40:1 to 15:2) gave 40a (12.0 mg, 15.5 mmol, 22%) as a colorless oil;

IR (film) ν 2955, 2884, 1743, 1690, 1472, 1320, 1173, 1114, 1038, 1008, 873, 832, 773 cm$^{-1}$; $^1$H NMR (400 MHz, CDCl$_3$) δ 0.09 (3H, s), 0.12 (3H, s), 0.55 (6H, q, J=7.7 Hz), 0.88 (9H, t, J=8.0 Hz), 0.96 (9H, s), 1.01 (3H, s), 1.06 (3H, d, J=7.1 Hz), 1.12 (3H, s), 1.20 (3H, d, J=7.1 Hz), 2.07-2.17 (1H, m), 2.19 (3H, s), 2.38 (1H, dd, J=14.3, 3.5 Hz), 2.39-2.49 (1H, m), 2.50 (1H, dd, J=14.3, 7.3 Hz), 2.73 (3H, s), 2.77-2.91 (2H, m), 2.96-3.09 (2H, m), 3.98 (1H, dd, J=8.9 Hz), 4.54 (1H, dd, J=7.3, 3.4 Hz), 5.28-5.38 (1H, m), 5.63 (1H, dd, J=9.6, 2.3 Hz), 5.77 (1H, dd, J=15.9, 8.5 Hz), 6.21-6.28 (1H, m), 6.60 (1H, s), 6.99 (1H, s); LRMS (ESI) calcd for $C_{39}H_{65}F_3NO_5SSi_2$ [M+H$^+$] 772.4, found 772.4.

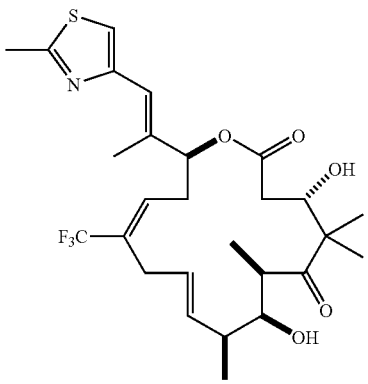

29

Compound 29: To a solution of 40a (67.7 mg, 87.7 μmol) in THF (2 mL) in a plastic tube was added HF.pyridine (1 mL) at 0° C., and the mixture was stirred at rt for 3 h. The reaction was quenched with dropwise addition of TMSOMe (15 mL) at 0° C. The mixture was stirred at rt for 3 h. After concentrated and dried under high vacuum, the residue was purified by flash column chromatography (SiO$_2$, hexane/EtOAc=1:1) gave 29 (46.7 mg, 85.9 μmol, 98%) as a white solid;

$^1$H NMR (400 MHz, CDCl$_3$) δ 1.05 (3H, s), 1.12 (3H, d, J=7.0 Hz), 1.23 (3H, d, J=6.8 Hz), 1.37 (3H, s), 2.04 (1H, brd, J=3.8 Hz, —OH), 2.12 (3H, s), 2.25-2.33 (1H, m), 2.38 (1H, dd, J=15.3, 3.0 Hz), 2.48 (1H, dd, J=15.4, 9.8 Hz), 2.54-2.61 (1H, m), 2.66-2.76 (1H, m), 2.71 (3H, s), 2.96 (1H, dd, J=16.5, 4.5 Hz), 3.02 (1H, dd, J=16.3, 6.5 Hz), 3.11 (1H, quint, J=6.7 Hz), 3.19 (1H, brs, =OH), 3.74 (1H, brs), 4.35 (1H, brd, J=9.5 Hz), 5.42 (1H, dd, J=6.2, 4.1 Hz), 5.60 (1H, ddd, J=15.8, 5.6, 4.5 Hz), 5.66 (1H, dd, J=15.8, 5.8 Hz), 6.24 (1H, t, J=7.2 Hz), 6.64 (1H, s), 7.00 (1H, s); LRMS (ESI) calcd for C$_{27}$H$_{37}$F$_3$NO$_5$S [M+H$^+$] 544.2, found 544.1.

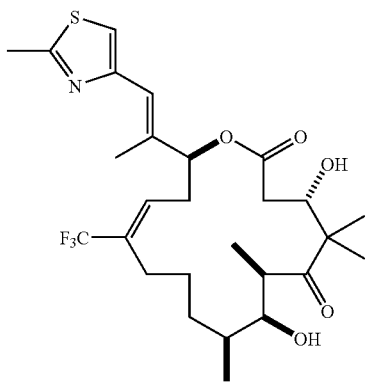

2

Compound 2: To a solution of 29 (1.22 mg, 2.24 μmol) and TrisNHNH$_2$ (26.7 mg, 89.6 μmol) in ClCH$_2$CH$_2$Cl (1 mL) at 50° C. was added Et$_3$N (12.5 μL, 89.6 μmol). The reaction was monitored by HPTLC (hexane/EtOAc/CH$_2$Cl$_2$=1/1/2). After stirred for 6.5 h, further TrisNHNH$_2$ (26.7 mg, 89.6 μmol) and Et$_3$N (12.5 μL, 89.6 μmol) were added to the mixture. After stirred for 14 h, the mixture was cooled to rt, diluted with EtOAc and filtered through a pad of silica gel, which was rinsed with EtOAc. After concentrated, the residue was purified by preparative TLC (hexane/EtOAc/CH$_2$Cl$_2$=1/1/2) gave 2 (1.16 mg, 2.13 μmol, 94%) as a white solid;

$^1$H NMR (400 MHz, CDCl$_3$) δ 1.03 (3H, d, J=7.0 Hz), 1.08 (3H, s), 1.19 (3H, d, J=6.8 Hz), 1.25-1.35 (2H, m), 1.37 (3H, s), 1.42-1.55 (2H, m), 1.65-1.82 (2H, m), 2.10 (3H, d, J=0.8 Hz), 2.21-2.47 (2H, m), 2.27 (1H, dd, J=14.2, 2.6 Hz), 2.48 (1H, dd, J=14.3, 10.8 Hz), 2.70 (3H, s), 2.70-2.28 (1H, m), 3.02 (1H, d, J=2.0 Hz, —OH), 3.19 (1H, qd, J=6.9, 2.2 Hz), 3.65 (1H, d, J=6.2 Hz, —OH), 3.69-3.72 (1H, m), 4.34 (1H, ddd, J=10.8, 6.2, 2.6 Hz), 5.28 (1H, dd, J=10.2, 2.2 Hz), 6.12 (1H, dd, J=10.2, 5.2 Hz), 6.61 (1H, s), 6.98 (1H, s); LRMS (ESI) calcd for C$_{27}$H$_{39}$F$_3$NO$_5$S [M+H$^+$] 546.3, found 546.2.

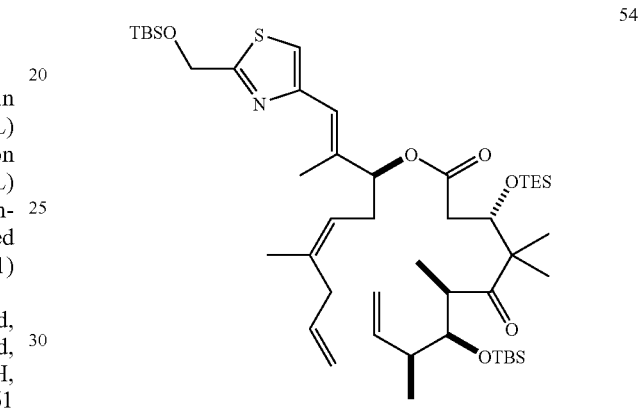

54

Compound 54: Acid 25 and alcohol 53 were azeotroped with dry benzene (3 mL×2) and dried under high vacuum before reaction. To a solution of alcohol 53 (68.0 mg, 0.173 mmol) in CH$_2$Cl$_2$ (1.3 mL) were added EDCI (37.8 mg, 0.197 mmol) and DMAP (24.1 mg, 0.197 mmol) at 0° C. To the mixture was added a solution of acid 25 (72.6 mg, as 0.123 mmol) in CH$_2$Cl$_2$ (0.7 mL) dropwise over 5 min at 0° C. After stirred at 0° C. for 1 h, the mixture was stirred at rt for 2.5 h. After concentrated, the residue was purified by flash column chromatography (SiO$_2$, hexane/EtOAc=30:1) gave 54 (99.5 mg, 0.114 mmol, 92% from t-butyl ester) as a colorless oil; [α]$_D^{25}$ −23.4 (c 0.56, CHCl$_3$); IR (film) ν 2955, 2931, 2880, 1735, 1696, 1506, 1472, 1386, 1362, 1294, 1254, 1174, 1104, 988, 878, 776, 742 cm$^{-1}$; $^1$H NMR (400 MHz, CDCl$_3$) δ 0.06 (3H, s), 0.06 (3H, s), 0.14 (6H, s), 0.63 (6H, q, J=8.0 Hz), 0.92 (9H, s), 0.94 (9H, t, J=8.0 Hz), 0.97 (9H, s), 1.02 (3H, d, J=6.6 Hz), 1.05 (3H, d, J=6.5 Hz), 1.07 (3H, s), 1.21 (3H, s), 1.67 (3H, s), 2.06 (3H, d, J=0.8 Hz), 2.05-2.14 (1H, m), 2.30 (1H, dd, J=16.9, 7.5 Hz), 2.33-2.53 (2H, m), 2.50 (1H, dd, J=16.9, 2.7 Hz), 2.76-2.80 (2H, m), 3.07 (1H, quint, J=7.0 Hz), 3.83 (1H, dd, J=7.0, 2.2 Hz), 4.35 (1H, dd, J=7.4, 2.8 Hz), 4.97 (2H, s), 4.97-5.07 (4H, m), 5.16 (1H, t, J=7.2 Hz), 5.24 (1H, t, J=6.9 Hz), 5.74 (1H, ddt, J=16.6, 10.0, 6.5 Hz), 5.91 (1H, ddd, J=17.6, 9.9, 7.7 Hz), 6.50 (1H, s), 7.06 (1H, s); $^{13}$C NMR (100 MHz, CDCl$_3$) δ −5.2 (2C), ±3.7, −3.3, 5.3 (3C), 7.2 (3C), 14.7, 15.2, 18.5, 18.7, 18.9, 20.3, 23.6, 23.7, 26.0 (3C), 26.4 (3C), 31.7, 36.7, 40.1, 43.8, 46.4, 53.3, 63.4, 74.2, 76.5, 79.6, 115.5, 115.6, 116.6, 120.5, 121.3, 135.8, 136.1, 137.4, 140.1, 153.0, 171.5, 172.2, 218.4; LRMS (ESI) calcd for C$_{47}$H$_{86}$NO$_6$SSi$_3$ [M+H$^+$] 876.6, found 876.5.

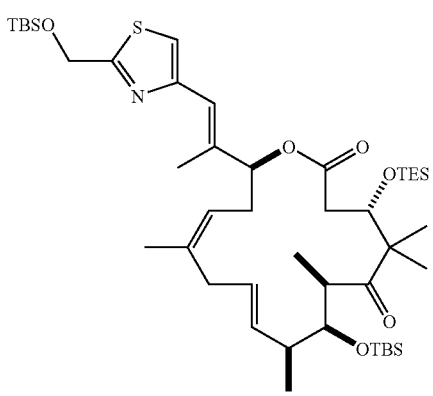

55

Compound 55: A solution of 54 (69.7 mg, 79.5 μmol) in toluene (158 mL) was heated to reflux and treated with a solution of Grubbs' catalyst (6.7 mg, 7.95 μmol) in toluene (2 mL). The mixture was stirred for 11 min, cooled to 0° C., filtered through a pad of silica gel, which was rinsed with hexane/EtOAc=3/1 (280 mL). The combine filtrate was concentrated and purified by flash column chromatography (SiO$_2$, hexane/Et$_2$O=20:1 to 15:1) gave 55 (18.4 mg, 21.7 μmol, 27%) as a colorless oil;

[α]$_D^{24}$ −40.4 (c 0.26, CHCl$_3$); IR (film) v 2955, 2930, 2879, 1740, 1694, 1472, 1387, 1362, 1253, 1200, 1107, 1007, 838, 776, 742 cm$^{-1}$; $^1$H NMR (400 MHz, CDCl$_3$) δ 0.08 (3H, s), 0.12 (3H, s), 0.15 (6H, s), 0.57 (6H, q, J=7.9 Hz), 0.88 (9H, t, J=8.0 Hz), 0.95 (9H, s), 0.97 (9H, s), 1.04 (3H, s), 1.06 (3H, d, J=7.1 Hz), 1.12 (3H, s), 1.17 (3H, d, J=7.0 Hz), 1.69 (3H, s), 2.06-2.30 (2H, m), 2.14 (3H, s), 2.45 (1H, dd, J=15.6, 3.6 Hz), 2.50 (1H, dd, J=14.9, 3.1 Hz), 2.63-2.75 (2H, m), 2.97-3.06 (1H, m), 3.10 (1H, dd, J=14.6, 7.7 Hz), 3.97 (1H, d, J=8.5 Hz), 4.44 (1H, dd, J=8.4, 2.9 Hz), 4.97 (2H, s), 5.22 (1H, dd, J=8.7, 5.2 Hz), 5.33-5.44 (2H, m), 5.70 (1H, dd, J=15.6, 8.1 Hz), 6.57 (1H, s), 7.07 (1H, s); LRMS (ESI) calcd for C$_{45}$H$_{82}$NO$_6$SSi$_3$ [M+H$^+$] 848.5, found 848.5.

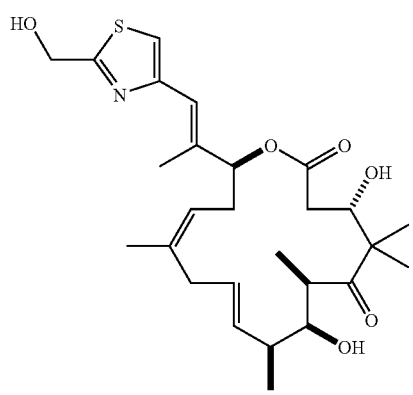

57

Compound 57: To a solution of 55 (61.8 mg, 72.8 μmol) in THF (2 mL) in a plastic tube was added HF.pyridine (1 mL) at 0° C., and the mixture was stirred at rt for 3.2 h. The reaction was quenched with dropwise addition of TMSOMe (15 mL) at 0° C. The mixture was stirred at rt for 2 h. After concentrated and dried under high vacuum, the residue was purified by flash column chromatography (SiO$_2$, hexane/EtOAc=1:3) gave 57 (32.4 mg, 64.1 μmol, 88%) as a white solid;

[α]$_D^{25}$ −108.4 (c 0.285, CHCl$_3$); IR (film) v 3422, 2968, 2919, 2729, 1689, 1449, 1377, 1252, 1152, 1064, 978 cm$^{-1}$;

$^1$H NMR (400 MHz, CDCl$_3$) δ 1.05 (3H, s), 1.12 (3H, d, J=6.9 Hz), 1.22 (3H, d, J=6.8 Hz), 1.32 (3H, s), 1.72 (3H, s), 2.08 (3H, s), 2.31-2.40 (3H, m), 2.43 (1H, dd, J=15.5, 3.5 Hz), 2.49 (1H, dd, J=15.5, 9.5 Hz), 2.55-2.67 (2H, m), 2.95 (1H, dd, J=14.6, 6.3 Hz), 3.13 (1H, quint, J=6.6 Hz), 3.34 (1H, brs, —OH), 3.75 (1H, dd, J=6.6, 2.4 Hz), 4.06 (1H, brs, —OH), 4.33 (1H, dd, J=9.4, 3.0 Hz), 4.92 (2H, s), 5.18 (1H, t, J=6.9 Hz), 5.33 (1H, dd, J=8.0, 2.5 Hz), 5.52 (1H, dd, J=15.8, 6.4 Hz), 5.59 (1H, ddd, J=15.8, 6.6, 5.0 Hz), 6.63 (1H, s), 7.13 (1H, s); $^{13}$C NMR (100 MHz, CDCl$_3$) δ 15.3, 16.3, 17.8, 19.2, 22.8, 23.7, 31.9, 35.1, 39.7, 40.2, 45.0, 53.4, 61.8, 71.7, 75.8, 78.1, 116.7, 119.0, 120.5, 130.0, 131.2, 137.6, 138.9, 152.5, 170.0, 170.7, 218.7; LRMS (ESI) calcd for C$_{27}$H$_{39}$NO$_6$SNa [M+Na$^+$] 528.2, found 528.0.

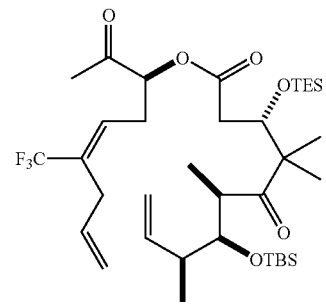

46

Compound 46: Acid 25 and alcohol 44 were azeotroped with dry benzene and dried under high vacuum before reaction. To a solution of alcohol 44 (59.2 mg, 0.266 mmol) in CH$_2$Cl$_2$ (2 mL) were added EDCI (63.4 mg, 0.331 mmol) and DMAP (40.4 mg, 0.331 mmol) at 0° C. To the mixture was added a solution of acid 25 (121 mg, as 0.207 mmol) in CH$_2$Cl$_2$ (1 mL+0.3 mL rinse) dropwise over 5 min at 0° C. After stirred at 0° C. for 0.5 h, the mixture was stirred at rt for 2.5 h. After concentrated, the residue was purified by flash column chromatography (SiO$_2$, hexane/EtOAc=20:1) gave 46 (124.9 mg, 0.177 mmol, 86% from t-butyl ester) as a colorless oil;

$^1$H NMR (400 MHz, CDCl$_3$) δ 0.08 (3H, s), 0.08 (3H, s), 0.60 (6H, q, J=7.8 Hz), 0.93 (9H, s), 0.94 (9H, t, J=8.0 Hz), 1.04 (3H, d, J=7.0 Hz), 1.04 (3H, d, J=7.0 Hz), 1.11 (3H, s), 1.23 (3H, s), 2.05-2.14 (1H, m), 2.17 (3H, s), 2.40 (1H, dd, J=16.9, 7.0 Hz), 2.59 (1H, dd, J=17.0, 3.6 Hz), 2.56-2.64 (2H, m), 2.90-3.01 (2H, m), 3.06 (1H, quint, J=7.0 Hz), 3.85 (1H, dd, J=7.3, 2.0 Hz), 4.38 (1H, d, J=7.0, 3.4 Hz), 4.97-5.14 (5H, m), 5.75 (1H, ddt, J=16.0, 9.9, 6.2 Hz), 5.92 (1H, ddd, J=17.8, 10.5, 7.8 Hz), 6.21 (1H, td, J=7.2, 1.5 Hz); LRMS (ESI) calcd for C$_{36}$H$_{63}$F$_3$O$_6$Si$_2$Na [M+Na$^+$] 727.4, found 727.3.

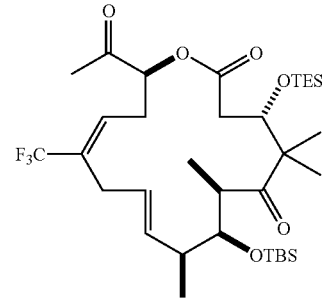

48

Compound 48: A solution of 46 (60.0 mg, 85.1 μmol) in toluene (170 mL) was heated to reflux and treated with a solution of Grubbs' catalyst (10.8 mg, 12.7 μmol) in toluene (2 mL). The mixture was stirred for 15 min, cooled to 0° C., filtered through a pad of silica gel, which was rinsed with hexane/EtOAc=3/1 (400 mL). The combine filtrate was concentrated and purified by flash column chromatography (SiO$_2$, hexane/Et$_2$O=10:1 to 5:1) gave 48 (41.0 mg, 60.6 μmol, 71%) as a colorless oil;

$^1$H NMR (400 MHz, CDCl$_3$) δ 0.08 (3H), 0.10 (3H, s), 0.60 (6H, q, J=7.8 Hz), 0.93 (9H, s), 0.94 (9H, t, J=7.8 Hz), 1.03 (3H, d, J=7.1 Hz), 1.08 (3H, s), 1.13 (3H, d, J=7.0 Hz), 1.17 (3H, s), 2.26 (3H, s), 2.25-2.34 (1H, m), 2.64 (1H, dd, J=15.5, 5.0 Hz), 2.68-2.75 (2H, m), 2.76 (1H, dd, J=15.6, 6.4 Hz), 2.85 (1H, dd, J=15.6, 5.7 Hz), 2.97 (1H, dq, J=8.3, 6.9 Hz), 3.04 (1H, dd, J=15.6, 6.3 Hz), 3.92 (1H, dd, J=8.3, 1.2 Hz), 4.36 (1H, t, J=5.3 Hz), 5.30-5.39 (2H, m), 5.58 (1H, dd, J=15.5, 8.0 Hz), 6.13 (1H, brt, J=7.2 Hz); LRMS (ESI) calcd for C$_{34}$H$_{59}$F$_3$O$_6$Si$_2$Na [M+Na$^+$] 699.4, found 699.4.

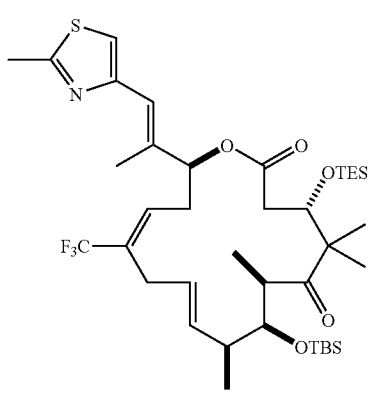

40a

Compound 40a (via Wittig reaction of ketone 48): To a solution of Wittig reagent (31.8 mg, 91.0 μmol) in THF (0.4 mL) was added n-BuLi (56.9 μL of a 1.6 M solution in hexane, 91.0 μmol) at 0° C. The mixture was stirred at 0° C. for 0.5 h and then cooled to −78° C. To the mixture was added dropwise a solution of ketone 48 (8.8 mg, 13.0 μmol) in THF (0.3 mL), and the resulting mixture was allowed to warm to −15° C. over 4.5 h. The reaction was quenched with sat. aq. NH$_4$Cl (2 mL) and extracted with EtOAc (8 mL×3). The combined organic layers were dried over Na$_2$SO$_4$ and concentrated. The residue was purified by flash column chromatography (SiO$_2$, hexane/Et$_2$O=10:1) gave 40a (7.0 mg, 9.07 μmol, 70%) and olefinic isomer (1.8 mg, 2.33 μmol, 18%) both as a colorless oil.

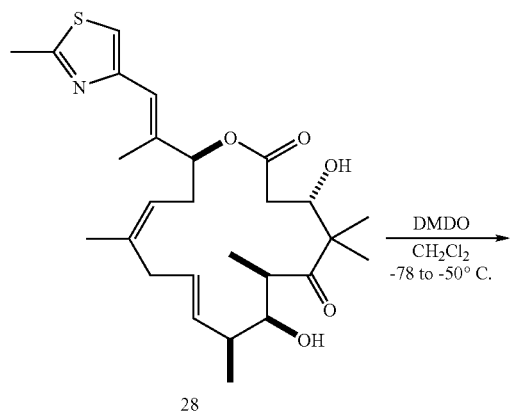

28

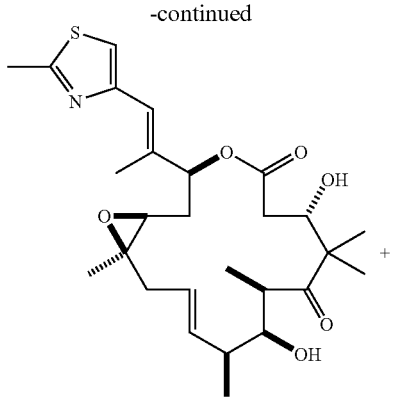

48

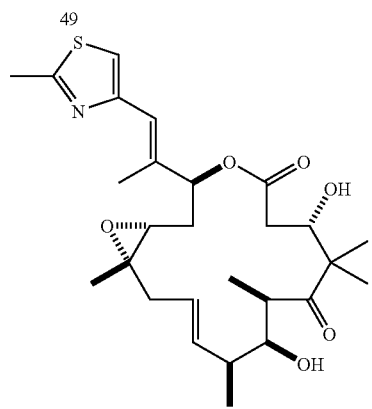

49

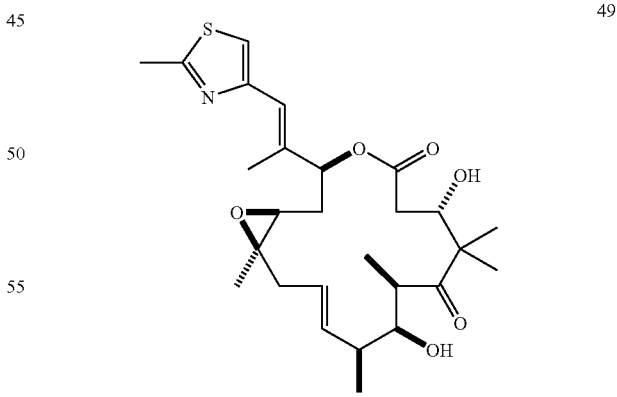

50

Compounds 49 and 50: A solution of 28 (12.2 mg, 24.9 μmol) in CH$_2$Cl$_2$ (1.25 mL) was cooled to −78° C. and treated with a cooled solution of DMDO (−78° C., 0.06 M in acetone, 914 μL, 54.8 μmol). The mixture was allowed to warm to −50° C. and stirred at −50° C. for 2.7 h. The excess DMDO was quenched at −50° C. by the addition of dimethylsulfide (117 μL) and the mixture was stirred at this temperature for 0.5 h. The solvent was removed in vacuo. Purification by preparative thin layer chromatography (hexane/EtOAc=1/2) gave β-epoxide 49 (3.0 mg, 5.93 μmol, 24%) and α-epoxide 50 (7.9 mg, 15.6 μmol, 63%) both as a colorless solid.

49

Compound 49: $^1$H NMR (400 MHz, CDCl$_3$) δ 1.03 (3H, s), 1.11 (3H, d, J=7.0 Hz), 1.14 (3H, d, J=6.9 Hz), 1.34 (3H, s), 1.36 (3H, s), 2.00 (1H, ddd, J=15.1, 7.3, 4.0 Hz), 2.14 (1H, dt, J=15.1, 5.2 Hz), 2.14 (3H, s), 2.21 (1H, dd, J=14.6, 8.0 Hz), 2.33 (1H, dd, J=14.7, 4.8 Hz), 2.47 (1H, dd, J=13.8, 3.3 Hz), 2.59 (1H, dd, J=13.8, 9.4 Hz), 2.73 (3H, s), 2.77 (1H, brs, OH), 2.93 (1H, dd, J=7.3, 4.8 Hz), 3.34 (1H, qd, J=6.9, 3.7 Hz), 3.75-3.82 (1H, m), 4.12-4.24 (2H, m, including OH), 5.54 (1H, ddd, J=15.7, 7.4, 5.0 Hz), 5.54-5.60 (1H, m), 5.64 (1H, dd, J=15.7, 5.6 Hz), 6.94 (1H, s), 7.01 (1H, s); LRMS (ESI) calcd for $C_{27}H_{40}NO_6S$ [M+H$^+$] 506.3, found 506.3.

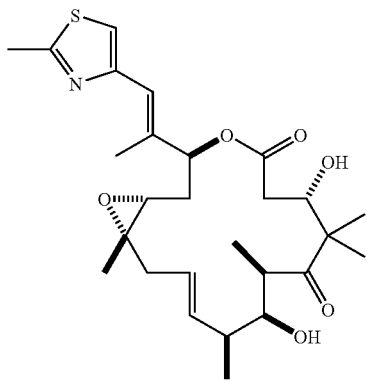
50

Compound 50: $^1$H NMR (400 MHz, CDCl$_3$) δ 1.00 (3H, s), 1.04 (3H, d, J=6.9 Hz), 1.12 (3H, d, J=7.0 Hz), 1.35 (3H, s), 1.35 (3H, s), 1.87 (1H, dt, J=15.0, 9.2 Hz), 2.03 (1H, dd, J=13.9, 9.2 Hz), 2.13 (3H, s), 2.13-2.19 (1H, m), 2.36 (1H, dd, J=13.9, 3.4 Hz), 2.39 (1H, dd, J=12.2, 2.1 Hz), 2.42-2.51 (1H, m), 2.49 (1H, dd, J=12.4, 10.9 Hz), 2.69 (1H, d, J=2.7 Hz), 2.72 (3H, s), 3.06 (1H, dd, J=9.7, 3.1 Hz), 3.54 (1H, qd, J=7.0, 2.0 Hz), 3.76-3.80 (1H, m), 4.07-4.14 (1H, m), 4.31 (1H, d, J=4.1 Hz), 5.52 (1H, dd, J=15.5, 8.7 Hz), 5.60 (1H, ddd, J=15.1, 9.4, 3.4 Hz), 5.71 (1H, d, J=8.4 Hz), 6.63 (1H, s), 6.99 (1H, s); LRMS (ESI) calcd for $C_{27}H_{39}NO_6SNa$ [M+Na$^+$] 528.2, found 528.2.

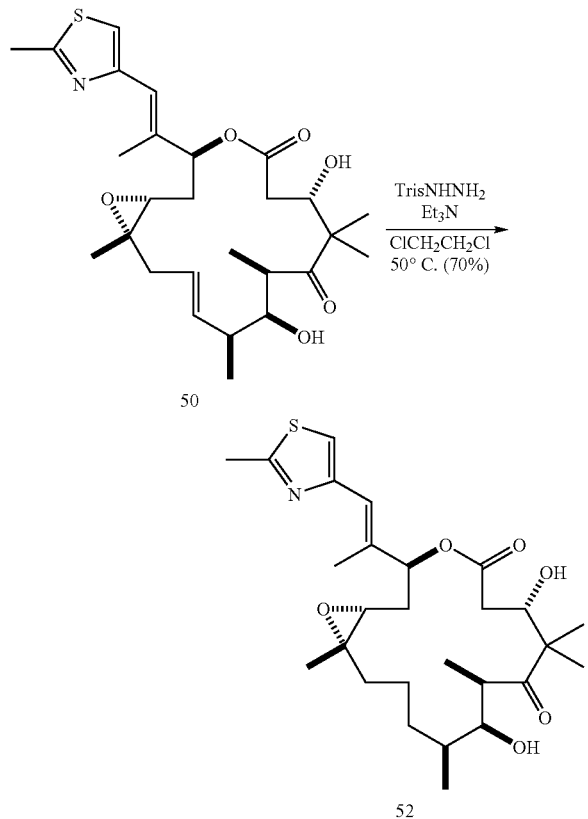

Compound 52: To a solution of 50 (1.7 mg, 3.4 μmol) and TrisNHNH$_2$ (40.1 mg, 0.134 mmol) in ClCH$_2$CH$_2$Cl (0.8 mL) at 50° C. was added Et$_3$N (18.7 μL, 0.134 mmol). The reaction was monitored by HPTLC (hexane/EtOAc=1/2). After stirred for 4 h, the mixture was cooled to rt, diluted with EtOAc and filtered through a pad of silica gel, which was rinsed with EtOAc. After concentrated, the residue was purified by preparative TLC (hexane/EtOAc=1/2) gave 52 (1.2 mg, 2.4 μmol, 70%) as a white solid.

$^1$H NMR (400 MHz, CDCl$_3$) δ 0.95 (3H, d, J=7.1 Hz), 1.04 (3H, s), 1.11 (3H, d, J=7.0 Hz), 1.28 (3H, s), 1.37 (3H, s), 1.35-1.44 (1H, m), 1.45-1.59 (4H, m), 1.71-1.82 (2H, m), 1.86 (1H, dt, J=15.3, 9.5 Hz), 2.10 (1H, dd, J=15.3, 3.6 Hz), 2.13 (3H, s), 2.40 (1H, dd, J=12.5, 2.5 Hz), 2.49 (1H, dd, J=12.5, 11.0 Hz), 2.74 (3H, s), 2.80 (1H, brs, OH), 3.07 (1H, dd, J=10.3, 3.3 Hz), 3.34 (1H, qd, J=7.0, 1.0 Hz), 3.89 (1H, brs, OH), 4.03-4.09 (1H, m), 4.12-4.17 (1H, m), 5.69 (1H, d, J=9.1 Hz), 6.63 (1H, s), 7.00 (1H, s); LRMS (ESI) calcd for $C_{27}H_{41}NO_6SNa$ [M+Na$^+$] 530.3, found 530.2.

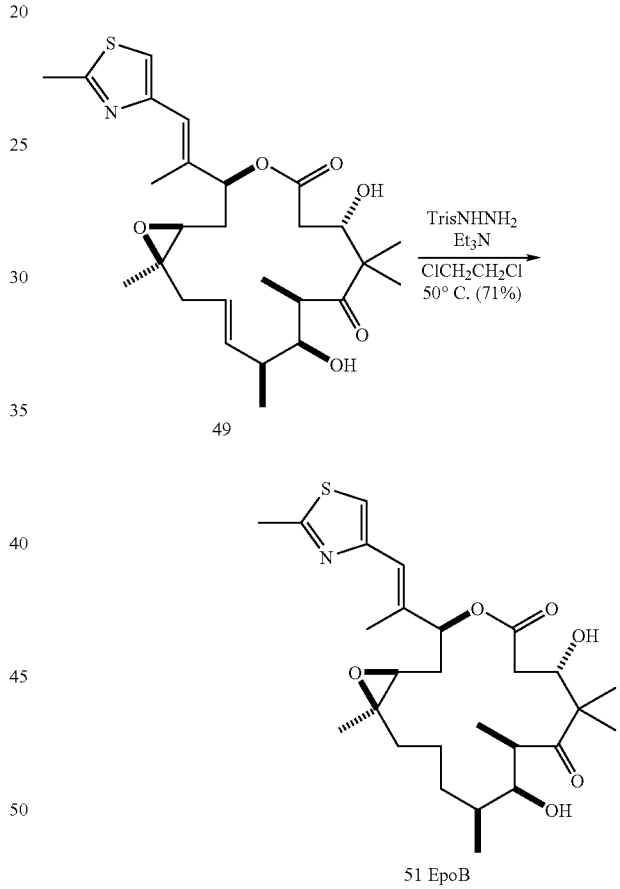

To a solution of 49 (0.7 mg, 1.38 μmol) and TrisNHNH$_2$ (20.6 mg, 69 μmol) in ClCH$_2$CH$_2$Cl (0.4 mL) at 50° C. was added Et$_3$N (9.6 μL, 69 μmol). The reaction was monitored by HPTLC (hexane/EtOAc=1/2). After stirred for 6 h, the mixture was cooled to rt, diluted with EtOAc and filtered through a pad of silica gel, which was rinsed with EtOAc. After concentrated, the residue was purified by preparative TLC (hexane/EtOAc=1/2) gave 51 (0.5 mg, 0.985 μmol, 71%) as a white solid.

The spectral data of 51 was identical to those reported of EpoB.

Example 5
Alternative Synthetic Strategies for Synthesizing Intermediates of Epothilones
The following examples offer methods of preparing the various intermediates in the synthesis of epothilone analogs. Optimization of the Syntheses of 9,10-dehydroEpothilones
Example 1
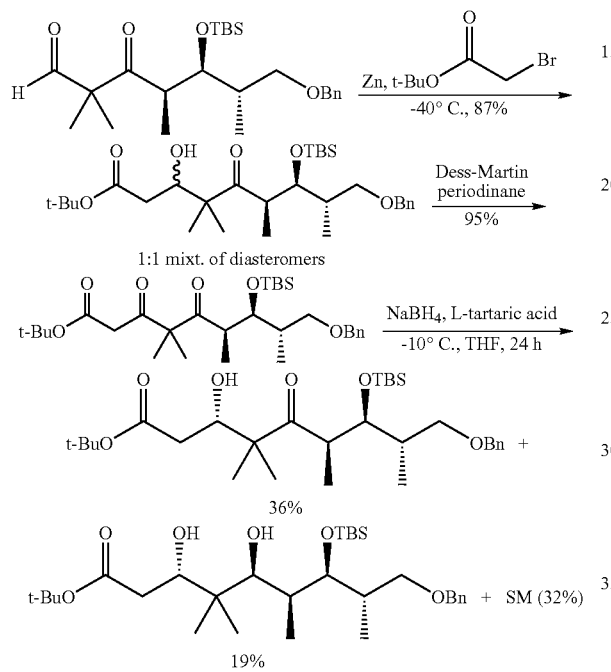
Example 2
Noyori Reductions
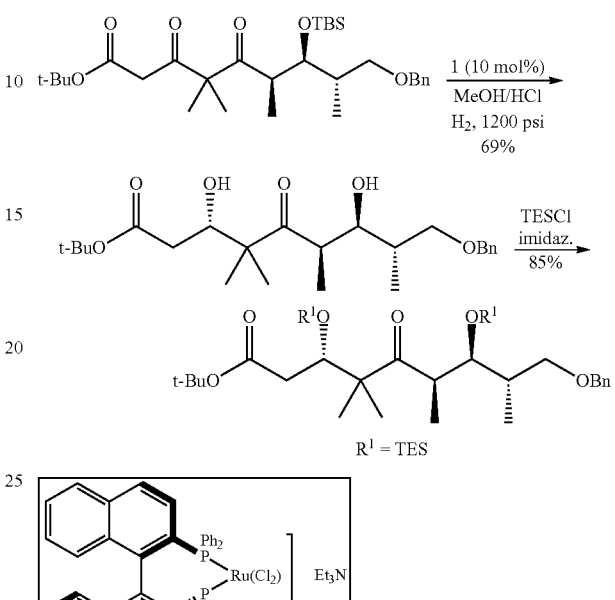
Example 3
Noyori Reductions
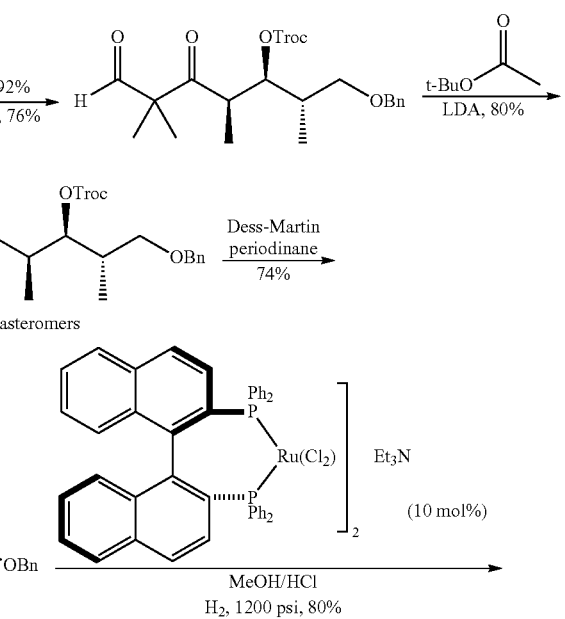

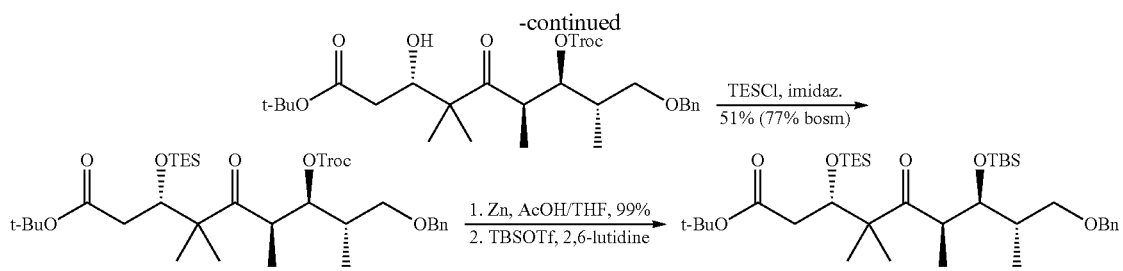
Example 4
Alternative Synthesis of the Key Diketone
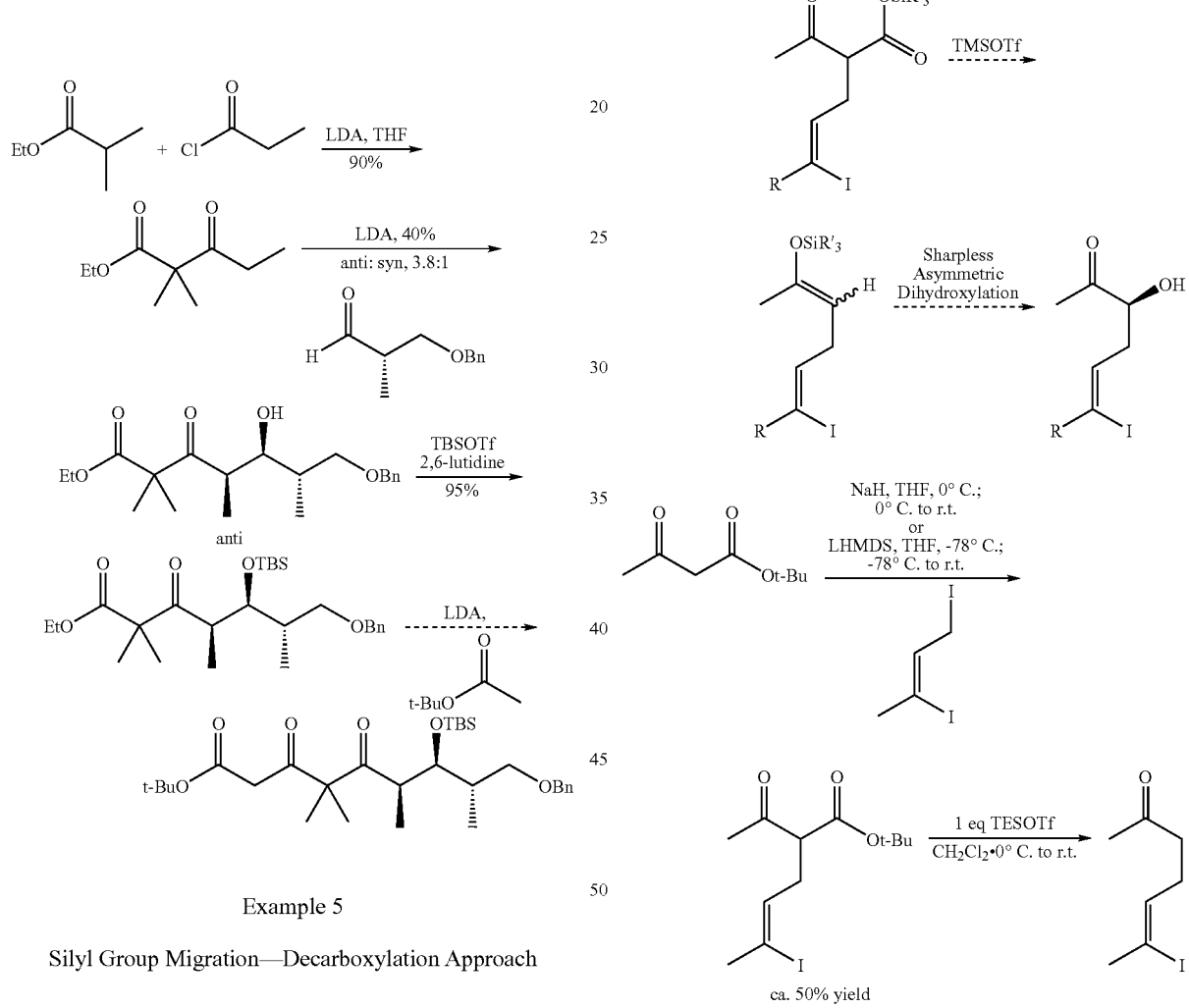
Example 5
Silyl Group Migration—Decarboxylation Approach
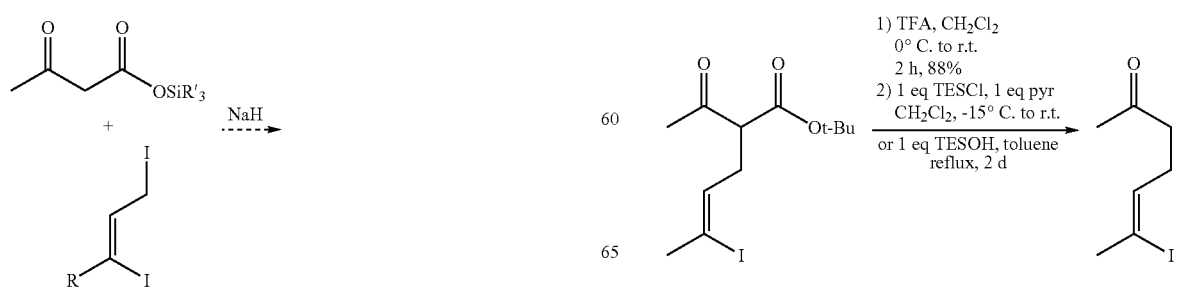

Example 6
Evans Auxiliary Approach: A New Generation of
Allyl Iodide Synthesis
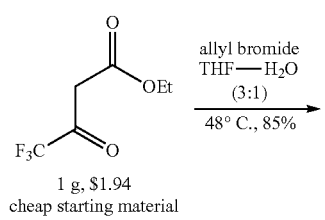
1 g, $1.94
cheap starting material
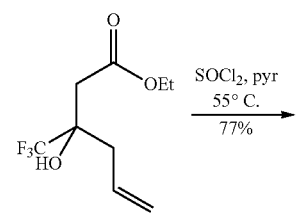
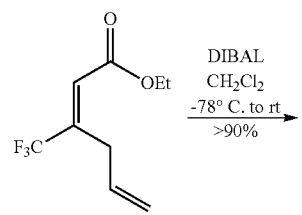
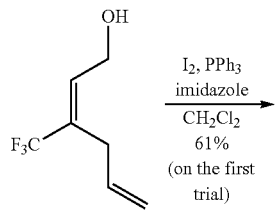
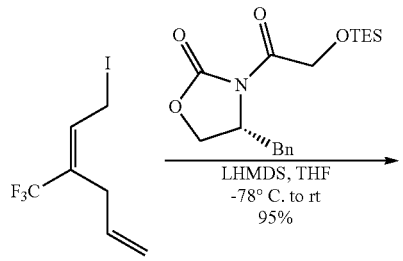
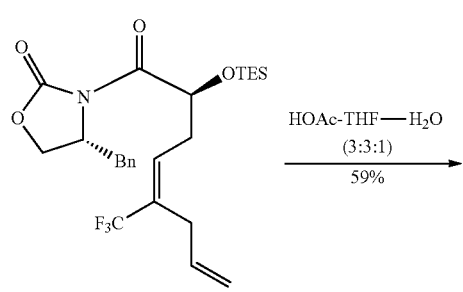
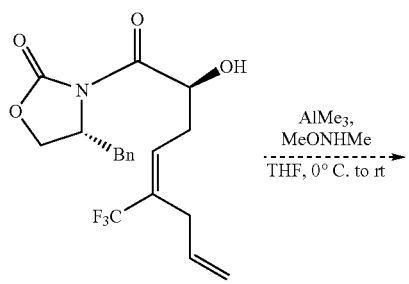
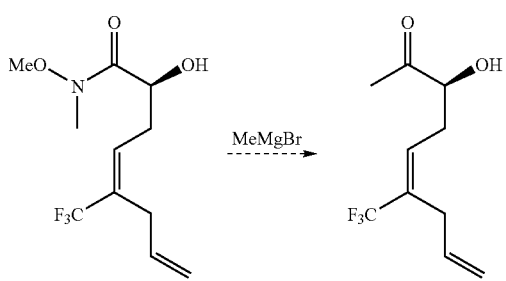
B
amenable for large scale reactions
Example 7
Kowalsky-Sharpless Approach: Utilization of Chiral Catalyst
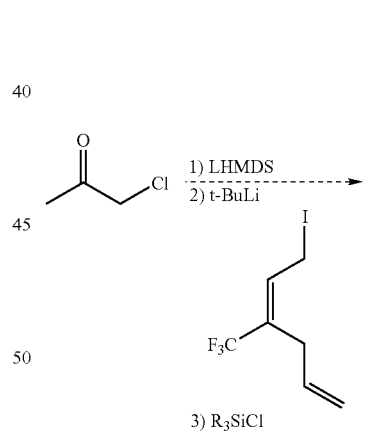
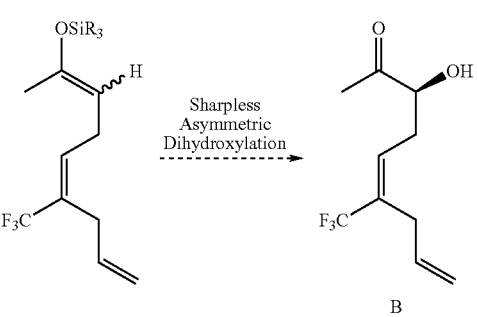
B

Example 8

Evans Auxiliary Approach to the Synthesis of the Allyl Iodide

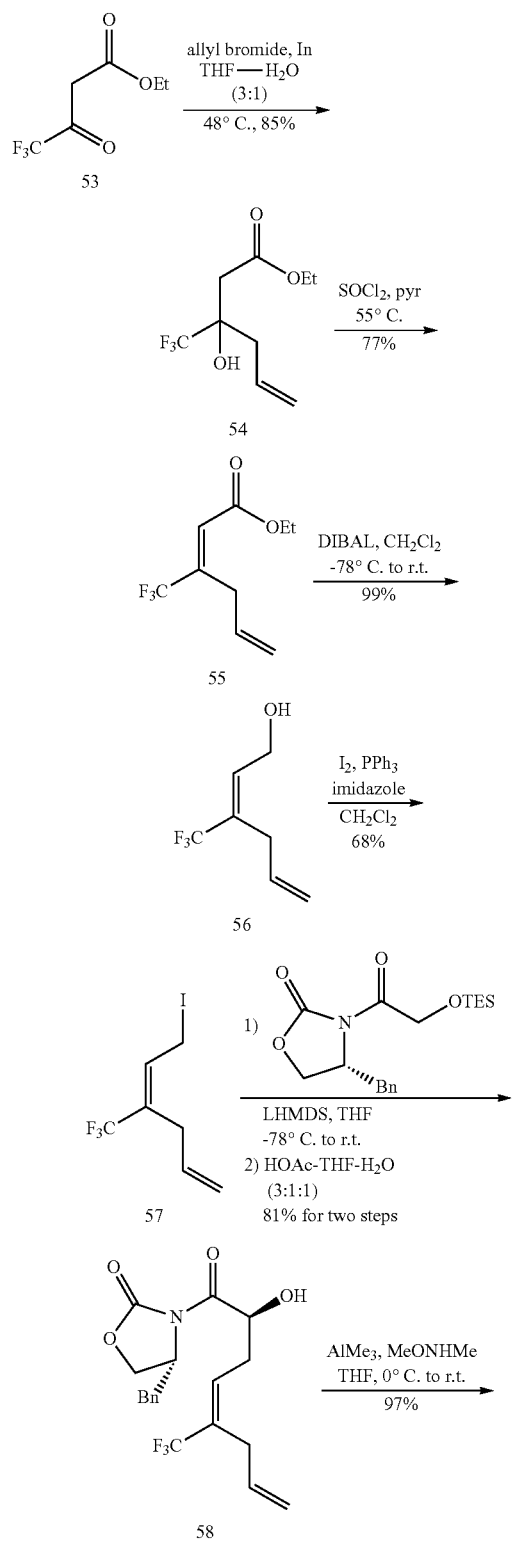

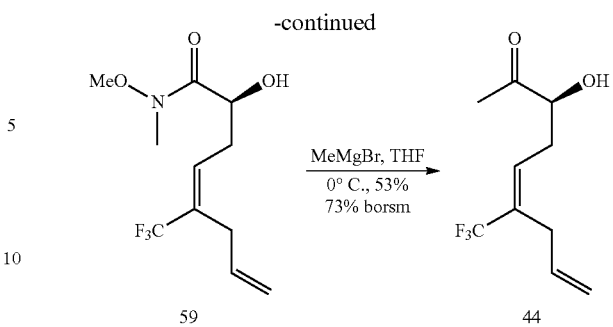

Chemical shifts are reported in δ values relative to chloroform (δ 7.24 for proton and δ 77.0 for carbon NMR).

Alcohol 54. To a solution of ethyl 4,4,4-trifluoroacetoacetate (24.0 mL, 0.164 mol) in THF-water (3:1=V:V, 320 mL) at room temperature were added allyl bromide (20.0 mL, 1.4 equiv) and indium (powder, −100 mesh, 25 g, 1.3 equiv) and the resulting mixture was stirred at 48° C. for 15 h. The reaction mixture was cooled to room temperature, quenched with 2 N aq. HCl (400 mL) and extracted with $CH_2Cl_2$ (400 mL, 2×200 mL). Combined organics were dried ($MgSO_4$), filtered, and concentrated in vacuo. Flash chromatography (hexanes→hexanes-ether 10:1→8:1→6:1→4:1) gave alcohol 54 as clear oil (31.64 g, 85% yield): IR (film) 3426 (br m), 2986 (m), 1713 (s), 1377 (m), 1345 (m), 1301 (m), 1232 (m), 1173 (s), 1095 (m), 1023 (m), 927 (m) cm$^{-1}$; $^1$H NMR (400 MHz, $CDCl_3$) δ 5.82 (m, 1H), 5.15 (m, 3H), 4.17 (m, 2H), 2.59 (m, 1H), 2.58 (d, J=3.4 Hz, 2H), 2.29 (dd, J=14.2, 8.6 Hz, 1H), 1.24 (t, J=7.2 Hz, 3H); $^{13}$C NMR (100 MHz, $CDCl_3$) δ 172.08, 130.89, 125.65 (q, J=280 Hz), 120.27, 73.79 (q, J=28 Hz), 61.55, 38.97, 35.65, 13.82; high resolution mass spectrum m/z 227.0895 [(M+H)$^+$; calcd for $C_9H_{14}O_3F_3$: 227.0895].

Ester 55. A mixture of alcohol 54 (16.71 g, 0.07386 mol) and pyridine (15.0 mL, 2.5 equiv) was cooled to −10° C. and treated with thionyl chloride (11.3 mL, 2.1 equiv) slowly over 11 min. The resulting mixture was warmed to 55° C. and stirred for 12 h. The reaction mixture was cooled to −5° C., quenched with water (200 mL) and extracted with $CH_2Cl_2$ (2×200 mL, 2×150 mL). Combined organics were washed with saturated $NaHCO_3$ (2×200 mL), and brine (200 mL), dried ($MgSO_4$), and concentrated in vacuo. Flash chromatography (pentane:ether 15:1) afforded ester 55 (11.90 g, 77% yield) as yellow oil: IR (film) 2986 (w), 1731 (s), 1308 (s), 1265 (w), 1227 (m), 1197 (s), 1133 (s), 1025 (m), 920 (w), 896 (w) cm$^{-1}$; $^1$H NMR (400 MHz, $CDCl_3$) δ 6.36 (s, 1H), 5.79 (ddt, J=16.9, 10.2, 6.6 Hz, 1H), 5.15 (dd, J=17.1, 1.5 Hz, 1H), 5.08 (dd, J=10.0, 1.4 Hz, 1H), 4.22 (q, J=7.1 Hz, 2H), 3.44 (d, J=6.5 Hz, 2H), 1.29 (t, J=7.1 Hz, 3H); $^{13}$C NMR (100 MHz, $CDCl_3$) δ 164.22, 143.37 (q, J=29 Hz), 132.71, 123.21 (q, J=274 Hz), 122.60 (q, J=6 Hz), 117.32, 60.85, 30.54, 13.85; high resolution mass spectrum m/z 209.0788 [(M+H)$^+$; calcd for $C_9H_{12}O_2F_3$: 209.0789].

Alcohol 56. To a cooled (−75° C.) solution of ester 55 (7.12 g, 0.0342 mol) in $CH_2Cl_2$ (120 mL) was added a solution of DIBAL-H (75 mL, 2.2 equiv) in $CH_2Cl_2$ (1.0 M) and the resulting mixture was warmed to room temperature over 3 h. The reaction mixture was cooled to 0° C., quenched with saturated $NH_4Cl$ (12 mL) and stirred at room temperature for 20 min. The reaction mixture was diluted with ether (200 mL), dried ($MgSO_4$), and concentrated in vacuo. Flash chromatography (pentane:ether 3:1→1:1) provided alcohol 56 (5.68 g, 99%) as clear oil: IR (film) 3331 (br s), 2929 (m), 1642 (m), 1445 (m), 1417 (w), 1348 (s), 1316 (s), 1217 (s), 1175 (s), 1119 (s), 1045 (m), 985 (s), 921 (m), 831 (w) cm$^{-1}$; $^1$H NMR (400 MHz, CDCl$_3$) δ 6.33 (td, J=6.1, 1.6 Hz, 1H), 5.75 (ddt, J=17.2, 10.0, 6.2 Hz, 1H), 5.07 (m, 2H), 4.29 (ddd, J=6.3, 4.3, 2.1 Hz, 2H), 2.95 (d, J=6.2 Hz, 2H); $^{13}$C NMR (100 MHz, CDCl$_3$) δ 134.45 (q, J=6 Hz), 133.38, 127.97 (q, J=29 Hz), 123.76 (q, J=271 Hz), 116.25, 57.87, 29.79

Iodide 57. A cooled (0° C.) solution of alcohol 56 (5.97 g, 0.0358 mol) in CH$_2$Cl$_2$ (50 mL) was treated with PPh$_3$ (11.17 g, 1.2 equiv), imidazole (3.55 g, 1.5 equiv) and I$_2$ (9.10 g, 1.1 equiv) and the resulting mixture was stirred at 0° C. for 10 min. The reaction mixture was quenched with saturated Na$_2$S$_2$O$_3$-saturated NaHCO$_3$ (1:1=V:V, 200 mL) and extracted with pentane (3×200 mL). Combined organice were washed with saturated Na$_2$S$_2$O$_3$-saturated NaHCO$_3$ (1:1=V:V, 200 mL), and brine (100 mL), dried (MgSO$_4$), and concentrated in vacuo. Flash chromatography (pentane) gave iodide 57 (6.69 g, 68%) as pale red oil: (IR Ifilm) 3083 (w), 2982 (w), 1636 (w), 1558 (w), 1456 (w), 1367 (w), 1317 (s), 1216 (m), 1181 (s), 1151 (s), 1120 (s), 989 (m), 921 (m), 896 (m) cm$^{-1}$; $^1$H NMR (400 MHz, CDCl$_3$) δ 6.45 (td, J=8.9, 1.5 Hz, 1H), 5.79 (ddt, J=16.8, 10.3, 6.2 Hz, 1H), 5.12 (m, 2H), 3.85 (ddd, J=8.9, 2.9, 1.4 Hz, 2H), 3.00 (dt, J=6.1, 1.4 Hz, 2H); $^{13}$C NMR (100 MHz, CDCl$_3$) δ 132.42, 131.64 (q, J=6 Hz), 129.63 (q, J=29 Hz), 123.64 (q, J=272 Hz), 117.00, 29.32, −4.27; low resolution mass spectrum m/z 298.7 [(M+Na)$^+$; calcd for C$_7$H$_8$F$_3$INa: 299.0].

α-Hydroxyoxazolidinone 58. To a cooled (−78° C.) of 57 (16.28 g, 1.92 equiv) (TES protected 4-Benzyl-3-hydroxy-acetyl-oxazolidin-2-one) in THF (160 mL) was added a solution of LHMDS (42.0 mL, 1.73 equiv) in THF (1.0 M) dropwise over 51 min and the resulting mixture was stirred at −78° C. for 35 min. The reaction mixture was treated with a solution of iodide XX (6.69 g, 24.2 mmol) in THF (10 mL) and the resulting mixture was allowed to warm to room temperature slowly overnight. The reaction mixture was quenched with saturated NaHCO$_3$ (200 mL) and extracted with EtOAc (3×200 mL). Combined organics were washed with saturated NH$_4$Cl (150 mL), brine (150 mL), dried (MgSO$_4$), and concentrated in vacuo. Flash chromatography (hexanes-EtOAc 6:1→3:1) provided a mixture of alkylation products (13.6 g) which were used for the next reaction without further purification. A solution of the alkylation products in HOAc-water-THF (3:1:1=V:V:V, 200 mL) was stirred at room temperature for 4 h. The reaction mixture was concentrated in vacuo to remove HOAc, quenched with saturated NaHCO$_3$ (400 mL), and extracted with EtOAc (3×200 mL). Combined organics were dried (MgSO$_4$), and concentrated in vacuo. Flash chromatography (hexanes:EtOAc 3:1→2:1) provided α-hydroxy-oxazolidinone 58 (7.55 g, 81% yield for two steps) as clear oil: [α]$_D^{20}$ (25° C.) −48.2° (c 1.08, CHCl$_3$); IR (film) 3486 (br s), 3030 (m), 2983 (s), 2925 (m), 1790 (s), 1682 (s), 1481 (m), 1393 (m), 1360 (m), 1217 (m), 1171 (m), 1113 (m), 992 (m), 919 (m), 847 (w) cm$^{-1}$; $^1$H NMR (400 MHz, CDCl$_3$) δ 7.32 (m, 3H), 7.17 (m, 2H), 6.33 (td, J=7.2, 1.5 Hz, 1H), 5.77 (ddt, J=16.6, 10.1, 6.2 Hz, 1H), 5.08 (m, 3H), 4.74 (ddt, J=4.8, 3.7, 4.4 Hz, 1H), 4.33 (dd, J=8.6, 8.6 Hz, 1H), 4.26 (dd, J=9.2, 3.4 Hz, 1H), 3.42 (br d, J=6.4 Hz, 1H), 3.24 (dd, J=13.5, 3.4 Hz, 1H), 2.99 (m, 2H), 2.79 (dd, J=13.5, 9.4 Hz, 1H), 2.70 (m, 1H), 2.50 (m, 1H); $^{13}$C NMR (125 MHz, CDCl$_3$) δ 173.93, 153.05, 134.43, 133.64, 129.98 (q, J=6 Hz), 129.82 (q, J=28 Hz), 129.29, 120.01, 127.58, 124.00 (q, J=272 Hz), 116.34, 69.60, 67.31, 54.95, 37.78, 32.29, 29.84; high resolution mass spectrum m/z 384.1421 [(M+H)$^+$; calcd for C$_{19}$H$_{21}$NO$_4$F$_3$: 384.1423].

α-Hydroxyamide 59. A suspension of (MeO)NHMe.HCl (10.1 g, 5.25 equiv) in THF (100 mL) at 0° C. was treated with a solution of AlMe$_3$ (50 mL, 5.1 equiv) in toluene (2.0 M) dropwise and the resulting clear solution was stirred at room temperature for 34 min, then added to a cooled (0° C.) solution of α-hydroxyoxazolidinone 58 (7.55 g, 19.7 mmol) in THF (70 mL). The resulting mixture was warmed to room temperature and stirred for 12 h. The reaction mixture was cooled to 0° C., quenched by slow addition of 1N aq. Tartaric acid (100 mL), stirred at room temperature for 25 min, and extracted with EtOAc (3×200 mL). Combined organics were dried (MgSO$_4$), and concentrated in vacuo. Flash chromatography (hexanes:EtOAc 2:1→1:1) gave α-hydroxyamide 59 (5.12 g, 97% yield) as clear oil: [α]$_D^{25}$ (24° C.) −57.2° (c 1.03, CHCl$_3$); IR (film) 3432 (br s), 3084 (w), 2980 (m), 2943 (m), 1652 (s), 1464 (m), 1373 (m), 1318 (m), 1214 (m), 1171 (m), 1112 (m), 991 (m), 919 (m), 818 (w) cm$^{-1}$; $^1$H NMR (400 MHz, CDCl$_3$) δ 6.32 (td, J=7.3, 1.5 Hz, 1H), 5.74 (ddt, J=16.9, 10.3, 6.1 Hz, 1H), 5.05 (m, 2H), 4.43 (dd, J=7.6, 3.5 Hz, 1H), 3.70 (s, 3H), 3.35 (br s, 1H), 3.24 (s, 3H), 2.94 (d, J=6.1 Hz, 2H), 2.59 (m, 1H), 2.36 (m, 1H); $^{13}$C NMR (100 MHz, CDCl$_3$) δ 173.43, 133.68, 130 59 (q, J=6 Hz), 129.25 (q, J=28 Hz), 124.05 (q, J=271 Hz), 116.17, 67.57, 61.44, 32.56, 32.38, 29.75; high resolution mass spectrum m/z 268.1161 [(M+H)$^+$; calcd for C$_{11}$H$_{17}$NO$_3$F$_3$: 268.1161].

α-Hydroxyketone 44. To a cooled (0° C.) solution of α-hydroxyamide 59 (4.87 g, 18.2 mmol) in THF (150 mL) was added a solution of MeMgBr (75 mL, 12 equiv) in ether (3.0 M). After 5 min, the reaction mixture was quenched with saturated NH$_4$Cl (250 mL), and extracted with EtOAc (5×200 mL). Combined organics were dried (MgSO$_4$), and concentrated in vacuo. Flash chromatography (hexanes:EtOAc 4:1→2:1→1:2) provided α-hydroxyketone 44 (2.16 g, 53% yield, 73% yield based on the recovered starting material) as clear oil and the starting material α-hydroxyamide 59 (1.30 g, 27% yield): [α]$_D^{20}$ (23° C.)+58.5° (c 1.30, CHCl$_3$); IR (film) 3460 (br s), 3085 (w), 2984 (m), 2926 (m), 1716 (s), 1679 (m), 1641 (m), 1417 (m), 1361 (m), 1319 (s), 1247 (m), 1216 (s), 1172 (s), 1113 (s), 1020 (m), 994 (m), 968 (w), 919 (m) cm$^{-1}$; $^1$H NMR (500 MHz, CDCl$_3$) δ 6.21 (t, J=7.0 Hz, 1H), 5.75 (ddt, J=16.7, 10.4, 6.2 Hz, 1H), 5.07 (m, 2H), 4.26 (dt, J=7.1, 4.5 Hz, 1H), 3.51 (d, J=4.7 Hz, 1H), 2.96 (d, J=6.1 Hz, 2H), 2.66 (m, 1H), 2.42 (m, 1H), 2.19 (s, 3H); $^{13}$C NMR (100 MHz, CDCl$_3$) δ 208.53, 133.43, 129.80 (q, J=28 Hz), 129.76 (q, J=6 Hz), 123.85 (q, J=271 Hz), 116.32, 75.36, 31.22, 29.81, 25.11; high resolution mass spectrum m/z 223.0945 [(M+H)$^+$; calcd for C$_{10}$H$_{14}$NO$_2$F$_3$: 223.0946].

Example 9

Catalytic Asymmetric Oxidation Approach

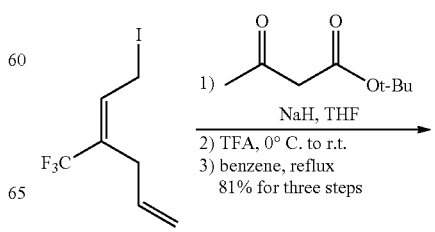

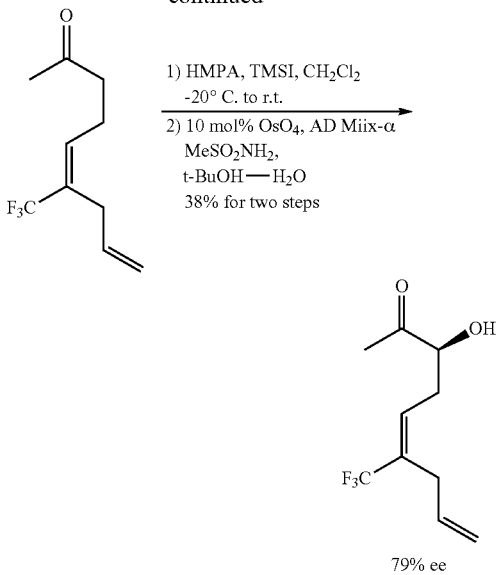

Example 10

In Vitro Studies

A typical experiment involves culturing cells (e.g., CCRF-CEM) at an initial density of 2-5×10⁴ cells per ml. They are maintained in a 5% $CO_2$-humidified atmosphere at 37° C. in RPMI medium 1640 (GIBCO/BRL) containing penicillin (100 units/ml), streptomycin (100 μg/ml) (GIBCO/BRL), and 5% heat-inactivated fetal bovine serum. For cells that were grown in suspension (such as CCRF-CEM and its sublines), cytotoxicitiy is measured by using the 2,-3-bis(2-methoxy-4-nitro-5-sulfophenyl)-5 carboxanilide)-2H terazodium hydroxide (XTT)-microculture tetrazonium method in duplicate in 96-well microtiter plates. For both methods, the absorbance of each well is measured with a microplate reader (EL-340, Bio-Tek, Burlington, Vt.). Each run entails six or seven concentrations of the tested drugs. Dose-effect relationship data are analyzed with the median-effect plot.

The CCRF-CEM human T cells, acute lymphoblastic leukemic cells, its teniposide-resistant subline (CCRF-CEM/VM₁) and vinblastine-resistant subline (CCRF-CEM/VBL₁₀₀) are obtained from W. T. Beck (University of Illinois, Chicago, Ill.).

In a typical experiment, as outlined generally above, certain of the inventive compounds (e.g., 9,10-dehydro-EpoD) demonstrated activity in CCRF-CEM cell lines and CCRF-CEM cell lines resistant to Taxol. Certain of these compounds exhibit $IC_{50}$s in the range of 0.0015 to about 0.120 for CCRF-CEM cell lines. Certain other compounds exhibit $IC_{50}$s in the range of 0.0015 to about 10.5. Certain of these compounds also exhibit $IC_{50}$s in the range of 0.011 to about 0.80 for CCRF-CEM/Taxol resistant cell lines and certain other compounds exhibit $IC_{50}$s in the range of about 0.011 to about 13.0 μM. In certain embodiments, 26F-EpoD exhibits activities in the range of 0.0015 μM for CCRF-CEM cell lines and in the range of 0.011 μM for CCRF-CEM/Taxol resistant cell lines.

Example 3

In Vivo Studies

Athymic nude mice bearing the nu/nu gene are typically used for tumor xenografts. Outbred, Swiss-background mice were obtained from Charles River Laboratories. Male mice 8 weeks or older weighing 22 g and up were used for most experiments. The drug was administered via the tail vein for 6 hr.-i.v. infusion. Each individual mouse was confined in a perforated Falcon polypropylene tube restrainer for drug administration. Tumor volume was assessed by measuring length×width×height (or width) using a caliper. The programmable Harvard PHD2000 syringe pump (Harvard Apparatus) with multi-track was used for i.v. infusion. All animal studies were conducted in accordance with the guidelines of the National Institutes of Health "Guide for the Care and Use of Animals" and the protocol approved by the Memorial Sloan-Kettering Cancer Center's Institutional Animal Care and Use Committee. In keeping with the policy of this committee for the humane treatment of tumor-bearing animals, mice were euthanized when tumors reached ≧10% of their total body weight.

Figure 8:
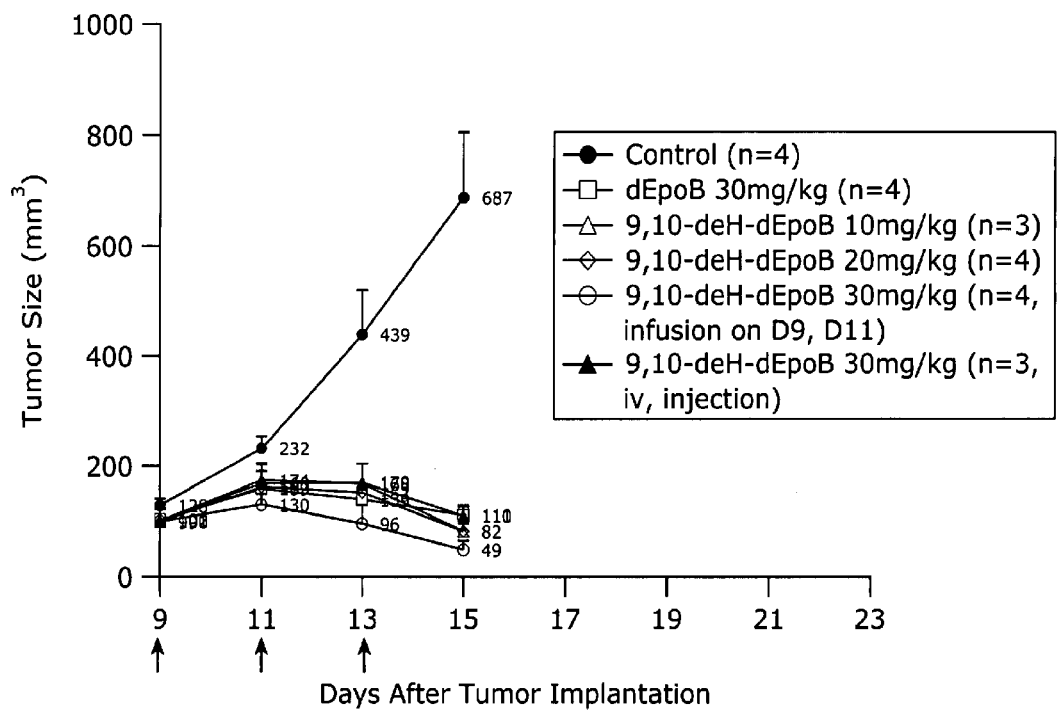
FIG. 8 shows the therapeutic effect of 9,10-dehydro-dEpoB and dEpoB in nude mice bearing human mammary carcinoma MX-1 xenograft.
Figure 53:
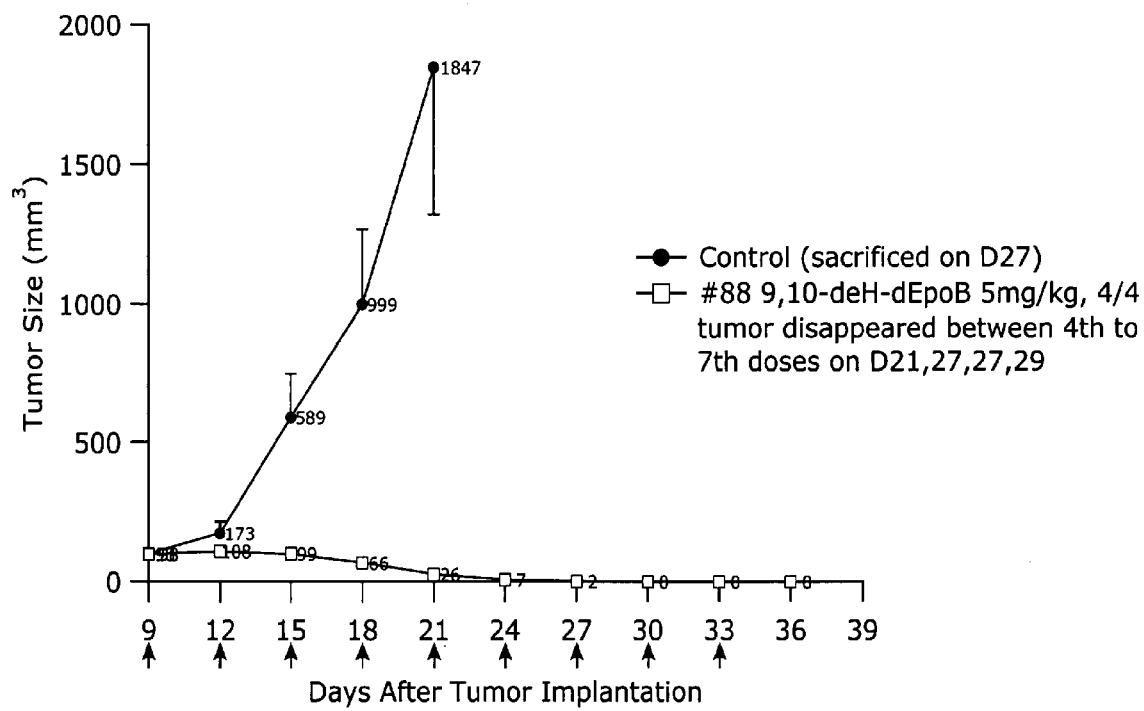
FIG. 53 shows the therapeutic effect of 9,10-dehydro-dEpoB in nude mice bearing MX-1 xenograft (Q3Dx9, 6 hr.-iv infusion).
Figure 54:
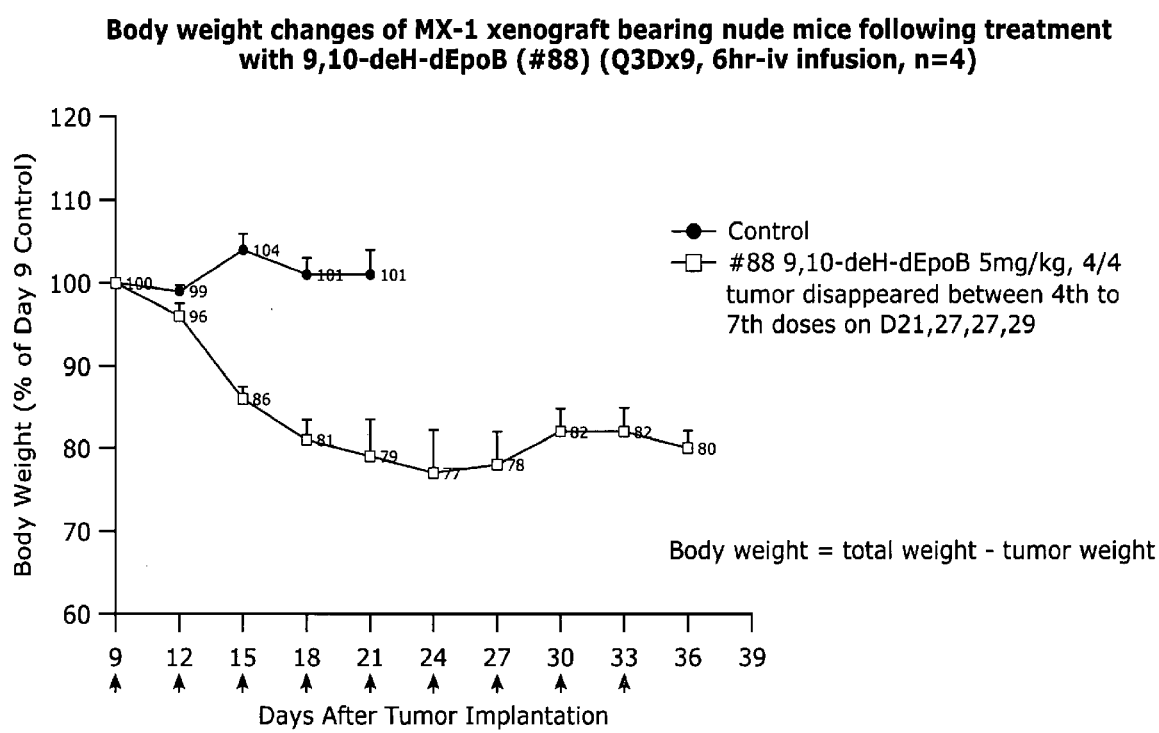
FIG. 54 shows changes in body weight of nude mice bearing an MX-1 xenograft following treatment with 9,10-dehydro-dEpoB (Q3Dx9, 6 hr-iv infusion).
Figure 55:
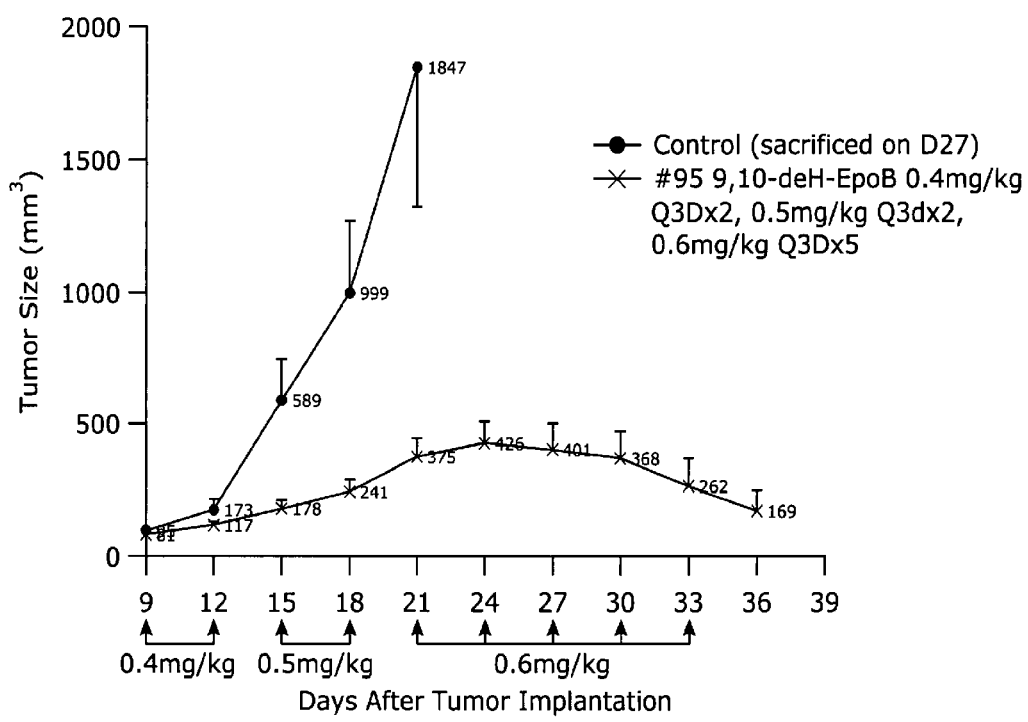
FIG. 55 shows the therapeutic effect of 9,10-dehydro-epothilone B in nude mice bearing MX-1 xenograft (Q3Dx9, 6 hour infusion).
Figure 56:
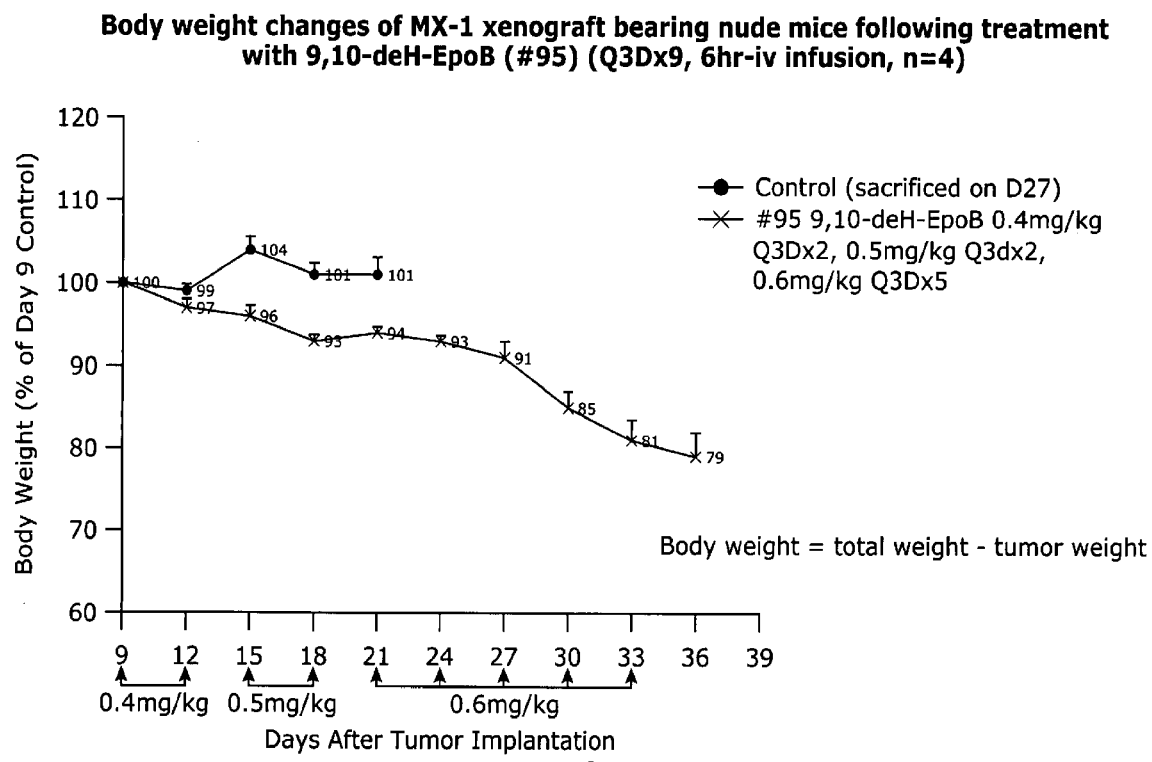
FIG. 56 shows changes in body weight of nude mice bearing MX-1 xenograft following treatment with 9,10-dehydro-epothilone B (Q3Dx9, 6 hr.-iv infusion).

As depicted in FIG. 8, 9,10-dehydro-EpoB was tested in nude mice bearing human mammary carcinoma MX-1. In general, 9,10-dehydro-EpoB was formulated as follows: 9,10-dehydro-EpoB was dissolved in ethanol and Cremophor was added (1:1) at a concentration of 20 mg/ml. This solution was diluted with saline for i.v. infusion (Q2DX3). The diluted solution was used for i.v. infusion within one hour. Tumor size and body weight were then measured using dosages of 10 mg/kg, 20 mg/kg, and 30 mg/kg over 15 days. Tumor size and body weight were also measured using a dosage regimen of 0.4 mg/kg Q3Dx2, 0.5 mg/kg Q3Dx2, and 0.6 mg/kg Q3Dx5 (see FIGS. 55 and 56). The every third day dosing regimen was used to reduce toxicity The compound, 9,10-dehydro-12,13-desoxyepothilone B (iso-490 epothilone), is three times more efficacious than dEpoB. 9,10-dehydro-12,13-desoxyepothilone D has been shown to arrest tumor growth after two to three infusions of 10 mg/kg or 20 mg/kg, each of which was administered every other day. Better results in mice were obtained using a dose of 30 mg/kg of 9,10-dehydro-12,13-desoxyepothilone B using two 6 hour infusion iv every other day. 9,10-dehydro-dEpoB at 5 mg/kg, Q3Dx9, 6 hr.-iv infusion, was also shown to achieve tumor disappearance in nude mice bearing MX-1 xenograft without mouse death and with only a moderate loss of body weight. This seems to have been accomplished by administering the epothilone analogs every third day to reduce toxicity (see FIGS. 53 and 54). In summary, 9,10-dehydro-12,13-desoxyepothilone B shows decreased toxicity as compared to other epothilones, greater potency in arresting tumor growth, and greater serum stability.

9,10-dehydro-Epo B when administered every other day nine times, 6 hour iv infusion, at 0.4 mg/kg, led to shrinkage of the tumor in nude mice with implanted human mammary carcinoma MX-1 xenografts; however, 1 out of 4 mice died due to toxicity. Administration every other day for 8 doses led to tumor growth suppression but no shrinkage of the tumor. When 9,10-dehydro-Epo B was administered every other day for 9 doses, the implanted tumor continued to shrink moderately from the second to the eighth day, but body weight recovered very slowly from 76% to 82% of the control during the same period. On the tenth day, one-fourth of tumor was gone. When a dosage of 0.6 mg/kg of 9,10-dehydro-EpoB was administered Q2Wx6, 6 hour infusion, to nude mice with HCT-116 xenografts, four out of four mice died of toxicity within three days after the sixth dosage.

26-trifluoro-9,10-dehydro-12,13-desoxy-epothilone B ($F_3$-deH-dEpoB) as shown in the Figures is curative at 20 mg/kg and 30 mg/kg, Q2Dx6, 6 hour infusions, in a nude mouse model implanted with human mammary carcinoma MX-1 xenografts. The data also suggests that 30 mg/kg Q2Dx6 is approximately the maximal tolerated dose. At 20 mg/kg, Q2Dx6, 6 hour infusion, 26-trifluoro-9,10-dehydro-12,13-dexoxy-epothilone B led to tumor shrinkage and disappearance in four out of four nude mice with human mammary carcinoma MX-1 xenografts. There was no reappearance of the tumor on the 20th day after stopping treatment. By comparison, dEpoB at 30 mg/kg achieved tumor disappearance in the same mouse model in five out of five mice; however, the tumor reappeared in 2 out of five mice on the 8th day after stopping treatment. Administration of 26-trifluoro-9,10-dehydro-12,13-desoxy-epothilone B at 20 mg/kg, Q2Dx6, 6 hr. iv infusion led to a transient drop in body weight of the mice up to 26%. This drop in body weight did not lead to death suggesting no severe toxicity toward vital organs. Two days after the last treatment, body weight began to recover. On the 16th day after treatment, body weight returned to 109% of the pretreatment control suggesting that toxicity, if any, is completely reversible. In comparison, dEpoB administered at 30 mg/kg led to a 31% decrease in body weight without lethality.

Figure 57:
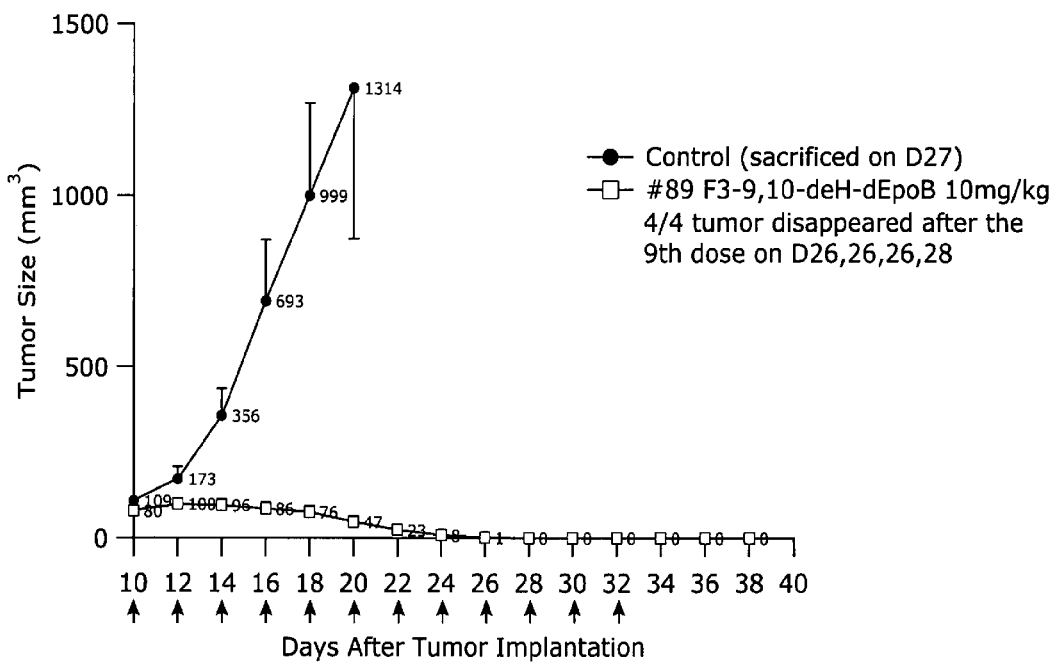
FIG. 57 shows the therapeutic effect at low doses of 26-trifluoro-9,10-dehydro-dEpoB in nude mice bearing MX-1 xenograft (6 hr.-i.v. infusion, Q2Dx12).
Figure 58:
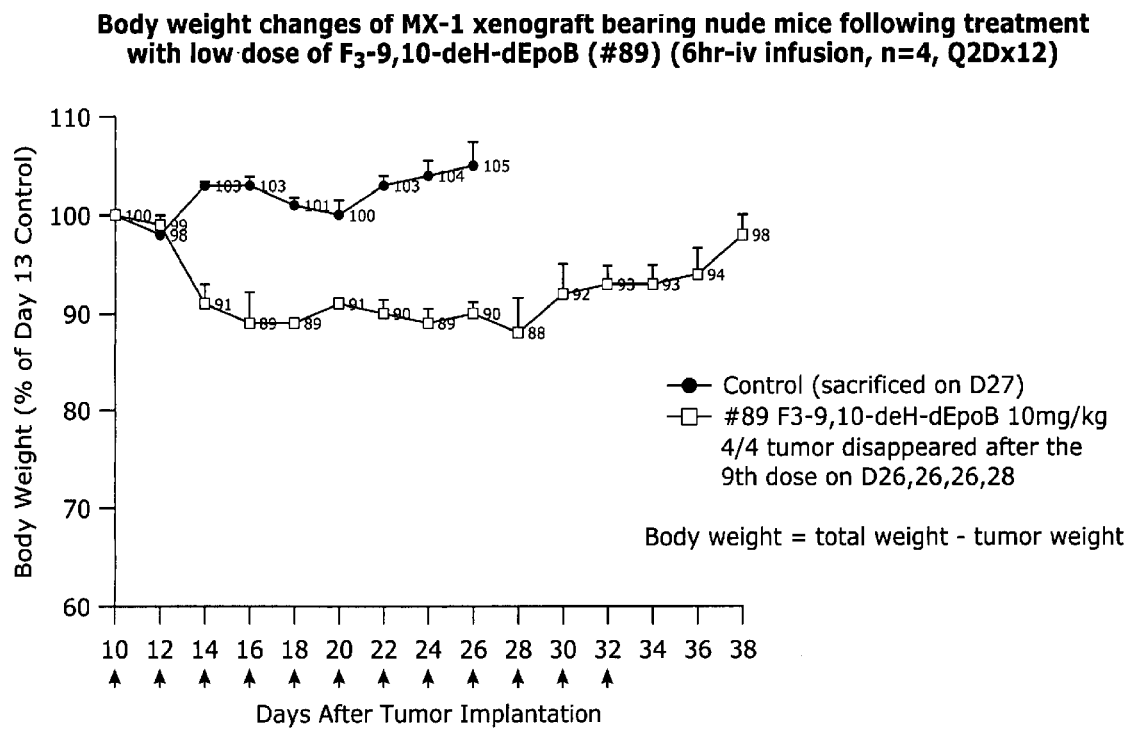
FIG. 58 shows changes in body weight of nude mice bearing a MX-1 xenograft following treatment with low doses of 26-trifluoro-9,10-dehydro-dEpoB (6 hr.-i.v. infusion, Q2Dx12).

When 26-trifluoro-9,10-dehydro-12,13-desoxy-epothilone B was administered at 30 mg/kg, Q2Dx6, 6 hour iv infusion, tumor disappearance was 2-3 days earlier than the 20 mg/kg dosage. Body weight dropped 27% at this higher dose and persisted 4 days without leading to lethality confirming no severe toxicity to vital organs. Four days after the last treatment at 30 mg/kg, body weight began to recover. On the 16th day after treatment, body weight returned to 98% of the pretreatment control again confirming the reversibility of toxicity. Treatment with 26-trifluoro-9,10-dehydro-dEpoB at 20 mg/kg and 30 mg/kg led to total tumor disappearance, and no relapse after 62 days was seen at the 30 mg/kg dose. Tumor disappearance was also achieved at 10 mg/kg by administering 9 doses with three additional doses given (FIG. 57). Only minor loss of body weight was observed at 10 mg/kg 26-trifluoro-9,10-dehydro-dEpoB (FIG. 58). No further loss of body weight was seen with continued treatment.

Conclusion. The 9,10-dehydro, 26-trifluoro, or both modifications to dEpoB result in a 1.5- to 5-fold increase in cytotoxicity in vitro and a 2- to 5-fold increase in half-life in mouse plasma in vitro. By using human solid tumor xenograft models in nude mice and using the Q2Dx5-9, 6 hr-i.v. infusion technique via tail vein at maximal tolerated doses, the antitumor efficacy and toxicity of 9,10-dehydro-epothilones were evaluated. The ability to achieve complete tumor growth suppression, tumor shrinkage, and disappearance allowed for further investigation to determine the relapse rate and cure rate after stopping treatment. 9,10-dehydro-EpoB, the most potent epothilone known in vitro, although highly efficacious, showed a narrow therapeutic safety margin in vivo. 9,10-dehydro-dEpoB at 4 mg/kg, 9,10-dehydro-EpoB at 0.4 mg/kg, and 21-hydroxy-9,10-dehydro-dEpoB at 3 mg/kg all strongly suppressed tumor growth for a sustained period of time and achieved some tumor shrinkage, and some achieved tumor disappearance. DEpoB at 30 mg/kg, 26-trifluoro-9,10-dehydro-dEpoB at 20 mg/kg, and paclitaxel at 20 mg/kg all showed strong suppression of tumor growth and achieved tumor shrinkage and disappearance of human mammary carcinoma MX-1 xenografts in all mice tested. 26-trifluoro-9,10-dehydro-dEpoB, when compared with dEpoB or paclitaxel, achieved a long term cure without a tumor relapse and showed an equally rapid recovery of body weight to the pretreatment control level.

The invention claimed is:

1. A method of stabilizing microtubule assemblies comprising administering a therapeutically effective amount of a compound of formula:

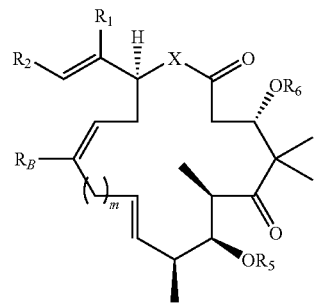

or a pharmaceutically acceptable salt thereof;
wherein:
$R_1$ is hydrogen or lower alkyl;
$R_2$ is a substituted or unsubstituted aryl, heteroaryl, arylalkyl, or heteroarylalkyl moiety;
$R_5$ and $R_6$ are each independently hydrogen or a protecting group;
X is O, S, $C(R_7)_2$, or $NR_7$, wherein each occurrence of $R_7$ is independently hydrogen or lower alkyl;
$R_B$ is, independently for each occurrence, hydrogen; halogen; —$OR_{B'}$; —$SR_{B'}$; —$N(R_{B'})_2$; —$CY_3$, —$CHY_2$, —$CH_2Y$, where Y is F, Br, Cl, I, $OR_{B'}$, $NHR_{B'}$, $N(R_{B'})_2$, or $SR_{B'}$; —$C(O)OR_{B'}$; —$C(O)R_{B'}$; —$CONHR_{B'}$; —$O(C{=}O)R_{B'}$; —$O(C{=}O)OR_{B'}$; —$NR_{B'}(C{=}O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C{=}O)R_{B'}$; —$O(C{=}O)OR_{B'}$; $NR_{B'}(C{=}O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; wherein each occurrence of $R_{B'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, heteroarylalkyl, heteroarylalkenyl, or heteroarylalkynyl moiety; and
m is 1, 2, 3, or 4;
to a subject in need thereof.

2. The method according to claim 1, wherein the compound is of the formula:

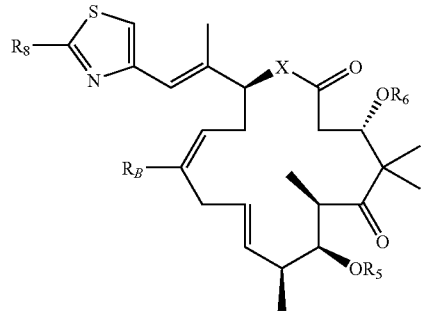

or a pharmaceutically acceptable salt thereof;
wherein:
X is O, S, $C(R_7)_2$, or $NR_7$, wherein each occurrence of $R_7$ is independently hydrogen or lower alkyl;
$R_5$ and $R_6$ are each independently hydrogen or a protecting group;
$R_B$ is hydrogen; halogen; —$OR_{B'}$; —$SR_{B'}$; —$N(R_{B'})_2$; —$CY_3$, —$CHY_2$, —$CH_2Y$, where Y is F, Br, Cl, I, $OR_{B'}$, $N(R_{B'})_2$, or $SR_{B'}$; —$C(O)OR_{B'}$; —$C(O)R_{B'}$; —CON- HR$_B$·; —O(C=O)R$_B$·; —O(C=O)OR$_B$·; —NR$_B$·; —(C=O)R$_B$·; N$_3$; N$_2$R$_B$·; cyclic acetal; or cyclic or acyclic, linear or branched aliphatic, heteroaliphatic, aryl, or heteroaryl, optionally substituted with one or more of hydrogen; halogen; —OR$_B$·; —SR$_B$·; —N(R$_B'$)$_2$; —C(O)OR$_B$·; —C(O)R$_B$·; —CONHR$_B$·; —O(C=O) R$_B$·; —O(C=O)OR$_B$·; —NR$_B'$(C=O)R$_B$·; N$_3$; N$_2$R$_B$'; cyclic acetal; or cyclic or acyclic, linear or branched substituted or unsubstituted aliphatic, heteroaliphatic, aryl, or heteroaryl moiety; or is an epothilone, desoxyepothilone, or analogues thereof or is a polymer; carbohydrate; photoaffinity label; or radiolabel; wherein each occurrence of R$_{B'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, heteroarylalkyl, heteroarylalkenyl, or heteroarylalkynyl moiety;

R$_8$ is independently hydrogen, halogen, —OR$_9$, —SR$_9$, —N(R$_9$)$_2$, —CY$_3$, —CHY$_2$, —CH$_2$Y, where Y is F, Br, Cl, I, OR$_{B'}$, NHR$_{B'}$, N(R$_{B'}$)$_2$, or SR$_{B'}$; —(CV$_2$)$_n$OR$_9$, —(CV$_2$)$_n$N(R$_9$)$_2$, —(CV$_2$)$_n$SR$_9$, —(C=O)R$_9$, —O(C=O)R$_9$, —(C=O)OR$_9$, —O(C=O)OR$_9$; —NH(C=O)R$_9$, —NH(C=O)OR$_9$, —(C=O)NHR$_9$, or a cyclic or acyclic, linear or branched aliphatic, heteroaliphatic, aryl, heteroaryl, arylalkyl, or heteroarylalkyl moiety optionally substituted with one or more occurrences of halogen, —OR$_9$, —SR$_9$, —N(R$_9$)$_2$, —(CV$_2$)$_n$OR$_9$, —(CV$_2$)$_n$N(R$_9$)$_2$, —(CV$_2$)$_n$SR$_9$, —(C=O)R$_9$, —O(C=O)R$_9$, —(C=O)OR$_9$, —O(C=O)OR$_9$; —NH(C=O)R$_9$, —NH(C=O)OR$_9$, —(C=O)NHR$_9$, or a cyclic or acyclic, linear or branched, substituted or unsubstituted aliphatic, heteroaliphatic, aryl, heteroaryl, arylalkyl, or heteroarylalkyl moiety, wherein each occurrence of R$_9$ is independently hydrogen; a protecting group; a cyclic or acyclic, linear or branched, substituted or unsubstituted aliphatic, heteroaliphatic, aryl, or heteroaryl moiety; or is an epothilone, desoxyepothilone or analogues thereof; a polymer; carbohydrate; photoaffinity label; or radiolabel; and wherein each occurrence of V is independently hydrogen, halogen, hydroxyl, thio, amino, alkylamino, or protected hydroxyl, thio or amino; each occurrence of t is independently 0, 1 or 2;

and each occurrence of n is independently 0-10;

wherein the therapeutically effective amount is an amount sufficient to deliver about 0.001 mg to about 40 mg compound per kg body weight.

3. The method according to claim 1, wherein the compound is of the formula:

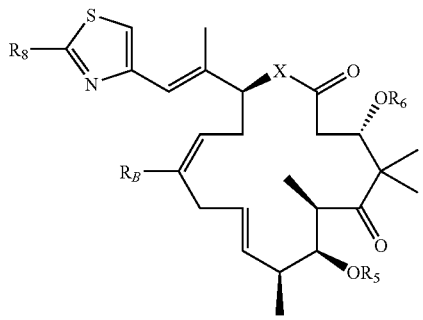

or a pharmaceutically acceptable salt thereof;

wherein:

X is O, S, C(R$_7$)$_2$, or NR$_7$, wherein each occurrence of R$_7$ is independently hydrogen or lower alkyl;

R$_5$ and R$_6$ are each independently hydrogen or a protecting group;

R$_B$ is hydrogen; halogen; —OR$_B$·; —SR$_B$·; —N(R$_B'$)$_2$; —CY$_3$, —CH$_2$Y, where Y is F, Br, Cl, I, OR$_{B'}$, NHR$_{B'}$, N(R$_{B'}$)$_2$, or SR$_{B'}$; —C(O)OR$_B$·; —C(O)R$_B$·; —CONHR$_B$·; —O(C=O)R$_B$·; —O(C=O)OR$_B$·; —NR$_B'$(C=O)R$_B$·; N$_3$·; N$_2$R$_B$·; cyclic acetal; or cyclic or acyclic, linear or branched aliphatic, heteroaliphatic, aryl, or heteroaryl, optionally substituted with one or more of hydrogen; halogen; —OR$_B$·; —SR$_B$·; —N(R$_B'$)$_2$; —C(O)OR$_B$·; —C(O)R$_B$·; —CONHR$_B$·; —O(C=O) R$_B$·; —O(C=O)OR$_B$·; —NR$_B'$(C=O)R$_B$·; N$_3$; N$_2$R$_B$·; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; wherein each occurrence of R$_{B'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, heteroarylalkyl, heteroarylalkenyl, or heteroarylalkynyl moiety;

R$_8$ is independently hydrogen, halogen, —OR$_9$, —SR$_9$, —N(R$_9$)$_2$, —CY$_3$, —CHY$_2$, where Y is F, Br, Cl, I, OR$_{B'}$, NHR$_{B'}$, N(R$_{B'}$)$_2$, or SR$_{B'}$; —(CV$_2$)$_n$OR$_9$, —(CV$_2$)$_n$N(R$_9$)$_2$, —(CV$_2$)$_n$SR$_9$, —(C=O)R$_9$, —O(C=O)R$_9$, —(C=O)OR$_9$, —O(C=O)OR$_9$; —NH(C=O)R$_9$, —NH(C=O)OR$_9$, —(C=O)NHR$_9$, or a cyclic or acyclic, linear or branched aliphatic, heteroaliphatic, aryl, heteroaryl, arylalkyl, or heteroarylalkyl moiety optionally substituted with one or more occurrences of halogen, —OR$_9$, —SR$_9$, —N(R$_9$)$_2$, —(CV$_2$)$_n$OR$_9$, —(CV$_2$)$_n$N(R$_9$)$_2$, —(CV$_2$)$_n$SR$_9$, —(C=O)R$_9$, —O(C=O)R$_9$, —(C=O)OR$_9$, —O(C=O)OR$_9$; —NH(C=O)R$_9$, —NH(C=O)OR$_9$, —(C=O)NHR$_9$, or a cyclic or acyclic, linear or branched, substituted or unsubstituted aliphatic, heteroaliphatic, aryl, heteroaryl, arylalkyl, or heteroarylalkyl moiety, wherein each occurrence of R$_9$ is independently hydrogen; a protecting group; a cyclic or acyclic, linear or branched, substituted or unsubstituted aliphatic, heteroaliphatic, aryl, or heteroaryl moiety; or is an epothilone, desoxyepothilone or analogues thereof; a polymer; carbohydrate; photoaffinity label; or radiolabel; and wherein each occurrence of V is independently hydrogen, halogen, hydroxyl, thio, amino, alkylamino, or protected hydroxyl, thio or amino; each occurrence of t is independently 0, 1 or 2; and each occurrence of n is independently 0-10;

wherein the therapeutically effective amount is an amount sufficient to deliver about 0.1 mg to about 25 mg compound per kg body weight.

4. The method according to claim 2 wherein R$_B$ is methyl.

5. The method according to claim 2, wherein R$_B$ is —CF$_3$.

6. The method according to claim 2, wherein R$_8$ is methyl.

7. The method according to claim 2, wherein R$_8$ is —CH$_2$OH.

8. The method according to claim 2, wherein R$_8$ is —CH$_2$NH$_2$.

9. The method according to claim 2, wherein the compound is of formula:

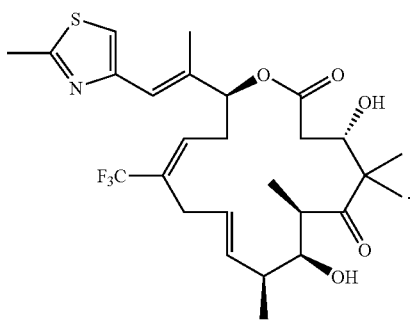

10. The method according to claim 2, wherein the compound is of formula:

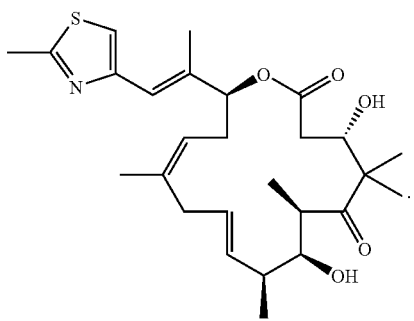

11. The method according to claim 1 wherein $R_2$ is a substituted or unsubstituted heteroaryl moiety.

12. The method according to claim 11, wherein the compound is of formula:

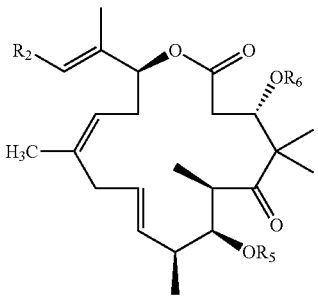

13. The method according to claim 12 wherein $R_2$ is a substituted isoxazolyl, $R_5$ is hydrogen, and $R_6$ is hydrogen.

14. The method according to claim 12 wherein $R_2$ is a substituted oxazolyl, $R_5$ is hydrogen, and $R_6$ is hydrogen.

15. The method according to claim 13 wherein the isoxazolyl group is substituted with an aliphatic moiety.

16. The method according to claim 15 wherein the isoxazolyl group is substituted with a $C_{1-4}$ alkyl group.

17. The method according to claim 16 wherein the isoxazolyl group is substituted with a methyl group.

18. The method according to claim 14 wherein the oxazolyl group is substituted with an aliphatic moiety.

19. The method according to claim 18 wherein the oxazolyl group is substituted with a $C_{1-4}$ alkyl group.

20. The method according to claim 19 wherein the oxazolyl group is substituted with a methyl group.

21. The method according to claim 11, wherein the compound is of formula:

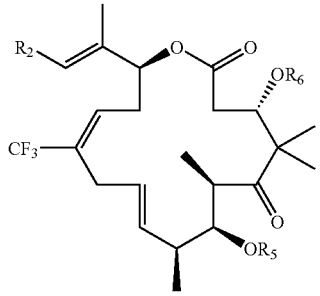

22. The method according to claim 21, wherein $R_2$ is substituted isoxazolyl, $R_5$ is hydrogen and $R_6$ is hydrogen.

23. The method according to claim 22 wherein the isoxazolyl group is substituted with an aliphatic moiety.

24. The method according to claim 23 wherein the isoxazolyl group is substituted with a $C_{1-4}$ alkyl group.

25. The method according to claim 24 wherein the isoxazolyl group is substituted with a methyl group.

26. The method according to claim 21, wherein $R_2$ is substituted oxazolyl, $R_5$ is hydrogen and $R_6$ is hydrogen.

27. The method according to claim 26 wherein the oxazolyl group is substituted with an aliphatic moiety.

28. The method according to claim 27 wherein the oxazolyl group is substituted with a $C_{1-4}$ alkyl group.

29. The method according to claim 28 wherein the oxazolyl group is substituted with a methyl group.

30. A method of treating cancer comprising administering to a subject in need thereof a therapeutically effective amount of a compound of the formula:

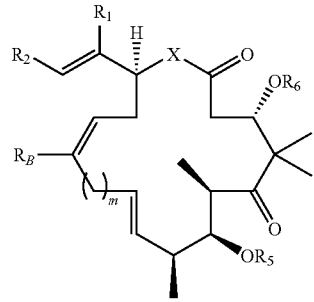

or a pharmaceutically acceptable salt thereof;
wherein:
$R_1$ is hydrogen or lower alkyl;
$R_2$ is a substituted or unsubstituted aryl, heteroaryl, arylalkyl, or heteroarylalkyl moiety;
$R_5$ and $R_6$ are each independently hydrogen or a protecting group;
X is O, S, $C(R_7)_2$, or $NR_7$, wherein each occurrence of $R_7$ is independently hydrogen or lower alkyl;
$R_B$ is, independently for each occurrence, hydrogen; halogen; —$OR_{B'}$; —$SR_{B'}$; —$N(R_{B'})_2$; —$CY_3$, —$CHY_2$, —$CH_2Y$, where Y is F, Br, Cl, I, $OR_{B'}$, $NHR_{B'}$, $N(R_{B'})_2$, or $SR_{B'}$; —$C(O)OR_{B'}$; —$C(O)R_{B'}$; —$CONHR_{B'}$; —$O(C\!=\!O)R_{B'}$; —$O(C\!=\!O)OR_{B'}$; —$NR_{B'}(C\!=\!O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —$N(R_{B'})_2$; —$C(O)OR_{B'}$—$C(O)R_{B'}$; —$CONHR_{B'}$; —$O(C\!=\!O)R_{B'}$; —$O(C\!=\!O)OR_{B'}$; $NR_{B'}(C\!=\!O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; wherein each occurrence of $R_{B'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, heteroarylalkyl, heteroarylalkenyl, or heteroarylalkynyl moiety; and m is 1, 2, 3, or 4;

wherein the cancer is selected from breast cancer, brain cancer, skin cancer, cervical cancer, colon cancer, rectal cancer, myeloid leukemia, lymphocytic leukemia, myelocytic leukemia, lymphoblastic leukemia, lung cancer, melanoma, malignant melanoma, non-Hodgkin's lymphoma, ovarian cancer, pancreatic cancer, prostate cancer and gastric cancer.

31. The method according to claim 30, wherein the compound is of the formula:

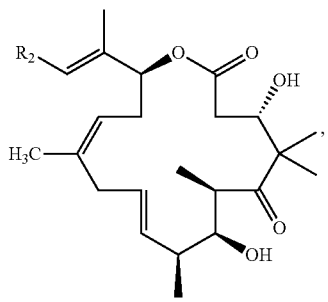

or a pharmaceutically acceptable salt thereof.

32. The method according to claim 31, wherein $R_2$ is substituted isoxazolyl.

33. The method according to claim 32, wherein the isoxazolyl group is substituted with an aliphatic moiety.

34. The method according to claim 33, wherein the isoxazolyl group is substituted with a $C_{1-4}$ alkyl group.

35. The method according to claim 34, wherein the isoxazolyl group is substituted with a methyl group.

36. The method according to claim 31, wherein $R_2$ is substituted oxazolyl.

37. The method according to claim 36, wherein the oxazolyl group is substituted with an aliphatic moiety.

38. The method according to claim 37, wherein the oxazolyl group is substituted with a $C_{1-4}$ alkyl group.

39. The method according to claim 38, wherein the oxazolyl group is substituted with a methyl group.

40. The method according to claim 30, wherein the compound is of the formula:

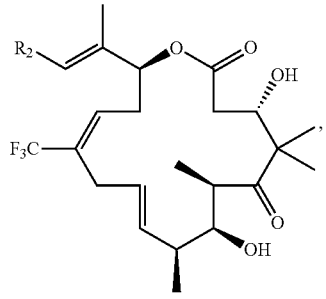

or a pharmaceutically acceptable salt thereof.

41. The method according to claim 40, wherein $R_2$ is substituted isoxazolyl.

42. The method according to claim 41, wherein the isoxazolyl group is substituted with an aliphatic moiety.

43. The method according to claim 42, wherein the isoxazolyl group is substituted with a $C_{1-4}$ alkyl group.

44. The method according to claim 43, wherein the isoxazolyl group is substituted with a methyl group.

45. The method according to claim 40, wherein $R_2$ is substituted oxazolyl.

46. The method according to claim 45, wherein the oxazolyl group is substituted with an aliphatic moiety.

47. The method according to claim 46, wherein the oxazolyl group is substituted with a $C_{1-4}$ alkyl group.

48. The method according to claim 47, wherein the oxazolyl group is substituted with a methyl group.

49. The method according to claim 30, wherein the compound is of formula:

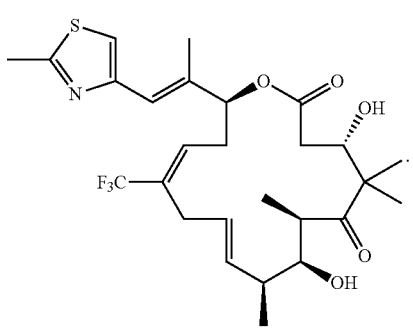

50. The method according to claim 30, wherein the compound is of formula:

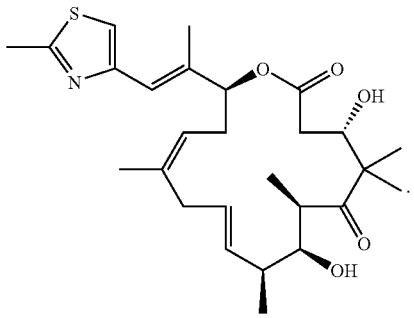

* * * * *